US012378536B1

(12) United States Patent
Bermudes et al.

(10) Patent No.: US 12,378,536 B1
(45) **Date of Patent: *Aug. 5, 2025**

(54) CHIMERIC PROTEIN TOXINS FOR EXPRESSION BY THERAPEUTIC BACTERIA

(71) Applicant: David Gordon Bermudes, Woodland Hills, CA (US)

(72) Inventors: David Gordon Bermudes, Woodland Hils, CA (US); David Quintero, Northridge, CA (US)

(73) Assignee: David Bermudes, Woodland Hills, CA (US)

(*) Notice: Subject to any disclaimer, the term of this patent is extended or adjusted under 35 U.S.C. 154(b) by 959 days.

This patent is subject to a terminal disclaimer.

(21) Appl. No.: 16/895,874

(22) Filed: Jun. 8, 2020

Related U.S. Application Data

(62) Division of application No. 15/151,194, filed on May 10, 2016, now Pat. No. 10,676,723.

(60) Provisional application No. 62/159,645, filed on May 11, 2015.

(51) Int. Cl.

| | |
|---|---|
| ***A61K 35/74*** | (2015.01) |
| ***C07K 7/08*** | (2006.01) |
| ***C07K 14/005*** | (2006.01) |
| ***C07K 14/195*** | (2006.01) |
| ***C07K 14/245*** | (2006.01) |
| ***C07K 14/415*** | (2006.01) |
| ***C12N 9/10*** | (2006.01) |
| *A61K 35/00* | (2006.01) |
| *A61K 38/00* | (2006.01) |

(52) U.S. Cl.
CPC ............ *C12N 9/1077* (2013.01); *A61K 35/74* (2013.01); *C07K 14/005* (2013.01); *C07K 14/245* (2013.01); *C07K 14/415* (2013.01); *C12Y 204/02036* (2013.01); *A61K 2035/11* (2013.01); *A61K 38/00* (2013.01); *C07K 2319/00* (2013.01); *C07K 2319/55* (2013.01); *C12N 2750/10022* (2013.01); *C12N 2750/10033* (2013.01)

(58) Field of Classification Search
None
See application file for complete search history.

(56) References Cited

U.S. PATENT DOCUMENTS

| | | | |
|---|---|---|---|
| 3,939,558 A | | 2/1976 | Riley |
| 4,436,727 A | | 3/1984 | Ribi |
| 4,703,008 A | | 10/1987 | Lin |
| 4,906,567 A | | 3/1990 | Connelly |
| 5,021,234 A | | 6/1991 | Ehrenfeld |
| D320,325 S | | 10/1991 | Barfield |
| 5,055,294 A | | 10/1991 | Gilroy |
| 5,057,417 A | | 10/1991 | Hammonds et al. |
| 5,082,927 A | | 1/1992 | Pastan et al. |
| 5,087,569 A | | 2/1992 | Gabay et al. |
| 5,098,833 A | | 3/1992 | Lasky et al. |
| 5,116,964 A | | 5/1992 | Capon et al. |
| 5,126,257 A | | 6/1992 | Gabay et al. |
| 5,143,830 A | | 9/1992 | Holland et al. |
| 5,143,905 A | | 9/1992 | Sivasubramanian et al. |
| 5,152,980 A | | 10/1992 | Strom et al. |
| 5,169,764 A | | 12/1992 | Shooter et al. |
| 5,177,308 A | | 1/1993 | Barton et al. |
| 5,187,153 A | * | 2/1993 | Cordell .................. A61P 17/02 530/324 |
| 5,202,422 A | | 4/1993 | Hiatt et al. |
| 5,206,353 A | | 4/1993 | Berger et al. |
| 5,223,409 A | | 6/1993 | Ladner et al. |
| 5,238,839 A | | 8/1993 | Cantor et al. |
| 5,250,515 A | | 10/1993 | Fuchs et al. |
| 5,254,799 A | | 10/1993 | De Greve et al. |
| 5,278,049 A | | 1/1994 | Baker et al. |
| 5,281,530 A | | 1/1994 | Sick et al. |
| 5,290,914 A | | 3/1994 | Wilcox et al. |
| 5,306,628 A | | 4/1994 | Sivasubramanian et al. |
| 5,306,631 A | | 4/1994 | Harrison et al. |
| 5,316,933 A | | 5/1994 | Yoshimatsu et al. |
| 5,317,096 A | | 5/1994 | De Greve et al. |
| 5,318,900 A | | 6/1994 | Habuka et al. |
| 5,328,984 A | | 7/1994 | Pastan et al. |
| 5,328,985 A | | 7/1994 | Sano et al. |

(Continued)

FOREIGN PATENT DOCUMENTS

| | | | |
|---|---|---|---|
| AU | 2007216854 | C1 | 10/2007 |
| AU | 2002225265 | B2 | 12/2007 |

(Continued)

OTHER PUBLICATIONS

Reagan-Shaw et al, Dose translation from animal to human studies revisited, 2007, pp. 659-661.*
D' Souza, Structural parameters modulating the cellular uptake of disulfide-rich cyclic cell-penetrating peptides: MCoTI-II and SFTI-1, European J of Medicinal Chemistry, 2014, pp. 10-18.*
Patyar et al. Bacteria in cancer therapy: a novel experimentalstrategy, Journal of Biomedical Science 2010, 17:21, pp. 1-9.*

(Continued)

*Primary Examiner* — Maria Marvich
(74) *Attorney, Agent, or Firm* — Hoffberg & Associates; Steven M. Hoffberg

(57) ABSTRACT

Bacteria with tumor-targeting capability express, surface displayed, secreted and/or released modified chimeric therapeutic proteins with enhanced therapeutic activity against a neoplastic tissue including solid tumors, lymphomas and leukemias. The bacteria may be attenuated, non-pathogenic, low pathogenic or a probiotic. The chimeric proteins may be protease sensitive and may optionally be further accompanied by co-expression of a secreted protease inhibitor as a separate molecule or as a fusion.

15 Claims, 15 Drawing Sheets

Specification includes a Sequence Listing.

(56) References Cited

U.S. PATENT DOCUMENTS 5,338,724 A 8/1994 Gabay et al.
5,344,762 A 9/1994 Karapetian
5,349,124 A 9/1994 Fischhoff et al.
5,354,675 A 10/1994 Iida et al.
5,356,795 A 10/1994 Leonard et al.
5,356,804 A 10/1994 Desnick et al.
5,366,874 A 11/1994 Eidels et al.
5,376,567 A 12/1994 McCormick et al.
5,380,831 A 1/1995 Adang et al.
5,382,524 A 1/1995 Desnick et al.
5,387,676 A 2/1995 Zavada et al.
5,387,744 A 2/1995 Curtiss, III et al.
5,389,368 A 2/1995 Gurtiss, III
5,399,490 A 3/1995 Balganesh et al.
5,403,484 A 4/1995 Ladner et al.
5,424,065 A 6/1995 Curtiss, III et al.
5,428,143 A 6/1995 Berger et al.
5,439,808 A 8/1995 Blake et al.
5,455,165 A 10/1995 Capon et al.
5,458,878 A 10/1995 Pastan et al.
5,460,961 A 10/1995 Deby et al.
5,466,463 A 11/1995 Ford
5,466,672 A 11/1995 Kushnaryov et al.
5,468,485 A 11/1995 Curtiss, III
5,470,719 A 11/1995 Meng et al.
5,491,075 A 2/1996 Desnick et al.
5,492,702 A 2/1996 Domingues
5,495,001 A 2/1996 McGrogan et al.
5,506,139 A 4/1996 Loosmore et al.
5,508,192 A 4/1996 Georgiou et al.
5,508,264 A 4/1996 Bradfisch et al.
5,512,658 A 4/1996 Pastan et al.
5,512,661 A 4/1996 Shooter et al.
5,514,582 A 5/1996 Capon et al.
5,525,502 A 6/1996 Thireos et al.
5,527,883 A 6/1996 Thompson et al.
5,529,932 A 6/1996 Lorenzetti et al.
5,543,312 A 8/1996 Mellors et al.
5,545,553 A 8/1996 Gotschlich
5,545,565 A 8/1996 De Greve et al.
5,562,907 A 10/1996 Arnon
5,567,600 A 10/1996 Adang et al.
5,567,862 A 10/1996 Adang et al.
5,569,597 A 10/1996 Grimsley et al.
5,571,544 A 11/1996 Domingues
5,571,698 A 11/1996 Ladner et al.
5,583,010 A 12/1996 Baumbach et al.
5,585,232 A 12/1996 Farr
5,585,269 A 12/1996 Earp, III et al.
5,587,455 A 12/1996 Berger et al.
5,589,337 A 12/1996 Farr
5,591,641 A 1/1997 Thorner et al.
5,593,881 A 1/1997 Thompson et al.
5,593,882 A 1/1997 Erbe et al.
5,602,030 A 2/1997 Ingrahm et al.
5,602,095 A 2/1997 Pastan et al.
5,604,115 A 2/1997 Sladek et al.
5,604,201 A 2/1997 Thomas et al.
5,614,191 A 3/1997 Puri et al.
5,616,482 A 4/1997 Williams
5,624,816 A 4/1997 Carraway et al.
5,624,832 A 4/1997 Fukuda et al.
5,631,150 A 5/1997 Harkki et al.
5,631,156 A 5/1997 Xiong et al.
5,631,228 A 5/1997 Oppenheim et al.
5,635,484 A 6/1997 Ayres et al.
5,635,599 A 6/1997 Pastan et al.
5,651,965 A 7/1997 Payne
5,652,122 A 7/1997 Frankel et al.
5,656,436 A 8/1997 Loosmore et al.
5,665,353 A 9/1997 Loosmore et al.
5,665,357 A 9/1997 Rose et al.
5,670,617 A 9/1997 Frankel et al.
5,674,980 A 10/1997 Frankel et al.
5,677,148 A 10/1997 Williams
5,683,868 A 11/1997 LaRossa et al.
5,686,600 A 11/1997 Carozzi et al.
5,703,039 A 12/1997 Williams et al.
5,705,151 A 1/1998 Dow et al.
5,705,156 A 1/1998 Pastan et al.
5,705,163 A 1/1998 Pastan et al.
5,712,369 A 1/1998 Old et al.
5,726,037 A 3/1998 Bodary et al.
5,731,163 A 3/1998 Vandyk et al.
5,733,543 A 3/1998 Nabel et al.
5,733,760 A 3/1998 Lu et al.
5,747,287 A 5/1998 Blake et al.
5,747,326 A 5/1998 Gerardy-Schahn et al.
5,747,641 A 5/1998 Frankel et al.
5,747,659 A 5/1998 Fioretti et al.
5,760,181 A 6/1998 De Greve et al.
5,763,250 A 6/1998 Williams et al.
5,767,241 A 6/1998 McEver
5,767,372 A 6/1998 De Greve et al.
5,770,420 A 6/1998 Lowe et al.
5,776,755 A 7/1998 Alitalo et al.
5,783,431 A 7/1998 Peterson et al.
5,786,179 A 7/1998 Kousoulas et al.
5,786,186 A 7/1998 Lancashire et al.
5,804,604 A 9/1998 Frankel et al.
5,821,081 A 10/1998 Boyd et al.
5,821,238 A 10/1998 Pastan et al.
5,824,485 A 10/1998 Thompson et al.
5,824,502 A 10/1998 Honjo et al.
5,824,509 A 10/1998 Aggarwal et al.
5,824,538 A 10/1998 Branstrom et al.
5,827,514 A 10/1998 Bradfisch et al.
5,830,702 A 11/1998 Portnoy et al.
5,837,488 A 11/1998 Garfinkel et al.
5,837,500 A 11/1998 Ladner et al.
5,840,554 A 11/1998 Thompson et al.
5,840,840 A 11/1998 Rybak et al.
5,843,707 A 12/1998 Larsen et al.
5,843,882 A 12/1998 Boyd et al.
5,843,898 A 12/1998 De Greve et al.
5,849,702 A 12/1998 Garfinkel et al.
5,854,044 A 12/1998 Pastan et al.
5,863,745 A 1/1999 Fitzgerald et al.
5,863,758 A 1/1999 Oppermann et al.
5,863,891 A 1/1999 Williams et al.
5,869,045 A 2/1999 Hellstrom et al.
5,869,302 A 2/1999 Loosmore et al.
5,877,012 A 3/1999 Estruch et al.
5,877,159 A 3/1999 Powell et al.
5,879,686 A 3/1999 Blake et al.
5,902,742 A 5/1999 Petter et al.
5,912,141 A 6/1999 Brojatsch et al.
5,912,230 A 6/1999 Oppenheim et al.
5,919,456 A 7/1999 Puri et al.
5,925,521 A 7/1999 Bandman et al.
5,928,892 A 7/1999 Hourcade et al.
5,932,209 A 8/1999 Thompson et al.
5,932,471 A 8/1999 Williams et al.
5,935,573 A 8/1999 Loosmore et al.
5,939,297 A 8/1999 Loosmore et al.
5,945,102 A 8/1999 de Faire et al.
5,945,322 A 8/1999 Gotschlich
5,955,073 A 9/1999 Rybak et al.
5,955,347 A 9/1999 Lowe
5,958,406 A 9/1999 de Faire et al.
5,962,430 A 10/1999 Loosmore et al.
5,962,653 A 10/1999 Boyd et al.
5,965,382 A 10/1999 Koths et al.
5,965,385 A 10/1999 Read et al.
5,965,415 A 10/1999 Radman et al.
5,965,428 A 10/1999 Gilmer et al.
5,976,852 A 11/1999 Cheng et al.
5,977,304 A 11/1999 Read et al.
5,980,896 A 11/1999 Hellstrom et al.
5,981,503 A 11/1999 Loosmore et al.
5,989,868 A 11/1999 Harrison et al.
5,993,827 A 11/1999 Sim et al.
5,994,625 A 11/1999 Melchers et al.
5,997,881 A 12/1999 Powell et al.

(56) References Cited

U.S. PATENT DOCUMENTS 5,998,587 A 12/1999 Boyd et al.
6,004,562 A 12/1999 Campagnari
6,005,089 A 12/1999 Lanza et al.
6,011,002 A 1/2000 Pastan et al.
6,013,523 A 1/2000 Adang et al.
6,015,876 A 1/2000 Boyd
6,015,891 A 1/2000 Adang et al.
6,015,897 A 1/2000 Theodore et al.
6,017,743 A 1/2000 Tsuji et al.
6,018,022 A 1/2000 Read et al.
6,020,145 A 2/2000 Hellstrom et al.
6,020,183 A 2/2000 Loosmore et al.
6,022,729 A 2/2000 Steinbuchel et al.
6,022,855 A 2/2000 Thomas et al.
6,025,183 A 2/2000 Soreq et al.
6,025,342 A 2/2000 Loosmore et al.
6,030,612 A 2/2000 de Faire et al.
6,030,624 A 2/2000 Russell et al.
6,030,780 A 2/2000 Vinkemeier et al.
6,033,663 A 3/2000 Ketcham et al.
6,033,890 A 3/2000 Jakobovits et al.
6,037,123 A 3/2000 Benton et al.
6,037,159 A 3/2000 Uchimura et al.
6,037,526 A 3/2000 Grimsley et al.
6,040,156 A 3/2000 Kawasaki et al.
6,051,237 A 4/2000 Paterson
6,051,405 A 4/2000 FitzGerald et al.
6,054,309 A 4/2000 Hirabayashi et al.
6,054,312 A 4/2000 Larocca et al.
6,069,127 A 5/2000 Koths et al.
6,069,301 A 5/2000 Carozzi et al.
6,074,840 A 6/2000 Bonadio et al.
6,080,849 A 6/2000 Bermudes et al.
6,083,688 A 7/2000 Lanza et al.
6,086,900 A 7/2000 Draper
6,090,567 A 7/2000 Jakobovits et al.
6,090,582 A 7/2000 Kikly et al.
6,090,931 A 7/2000 Edwards et al.
6,093,539 A 7/2000 Maddon et al.
6,096,529 A 8/2000 Gilbert et al.
6,107,279 A 8/2000 Estruch et al.
6,107,546 A 8/2000 De Greve et al.
6,110,899 A 8/2000 Lonetto
6,111,089 A 8/2000 Fukuda
6,114,125 A 9/2000 Loosmore et al.
6,117,651 A 9/2000 Schultz et al.
6,117,977 A 9/2000 Lasky et al.
6,124,446 A 9/2000 Hillman et al.
6,137,033 A 10/2000 Estruch et al.
6,140,066 A 10/2000 Lorberboum-Galski et al.
6,143,551 A 11/2000 Goebel
6,146,845 A 11/2000 Kikly et al.
6,146,849 A 11/2000 Pierce et al.
6,147,057 A 11/2000 Loosmore et al.
6,150,170 A 11/2000 Powell et al.
6,153,580 A 11/2000 Loosmore et al.
6,166,290 A 12/2000 Rea et al.
6,172,281 B1 1/2001 Van Mellaert et al.
6,177,083 B1 1/2001 Lubitz
6,187,541 B1 2/2001 Benton et al.
6,190,657 B1 2/2001 Pawelek et al.
6,193,982 B1 2/2001 Boyd
6,200,779 B1 3/2001 Lonetto
6,207,156 B1 3/2001 Kuchroo et al.
6,207,417 B1 3/2001 Zsebo et al.
6,207,427 B1 3/2001 Hashimoto et al.
6,207,648 B1 3/2001 Waxman et al.
6,217,869 B1 4/2001 Meyer et al.
6,218,148 B1 4/2001 Zsebo et al.
6,228,588 B1 5/2001 Benton et al.
6,232,110 B1 5/2001 Pallas et al.
6,238,914 B1 5/2001 Boyce
6,242,210 B1 6/2001 Bjorck et al.
6,242,211 B1 6/2001 Peterson et al.
6,245,737 B1 6/2001 Boyd et al.
6,245,892 B1 6/2001 Oaks et al.
6,248,329 B1 6/2001 Chandrashekar et al.
6,251,406 B1 6/2001 Haefliger et al.
6,261,800 B1 7/2001 Nikolics et al.
6,268,193 B1 7/2001 Lowe
6,271,011 B1 8/2001 Lee et al.
6,271,368 B1 8/2001 Lentzen et al.
6,274,339 B1 8/2001 Moore et al.
6,277,379 B1 8/2001 Oaks et al.
6,277,574 B1 8/2001 Walker et al.
6,280,989 B1 8/2001 Kapitonov et al.
6,284,493 B1 9/2001 Roth
6,291,156 B1 9/2001 Estruch et al.
6,296,843 B1 10/2001 Debinski
6,302,685 B1 10/2001 Lobel et al.
6,303,571 B1 10/2001 Lonetto
6,310,046 B1 10/2001 Duffy et al.
6,312,907 B1 11/2001 Guo et al.
6,316,003 B1 11/2001 Frankel et al.
6,316,609 B1 11/2001 Dillon et al.
6,323,003 B1 11/2001 Black, Jr.
6,329,002 B1 12/2001 Kim et al.
6,331,413 B1 12/2001 Adler et al.
6,333,182 B1 12/2001 Coleman et al.
6,333,396 B1 12/2001 Filpula et al.
6,338,953 B1 1/2002 Boyce et al.
6,338,955 B2 1/2002 Oguri et al.
6,342,382 B1 1/2002 Gotschlich
6,348,344 B1 2/2002 Ayal-Hershkovitz et al.
6,355,790 B1 3/2002 Rosenblatt et al.
6,358,724 B1 3/2002 Wong-Madden et al.
6,365,381 B2 4/2002 Hashimoto et al.
6,369,213 B1 4/2002 Schnepf et al.
6,375,947 B1 4/2002 Bolen et al.
6,376,234 B1 4/2002 Grimsley et al.
6,379,913 B1 4/2002 Bandman et al.
6,383,496 B1 5/2002 Curtiss, III et al.
6,387,648 B1 5/2002 Levi et al.
6,387,702 B1 5/2002 Stemmer
6,395,513 B1 5/2002 Foster et al.
6,399,326 B1 6/2002 Chiang et al.
6,399,336 B1 6/2002 Paulson et al.
6,410,012 B1 6/2002 Sizemore et al.
6,410,687 B1 6/2002 Vale et al.
6,416,988 B1 7/2002 Conklin et al.
6,420,135 B1 7/2002 Kunsch et al.
6,420,149 B1 7/2002 Fukuda et al.
6,420,336 B1 7/2002 Boyd
6,420,527 B1 7/2002 Bolen et al.
6,423,525 B1 7/2002 Landry
6,428,788 B1 8/2002 Debinski et al.
6,428,790 B1 8/2002 Boyd
6,428,999 B1 8/2002 Ito et al.
6,429,304 B1 8/2002 Vale et al.
6,429,360 B1 8/2002 Estruch et al.
6,436,687 B1 8/2002 Yu et al.
6,447,777 B1 9/2002 Terman et al.
6,447,784 B1 9/2002 Bermudes et al.
6,451,312 B1 9/2002 Thorpe
6,455,288 B1 9/2002 Jakobovits et al.
6,458,573 B1 10/2002 Landry
6,472,518 B1 10/2002 Ribot et al.
6,475,482 B1 11/2002 Bermudes et al.
6,475,763 B1 11/2002 Ayal-Hershkovitz et al.
6,482,647 B1 11/2002 Stemmer
6,492,152 B1 12/2002 Canfield et al.
6,500,419 B1 12/2002 Hone et al.
6,503,744 B1 1/2003 Gilbert et al.
6,506,550 B1 1/2003 Fulton et al.
6,514,724 B1 2/2003 McMahon et al.
6,518,061 B1 2/2003 Puri et al.
6,521,439 B2 2/2003 Folkman et al.
6,524,792 B1 2/2003 Renner et al.
6,524,820 B1 2/2003 Pierce et al.
6,531,133 B1 3/2003 Lorberboum-Galski et al.
6,531,306 B1 3/2003 Hockensmith et al.
6,534,311 B2 3/2003 Stewart et al.
6,537,558 B2 3/2003 Kaniga
6,545,126 B1 4/2003 Johnson et al.

(56) References Cited

U.S. PATENT DOCUMENTS

| | | | |
|---|---|---|---|
| 6,548,287 | B1 | 4/2003 | Powell et al. |
| 6,551,618 | B2 | 4/2003 | Baird et al. |
| 6,551,795 | B1 | 4/2003 | Rubenfield et al. |
| 6,555,343 | B1 | 4/2003 | DeSauvage et al. |
| 6,558,953 | B1 | 5/2003 | Gonsalves et al. |
| 6,570,000 | B1 | 5/2003 | Maddon et al. |
| 6,570,005 | B1 | 5/2003 | Schnepf et al. |
| 6,573,082 | B1 | 6/2003 | Choi et al. |
| 6,576,232 | B1 | 6/2003 | Debinski et al. |
| 6,582,948 | B1 | 6/2003 | Bolen et al. |
| 6,582,950 | B1 | 6/2003 | Smith et al. |
| 6,585,975 | B1 | 7/2003 | Kleanthous et al. |
| 6,586,392 | B2 | 7/2003 | Boyd |
| 6,596,849 | B1 | 7/2003 | Roffler et al. |
| 6,599,912 | B1 | 7/2003 | Au et al. |
| 6,605,286 | B2 | 8/2003 | Steidler et al. |
| 6,605,592 | B2 | 8/2003 | Ni et al. |
| 6,605,697 | B1 | 8/2003 | Kwon et al. |
| 6,607,897 | B2 | 8/2003 | Vogel et al. |
| 6,617,118 | B2 | 9/2003 | Roffler et al. |
| 6,630,303 | B1 | 10/2003 | Benton et al. |
| 6,632,935 | B2 | 10/2003 | Shigenobu et al. |
| 6,635,246 | B1 | 10/2003 | Barrett et al. |
| 6,635,468 | B2 | 10/2003 | Ashkenazi et al. |
| 6,635,740 | B1 | 10/2003 | Enright et al. |
| 6,638,718 | B1 | 10/2003 | Benton et al. |
| 6,638,912 | B2 | 10/2003 | Bhatnagar et al. |
| 6,642,041 | B2 | 11/2003 | Chen et al. |
| 6,645,490 | B2 | 11/2003 | Yarkoni et al. |
| 6,646,113 | B1 | 11/2003 | Dreyfuss et al. |
| 6,673,915 | B1 | 1/2004 | Luster et al. |
| 6,680,058 | B1 | 1/2004 | Enright et al. |
| 6,680,187 | B2 | 1/2004 | Moeckel et al. |
| 6,680,374 | B2 | 1/2004 | Oaks et al. |
| 6,682,728 | B1 | 1/2004 | Finkel et al. |
| 6,682,729 | B1 | 1/2004 | Powell et al. |
| 6,682,910 | B2 | 1/2004 | Powell |
| 6,685,935 | B1 | 2/2004 | Pawelek et al. |
| 6,689,586 | B2 | 2/2004 | Moeckel et al. |
| 6,689,604 | B1 | 2/2004 | Gilbert et al. |
| 6,692,942 | B2 | 2/2004 | Filpula et al. |
| 6,693,183 | B2 | 2/2004 | Natsuka et al. |
| 6,696,411 | B1 | 2/2004 | MacLeod |
| 6,699,705 | B2 | 3/2004 | Gilbert et al. |
| 6,699,969 | B1 | 3/2004 | Vale et al. |
| 6,703,223 | B2 | 3/2004 | Bathe et al. |
| 6,703,233 | B1 | 3/2004 | Galen |
| 6,709,656 | B1 | 3/2004 | Boren et al. |
| 6,709,830 | B2 | 3/2004 | Witte et al. |
| 6,709,834 | B2 | 3/2004 | Gilbert et al. |
| 6,713,277 | B1 | 3/2004 | Moore et al. |
| 6,716,582 | B2 | 4/2004 | Gonye et al. |
| 6,720,410 | B2 | 4/2004 | Cerny et al. |
| 6,723,540 | B1 | 4/2004 | Harkki et al. |
| 6,727,086 | B2 | 4/2004 | Bathe et al. |
| 6,734,002 | B2 | 5/2004 | Bathe et al. |
| 6,743,577 | B2 | 6/2004 | Boyd |
| 6,743,893 | B2 | 6/2004 | Engler et al. |
| 6,746,671 | B2 | 6/2004 | Steidler et al. |
| 6,746,854 | B2 | 6/2004 | Bathe et al. |
| 6,752,992 | B2 | 6/2004 | Schnepf et al. |
| 6,753,164 | B2 | 6/2004 | Ni et al. |
| 6,759,215 | B1 | 7/2004 | Zsebo et al. |
| 6,759,224 | B2 | 7/2004 | Farwick et al. |
| 6,759,230 | B1 | 7/2004 | Bulla, Jr. et al. |
| 6,764,853 | B2 | 7/2004 | Filpula et al. |
| 6,770,466 | B2 | 8/2004 | Shi et al. |
| 6,770,632 | B1 | 8/2004 | Aghi et al. |
| 6,777,206 | B2 | 8/2004 | Farwick et al. |
| 6,780,405 | B1 | 8/2004 | Curtiss, III et al. |
| 6,780,624 | B2 | 8/2004 | Gotschlich |
| 6,780,847 | B2 | 8/2004 | Boyd |
| 6,783,966 | B1 | 8/2004 | Kojima et al. |
| 6,783,967 | B2 | 8/2004 | Moeckel et al. |
| 6,783,971 | B2 | 8/2004 | Coleman et al. |
| 6,784,164 | B2 | 8/2004 | Masure et al. |
| 6,787,643 | B2 | 9/2004 | Dillon et al. |
| 6,797,509 | B1 | 9/2004 | Dunican et al. |
| 6,803,192 | B1 | 10/2004 | Chen |
| 6,811,788 | B2 | 11/2004 | Yu |
| 6,812,006 | B2 | 11/2004 | Moeckel et al. |
| 6,818,449 | B2 | 11/2004 | Fong et al. |
| 6,822,071 | B1 | 11/2004 | Stephens et al. |
| 6,822,085 | B2 | 11/2004 | Farwick et al. |
| 6,824,782 | B2 | 11/2004 | Whitlow et al. |
| 6,825,019 | B2 | 11/2004 | Gilbert et al. |
| 6,825,029 | B2 | 11/2004 | Dunican et al. |
| 6,825,030 | B2 | 11/2004 | Mockel et al. |
| 6,828,121 | B2 | 12/2004 | Chen |
| 6,828,146 | B2 | 12/2004 | Desnoyers et al. |
| 6,828,419 | B2 | 12/2004 | Adler et al. |
| 6,831,060 | B2 | 12/2004 | DeSauvage et al. |
| 6,833,130 | B1 | 12/2004 | Paton et al. |
| 6,833,253 | B2 | 12/2004 | Choi |
| 6,833,255 | B1 | 12/2004 | Stewart et al. |
| 6,838,267 | B2 | 1/2005 | Moeckel et al. |
| 6,841,535 | B2 | 1/2005 | Divita et al. |
| 6,841,718 | B2 | 1/2005 | Alberte et al. |
| 6,844,176 | B1 | 1/2005 | Bathe et al. |
| 6,844,178 | B2 | 1/2005 | Bolen et al. |
| 6,846,484 | B2 | 1/2005 | Vallera et al. |
| 6,846,667 | B1 | 1/2005 | Crooke et al. |
| 6,855,688 | B2 | 2/2005 | McKerracher |
| 6,858,407 | B2 | 2/2005 | Feder et al. |
| 6,858,415 | B2 | 2/2005 | Coleman et al. |
| 6,861,231 | B2 | 3/2005 | Shao |
| 6,863,894 | B2 | 3/2005 | Bermudes et al. |
| 6,872,393 | B2 | 3/2005 | Whitlow et al. |
| 6,872,526 | B2 | 3/2005 | Short et al. |
| 6,872,537 | B1 | 3/2005 | Vale et al. |
| 6,875,586 | B2 | 4/2005 | Moeckel et al. |
| 6,884,603 | B2 | 4/2005 | Debinski et al. |
| 6,884,770 | B1 | 4/2005 | Galdes et al. |
| 6,887,663 | B1 | 5/2005 | Choi et al. |
| 6,890,744 | B2 | 5/2005 | Bathe et al. |
| 6,902,916 | B2 | 6/2005 | Moeckel et al. |
| 6,902,932 | B2 | 6/2005 | Altman et al. |
| 6,905,867 | B2 | 6/2005 | Gilbert et al. |
| 6,911,337 | B2 | 6/2005 | Gilbert et al. |
| 6,913,906 | B2 | 7/2005 | Bolen et al. |
| 6,913,908 | B2 | 7/2005 | Mockel et al. |
| 6,913,919 | B2 | 7/2005 | Botstein et al. |
| 6,916,636 | B2 | 7/2005 | Marx et al. |
| 6,916,648 | B2 | 7/2005 | Goddard et al. |
| 6,916,918 | B2 | 7/2005 | Yu et al. |
| 6,919,079 | B1 | 7/2005 | Fishman et al. |
| 6,921,651 | B2 | 7/2005 | Farwick et al. |
| 6,921,659 | B2 | 7/2005 | Joly |
| 6,923,972 | B2 | 8/2005 | Bermudes et al. |
| 6,924,134 | B2 | 8/2005 | Farwick et al. |
| 6,927,052 | B2 | 8/2005 | Bathe et al. |
| 6,929,930 | B2 | 8/2005 | Choi et al. |
| 6,933,271 | B2 | 8/2005 | Yarkoni et al. |
| 6,936,448 | B2 | 8/2005 | Holmes et al. |
| 6,939,692 | B2 | 9/2005 | Bathe et al. |
| 6,939,694 | B2 | 9/2005 | Mockel et al. |
| 6,939,695 | B2 | 9/2005 | Moeckel et al. |
| 6,943,001 | B2 | 9/2005 | Zhao et al. |
| 6,943,241 | B2 | 9/2005 | Isogai et al. |
| 6,946,262 | B2 | 9/2005 | Ferrara et al. |
| 6,946,271 | B2 | 9/2005 | Farwick et al. |
| 6,949,372 | B2 | 9/2005 | Betenbaugh et al. |
| 6,951,737 | B2 | 10/2005 | Desnoyers et al. |
| 6,951,738 | B2 | 10/2005 | Ni et al. |
| 6,953,835 | B2 | 10/2005 | Fischhoff et al. |
| 6,955,953 | B2 | 10/2005 | Yamazaki et al. |
| 6,962,696 | B1 | 11/2005 | Bermudes et al. |
| 6,962,703 | B2 | 11/2005 | Foster et al. |
| 6,962,800 | B2 | 11/2005 | Kiy et al. |
| 6,969,517 | B2 | 11/2005 | Gillies et al. |
| 6,972,185 | B2 | 12/2005 | Desnoyers et al. |
| 6,972,186 | B2 | 12/2005 | Desnoyers et al. |
| 6,974,689 | B1 | 12/2005 | Ashkenazi et al. |
| 6,974,696 | B2 | 12/2005 | Botstein et al. |

(56) References Cited

U.S. PATENT DOCUMENTS

| | | | |
|---|---|---|---|
| 6,974,893 | B2 | 12/2005 | Shanklin et al. |
| 6,979,538 | B2 | 12/2005 | Ladner et al. |
| 6,979,556 | B2 | 12/2005 | Simmons et al. |
| 6,979,733 | B2 | 12/2005 | Zhao et al. |
| 6,987,096 | B1 | 1/2006 | Boyd et al. |
| 6,987,176 | B1 | 1/2006 | Guerry et al. |
| 6,992,174 | B2 | 1/2006 | Gillies et al. |
| 6,995,000 | B2 | 2/2006 | Bathe et al. |
| 6,995,002 | B2 | 2/2006 | Molenaar et al. |
| 7,001,884 | B2 | 2/2006 | Komiyama et al. |
| 7,015,027 | B1 | 3/2006 | Redshaw |
| 7,018,811 | B2 | 3/2006 | Botstein et al. |
| 7,019,124 | B2 | 3/2006 | Desnoyers et al. |
| 7,022,498 | B2 | 4/2006 | Desnoyers et al. |
| 7,026,158 | B2 | 4/2006 | Farwick et al. |
| 7,026,449 | B2 | 4/2006 | Baker et al. |
| 7,029,875 | B2 | 4/2006 | Desnoyers et al. |
| 7,029,904 | B2 | 4/2006 | Farwick et al. |
| 7,033,785 | B2 | 4/2006 | Desnoyers et al. |
| 7,033,786 | B2 | 4/2006 | Baker et al. |
| 7,033,825 | B2 | 4/2006 | Goddard et al. |
| 7,033,991 | B2 | 4/2006 | Lindberg et al. |
| 7,034,136 | B2 | 4/2006 | Goddard et al. |
| 7,037,679 | B2 | 5/2006 | Desnoyers et al. |
| 7,037,689 | B2 | 5/2006 | Bathe et al. |
| 7,037,710 | B2 | 5/2006 | Goddard et al. |
| 7,038,034 | B2 | 5/2006 | Farwick et al. |
| 7,041,441 | B1 | 5/2006 | Steven et al. |
| 7,041,814 | B1 | 5/2006 | Weinstock et al. |
| 7,045,122 | B2 | 5/2006 | Nuijten et al. |
| 7,048,935 | B2 | 5/2006 | Boyd |
| 7,049,096 | B2 | 5/2006 | Feder et al. |
| 7,049,106 | B2 | 5/2006 | Farwick et al. |
| 7,052,702 | B1 | 5/2006 | Duggan et al. |
| 7,052,889 | B2 | 5/2006 | Jenuwein et al. |
| 7,052,903 | B2 | 5/2006 | Black, Jr. |
| 7,053,266 | B2 | 5/2006 | Tuli |
| 7,056,510 | B1 | 6/2006 | Choi et al. |
| 7,056,700 | B2 | 6/2006 | Galen |
| 7,056,721 | B2 | 6/2006 | Dunn-Coleman et al. |
| 7,056,736 | B2 | 6/2006 | Ashkenazi et al. |
| 7,056,737 | B2 | 6/2006 | Feder et al. |
| 7,060,475 | B2 | 6/2006 | Usuda et al. |
| 7,060,479 | B2 | 6/2006 | Dumas Milne Edwards et al. |
| 7,060,812 | B2 | 6/2006 | Desnoyers et al. |
| 7,067,110 | B1 | 6/2006 | Gillies et al. |
| 7,067,288 | B2 | 6/2006 | Molenaar et al. |
| 7,067,306 | B2 | 6/2006 | Singhvi et al. |
| 7,070,979 | B2 | 7/2006 | Botstein et al. |
| 7,074,589 | B1 | 7/2006 | Ullrich et al. |
| 7,074,592 | B2 | 7/2006 | Ashkenazi et al. |
| 7,078,185 | B2 | 7/2006 | Farnet et al. |
| 7,078,186 | B2 | 7/2006 | Ni et al. |
| 7,078,204 | B2 | 7/2006 | Yokoi et al. |
| 7,078,207 | B2 | 7/2006 | Gilbert et al. |
| 7,078,502 | B2 | 7/2006 | Moeckel et al. |
| 7,083,791 | B2 | 8/2006 | Sleeman et al. |
| 7,083,794 | B2 | 8/2006 | Curtiss, III et al. |
| 7,083,942 | B2 | 8/2006 | Bathe et al. |
| 7,083,946 | B2 | 8/2006 | Baker et al. |
| 7,083,978 | B2 | 8/2006 | Desnoyers et al. |
| 7,084,105 | B2 | 8/2006 | Chakrabarty et al. |
| 7,087,404 | B2 | 8/2006 | Desnoyers et al. |
| 7,087,738 | B2 | 8/2006 | Botstein et al. |
| 7,090,835 | B2 | 8/2006 | Gabriel et al. |
| 7,091,315 | B1 | 8/2006 | Ruben et al. |
| 7,091,321 | B2 | 8/2006 | Gillies et al. |
| 7,094,563 | B2 | 8/2006 | Wong-Madden et al. |
| 7,094,567 | B2 | 8/2006 | Ashkenazi et al. |
| 7,094,572 | B2 | 8/2006 | Ramanathan et al. |
| 7,101,690 | B2 | 9/2006 | Moeckel et al. |
| 7,101,977 | B2 | 9/2006 | Rosenblum et al. |
| 7,105,169 | B2 | 9/2006 | Boyd |
| 7,105,302 | B2 | 9/2006 | Bathe et al. |
| 7,105,321 | B2 | 9/2006 | Moeckel et al. |
| 7,109,033 | B2 | 9/2006 | Harper et al. |
| 7,109,315 | B2 | 9/2006 | Bryan et al. |
| 7,112,317 | B2 | 9/2006 | Thorpe et al. |
| 7,115,402 | B2 | 10/2006 | Feder et al. |
| 7,118,879 | B2 | 10/2006 | Ladner et al. |
| 7,119,193 | B2 | 10/2006 | Gottesman et al. |
| 7,122,185 | B2 | 10/2006 | Olson et al. |
| 7,122,358 | B2 | 10/2006 | Feder et al. |
| 7,122,367 | B2 | 10/2006 | Milcamps et al. |
| 7,122,375 | B2 | 10/2006 | Goddard et al. |
| 7,125,541 | B2 | 10/2006 | Thorpe et al. |
| 7,125,548 | B2 | 10/2006 | Smith |
| 7,125,718 | B2 | 10/2006 | Powell et al. |
| 7,129,066 | B2 | 10/2006 | Farwick et al. |
| 7,129,085 | B2 | 10/2006 | Feder et al. |
| 7,129,212 | B2 | 10/2006 | Narva et al. |
| 7,132,283 | B2 | 11/2006 | Fong et al. |
| 7,135,313 | B2 | 11/2006 | Bathe et al. |
| 7,138,252 | B2 | 11/2006 | Bachmann et al. |
| 7,138,258 | B2 | 11/2006 | Gilbert et al. |
| 7,138,259 | B2 | 11/2006 | Beavo et al. |
| 7,141,418 | B2 | 11/2006 | Kunsch et al. |
| 7,144,724 | B2 | 12/2006 | Farwick et al. |
| 7,148,321 | B2 | 12/2006 | Gillies et al. |
| 7,150,872 | B2 | 12/2006 | Whitlow et al. |
| 7,153,678 | B2 | 12/2006 | Jackson et al. |
| 7,157,418 | B1 | 1/2007 | McDonald et al. |
| 7,160,703 | B2 | 1/2007 | Moeckel et al. |
| 7,160,711 | B2 | 1/2007 | Bathe et al. |
| 7,163,797 | B2 | 1/2007 | Ruben et al. |
| 7,166,702 | B1 | 1/2007 | McDonald et al. |
| 7,169,565 | B2 | 1/2007 | Ruben et al. |
| 7,169,904 | B2 | 1/2007 | Gillies et al. |
| 7,169,912 | B2 | 1/2007 | Desnoyers et al. |
| 7,173,105 | B2 | 2/2007 | Moeckel et al. |
| 7,183,066 | B2 | 2/2007 | Fernandez-Salas et al. |
| 7,183,379 | B2 | 2/2007 | Feder et al. |
| 7,186,564 | B2 | 3/2007 | Chen et al. |
| 7,186,804 | B2 | 3/2007 | Gillies et al. |
| 7,189,529 | B2 | 3/2007 | Ashkenazi et al. |
| 7,189,530 | B2 | 3/2007 | Botstein et al. |
| 7,189,539 | B2 | 3/2007 | Ramanathan et al. |
| 7,189,836 | B2 | 3/2007 | Gilbert et al. |
| 7,192,736 | B2 | 3/2007 | McDonald et al. |
| 7,192,933 | B1 | 3/2007 | Boyce |
| 7,195,754 | B1 | 3/2007 | Glatkowski et al. |
| 7,195,757 | B2 | 3/2007 | Curtiss, III et al. |
| 7,198,912 | B2 | 4/2007 | Ramanathan et al. |
| 7,202,056 | B2 | 4/2007 | Lee et al. |
| 7,202,059 | B2 | 4/2007 | Habermann et al. |
| 7,202,061 | B2 | 4/2007 | Farwick et al. |
| 7,202,353 | B2 | 4/2007 | Gilbert et al. |
| 7,205,144 | B2 | 4/2007 | Mockel et al. |
| 7,208,285 | B2 | 4/2007 | Steward et al. |
| 7,208,293 | B2 | 4/2007 | Ladner et al. |
| 7,208,304 | B2 | 4/2007 | Gilbert et al. |
| 7,208,312 | B1 | 4/2007 | Desnoyers et al. |
| 7,208,313 | B2 | 4/2007 | McCart et al. |
| 7,208,466 | B1 | 4/2007 | Foster et al. |
| 7,211,253 | B1 | 5/2007 | Way |
| 7,211,657 | B2 | 5/2007 | Gilbert et al. |
| 7,214,526 | B2 | 5/2007 | Bathe et al. |
| 7,214,792 | B2 | 5/2007 | Bulla et al. |
| 7,217,548 | B2 | 5/2007 | Yoshida et al. |
| 7,217,549 | B2 | 5/2007 | Gilbert et al. |
| 7,217,809 | B2 | 5/2007 | Schultz et al. |
| 7,220,555 | B2 | 5/2007 | Paulson et al. |
| 7,220,848 | B2 | 5/2007 | Gilbert et al. |
| 7,223,557 | B2 | 5/2007 | Lee et al. |
| 7,223,586 | B2 | 5/2007 | Ferrara et al. |
| 7,226,761 | B2 | 6/2007 | Miasnikov et al. |
| 7,226,763 | B2 | 6/2007 | Bathe et al. |
| 7,226,791 | B2 | 6/2007 | Carman et al. |
| 7,229,791 | B2 | 6/2007 | Bathe et al. |
| 7,229,802 | B2 | 6/2007 | Bathe et al. |
| 7,232,672 | B2 | 6/2007 | Weiner et al. |
| 7,235,234 | B1 | 6/2007 | Branstrom et al. |
| 7,238,509 | B2 | 7/2007 | Gilbert et al. |
| 7,244,601 | B2 | 7/2007 | Gilbert et al. |

(56) References Cited

U.S. PATENT DOCUMENTS 7,244,833 B2 7/2007 Yu et al.
7,247,296 B2 7/2007 Redshaw
7,247,717 B2 7/2007 Chen et al.
7,252,977 B2 8/2007 Bathe et al.
7,256,267 B2 8/2007 Chen et al.
7,258,863 B2 8/2007 Oaks et al.
7,259,296 B2 8/2007 Schmulling et al.
7,262,039 B1 8/2007 Narimatsu et al.
7,262,040 B2 8/2007 Schultz et al.
7,267,973 B2 9/2007 Backer et al.
7,270,815 B2 9/2007 Sasisekharan et al.
7,270,984 B1 9/2007 Pompejus et al.
7,271,243 B2 9/2007 Dumas Milne Edwards et al.
7,273,706 B2 9/2007 Feder et al.
7,276,354 B2 10/2007 Feder et al.
7,279,310 B2 10/2007 Narimatsu et al.
7,285,635 B2 10/2007 Rosenblum et al.
7,288,255 B1 10/2007 Shlomchik et al.
7,291,491 B2 11/2007 Fukuda et al.
7,297,340 B2 11/2007 Apicella
7,303,905 B2 12/2007 Breves et al.
7,306,932 B2 12/2007 Bathe et al.
7,307,159 B2 12/2007 DeAngelis
7,309,600 B2 12/2007 Apicella et al.
7,318,927 B2 1/2008 Perez et al.
7,318,928 B2 1/2008 Wu et al.
7,320,791 B2 1/2008 Roffler et al.
7,320,887 B2 1/2008 Kottwitz et al.
7,323,549 B2 1/2008 Lauder et al.
7,326,546 B2 2/2008 Matsuno et al.
7,326,557 B2 2/2008 San et al.
7,332,304 B2 2/2008 Deng et al.
7,332,310 B2 2/2008 Nakagawa et al.
7,332,316 B2 2/2008 Schmulling et al.
7,332,567 B2 2/2008 Steward et al.
7,335,361 B2 2/2008 Liao et al.
7,338,790 B2 3/2008 Thierbach et al.
7,338,799 B2 3/2008 Blakely et al.
7,339,037 B2 3/2008 Boyd et al.
7,344,710 B2 3/2008 Dang et al.
7,344,882 B2 3/2008 Lee et al.
7,345,148 B2 3/2008 Feder et al.
7,348,161 B2 3/2008 Gay et al.
7,351,568 B2 4/2008 Dunn-Coleman et al.
7,354,592 B2 4/2008 Bermudes et al.
7,357,934 B2 4/2008 Donovan et al.
7,358,074 B2 4/2008 Jackson et al.
7,358,084 B2 4/2008 Kolkman
7,364,787 B2 4/2008 Ito et al.
7,365,159 B2 4/2008 O'Reilly et al.
7,368,108 B2 5/2008 DeFrees et al.
7,368,284 B2 5/2008 Koike
7,371,559 B2 5/2008 Boone et al.
7,371,723 B2 5/2008 Rosenblum et al.
7,371,838 B2 5/2008 Gilbert et al.
7,374,896 B2 5/2008 Steward et al.
7,378,258 B2 5/2008 Doucette-Stamm et al.
7,378,514 B2 5/2008 Doucette-Stamm et al.
7,381,544 B2 6/2008 Gilbert et al.
7,390,633 B2 6/2008 Liu et al.
7,390,646 B2 6/2008 Andino-Pavlovsky et al.
7,393,525 B2 7/2008 Powell et al.
7,393,675 B2 7/2008 Pompejus et al.
7,396,824 B2 7/2008 Sasisekharan et al.
7,399,607 B2 7/2008 Williams et al.
7,404,963 B2 7/2008 Sotomayor et al.
7,405,081 B2 7/2008 Pan
7,405,235 B2 7/2008 Levy et al.
7,407,787 B2 8/2008 Barrangou et al.
7,410,791 B2 8/2008 Singhvi et al.
7,413,877 B2 8/2008 Collier et al.
7,414,119 B2 8/2008 Greenberg et al.
7,416,863 B2 8/2008 Moeckel et al.
7,420,030 B2 9/2008 Arap et al.
7,429,474 B2 9/2008 Sasisekharan et al.
7,432,085 B2 10/2008 Hara et al.
7,432,357 B2 10/2008 Gillies
7,435,808 B2 10/2008 Wu et al.
7,439,059 B2 10/2008 Black, Jr.
7,442,523 B2 10/2008 Doucette-Stamm et al.
7,452,531 B2 11/2008 Bermudes et al.
7,452,543 B2 11/2008 Chaddock et al.
7,459,309 B2 12/2008 Dreyfuss et al.
7,459,538 B2 12/2008 Gillies et al.
7,462,350 B2 12/2008 Gillies et al.
7,462,482 B2 12/2008 Malik et al.
7,465,447 B2 12/2008 Gillies et al.
7,470,667 B2 12/2008 Luo et al.
7,485,439 B2 2/2009 Folkman et al.
7,491,529 B2 2/2009 Goddard et al.
7,491,799 B2 2/2009 Steward et al.
7,494,798 B2 2/2009 Berka et al.
7,494,801 B2 2/2009 Yazaki et al.
7,495,069 B2 2/2009 Steward et al.
7,504,242 B2 3/2009 Dunican et al.
7,504,247 B2 3/2009 Sasisekharan et al.
7,507,406 B2 3/2009 Gillies et al.
7,510,859 B2 3/2009 Wieland et al.
7,514,089 B2 4/2009 Bermudes et al.
7,514,538 B2 4/2009 Goddard et al.
7,517,526 B2 4/2009 Gillies et al.
7,517,667 B2 4/2009 Murphy et al.
7,524,657 B2 4/2009 Bathe et al.
7,544,486 B2 6/2009 Ting et al.
7,557,186 B2 7/2009 Tuli
7,563,602 B2 7/2009 Thierbach et al.
7,566,777 B2 7/2009 Enright et al.
7,569,226 B2 8/2009 Weber et al.
7,569,376 B2 8/2009 Bayer et al.
7,569,384 B2 8/2009 Rosen et al.
7,569,386 B2 8/2009 DeAngelis
7,569,547 B2 8/2009 Lindberg et al.
7,572,618 B2 8/2009 Mintier et al.
7,582,445 B2 9/2009 Anan et al.
7,585,650 B2 9/2009 Bathe et al.
7,588,767 B2 9/2009 Szalay et al.
7,588,771 B2 9/2009 Szalay et al.
7,589,179 B2 9/2009 Gillies et al.
7,595,054 B2 9/2009 Liao et al.
7,598,027 B2 10/2009 Fernandez-Salas et al.
7,598,058 B2 10/2009 Debinski et al.
7,598,067 B2 10/2009 Beavo et al.
7,601,341 B2 10/2009 Rosenblum
7,601,814 B2 10/2009 Gillies et al.
7,611,712 B2 11/2009 Karp
7,611,883 B2 11/2009 Cranenburgh
7,615,223 B2 11/2009 Thorpe et al.
7,618,635 B2 11/2009 Chang et al.
7,618,798 B2 11/2009 Bathe et al.
7,622,564 B2 11/2009 Ge et al.
7,626,000 B2 12/2009 Doucette-Stamm et al.
7,629,150 B2 12/2009 Narimatsu et al.
7,632,504 B2 12/2009 Whitlow et al.
7,632,655 B2 12/2009 Williams et al.
7,632,924 B2 12/2009 Cho et al.
7,635,574 B2 12/2009 Williams et al.
7,635,598 B2 12/2009 Cook et al.
7,635,682 B2 12/2009 Denmeade et al.
7,635,765 B2 12/2009 Farnet et al.
7,638,282 B2 12/2009 Bakaletz et al.
7,638,294 B2 12/2009 Williams et al.
7,638,299 B2 12/2009 Cho et al.
7,645,570 B2 1/2010 Fernandez-Salas et al.
7,645,577 B2 1/2010 Adderson et al.
7,655,770 B1 2/2010 Cheikh et al.
7,655,774 B2 2/2010 Mullins et al.
7,655,781 B2 2/2010 Shemesh et al.
7,658,933 B2 2/2010 Foster et al.
7,662,398 B2 2/2010 Szalay et al.
7,662,933 B2 2/2010 Kinstler et al.
7,666,419 B2 2/2010 Olson et al.
7,666,627 B2 2/2010 Gal et al.
7,667,018 B2 2/2010 Jakobovits et al.
7,670,595 B2 3/2010 Gillies et al.

(56) References Cited

U.S. PATENT DOCUMENTS 7,670,835 B2 3/2010 Smith
7,674,601 B2 3/2010 Williams et al.
7,678,550 B1 3/2010 Steward et al.
7,687,474 B2 3/2010 Matin et al.
7,691,383 B2 4/2010 Chakrabarty et al.
7,691,599 B2 4/2010 Rubin
7,691,983 B2 4/2010 Fernandez-Salas et al.
7,693,664 B2 4/2010 Takami et al.
7,695,711 B2 4/2010 Myette et al.
7,696,173 B2 4/2010 Collier et al.
7,700,104 B2 4/2010 Hensel et al.
7,700,313 B2 4/2010 Schischka et al.
7,700,317 B2 4/2010 Ambrose et al.
7,700,349 B2 4/2010 Romaine et al.
7,700,557 B2 4/2010 Backer et al.
7,700,830 B2 4/2010 Corbin et al.
7,704,506 B2 4/2010 Fishman et al.
7,705,195 B2 4/2010 French et al.
7,709,608 B2 5/2010 Steward et al.
7,718,180 B2 5/2010 Karp
7,718,363 B2 5/2010 Brines et al.
7,718,618 B2 5/2010 Gallo et al.
7,718,766 B2 5/2010 Steward et al.
7,722,867 B2 5/2010 Umana et al.
7,723,069 B2 5/2010 Soll et al.
7,723,472 B2 5/2010 Szoka et al.
7,727,538 B2 6/2010 Quinn et al.
7,727,741 B2 6/2010 Umana et al.
7,734,420 B2 6/2010 Palsson et al.
7,736,872 B2 6/2010 Paulsel et al.
7,736,898 B1 6/2010 Fulton et al.
7,740,835 B2 6/2010 Fujimori et al.
7,740,853 B2 6/2010 Fishman et al.
7,741,091 B2 6/2010 DeAngelis et al.
7,741,278 B2 6/2010 Rosenblum et al.
7,749,518 B2 7/2010 Masignani et al.
7,749,746 B2 7/2010 Raitano et al.
7,749,759 B2 7/2010 Fernandez-Salas et al.
7,754,221 B2 7/2010 Szalay et al.
7,754,420 B2 7/2010 Boyd
7,754,446 B2 7/2010 Bathe et al.
7,758,855 B2 7/2010 Kopecko et al.
7,759,091 B2 7/2010 Rosenblum et al.
7,763,250 B2 7/2010 Rosenthal et al.
7,763,420 B2 7/2010 Stritzker et al.
7,767,405 B2 8/2010 Gillies et al.
7,767,643 B2 8/2010 Brines et al.
7,771,981 B2 8/2010 DeAngelis
7,776,323 B2 8/2010 Smith
7,776,823 B2 8/2010 Gallo et al.
7,785,779 B2 8/2010 Kroger et al.
7,785,840 B2 8/2010 Bathe et al.
7,785,861 B2 8/2010 Devroe et al.
7,786,288 B2 8/2010 Karp
7,790,177 B2 9/2010 Karp
7,790,415 B2 9/2010 Gillies et al.
7,790,860 B2 9/2010 Thorpe et al.
7,803,531 B2 9/2010 Fulton et al.
7,803,604 B2 9/2010 Breves et al.
7,803,618 B2 9/2010 Gillies et al.
7,803,769 B2 9/2010 Sullivan et al.
7,803,918 B2 9/2010 van der Hoek
7,803,923 B2 9/2010 Han et al.
7,807,434 B2 10/2010 Dunn-Coleman et al.
7,807,441 B2 10/2010 Steinaa et al.
7,807,620 B2 10/2010 Lustbader
7,811,799 B2 10/2010 Dunn-Coleman et al.
7,816,086 B2 10/2010 Bakaletz et al.
7,816,320 B2 10/2010 Hays et al.
7,820,184 B2 10/2010 Stritzker et al.
7,820,623 B2 10/2010 Sullivan et al.
7,824,894 B2 11/2010 Barrangou et al.
7,824,895 B2 11/2010 Short et al.
7,825,093 B2 11/2010 Sullivan et al.
7,829,310 B2 11/2010 Paulsel et al.
7,833,979 B2 11/2010 Sullivan et al.
7,834,164 B2 11/2010 Sullivan et al.
7,834,166 B2 11/2010 Doucette-Stamm et al.
7,838,260 B2 11/2010 Steward et al.
7,838,265 B2 11/2010 Paulsel et al.
7,842,290 B2 11/2010 Holden
7,842,492 B2 11/2010 Myette et al.
7,846,678 B2 12/2010 Pepe et al.
7,846,689 B2 12/2010 Paulsel et al.
7,846,706 B2 12/2010 Mintier et al.
7,846,722 B2 12/2010 Williams et al.
7,847,079 B2 12/2010 Rosen et al.
7,850,970 B2 12/2010 Shapiro
7,858,344 B2 12/2010 Paulsel et al.
7,863,032 B2 1/2011 Berka et al.
7,867,484 B2 1/2011 Samulski et al.
7,867,732 B2 1/2011 Hori et al.
7,869,957 B2 1/2011 Palsson et al.
7,883,866 B2 2/2011 Paulsel et al.
7,887,794 B2 2/2011 Luquet et al.
7,887,810 B2 2/2011 Foster et al.
7,887,816 B2 2/2011 Feldman et al.
7,888,071 B2 2/2011 Gillies et al.
7,888,321 B2 2/2011 Cooper et al.
7,892,560 B2 2/2011 Foster et al.
7,892,803 B2 2/2011 Tanner et al.
7,892,825 B2 2/2011 Barr et al.
7,893,007 B2 2/2011 Ladner et al.
7,893,033 B2 2/2011 Hung et al.
7,893,230 B2 2/2011 Doucette-Stamm et al.
7,893,231 B2 2/2011 Bathe et al.
7,893,238 B2 2/2011 Doucette-Stamm et al.
7,901,691 B2 3/2011 Tuli et al.
7,901,913 B2 3/2011 Dunican et al.
7,906,628 B2 3/2011 Hung et al.
7,910,102 B2 3/2011 Sullivan et al.
7,910,715 B2 3/2011 Bathe et al.
7,915,218 B2 3/2011 Capecchi et al.
7,915,394 B2 3/2011 Schischka et al.
7,919,311 B2 4/2011 Black, Jr.
7,919,591 B2 4/2011 Sheffer et al.
7,923,221 B1 4/2011 Cabilly et al.
7,927,612 B2 4/2011 Yu
7,939,319 B2 5/2011 Polack et al.
7,939,496 B2 5/2011 Cho et al.
7,943,571 B2 5/2011 Rosenblum et al.
7,943,754 B2 5/2011 Bentwich et al.
7,947,473 B2 5/2011 Buechler et al.
7,947,822 B2 5/2011 Nabel et al.
7,951,557 B2 5/2011 Shaaltiel et al.
7,951,560 B2 5/2011 Myette et al.
7,955,590 B2 6/2011 Gillies et al.
7,955,600 B2 6/2011 Hensel et al.
7,959,926 B2 6/2011 Buechler et al.
7,960,514 B2 6/2011 Lauder et al.
7,964,362 B2 6/2011 Lee et al.
7,968,684 B2 6/2011 Ghayur et al.
7,968,699 B2 6/2011 Haefner et al.
7,973,150 B2 7/2011 Gillies et al.
7,977,080 B2 7/2011 Gramatikova et al.
7,977,084 B2 7/2011 Sun et al.
7,981,659 B2 7/2011 Kadoya et al.
7,989,202 B1 8/2011 Mach et al.
7,993,905 B2 8/2011 Singhvi et al.
7,998,461 B2 8/2011 Forbes et al.
8,003,753 B2 8/2011 Steward et al.
8,007,781 B2 8/2011 Wu et al.
8,008,047 B2 8/2011 Iyo et al.
8,008,283 B2 8/2011 Hochman et al.
8,008,465 B2 8/2011 Fernandez-Salas et al.
8,012,733 B2 9/2011 Dijk et al.
8,012,931 B2 9/2011 Cujec et al.
8,013,113 B2 9/2011 Steward et al.
8,017,741 B2 9/2011 Fernandez-Salas et al.
8,021,662 B2 9/2011 Szalay et al.
8,021,859 B2 9/2011 Steward et al.
8,022,172 B2 9/2011 Williams et al.
8,022,186 B2 9/2011 Sheffer et al.
8,026,386 B2 9/2011 Burk et al.

(56) References Cited

U.S. PATENT DOCUMENTS 8,029,789 B2 10/2011 Jung et al.
8,030,023 B2 10/2011 Adams et al.
8,030,447 B2 10/2011 Motin et al.
8,030,542 B2 10/2011 Corbin et al.
8,034,997 B2 10/2011 Bogdanova et al.
8,043,608 B2 10/2011 Gillies et al.
8,043,829 B2 10/2011 Sullivan et al.
8,043,831 B2 10/2011 Rosenblum et al.
8,043,839 B2 10/2011 Weiner et al.
8,044,191 B2 10/2011 Kroger et al.
8,048,643 B2 11/2011 Steward et al.
8,048,646 B2 11/2011 Ting et al.
8,048,651 B2 11/2011 Zelder et al.
8,053,208 B2 11/2011 Steward et al.
8,053,209 B2 11/2011 Steward et al.
8,053,560 B2 11/2011 Sheffer et al.
8,062,885 B2 11/2011 Mach et al.
8,066,987 B2 11/2011 Moore et al.
8,066,994 B2 11/2011 Gillies et al.
8,067,179 B2 11/2011 Georgiou et al.
8,067,231 B2 11/2011 Fernandez-Salas et al.
8,067,377 B2 11/2011 Arap et al.
8,067,530 B2 11/2011 O'Keefe et al.
8,071,365 B2 12/2011 Kroger et al.
8,080,391 B2 12/2011 Buechler et al.
8,080,395 B2 12/2011 Bathe et al.
8,088,620 B2 1/2012 Bestel-Corre et al.
8,093,032 B2 1/2012 Kumar et al.
8,093,037 B2 1/2012 Picataggio et al.
8,093,356 B2 1/2012 Hays et al.
8,097,436 B2 1/2012 Umana et al.
8,097,440 B1 1/2012 Buelter et al.
8,097,702 B2 1/2012 Cho et al.
8,101,168 B2 1/2012 Hassan et al.
8,101,349 B2 1/2012 Garcia et al.
8,101,396 B2 1/2012 Sabbadini et al.
8,101,826 B2 1/2012 Romano
8,105,602 B2 1/2012 Parry et al.
8,105,603 B2 1/2012 Kelley et al.
8,105,608 B2 1/2012 Low et al.
8,105,804 B2 1/2012 Mintier et al.
8,114,630 B2 2/2012 Kraynov et al.
8,114,974 B2 2/2012 Picataggio et al.
8,119,354 B2 2/2012 Katanaev
8,119,372 B2 2/2012 Bathe et al.
8,119,377 B2 2/2012 Yi et al.
8,119,603 B2 2/2012 Cho et al.
8,124,098 B2 2/2012 Masignani et al.
8,124,357 B2 2/2012 Fernandez-Salas et al.
8,124,381 B2 2/2012 Deng et al.
8,124,729 B2 2/2012 Feder et al.
8,128,922 B2 3/2012 Wu et al.
8,128,940 B2 3/2012 Steward et al.
8,129,166 B2 3/2012 Sabbadini et al.
8,133,493 B2 3/2012 Curtiss, III
8,137,904 B2 3/2012 Szalay et al.
8,137,928 B2 3/2012 Schwartz et al.
8,138,311 B2 3/2012 Rosenblum et al.
8,143,216 B2 3/2012 Cho et al.
8,153,404 B2 4/2012 Bathe et al.
8,153,414 B2 4/2012 Caplan et al.
8,158,132 B2 4/2012 Foster et al.
8,163,532 B2 4/2012 Zelder et al.
8,163,695 B2 4/2012 Hays et al.
8,168,417 B2 5/2012 Berka et al.
8,173,397 B2 5/2012 Gal et al.
8,178,108 B2 5/2012 Buechler et al.
8,178,319 B2 5/2012 Pahlsson et al.
8,178,339 B2 5/2012 Campbell et al.
8,178,494 B2 5/2012 Hays et al.
8,183,354 B2 5/2012 DeVico et al.
8,187,834 B2 5/2012 Foster et al.
8,198,045 B2 6/2012 DeFrees et al.
8,198,430 B2 6/2012 Prior et al.
8,202,706 B2 6/2012 Bathe et al.
8,206,700 B2 6/2012 Horwitz et al.
8,221,769 B2 7/2012 Szalay et al.
8,227,217 B2 7/2012 Liu et al.
8,227,230 B2 7/2012 Shaaltiel et al.
8,227,236 B2 7/2012 Picataggio et al.
8,231,878 B2 7/2012 Colonna et al.
8,232,371 B2 7/2012 Cho et al.
8,236,315 B2 8/2012 Lazarides et al.
8,236,494 B2 8/2012 Bakaletz et al.
8,236,531 B2 8/2012 Asahara et al.
8,241,623 B1 8/2012 Bermudes
8,244,484 B2 8/2012 Lee et al.
8,246,945 B2 8/2012 Caplan et al.
8,247,225 B2 8/2012 Kopecko et al.
8,252,579 B2 8/2012 Meynial-Salles et al.
8,257,914 B2 9/2012 Fernandez-Salas et al.
8,257,949 B2 9/2012 Wakarchuk et al.
8,258,100 B2 9/2012 Enright et al.
8,258,262 B2 9/2012 Kinstler et al.
8,278,065 B2 10/2012 Nicolaides et al.
8,278,418 B2 10/2012 Tian et al.
8,282,919 B2 10/2012 Eisenstark et al.
8,283,114 B2 10/2012 Bakaletz et al.
8,283,152 B2 10/2012 Kim et al.
8,283,319 B2 10/2012 Schulte et al.
8,283,456 B2 10/2012 Gin et al.
8,293,503 B2 10/2012 Slater et al.
8,293,514 B2 10/2012 Bathe et al.
8,298,791 B2 10/2012 Matsuno et al.
8,298,807 B2 10/2012 Soucaille et al.
8,304,604 B2 11/2012 Lira et al.
8,304,605 B2 11/2012 Lira et al.
8,323,959 B2 12/2012 Szalay et al.
8,323,961 B2 12/2012 Nabel et al.
8,324,362 B2 12/2012 Chen et al.
8,329,886 B2 12/2012 Bardroff et al.
8,338,575 B2 12/2012 Lauder et al.
8,343,509 B2 1/2013 Stritzker et al.
8,343,752 B2 1/2013 Picataggio et al.
8,344,207 B2 1/2013 Bogdanova et al.
8,349,570 B2 1/2013 Pepe et al.
8,354,264 B2 1/2013 Mintier et al.
8,357,486 B2 1/2013 Stritzker et al.
8,362,207 B2 1/2013 Debinski et al.
8,367,403 B2 2/2013 Slater et al.
8,367,621 B2 2/2013 Ruoslahti et al.
8,372,601 B2 2/2013 Metcalf et al.
8,372,620 B2 2/2013 Sibbesen et al.
8,372,625 B2 2/2013 Walsh et al.
8,383,365 B2 2/2013 Cujec et al.
8,383,388 B2 2/2013 Oyhenart et al.
8,394,607 B2 3/2013 Ebens, Jr. et al.
8,394,610 B2 3/2013 Gulevich et al.
8,404,226 B2 3/2013 Brines et al.
8,409,563 B2 4/2013 Asahara et al.
8,409,825 B2 4/2013 Chiba et al.
8,415,118 B2 4/2013 Huang et al.
8,420,350 B2 4/2013 Nakamura et al.
8,420,779 B2 4/2013 Walker et al.
8,420,792 B2 4/2013 Tian et al.
8,426,187 B2 4/2013 Georgiou et al.
8,426,571 B2 4/2013 Raitano et al.
8,431,373 B2 4/2013 Yi et al.
8,435,506 B2 5/2013 Hassan et al.
8,436,031 B2 5/2013 Kim
8,440,207 B2 5/2013 Bermudes
8,445,227 B2 5/2013 Bobrowicz et al.
8,445,241 B2 5/2013 Dunican et al.
8,445,254 B2 5/2013 Curtiss, III et al.
8,445,650 B2 5/2013 Simpson et al.
8,449,876 B2 5/2013 Shaaltiel et al.
8,455,683 B2 6/2013 Burk et al.
8,461,422 B2 6/2013 Lira et al.
8,465,755 B2 6/2013 Curtiss, III et al.
8,470,991 B2 6/2013 Gillies et al.
8,475,807 B2 7/2013 Perez
8,492,109 B2 7/2013 Oyler et al.
8,497,081 B2 7/2013 Fernandez-Salas et al.
8,501,190 B2 8/2013 Prescott et al.

(56) References Cited

U.S. PATENT DOCUMENTS 8,506,947 B2 8/2013 McCart et al.
8,507,227 B2 8/2013 Samain
8,507,235 B2 8/2013 Chotani et al.
8,507,249 B2 8/2013 Finlay et al.
8,507,250 B2 8/2013 Liu et al.
8,512,984 B2 8/2013 Foster et al.
8,513,396 B2 8/2013 Boone et al.
8,513,493 B2 8/2013 Baum et al.
8,518,417 B1 8/2013 Steward et al.
8,524,220 B1 9/2013 Bermudes
8,524,241 B2 9/2013 Seed et al.
8,524,484 B2 9/2013 Sabbadini et al.
8,530,225 B2 9/2013 Rosenblum et al.
8,535,909 B2 9/2013 Woldike et al.
8,535,941 B2 9/2013 Fernandez-Salas et al.
8,540,992 B2 9/2013 Naso et al.
8,541,201 B2 9/2013 Min et al.
8,551,471 B2 10/2013 Filutowicz et al.
8,557,232 B2 10/2013 Gillies et al.
8,568,707 B2 10/2013 Szalay et al.
8,569,016 B2 10/2013 Obayashi et al.
8,575,316 B2 11/2013 Hiruma et al.
8,586,022 B2 11/2013 Szalay et al.
8,586,332 B2 11/2013 Samain et al.
8,591,862 B2 11/2013 Brahmbhatt et al.
8,592,187 B2 11/2013 Bathe et al.
8,603,779 B2 12/2013 Foster et al.
8,603,824 B2 12/2013 Ramseier et al.
8,604,004 B2 12/2013 Kahne et al.
8,604,178 B2 12/2013 Bottje et al.
8,606,553 B2 12/2013 Palsson
8,609,358 B2 12/2013 Sebastian et al.
8,623,350 B1 1/2014 Bermudes
8,623,622 B2 1/2014 Srienc et al.
8,623,999 B2 1/2014 Steward et al.
8,628,782 B2 1/2014 Berkower
8,628,917 B2 1/2014 Bakaletz et al.
8,629,246 B2 1/2014 Humphreys et al.
8,632,995 B2 1/2014 Sun et al.
8,633,305 B2 1/2014 Shapiro
8,635,031 B2 1/2014 Palsson
8,637,295 B1 1/2014 Claes et al.
8,642,257 B2 2/2014 Szalay et al.
8,642,292 B2 2/2014 Sandig et al.
8,647,642 B2 2/2014 Bermudes
8,652,773 B2 2/2014 Bakaletz et al.
8,652,808 B2 2/2014 Jennewein et al.
8,652,838 B2 2/2014 Shen et al.
8,663,634 B2 3/2014 Koenig et al.
8,663,962 B2 3/2014 Zhang et al.
8,673,601 B2 3/2014 Burgard et al.
8,674,062 B2 3/2014 Dunn-Coleman et al.
8,674,083 B2 3/2014 Presta
8,680,236 B2 3/2014 Luft et al.
8,685,392 B2 4/2014 Helmerhorst et al.
8,685,718 B2 4/2014 Wisniewski et al.
8,685,939 B2 4/2014 Wei et al.
8,686,218 B2 4/2014 Romaine et al.
8,691,952 B2 4/2014 Super et al.
8,697,398 B2 4/2014 Doherty et al.
8,697,414 B2 4/2014 Steward et al.
8,697,642 B2 4/2014 Lira et al.
8,703,153 B2 4/2014 Telfer et al.
8,703,471 B2 4/2014 Aebi et al.
8,709,813 B2 4/2014 Kopecko et al.
8,715,641 B2 5/2014 Filutowicz et al.
8,716,450 B2 5/2014 Ghayur et al.
8,722,584 B2 5/2014 Delisa et al.
8,722,618 B2 5/2014 Jacobs et al.
8,722,668 B2 5/2014 Hochman
8,722,855 B2 5/2014 Ghayur et al.
8,722,869 B2 5/2014 Fang et al.
8,728,795 B2 5/2014 Kroger et al.
8,728,798 B2 5/2014 Picataggio et al.
8,734,779 B2 5/2014 Hamaji et al.
8,734,814 B2 5/2014 Datta et al.
8,735,159 B2 5/2014 Zelder et al.
8,735,539 B2 5/2014 Kraynov et al.
8,735,546 B2 5/2014 Ghayur et al.
8,735,560 B1 5/2014 English et al.
8,741,313 B2 6/2014 Sable et al.
8,741,608 B2 6/2014 Claes et al.
8,741,620 B2 6/2014 Shaaltiel et al.
8,741,623 B2 6/2014 Zelder et al.
8,748,373 B2 6/2014 Chai et al.
8,753,604 B2 6/2014 Ruoslahti et al.
8,758,741 B2 6/2014 Takagi et al.
8,758,764 B2 6/2014 Masignani et al.
8,758,771 B2 6/2014 Finlay et al.
8,759,086 B2 6/2014 Mach et al.
8,759,494 B2 6/2014 Bachmann et al.
8,765,407 B2 7/2014 Iyo et al.
8,771,669 B1 7/2014 Bermudes
8,771,671 B2 7/2014 Spencer et al.
8,771,707 B2 7/2014 Chapman et al.
8,771,708 B2 7/2014 Evans et al.
8,771,991 B2 7/2014 Gilbert et al.
8,778,634 B2 7/2014 Foster et al.
8,778,652 B2 7/2014 Subbian et al.
8,778,880 B2 7/2014 Cho et al.
8,784,836 B2 7/2014 Szalay et al.
8,790,641 B2 7/2014 Shaaltiel et al.
8,791,237 B2 7/2014 Paterson et al.
8,795,730 B2 8/2014 Vachon
8,809,027 B1 8/2014 Lynch et al.
8,815,251 B2 8/2014 Caplan et al.
8,815,558 B2 8/2014 Frost et al.
RE45,170 E 9/2014 Smith
8,821,893 B2 9/2014 Dattwyler et al.
8,822,194 B2 9/2014 Zhao et al.
8,822,645 B2 9/2014 Ghayur et al.
8,822,664 B2 9/2014 Cicortas Gunnarsson et al.
8,828,681 B2 9/2014 Bell, III et al.
8,835,107 B2 9/2014 Van Der Hoek
8,835,162 B2 9/2014 Kwon et al.
8,835,606 B2 9/2014 Gillies
8,841,253 B2 9/2014 Murphy et al.
8,846,363 B2 9/2014 Myette et al.
8,852,603 B2 10/2014 Foster et al.
8,852,890 B2 10/2014 Cervin et al.
8,852,927 B2 10/2014 Szalay et al.
8,853,154 B2 10/2014 Cload et al.
8,853,362 B2 10/2014 Tissot et al.
8,865,153 B2 10/2014 Szalay et al.
8,865,442 B2 10/2014 Chotani et al.
8,871,491 B2 10/2014 Wacker et al.
8,871,906 B2 10/2014 Pastan et al.
8,883,464 B2 11/2014 Lynch et al.
8,889,121 B2 11/2014 Curtiss, III et al.
8,889,383 B2 11/2014 Beck et al.
8,889,842 B2 11/2014 Gin et al.
8,895,277 B2 11/2014 Beatty et al.
8,906,653 B2 12/2014 Volkert et al.
8,906,662 B2 12/2014 Nataro et al.
8,906,676 B2 12/2014 Cho et al.
8,907,064 B2 12/2014 Cho et al.
8,907,066 B2 12/2014 Lo et al.
8,907,071 B2 12/2014 Sullivan et al.
8,912,313 B2 12/2014 Reth et al.
8,920,798 B2 12/2014 Han et al.
8,920,809 B2 12/2014 Dirienzo
8,926,973 B2 1/2015 Gillies et al.
8,926,993 B2 1/2015 Dubensky, Jr. et al.
8,932,598 B2 1/2015 Song et al.
8,946,148 B2 2/2015 Miao et al.
8,951,759 B2 2/2015 Claes et al.
8,951,992 B2 2/2015 Nathan et al.
8,956,849 B2 2/2015 Bottje et al.
8,956,859 B1 2/2015 Bermudes
8,957,195 B2 2/2015 Super et al.
8,961,990 B2 2/2015 Hargis et al.
8,962,275 B2 2/2015 Liang et al.
8,962,816 B2 2/2015 Ertl et al.
8,969,529 B2 3/2015 O'Brien et al.

(56) References Cited

U.S. PATENT DOCUMENTS 8,969,538 B2 3/2015 Rosen et al.
8,969,542 B2 3/2015 Buyse et al.
8,975,040 B2 3/2015 Naso et al.
8,975,051 B2 3/2015 McAuliffe et al.
8,981,061 B2 3/2015 Colonna et al.
8,993,265 B2 3/2015 Cload et al.
8,993,295 B2 3/2015 Seed et al.
8,993,297 B2 3/2015 Ronin et al.
8,993,305 B2 3/2015 Beck et al.
8,999,949 B2 4/2015 Spencer et al.
9,000,036 B2 4/2015 Yu
9,005,600 B2 4/2015 Debinski et al.
9,005,949 B2 4/2015 Oxvig et al.
9,006,520 B2 4/2015 Lira et al.
9,011,866 B2 4/2015 Wu et al.
9,012,152 B2 4/2015 Engelberg-Kulka et al.
9,012,186 B2 4/2015 Cann et al.
9,012,195 B2 4/2015 Foster et al.
9,012,226 B2 4/2015 Williams
9,017,966 B2 4/2015 Williams et al.
9,017,986 B2 4/2015 Sabbadini et al.
9,018,014 B2 4/2015 Slater et al.
9,023,635 B2 5/2015 Bayer et al.
9,029,104 B2 5/2015 Samsonova et al.
9,029,136 B2 5/2015 Heidtman et al.
9,029,508 B2 5/2015 Ghayur et al.
9,034,642 B2 5/2015 Bakaletz et al.
9,037,445 B2 5/2015 Oltvai et al.
9,040,059 B2 5/2015 Curtiss, III et al.
9,045,742 B2 6/2015 Curtiss, III et al.
9,045,745 B2 6/2015 Subbian et al.
9,045,762 B2 6/2015 Reth et al.
9,045,766 B2 6/2015 Meade et al.
9,050,285 B2 6/2015 Curtiss, III et al.
9,051,565 B2 6/2015 Delisa et al.
9,051,588 B2 6/2015 Soucaille et al.
9,062,297 B2 6/2015 Curtiss, III et al.
9,068,187 B1 6/2015 Bermudes
9,072,736 B2 7/2015 Foster et al.
9,074,229 B2 7/2015 Reth et al.
9,079,971 B2 7/2015 Cujec et al.
9,085,638 B2 7/2015 Wu et al.
9,085,765 B2 7/2015 Campbell et al.
9,090,889 B2 7/2015 Nunn, Jr. et al.
9,090,928 B2 7/2015 Park et al.
9,096,651 B2 8/2015 Igawa et al.
9,102,729 B2 8/2015 Masignani et al.
9,102,958 B2 8/2015 Botes et al.
9,102,960 B2 8/2015 Botes et al.
9,109,229 B2 8/2015 Ramseier et al.
9,121,024 B2 9/2015 Tian et al.
9,121,025 B2 9/2015 Tian et al.
9,121,038 B2 9/2015 Beck et al.
9,125,854 B2 9/2015 Bottje et al.
9,125,855 B2 9/2015 Pasmans et al.
9,139,635 B2 9/2015 Foster et al.
9,139,844 B2 9/2015 Meade et al.
9,150,827 B2 10/2015 Wendisch et al.
9,150,868 B2 10/2015 Tokuda et al.
9,150,885 B2 10/2015 Shibamoto
9,155,798 B2 10/2015 Vallera
9,156,899 B2 10/2015 Tian et al.
9,161,974 B2 10/2015 Dubensky et al.
9,163,219 B2 10/2015 Curtiss, III et al.
9,163,263 B2 10/2015 Beck et al.
9,169,468 B2 10/2015 Zhang et al.
9,169,502 B2 10/2015 Wittmann et al.
9,175,083 B2 11/2015 Cho et al.
9,187,523 B2 11/2015 Motin et al.
9,187,762 B2 11/2015 Albert et al.
9,198,960 B2 12/2015 Dubensky, Jr. et al.
9,200,251 B1 12/2015 Bermudes
9,200,289 B1 12/2015 Bermudes
9,206,456 B2 12/2015 Lenormand
9,221,877 B2 12/2015 Hansel et al.
9,226,957 B2 1/2016 Bottje et al.
9,228,017 B2 1/2016 Igawa et al.
9,233,137 B2 1/2016 de Muinck et al.
9,234,208 B1 1/2016 Lira et al.
9,243,301 B2 1/2016 Foster et al.
9,248,177 B2 2/2016 Tang et al.
9,249,430 B2 2/2016 Marliere
9,260,472 B2 2/2016 Cho et al.
9,260,729 B2 2/2016 Sun et al.
9,267,156 B2 2/2016 Amano et al.
9,284,573 B2 3/2016 Meade et al.
9,297,015 B2 3/2016 Curtiss, III et al.
9,303,264 B2 4/2016 Curtiss et al.
9,309,327 B2 4/2016 Humphreys et al.
9,315,817 B2 4/2016 Bermudes
9,315,831 B2 4/2016 Blake et al.
9,321,847 B2 4/2016 Benhar et al.
9,328,148 B2 5/2016 Joens et al.
9,334,313 B2 5/2016 Masignani et al.
9,334,508 B2 5/2016 Pearlman et al.
9,340,615 B2 5/2016 Maeda et al.
9,340,793 B2 5/2016 Muramatsu et al.
9,365,625 B1 6/2016 Bermudes
9,365,874 B2 6/2016 Burk et al.
9,371,531 B2 6/2016 Slater et al.
9,388,394 B2 7/2016 Heinrichs et al.
9,388,397 B2 7/2016 Rosenblum et al.
9,388,417 B2 7/2016 Lee et al.
9,388,419 B2 7/2016 Lynch et al.
9,388,431 B2 7/2016 McAuliffe et al.
9,399,058 B2 7/2016 Prescott et al.
9,421,252 B2 8/2016 Bermudes
9,422,578 B2 8/2016 Pearlman et al.
9,422,580 B2 8/2016 Pearlman et al.
9,428,778 B2 8/2016 Lynch et al.
9,434,778 B2 9/2016 Morin et al.
9,434,966 B2 9/2016 Picataggio et al.
9,441,251 B2 9/2016 Lee et al.
9,447,405 B2 9/2016 Johnson et al.
9,449,144 B2 9/2016 Oltvai et al.
9,452,205 B2 9/2016 Pascual et al.
9,452,222 B2 9/2016 Kraynov et al.
9,464,129 B2 10/2016 Carreno Serraima et al.
9,464,288 B2 10/2016 Soll et al.
9,469,857 B2 10/2016 Slater et al.
9,474,807 B2 10/2016 Foster et al.
9,486,513 B1 11/2016 Bermudes
9,487,798 B2 11/2016 Lira et al.
9,488,660 B2 11/2016 Miao et al.
9,492,534 B2 11/2016 Szalay et al.
9,499,835 B2 11/2016 Meade et al.
9,504,735 B2 11/2016 Sanders
9,517,273 B2 12/2016 Cujec et al.
9,567,386 B2 2/2017 Kraynov et al.
9,567,594 B2 2/2017 Park et al.
9,567,602 B2 2/2017 Meade et al.
9,580,716 B2 2/2017 Park et al.
9,593,339 B1 3/2017 Bermudes
9,597,379 B1 3/2017 Bermudes
9,598,685 B2 3/2017 Dong et al.
9,616,114 B1 4/2017 Bermudes
9,617,349 B2 4/2017 Gillies
9,631,004 B2 4/2017 Morin et al.
9,644,014 B2 5/2017 Tian et al.
9,657,085 B1 5/2017 Bermudes
9,663,795 B2 5/2017 Meade et al.
9,670,269 B2 6/2017 Igawa et al.
9,694,063 B2 7/2017 Scarselli et al.
9,694,064 B2 7/2017 Boutriau et al.
9,701,725 B2 7/2017 Wu et al.
9,718,850 B2 8/2017 Gin et al.
9,730,994 B2 8/2017 Pietrobon et al.
9,737,592 B1 8/2017 Bermudes et al.
9,739,773 B1 8/2017 Bermudes
9,758,551 B2 9/2017 Wu et al.
9,764,006 B2 9/2017 Wang et al.
9,771,404 B2 9/2017 Debinski et al.
9,796,982 B2 10/2017 Meade et al.
9,801,931 B2 10/2017 O'Brien et al.

(56) References Cited

U.S. PATENT DOCUMENTS 9,828,429 B2 11/2017 Igawa et al.
9,828,438 B2 11/2017 Humphreys et al.
9,868,948 B2 1/2018 Igawa et al.
9,878,023 B1 1/2018 Bermudes
9,890,377 B2 2/2018 Igawa et al.
9,937,260 B2 4/2018 Hansel et al.
9,938,333 B2 4/2018 Kraynov et al.
9,962,450 B2 5/2018 Kraynov et al.
9,975,936 B2 5/2018 Cujec et al.
11,180,535 B1 * 11/2021 Bermudes .......... A61K 39/0275
2001/0006642 A1 7/2001 Steidler et al.
2001/0009957 A1 7/2001 Oaks et al.
2001/0028881 A1 10/2001 Roffler et al.
2001/0029024 A1 10/2001 Kodadek
2001/0029043 A1 10/2001 Haefliger et al.
2001/0031485 A1 10/2001 Backer et al.
2001/0041333 A1 11/2001 Short et al.
2001/0046498 A1 11/2001 Ruoslahti et al.
2001/0053371 A1 12/2001 Debinski et al.
2002/0006645 A1 1/2002 Hashimoto et al.
2002/0012939 A1 1/2002 Palsson
2002/0015940 A1 2/2002 Rao et al.
2002/0016982 A1 2/2002 Romaine et al.
2002/0026655 A1 2/2002 Bermudes et al.
2002/0028914 A1 3/2002 Yarkoni et al.
2002/0031809 A1 3/2002 Moeckel et al.
2002/0031810 A1 3/2002 Moeckel et al.
2002/0032323 A1 3/2002 Kunsch et al.
2002/0037568 A1 3/2002 Molenaar et al.
2002/0039766 A1 4/2002 Bathe et al.
2002/0042105 A1 4/2002 Bathe et al.
2002/0042382 A1 4/2002 Duffy et al.
2002/0044919 A1 4/2002 Yu
2002/0045224 A1 4/2002 Mockel et al.
2002/0048795 A1 4/2002 Farwick et al.
2002/0051993 A1 5/2002 Farwick et al.
2002/0052486 A1 5/2002 Bathe et al.
2002/0055114 A1 5/2002 Bathe et al.
2002/0055115 A1 5/2002 Farwick et al.
2002/0055152 A1 5/2002 Farwick et al.
2002/0058277 A1 5/2002 Bathe et al.
2002/0061545 A1 5/2002 Choi et al.
2002/0064839 A1 5/2002 Marx et al.
2002/0068336 A1 6/2002 Moeckel et al.
2002/0072104 A1 6/2002 Landry
2002/0078473 A1 6/2002 Estruch et al.
2002/0081672 A1 6/2002 Mockel et al.
2002/0081674 A1 6/2002 Moeckel et al.
2002/0082236 A1 6/2002 Black
2002/0086372 A1 7/2002 Mockel et al.
2002/0086373 A1 7/2002 Farwick et al.
2002/0086374 A1 7/2002 Farwick et al.
2002/0086404 A1 7/2002 Moeckel et al.
2002/0090685 A1 7/2002 Bathe et al.
2002/0098554 A1 7/2002 Farwick et al.
2002/0102242 A1 8/2002 Briles et al.
2002/0102663 A1 8/2002 Farwick et al.
2002/0102668 A1 8/2002 Farwick et al.
2002/0102669 A1 8/2002 Farwick et al.
2002/0103338 A1 8/2002 Choi
2002/0103356 A1 8/2002 Mockel et al.
2002/0103357 A1 8/2002 Bathe et al.
2002/0106380 A1 8/2002 Hung et al.
2002/0106672 A1 8/2002 Farwick et al.
2002/0106749 A1 8/2002 Farwick et al.
2002/0106750 A1 8/2002 Farwick et al.
2002/0106751 A1 8/2002 Farwick et al.
2002/0106755 A1 8/2002 Bathe et al.
2002/0106756 A1 8/2002 Bathe et al.
2002/0106757 A1 8/2002 Farwick et al.
2002/0106758 A1 8/2002 Farwick et al.
2002/0106759 A1 8/2002 Farwick et al.
2002/0106760 A1 8/2002 Bathe et al.
2002/0107374 A1 8/2002 Pallas et al.
2002/0107377 A1 8/2002 Farwick et al.
2002/0107379 A1 8/2002 Marx et al.
2002/0110879 A1 8/2002 Bathe et al.
2002/0111468 A1 8/2002 Bathe et al.
2002/0115159 A1 8/2002 Farwick et al.
2002/0115160 A1 8/2002 Farwick et al.
2002/0115161 A1 8/2002 Farwick et al.
2002/0115162 A1 8/2002 Farwick et al.
2002/0119537 A1 8/2002 Moeckel et al.
2002/0119549 A1 8/2002 Moeckel et al.
2002/0120116 A1 8/2002 Kunsch et al.
2002/0123053 A1 9/2002 Luo et al.
2002/0127661 A1 9/2002 Farwick et al.
2002/0127687 A1 9/2002 Shigenobu et al.
2002/0127702 A1 9/2002 Bernstein et al.
2002/0132323 A1 9/2002 Moeckel et al.
2002/0137065 A1 9/2002 Farwick et al.
2002/0137073 A1 9/2002 Bathe et al.
2002/0142006 A1 10/2002 McGhee et al.
2002/0142404 A1 10/2002 Farwick et al.
2002/0146430 A1 10/2002 Galen
2002/0146782 A1 10/2002 Bathe et al.
2002/0150881 A1 10/2002 Ladner et al.
2002/0151001 A1 10/2002 Moeckel et al.
2002/0151063 A1 10/2002 Lasham et al.
2002/0151700 A1 10/2002 Farwick et al.
2002/0155519 A1 10/2002 Lindner et al.
2002/0155554 A1 10/2002 Bathe et al.
2002/0155557 A1 10/2002 Moeckel et al.
2002/0159972 A1 10/2002 Debinski et al.
2002/0168732 A1 11/2002 Moeckel et al.
2002/0176848 A1 11/2002 Sizemore et al.
2002/0177551 A1 11/2002 Terman
2002/0182689 A1 12/2002 Bathe et al.
2002/0192223 A1 12/2002 Hellstrom et al.
2002/0192674 A1 12/2002 Hermann et al.
2002/0197276 A1 12/2002 Oaks et al.
2002/0197605 A1 12/2002 Nakagawa et al.
2003/0008839 A1 1/2003 van Rooij et al.
2003/0009015 A1 1/2003 Ulrich et al.
2003/0022835 A1 1/2003 Watson et al.
2003/0031628 A1 2/2003 Zhao et al.
2003/0031666 A1 2/2003 Debinski et al.
2003/0031681 A1 2/2003 McCart et al.
2003/0031683 A1 2/2003 Curtiss et al.
2003/0036644 A1 2/2003 Ulrich
2003/0040619 A1 2/2003 Edwards et al.
2003/0044943 A1 3/2003 Farwick et al.
2003/0045492 A1 3/2003 Tang et al.
2003/0049264 A1 3/2003 Foster et al.
2003/0049648 A1 3/2003 Choi
2003/0059400 A1 3/2003 Szalay
2003/0059792 A1 3/2003 Palsson et al.
2003/0059923 A1 3/2003 Feder et al.
2003/0068328 A1 4/2003 Vladoianu et al.
2003/0068611 A1 4/2003 Larossa et al.
2003/0068791 A1 4/2003 Miasnikov et al.
2003/0072737 A1 4/2003 Brines et al.
2003/0073217 A1 4/2003 Barr et al.
2003/0077677 A1 4/2003 Short et al.
2003/0082219 A1 5/2003 Warren et al.
2003/0086919 A1 5/2003 Rosenblum et al.
2003/0087827 A1 5/2003 Lindberg et al.
2003/0092026 A1 5/2003 Rey et al.
2003/0092066 A1 5/2003 Vinkemeier et al.
2003/0092137 A1 5/2003 Farwick et al.
2003/0092139 A1 5/2003 Wolf et al.
2003/0092164 A1 5/2003 Gross et al.
2003/0100054 A1 5/2003 Bathe et al.
2003/0100071 A1 5/2003 Apicella et al.
2003/0100080 A1 5/2003 Farwick et al.
2003/0100099 A1 5/2003 Moeckel et al.
2003/0100108 A1 5/2003 Altman et al.
2003/0100488 A1 5/2003 Boyle
2003/0103958 A1 6/2003 Short et al.
2003/0104988 A1 6/2003 Brines et al.
2003/0105319 A1 6/2003 Schnepf et al.
2003/0106096 A1 6/2003 Barry
2003/0109014 A1 6/2003 Burke et al.
2003/0109026 A1 6/2003 Bermudes et al.

(56) References Cited

U.S. PATENT DOCUMENTS

2003/0113293 A1 6/2003 Bermudes et al.
2003/0113343 A1 6/2003 Tuomanen et al.
2003/0113717 A1 6/2003 Ladner et al.
2003/0113879 A1 6/2003 Farwick et al.
2003/0115630 A1 6/2003 Romano
2003/0119154 A1 6/2003 Dunican et al.
2003/0124561 A1 7/2003 Mach et al.
2003/0125278 A1 7/2003 Tang et al.
2003/0129132 A1 7/2003 Puri et al.
2003/0129193 A1 7/2003 Thorpe et al.
2003/0131372 A1 7/2003 Copenhaver et al.
2003/0131376 A1 7/2003 Okubara et al.
2003/0138917 A1 7/2003 Dunican et al.
2003/0143558 A1 7/2003 Mitchell et al.
2003/0143650 A1 7/2003 Steward et al.
2003/0143651 A1 7/2003 Steward et al.
2003/0143676 A1 7/2003 Strachan et al.
2003/0144490 A1 7/2003 Edwards et al.
2003/0153527 A1 8/2003 Powell et al.
2003/0157113 A1 8/2003 Terman
2003/0157551 A1 8/2003 Bathe et al.
2003/0157666 A1 8/2003 Farwick et al.
2003/0158390 A1 8/2003 Fishman et al.
2003/0165875 A1 9/2003 Colonna et al.
2003/0166140 A1 9/2003 Chen et al.
2003/0166541 A1 9/2003 Ruben et al.
2003/0166884 A1 9/2003 Moeckel et al.
2003/0170211 A1 9/2003 Goudsmit et al.
2003/0170276 A1 9/2003 Bermudes et al.
2003/0170780 A1 9/2003 Moeckel et al.
2003/0170897 A1 9/2003 Imai et al.
2003/0175911 A1 9/2003 Hans et al.
2003/0180289 A1 9/2003 Foster et al.
2003/0186416 A1 10/2003 Pallas et al.
2003/0188335 A1 10/2003 Tuli
2003/0188336 A1 10/2003 Corbin et al.
2003/0194798 A1 10/2003 Surber et al.
2003/0198991 A1 10/2003 Moeckel et al.
2003/0199045 A1 10/2003 Burke et al.
2003/0202990 A1 10/2003 Donovan et al.
2003/0203377 A1 10/2003 Milne Edwards et al.
2003/0207271 A1 11/2003 Holwitt et al.
2003/0211476 A1 11/2003 O'Mahony et al.
2003/0211599 A1 11/2003 Sabbadini et al.
2003/0219462 A1 11/2003 Steward et al.
2003/0219722 A1 11/2003 Ladner et al.
2003/0219736 A1 11/2003 Gonye et al.
2003/0219881 A1 11/2003 Brigitte et al.
2003/0219886 A1 11/2003 Ladner et al.
2003/0224363 A1 12/2003 Park et al.
2003/0228678 A1 12/2003 Bathe et al.
2003/0229065 A1 12/2003 Levy et al.
2004/0005539 A1 1/2004 Ladner et al.
2004/0005695 A1 1/2004 Miksch et al.
2004/0005700 A1 1/2004 Surber et al.
2004/0009485 A1 1/2004 Gonye et al.
2004/0009490 A1 1/2004 Glenn et al.
2004/0009578 A1 1/2004 Bathe et al.
2004/0009936 A1 1/2004 Tang et al.
2004/0013658 A1 1/2004 Fulton et al.
2004/0014156 A1 1/2004 Roffler et al.
2004/0014177 A1 1/2004 Navran, Jr. et al.
2004/0018203 A1 1/2004 Pastan et al.
2004/0018967 A1 1/2004 Enright et al.
2004/0022805 A1 2/2004 Narum et al.
2004/0023205 A1 2/2004 Ladner et al.
2004/0023266 A1 2/2004 Vivekananda et al.
2004/0023282 A1 2/2004 Luo et al.
2004/0033549 A1 2/2004 Greenberg et al.
2004/0038307 A1 2/2004 Lee et al.
2004/0038372 A1 2/2004 Bathe et al.
2004/0043029 A1 3/2004 Hellstrom et al.
2004/0043458 A1 3/2004 Bathe et al.
2004/0052802 A1 3/2004 Nuijten et al.
2004/0054142 A1 3/2004 Cassart et al.
2004/0058849 A1 3/2004 Sleeman et al.
2004/0063181 A1 4/2004 Duncan et al.
2004/0067561 A1 4/2004 Bathe et al.
2004/0067562 A1 4/2004 Bathe et al.
2004/0071729 A1 4/2004 Adderson et al.
2004/0072218 A1 4/2004 Quan Pan
2004/0072270 A1 4/2004 Fernandez-Salas et al.
2004/0072723 A1 4/2004 Palsson et al.
2004/0072755 A1* 4/2004 Stennicke .......... C07K 5/06191
514/15.6
2004/0073008 A1 4/2004 Iglesias Perez et al.
2004/0077540 A1 4/2004 Quay
2004/0082002 A1 4/2004 Choi
2004/0091505 A1 5/2004 Abad et al.
2004/0091969 A1 5/2004 Agarwal et al.
2004/0091976 A1 5/2004 Deng et al.
2004/0096426 A1 5/2004 Chen et al.
2004/0101531 A1 5/2004 Curtiss et al.
2004/0101932 A1 5/2004 Naleway et al.
2004/0106185 A1 6/2004 Ranganathan
2004/0106553 A1 6/2004 Alekshun et al.
2004/0110939 A1 6/2004 Dumas Milne Edwards et al.
2004/0115174 A1 6/2004 Gilboa et al.
2004/0115788 A1 6/2004 Zheng et al.
2004/0117863 A1 6/2004 Edge et al.
2004/0122216 A1 6/2004 Nielsen et al.
2004/0128716 A1 7/2004 Narva et al.
2004/0133930 A1 7/2004 Cooper et al.
2004/0136959 A1 7/2004 Puri
2004/0142373 A1 7/2004 Gonye et al.
2004/0142454 A1 7/2004 Molenaar et al.
2004/0146922 A1 7/2004 Gonye et al.
2004/0166565 A1 8/2004 Backer et al.
2004/0170987 A1 9/2004 Usuda et al.
2004/0171123 A1 9/2004 Rosen et al.
2004/0171130 A1 9/2004 Yokoi et al.
2004/0180359 A1 9/2004 Moeckel et al.
2004/0180371 A1 9/2004 Clayman et al.
2004/0180380 A1 9/2004 Lee et al.
2004/0191787 A1 9/2004 Tanner et al.
2004/0202648 A1 10/2004 Cabezon et al.
2004/0202663 A1 10/2004 Hu et al.
2004/0208897 A1 10/2004 Curtiss et al.
2004/0209285 A1 10/2004 Moeckel et al.
2004/0210398 A1 10/2004 Palsson et al.
2004/0214219 A1 10/2004 Dunican et al.
2004/0214236 A1 10/2004 Brines et al.
2004/0214783 A1 10/2004 Terman
2004/0219169 A1 11/2004 Bermudes et al.
2004/0220386 A1 11/2004 Steward et al.
2004/0229243 A1 11/2004 Levy
2004/0229255 A1 11/2004 Hermann et al.
2004/0229338 A1 11/2004 King
2004/0234455 A1 11/2004 Szalay
2004/0234956 A1 11/2004 Kabat et al.
2004/0234998 A1 11/2004 Sibbesen et al.
2004/0247611 A1 12/2004 Bargatze et al.
2004/0247617 A1 12/2004 Liao et al.
2004/0253628 A1 12/2004 Bathe et al.
2004/0258688 A1 12/2004 Hawiger et al.
2004/0266003 A1 12/2004 Powell et al.
2004/0266674 A1 12/2004 Mills et al.
2005/0003400 A1 1/2005 Boyle
2005/0003423 A1 1/2005 Moeckel et al.
2005/0008618 A1 1/2005 Kaufman et al.
2005/0008649 A1 1/2005 Shin et al.
2005/0009750 A1 1/2005 Sleeman et al.
2005/0013822 A1 1/2005 Oaks et al.
2005/0019335 A1 1/2005 Lowery et al.
2005/0026866 A1 2/2005 Pawelek
2005/0031643 A1 2/2005 Szalay et al.
2005/0032157 A1 2/2005 Gal et al.
2005/0032179 A1 2/2005 Moeckel et al.
2005/0036987 A1 2/2005 Pawelek et al.
2005/0042216 A1 2/2005 Frantz et al.
2005/0042229 A1 2/2005 Yang et al.
2005/0043526 A1 2/2005 Bathe et al.
2005/0053589 A1 3/2005 Debinski et al.
2005/0053958 A1 3/2005 Roth et al.

(56) References Cited

U.S. PATENT DOCUMENTS

2005/0055746 A1 3/2005 Michaud et al.
2005/0059122 A1 3/2005 Shen
2005/0059592 A1 3/2005 Kiener et al.
2005/0063994 A1 3/2005 Caplan et al.
2005/0064526 A1 3/2005 Ulrich et al.
2005/0064527 A1 3/2005 Levy et al.
2005/0064562 A1 3/2005 Farwick et al.
2005/0069491 A1 3/2005 Szalay et al.
2005/0069532 A1 3/2005 Weinrauch et al.
2005/0069894 A1 3/2005 Gottesman et al.
2005/0069911 A1 3/2005 Lee et al.
2005/0070005 A1 3/2005 Keller
2005/0070007 A1 3/2005 Romaine et al.
2005/0074463 A1 4/2005 Autran et al.
2005/0074802 A1 4/2005 Rey et al.
2005/0079573 A1 4/2005 Sibbesen
2005/0079588 A1 4/2005 Sindelar et al.
2005/0084972 A1 4/2005 Barr et al.
2005/0089552 A1 4/2005 Altman et al.
2005/0089976 A1 4/2005 Moeckel et al.
2005/0089986 A1 4/2005 Bathe et al.
2005/0100973 A1 5/2005 Steward et al.
2005/0106151 A1 5/2005 Shapiro
2005/0106597 A1 5/2005 Choi
2005/0112139 A1 5/2005 Karp
2005/0112140 A1 5/2005 Karp
2005/0112141 A1 5/2005 Terman
2005/0112642 A1 5/2005 Sleeman et al.
2005/0112664 A1 5/2005 Mockel et al.
2005/0112730 A1 5/2005 Dunican et al.
2005/0112732 A1 5/2005 Bathe et al.
2005/0112733 A1 5/2005 Burke et al.
2005/0112751 A1 5/2005 Fang et al.
2005/0118187 A1 6/2005 Yu
2005/0118193 A1 6/2005 Andino-Pavlovsky et al.
2005/0124678 A1 6/2005 Levy et al.
2005/0130264 A1 6/2005 Moeckel et al.
2005/0130277 A1 6/2005 Bathe et al.
2005/0136404 A1 6/2005 Doucette-Stamm et al.
2005/0147590 A1 7/2005 Sabbadini et al.
2005/0148504 A1 7/2005 Katunuma et al.
2005/0158295 A1 7/2005 Swiercz et al.
2005/0166274 A1 7/2005 French et al.
2005/0180963 A1 8/2005 Adams et al.
2005/0180985 A9 8/2005 Vladoianu et al.
2005/0181439 A1 8/2005 Choi et al.
2005/0181464 A1 8/2005 Edwards et al.
2005/0181488 A1 8/2005 Akhverdian et al.
2005/0191684 A1 9/2005 Zimenkov et al.
2005/0202409 A1 9/2005 Takami et al.
2005/0202535 A1 9/2005 Collier et al.
2005/0203007 A1 9/2005 Komiyama et al.
2005/0208033 A1 9/2005 Luquet et al.
2005/0214317 A1 9/2005 Karp
2005/0214318 A1 9/2005 Karp
2005/0221439 A1 10/2005 Bakaletz et al.
2005/0221450 A1 10/2005 Mockel et al.
2005/0221454 A1 10/2005 Bathe
2005/0227917 A1 10/2005 Williams et al.
2005/0233424 A1 10/2005 Farwick et al.
2005/0241015 A1 10/2005 Mach et al.
2005/0241016 A1 10/2005 Mach et al.
2005/0249706 A1 11/2005 Bermudes et al.
2005/0249748 A1 11/2005 Dubensky, Jr. et al.
2005/0250196 A1 11/2005 Paton et al.
2005/0251885 A1 11/2005 Michaud et al.
2005/0255088 A1 11/2005 Bermudes et al.
2005/0255566 A1 11/2005 Bathe et al.
2005/0256049 A1 11/2005 Yarkoni et al.
2005/0257282 A1 11/2005 Mach et al.
2005/0260225 A1 11/2005 Goldberg et al.
2005/0260670 A1 11/2005 Colonna et al.
2005/0266536 A1 12/2005 Wolf et al.
2005/0266560 A1 12/2005 Preuss et al.
2005/0267103 A1 12/2005 Hochman
2005/0268359 A1 12/2005 Mach et al.
2005/0272060 A1 12/2005 Tuli
2005/0273882 A1 12/2005 Romano
2005/0281828 A1 12/2005 Bowdish et al.
2005/0282239 A1 12/2005 Allbritton et al.
2005/0282259 A1 12/2005 Moeckel et al.
2005/0287639 A1 12/2005 Kwon et al.
2006/0008465 A1 1/2006 Steinaa et al.
2006/0009633 A9 1/2006 Dumas Milne Edwards et al.
2006/0014212 A1 1/2006 Benkovic et al.
2006/0014259 A9 1/2006 Burke et al.
2006/0015969 A1 1/2006 Larrick et al.
2006/0018914 A1 1/2006 Hellstrom et al.
2006/0019356 A1 1/2006 Usuda et al.
2006/0019357 A1 1/2006 Moeckel et al.
2006/0024668 A1 2/2006 Hoek
2006/0025387 A1 2/2006 Hochman
2006/0026695 A1 2/2006 Edge et al.
2006/0030010 A1 2/2006 Usuda et al.
2006/0034799 A1 2/2006 Brines et al.
2006/0035270 A1 2/2006 Lee et al.
2006/0035320 A1 2/2006 Tissot et al.
2006/0035371 A1 2/2006 Zheng et al.
2006/0035813 A1 2/2006 Sternberg et al.
2006/0039929 A1 2/2006 Fernandez-Salas et al.
2006/0040317 A1 2/2006 Farwick et al.
2006/0051356 A1 3/2006 Foster et al.
2006/0051370 A1 3/2006 Szalay et al.
2006/0051839 A1 3/2006 Robinson et al.
2006/0057152 A1 3/2006 Marshall
2006/0063221 A1 3/2006 Williams et al.
2006/0063222 A1 3/2006 Williams et al.
2006/0073168 A1 4/2006 Stephens et al.
2006/0083716 A1 4/2006 Kaufman et al.
2006/0084113 A1 4/2006 Ladner et al.
2006/0088910 A1 4/2006 Nguyen
2006/0089350 A1 4/2006 Hochman et al.
2006/0094672 A1 5/2006 Pasqualini et al.
2006/0104955 A1 5/2006 Redshaw
2006/0110747 A1 5/2006 Ramseier et al.
2006/0112447 A1 5/2006 Bogdanova et al.
2006/0115483 A1 6/2006 Sleeman et al.
2006/0121056 A1 6/2006 Chaddock et al.
2006/0127408 A1 6/2006 Young et al.
2006/0134761 A1 6/2006 Moeckel et al.
2006/0134791 A1 6/2006 Black
2006/0135754 A1 6/2006 Christensen et al.
2006/0140975 A1 6/2006 Curtiss et al.
2006/0153876 A1 7/2006 Sanders
2006/0154314 A9 7/2006 Steward et al.
2006/0156440 A1 7/2006 Michaud et al.
2006/0160152 A1 7/2006 Vinkemeier et al.
2006/0160799 A1 7/2006 Alekshun et al.
2006/0166338 A1 7/2006 Bathe et al.
2006/0167229 A1 7/2006 Wong et al.
2006/0174357 A1 8/2006 Velander et al.
2006/0177912 A1 8/2006 Farwick et al.
2006/0182685 A1 8/2006 Bishai et al.
2006/0182762 A1 8/2006 Irene Martina Maas et al.
2006/0216283 A1 9/2006 Foster et al.
2006/0216757 A1 9/2006 Brines et al.
2006/0222633 A1 10/2006 Shlomchik et al.
2006/0223142 A1 10/2006 Dumas Milne Edwards et al.
2006/0228712 A1 10/2006 Nakagawa et al.
2006/0229336 A1 10/2006 Kazmierski et al.
2006/0233829 A1 10/2006 Curtiss
2006/0234331 A1 10/2006 Yazaki et al.
2006/0234358 A1 10/2006 Anderlei et al.
2006/0234943 A1 10/2006 Wong
2006/0239968 A1 10/2006 Arap et al.
2006/0241050 A1 10/2006 Cameron et al.
2006/0246554 A1 11/2006 Thierbach et al.
2006/0263368 A1 11/2006 Rosenblum et al.
2006/0269540 A1 11/2006 Robert et al.
2006/0269561 A1 11/2006 Paterson et al.
2006/0270043 A1 11/2006 Blattner et al.
2006/0275823 A1 12/2006 Kodadek
2006/0275874 A1 12/2006 Matsuno et al.
2006/0275897 A1 12/2006 Nabel et al.

(56) References Cited

U.S. PATENT DOCUMENTS

2006/0280749 A1 12/2006 Rosenblum et al.
2006/0281908 A1 12/2006 Callen
2006/0286639 A1 12/2006 Dumas Milne Edwards et al.
2007/0004666 A1 1/2007 Lasham et al.
2007/0006340 A1 1/2007 Lang et al.
2007/0009489 A1 1/2007 Bermudes et al.
2007/0009900 A1 1/2007 Doucette-Stamm et al.
2007/0009901 A1 1/2007 Doucette-Stamm et al.
2007/0009902 A1 1/2007 Doucette-Stamm et al.
2007/0009903 A1 1/2007 Doucette-Stamm et al.
2007/0009904 A1 1/2007 Doucette-Stamm et al.
2007/0009905 A1 1/2007 Doucette-Stamm et al.
2007/0009906 A1 1/2007 Doucette-Stamm et al.
2007/0009932 A1 1/2007 Stephanopoulos et al.
2007/0015271 A1 1/2007 Rosen et al.
2007/0020327 A1 1/2007 Fikes et al.
2007/0025981 A1 2/2007 Szalay et al.
2007/0026507 A1 2/2007 Olivo et al.
2007/0028324 A1 2/2007 Corbin et al.
2007/0031382 A1 2/2007 Powell et al.
2007/0031852 A1 2/2007 Doucette-Stamm et al.
2007/0032639 A1 2/2007 Gottesman et al.
2007/0037744 A1 2/2007 Gallo et al.
2007/0038419 A1 2/2007 Usuda et al.
2007/0041997 A1 2/2007 Finlay et al.
2007/0059709 A1 3/2007 Benton et al.
2007/0059799 A1 3/2007 Sette et al.
2007/0059801 A1 3/2007 Doucette-Stamm et al.
2007/0059802 A1 3/2007 Doucette-Stamm et al.
2007/0059807 A1 3/2007 Wisniewski et al.
2007/0059836 A1 3/2007 Black
2007/0065820 A1 3/2007 Jiang et al.
2007/0065908 A1 3/2007 Gallo et al.
2007/0071675 A1 3/2007 Wu et al.
2007/0071773 A1 3/2007 Hanski et al.
2007/0072279 A1 3/2007 Meynial-Salles et al.
2007/0087403 A1 4/2007 Bestel-Corre et al.
2007/0092951 A1 4/2007 Bathe et al.
2007/0104689 A1 5/2007 Gillies et al.
2007/0110721 A1 5/2007 Cranenburgh
2007/0110752 A1 5/2007 Murison et al.
2007/0111291 A1 5/2007 Bathe et al.
2007/0116671 A1 5/2007 Prakash et al.
2007/0116725 A1 5/2007 Vladoianu et al.
2007/0118934 A1 5/2007 Yu et al.
2007/0122832 A1 5/2007 Mockel et al.
2007/0122858 A1 5/2007 Fernandez-Salas et al.
2007/0122881 A1 5/2007 Surber
2007/0134264 A1 6/2007 Marshall
2007/0134768 A1 6/2007 Zelder et al.
2007/0141680 A1 6/2007 Bathe et al.
2007/0143871 A1 6/2007 French et al.
2007/0154458 A1 7/2007 McCart et al.
2007/0154986 A1 7/2007 Kunsch et al.
2007/0178116 A1 8/2007 Adderson et al.
2007/0178492 A1 8/2007 Gross et al.
2007/0178505 A1 8/2007 Fischer et al.
2007/0184048 A1 8/2007 Foster et al.
2007/0184517 A1 8/2007 Schultz et al.
2007/0184528 A1 8/2007 Pierce et al.
2007/0184543 A1 8/2007 Pierce et al.
2007/0191262 A1 8/2007 Racila et al.
2007/0192905 A1 8/2007 Piller et al.
2007/0202572 A1 8/2007 Szalay et al.
2007/0202578 A1 8/2007 Samain et al.
2007/0202591 A1 8/2007 Ulrich
2007/0212311 A1 9/2007 Burne et al.
2007/0212711 A1 9/2007 Choi et al.
2007/0212727 A1 9/2007 Szalay et al.
2007/0224666 A1 9/2007 Bathe et al.
2007/0231820 A1 10/2007 Weiner et al.
2007/0231867 A1 10/2007 Choi et al.
2007/0243303 A1 10/2007 Dan Hengst et al.
2007/0243565 A1 10/2007 Williams et al.
2007/0243616 A1 10/2007 Church et al.
2007/0244047 A1 10/2007 Rosen et al.
2007/0254329 A1 11/2007 Rubin
2007/0254846 A1 11/2007 Wong et al.
2007/0254850 A1 11/2007 Lieberman et al.
2007/0258889 A1 11/2007 Douglas et al.
2007/0259408 A1 11/2007 Bathe et al.
2007/0259417 A1 11/2007 Ladner et al.
2007/0264689 A1 11/2007 Gross et al.
2007/0269369 A1 11/2007 Gegg et al.
2007/0269414 A1 11/2007 Okano et al.
2007/0269871 A1 11/2007 Zelder et al.
2007/0275423 A1 11/2007 Sebastian et al.
2007/0281342 A1 12/2007 DeAngelis
2007/0287171 A1 12/2007 Inouye
2007/0298012 A1 * 12/2007 King ...................... A61K 48/00 514/110
2007/0299008 A1 12/2007 Rummel
2008/0003240 A1 1/2008 Fernandez-Salas et al.
2008/0004206 A1 1/2008 Rosen et al.
2008/0009041 A1 1/2008 Mizoguchi et al.
2008/0009446 A1 1/2008 Yu et al.
2008/0014618 A1 1/2008 Bathe et al.
2008/0019994 A1 1/2008 Brunham et al.
2008/0031877 A1 2/2008 Covacci et al.
2008/0032318 A1 2/2008 Steward et al.
2008/0032374 A1 2/2008 Zelder et al.
2008/0038274 A1 2/2008 Foster et al.
2008/0038296 A1 * 2/2008 Brahmbhatt ....... A61K 48/0008 424/234.1
2008/0038756 A1 2/2008 Steward et al.
2008/0038779 A1 2/2008 Miasnikov et al.
2008/0038787 A1 2/2008 Zelder et al.
2008/0050774 A1 2/2008 Berka et al.
2008/0050786 A1 2/2008 Bathe et al.
2008/0063666 A1 3/2008 Allende
2008/0064054 A1 3/2008 Fernandez-Salas et al.
2008/0064062 A1 3/2008 Leonhartsberger et al.
2008/0064762 A1 3/2008 Fuchs et al.
2008/0070255 A1 3/2008 Tanner et al.
2008/0070840 A1 3/2008 Min et al.
2008/0076157 A1 3/2008 Leonhartsberger et al.
2008/0089862 A1 4/2008 Benhar et al.
2008/0090770 A1 4/2008 Belmares et al.
2008/0095806 A1 4/2008 Bathurst et al.
2008/0102115 A1 5/2008 Oyhenart et al.
2008/0118948 A1 5/2008 Kroger et al.
2008/0124355 A1 5/2008 Bermudes
2008/0131903 A1 6/2008 Thierbach et al.
2008/0131927 A1 6/2008 Schischka et al.
2008/0146786 A1 6/2008 Steward et al.
2008/0160121 A1 7/2008 Donovan et al.
2008/0160561 A1 7/2008 Fernandez-Salas et al.
2008/0160585 A1 7/2008 Zelder et al.
2008/0166739 A1 7/2008 Steward et al.
2008/0166757 A1 7/2008 Bron et al.
2008/0166764 A1 7/2008 Schloesser et al.
2008/0166775 A1 7/2008 Kroger et al.
2008/0171014 A1 7/2008 Wu et al.
2008/0171348 A1 7/2008 Steward et al.
2008/0176249 A1 7/2008 Steward et al.
2008/0176295 A1 7/2008 Zelder et al.
2008/0176336 A1 7/2008 Steward et al.
2008/0181892 A1 7/2008 Ledbetter et al.
2008/0182295 A1 7/2008 Patkar et al.
2008/0182799 A1 7/2008 Fernandez-Salas et al.
2008/0187520 A1 8/2008 Polack et al.
2008/0187960 A1 8/2008 Foster et al.
2008/0193373 A1 8/2008 Stritzker et al.
2008/0193470 A1 8/2008 Masignani et al.
2008/0193974 A1 8/2008 Coleman et al.
2008/0194481 A1 8/2008 Rosen et al.
2008/0199926 A1 8/2008 Burgard et al.
2008/0206271 A1 8/2008 Liao et al.
2008/0206284 A1 8/2008 Williams et al.
2008/0206814 A1 8/2008 Lee et al.
2008/0206818 A1 8/2008 Wich et al.
2008/0213316 A1 9/2008 Tarasenko
2008/0213796 A1 9/2008 Steward et al.
2008/0214469 A1 9/2008 Lam et al.

(56) References Cited

U.S. PATENT DOCUMENTS

2008/0220456 A1 9/2008 Williams et al.
2008/0226551 A1 9/2008 Waugh et al.
2008/0227704 A1 9/2008 Kamens
2008/0233623 A1 9/2008 Chang et al.
2008/0242620 A1 10/2008 Wong et al.
2008/0249013 A1 10/2008 Cabezon et al.
2008/0254511 A1 10/2008 Dassler et al.
2008/0260769 A1 10/2008 Capecchi et al.
2008/0261269 A1 10/2008 Bathe et al.
2008/0261869 A1 10/2008 Shapiro
2008/0267966 A1 10/2008 Masignani et al.
2008/0268502 A1 10/2008 Haefner et al.
2008/0269070 A1 10/2008 Ramseier et al.
2008/0270096 A1 10/2008 Palsson
2008/0274155 A1 11/2008 Barton et al.
2008/0274265 A1 11/2008 Bathe et al.
2008/0274516 A1 11/2008 Kroger et al.
2008/0280346 A1 11/2008 de Lorenzo Prieto et al.
2008/0280354 A1 11/2008 Perez et al.
2008/0286290 A1 11/2008 Furusako et al.
2008/0286306 A1 11/2008 Nabel et al.
2008/0286841 A1 11/2008 Kroger et al.
2008/0288264 A1 11/2008 Mach et al.
2008/0293084 A1 11/2008 Williams et al.
2008/0293085 A1 11/2008 Williams et al.
2008/0293100 A1 11/2008 Wendisch et al.
2008/0305119 A1 12/2008 Dewhurst et al.
2008/0305509 A1 12/2008 Williams et al.
2008/0305510 A1 12/2008 Williams et al.
2008/0305533 A1 12/2008 Yi et al.
2008/0311081 A1 12/2008 Fruehauf et al.
2008/0311096 A1 12/2008 Lang et al.
2008/0311125 A1 12/2008 O'Keefe et al.
2008/0317731 A1 12/2008 Gramatikova et al.
2008/0318286 A1 12/2008 Choi et al.
2008/0319167 A1 12/2008 Foster et al.
2009/0004215 A1 1/2009 Tuli et al.
2009/0004705 A1 1/2009 Kroger et al.
2009/0004744 A1 1/2009 Surber et al.
2009/0004745 A1 1/2009 Choi et al.
2009/0010917 A1 1/2009 Rosenblum et al.
2009/0010956 A1 1/2009 Rikihisa
2009/0011490 A1 1/2009 Sabbadini et al.
2009/0011974 A1 1/2009 Bocharov et al.
2009/0011995 A1 1/2009 Lee et al.
2009/0019609 A1 1/2009 Romano
2009/0023157 A1 1/2009 Lee et al.
2009/0023182 A1 1/2009 Schilling
2009/0023649 A1 1/2009 Backer et al.
2009/0028890 A1 1/2009 Karp
2009/0029425 A1 1/2009 Zelder et al.
2009/0035827 A1 2/2009 Stephens et al.
2009/0042231 A1 2/2009 Steward et al.
2009/0042248 A1 2/2009 Gal et al.
2009/0042278 A1 2/2009 Barr et al.
2009/0042785 A1 2/2009 Matschiner et al.
2009/0053186 A1 2/2009 Hu et al.
2009/0053746 A1 2/2009 Steward et al.
2009/0053794 A1 2/2009 Bathe et al.
2009/0054323 A1 2/2009 Oliner et al.
2009/0061006 A1 3/2009 Leuschner et al.
2009/0061445 A1 3/2009 Oltvai et al.
2009/0062139 A1 3/2009 Short et al.
2009/0068226 A1 3/2009 Ulrich et al.
2009/0069241 A1 3/2009 Barnstable et al.
2009/0069248 A1 3/2009 Motin et al.
2009/0075333 A1 3/2009 Campbell et al.
2009/0081193 A1 3/2009 Sasisekharan et al.
2009/0081199 A1 3/2009 Colonna et al.
2009/0081673 A1 3/2009 Shen et al.
2009/0082549 A1 3/2009 Fishman et al.
2009/0092632 A1 4/2009 Lee
2009/0098049 A1 4/2009 Dowdy et al.
2009/0111160 A1 4/2009 Collier et al.
2009/0117047 A1 5/2009 Szalay et al.
2009/0117048 A1 5/2009 Szalay et al.
2009/0117049 A1 5/2009 Szalay et al.
2009/0117572 A1 5/2009 Fernandez-Salas et al.
2009/0118475 A1 5/2009 Steward et al.
2009/0123382 A1 5/2009 Szalay et al.
2009/0123426 A1 5/2009 Li et al.
2009/0123921 A1 5/2009 Georgiou et al.
2009/0130709 A1 5/2009 Hamilton
2009/0131401 A1 5/2009 Levy et al.
2009/0131645 A1 5/2009 Foster et al.
2009/0136519 A1 5/2009 Brines et al.
2009/0136542 A1 5/2009 Karp
2009/0142343 A1 6/2009 Fuh et al.
2009/0155238 A1 6/2009 Weiner et al.
2009/0155866 A1 6/2009 Burk et al.
2009/0156794 A1 6/2009 Black, Jr.
2009/0162341 A1 6/2009 Foster et al.
2009/0162356 A1 6/2009 Lookeren Campagne
2009/0162933 A1 6/2009 Kiener et al.
2009/0169517 A1 7/2009 Bermudes et al.
2009/0169566 A1 7/2009 Rawlin et al.
2009/0170155 A1 7/2009 Johnson et al.
2009/0170170 A1 7/2009 Choi et al.
2009/0170812 A1 7/2009 Alekshun et al.
2009/0175829 A1 7/2009 Forbes et al.
2009/0175897 A1 7/2009 Tang et al.
2009/0180955 A1 7/2009 Stritzker et al.
2009/0180987 A1 7/2009 Stritzker et al.
2009/0181894 A1 7/2009 Yarkoni et al.
2009/0186377 A1 7/2009 Johnson et al.
2009/0186384 A1 7/2009 Matsuno et al.
2009/0191583 A1 7/2009 Fernandez-Salas et al.
2009/0191599 A1 7/2009 Devroe et al.
2009/0203070 A1 8/2009 Devroe et al.
2009/0203103 A1 8/2009 Pierce et al.
2009/0208534 A1 8/2009 Xu et al.
2009/0209749 A1 8/2009 Mach et al.
2009/0214506 A1 8/2009 Hardy et al.
2009/0215130 A1 8/2009 Iyo et al.
2009/0215133 A1 8/2009 Bathe et al.
2009/0215754 A1 8/2009 Hochman et al.
2009/0217396 A1 8/2009 Kyrkaniders et al.
2009/0220480 A1 9/2009 Gray et al.
2009/0220540 A1 9/2009 Marshall
2009/0221055 A1 9/2009 Kadoya et al.
2009/0226372 A1 9/2009 Ruoslahti et al.
2009/0226919 A1 9/2009 Gulevich et al.
2009/0232801 A1 9/2009 Hillen et al.
2009/0232804 A1 9/2009 Lazarides et al.
2009/0233844 A1 9/2009 Brines et al.
2009/0234101 A1 9/2009 Ladner et al.
2009/0238789 A1 9/2009 Guyon et al.
2009/0238798 A1 9/2009 Bogdanova et al.
2009/0239797 A1 9/2009 Cooper et al.
2009/0240073 A1 9/2009 Barry
2009/0246220 A1 10/2009 Ertl et al.
2009/0246832 A1 10/2009 Wakarchuk et al.
2009/0246836 A1 10/2009 Kroger et al.
2009/0246838 A1 10/2009 Zelder et al.
2009/0253164 A1 10/2009 Unrean et al.
2009/0258401 A1 10/2009 Iyo et al.
2009/0258935 A1 10/2009 Zheng et al.
2009/0263836 A1 10/2009 Fernandez-Salas et al.
2009/0271894 A1 10/2009 Benfey et al.
2009/0275097 A1 11/2009 Sun et al.
2009/0275104 A1 11/2009 Berka et al.
2009/0280542 A1 11/2009 Bathe et al.
2009/0291457 A1 11/2009 Foster et al.
2009/0294288 A1 12/2009 May et al.
2009/0297560 A1 12/2009 Dattwyler et al.
2009/0298136 A1 12/2009 Zelder et al.
2009/0299044 A1 12/2009 Sullivan et al.
2009/0300779 A1 12/2009 Zhao et al.
2009/0304693 A1 12/2009 Ghayur et al.
2009/0305296 A1 12/2009 Bengtsson et al.
2009/0311253 A1 12/2009 Ghayur et al.
2009/0311744 A1 12/2009 DeFrees et al.
2009/0311756 A1 12/2009 Zelder et al.
2009/0317404 A1 12/2009 Markham

(56) References Cited

U.S. PATENT DOCUMENTS

2009/0317418 A1 12/2009 Catanzaro et al.
2009/0317839 A1 12/2009 Fernandez-Salas et al.
2009/0324576 A1 12/2009 Padmanabhan et al.
2009/0324651 A1 12/2009 Old et al.
2009/0325242 A1 12/2009 Bathe et al.
2009/0325298 A1 12/2009 Kernodle
2009/0325866 A1 12/2009 Kim et al.
2010/0003727 A1 1/2010 Zelder et al.
2010/0008851 A1 1/2010 Nicolaides et al.
2010/0008946 A1 1/2010 Szalay et al.
2010/0011456 A1 1/2010 Mathur et al.
2010/0015672 A1 1/2010 Takagi et al.
2010/0015674 A1 1/2010 Zelder et al.
2010/0016227 A1 1/2010 Enright et al.
2010/0021510 A1 1/2010 Carreno Serraima et al.
2010/0021978 A1 1/2010 Burk et al.
2010/0022584 A1 1/2010 Kenyon et al.
2010/0028340 A1 2/2010 Mueller et al.
2010/0034822 A1 2/2010 Masignani et al.
2010/0040537 A1 2/2010 Gu et al.
2010/0040640 A1 2/2010 Lanar et al.
2010/0041107 A1 2/2010 Herold et al.
2010/0047239 A1 2/2010 Wu et al.
2010/0047245 A1 2/2010 Lacy et al.
2010/0055727 A1 3/2010 Steward et al.
2010/0055761 A1 3/2010 Seed et al.
2010/0062016 A1 3/2010 Szalay et al.
2010/0062438 A1 3/2010 Danchin
2010/0062535 A1 3/2010 Kroger et al.
2010/0064393 A1 3/2010 Berka et al.
2010/0068173 A1 3/2010 Yu et al.
2010/0069610 A1 3/2010 Steward et al.
2010/0074900 A1 3/2010 Ghayur et al.
2010/0074933 A1 3/2010 Prakash et al.
2010/0075346 A1 3/2010 Steward et al.
2010/0075357 A1 3/2010 Steward et al.
2010/0075358 A1 3/2010 Steward et al.
2010/0080815 A1 4/2010 Zavada et al.
2010/0081155 A1 4/2010 Williams et al.
2010/0081156 A1 4/2010 Williams et al.
2010/0081157 A1 4/2010 Steward et al.
2010/0081158 A1 4/2010 Steward et al.
2010/0086546 A1 4/2010 Lee et al.
2010/0092438 A1 4/2010 Fruehauf et al.
2010/0093639 A1 4/2010 Waugh et al.
2010/0095398 A1 4/2010 Meana et al.
2010/0104560 A1 4/2010 Chapman et al.
2010/0104607 A1 4/2010 Engelberg-Kulka et al.
2010/0105106 A1 4/2010 Ronin et al.
2010/0111998 A1 5/2010 Nabel et al.
2010/0112670 A1 5/2010 Giacalone et al.
2010/0119550 A1 5/2010 Gomi et al.
2010/0119588 A1 5/2010 Sato et al.
2010/0120105 A1 5/2010 Anthony et al.
2010/0121042 A1 5/2010 Fernandez-Salas et al.
2010/0124558 A1 5/2010 Curtiss, III et al.
2010/0135961 A1 6/2010 Bermudes
2010/0135973 A1 6/2010 Eisenstark et al.
2010/0136027 A1 6/2010 Kim
2010/0136048 A1 6/2010 Bermudes
2010/0136657 A1 6/2010 Jokinen et al.
2010/0137162 A1 6/2010 Retallack et al.
2010/0137192 A1 6/2010 Shapiro
2010/0143997 A1 6/2010 Buelter et al.
2010/0144543 A1 6/2010 Witcher et al.
2010/0150965 A1 6/2010 Kopecko et al.
2010/0151494 A1 6/2010 Steward et al.
2010/0158952 A1 6/2010 Goletz
2010/0159523 A1 6/2010 Bathe et al.
2010/0160609 A1 6/2010 Fernandez-Salas et al.
2010/0160612 A1 6/2010 Skerra et al.
2010/0166802 A1 7/2010 Caplan et al.
2010/0168387 A1 7/2010 Tuli
2010/0169988 A1 7/2010 Kohli et al.
2010/0172976 A1 7/2010 Satishchandran et al.
2010/0183516 A1 7/2010 Ribbert et al.
2010/0184157 A1 7/2010 Williams et al.
2010/0184613 A1 7/2010 Lee et al.
2010/0189686 A1 7/2010 Rosen et al.
2010/0189691 A1 7/2010 Fruehauf et al.
2010/0189740 A1 7/2010 Michon et al.
2010/0189774 A1 7/2010 Lenormand
2010/0196315 A1 8/2010 Lacy et al.
2010/0196959 A1 8/2010 Schischka et al.
2010/0197563 A1* 8/2010 Wight .................... A61P 19/00 435/375
2010/0209405 A1 8/2010 Altman et al.
2010/0209955 A1 8/2010 Oyler et al.
2010/0215679 A1 8/2010 Horwitz et al.
2010/0215682 A1 8/2010 Berkower
2010/0216720 A1 8/2010 Brophy et al.
2010/0221179 A1 9/2010 Hsieh et al.
2010/0221779 A1 9/2010 Short et al.
2010/0227850 A1 9/2010 Alekshun et al.
2010/0233079 A1 9/2010 Jakob et al.
2010/0233195 A1 9/2010 Delisa et al.
2010/0233814 A1 9/2010 Williams
2010/0239546 A1 9/2010 Fruehauf et al.
2010/0247544 A1 9/2010 Vachon
2010/0247560 A1 9/2010 Simpson et al.
2010/0249026 A1 9/2010 Rosen et al.
2010/0255022 A1 10/2010 Prescott et al.
2010/0255036 A1 10/2010 Hassan et al.
2010/0255544 A1 10/2010 Bathe et al.
2010/0255553 A1 10/2010 Srienc et al.
2010/0260668 A1 10/2010 Ghayur et al.
2010/0261201 A1 10/2010 Katanaev
2010/0261257 A1 10/2010 Bathe et al.
2010/0269223 A1 10/2010 Lira et al.
2010/0272750 A1 10/2010 Buyse et al.
2010/0278819 A1 11/2010 Bossuyt et al.
2010/0279923 A1 11/2010 Schulte et al.
2010/0280222 A1 11/2010 Steward et al.
2010/0281577 A1 11/2010 Mulet Salort et al.
2010/0285547 A1 11/2010 Soucaille et al.
2010/0285564 A1 11/2010 Skerra et al.
2010/0286060 A1 11/2010 Oliner et al.
2010/0286251 A1 11/2010 Rubin
2010/0290996 A1 11/2010 Nickerson et al.
2010/0291033 A1 11/2010 Rosen et al.
2010/0291088 A1 11/2010 Ghayur et al.
2010/0292091 A1 11/2010 Levy
2010/0292429 A1 11/2010 Volkert et al.
2010/0303822 A1 12/2010 Masignani et al.
2010/0305306 A1 12/2010 Colonna et al.
2010/0310560 A1 12/2010 Colonna et al.
2010/0310593 A1 12/2010 Brazer et al.
2010/0311147 A1 12/2010 Bathe et al.
2010/0317007 A1 12/2010 Palsson et al.
2010/0317569 A1 12/2010 Lira et al.
2010/0319087 A1 12/2010 Corbin et al.
2010/0319092 A1 12/2010 Lira et al.
2010/0319093 A1 12/2010 Lira et al.
2010/0333235 A1 12/2010 Mach et al.
2011/0002910 A1 1/2011 Rosenblum et al.
2011/0003963 A1 1/2011 Zelder et al.
2011/0008392 A1 1/2011 Buck et al.
2011/0008828 A1 1/2011 Kwon et al.
2011/0014666 A1 1/2011 Voelker et al.
2011/0014672 A1 1/2011 Chotani et al.
2011/0014701 A1 1/2011 Ghosh
2011/0021416 A1 1/2011 Shapiro
2011/0027309 A1 2/2011 Bottje et al.
2011/0027349 A1 2/2011 Sable et al.
2011/0028397 A1 2/2011 Tozser et al.
2011/0033501 A1 2/2011 Curtiss, III et al.
2011/0038865 A1 2/2011 Shin et al.
2011/0038917 A1 2/2011 Kappers et al.
2011/0039313 A1 2/2011 Verseck et al.
2011/0044980 A1 2/2011 Ghayur et al.
2011/0045587 A1 2/2011 Sullivan et al.
2011/0053253 A1 3/2011 Kim et al.
2011/0054442 A1 3/2011 Sanders
2011/0065091 A1 3/2011 Van Der Hoek

(56) References Cited

U.S. PATENT DOCUMENTS

2011/0086407 A1 4/2011 Berka et al.
2011/0091372 A1 4/2011 Ghayur et al.
2011/0091463 A1 4/2011 Ghayur et al.
2011/0091493 A1 4/2011 Moahamadzadeh et al.
2011/0093965 A1 4/2011 O'Donoghue et al.
2011/0104146 A1 5/2011 Faraday
2011/0104163 A1 5/2011 Dimitrov et al.
2011/0104196 A1 5/2011 Karp
2011/0104240 A1 5/2011 Jones et al.
2011/0104789 A1 5/2011 Wu et al.
2011/0106000 A1 5/2011 Jones et al.
2011/0111015 A1 5/2011 Bottje et al.
2011/0111458 A1 5/2011 Masuda et al.
2011/0111481 A1 5/2011 Li
2011/0111496 A1 5/2011 Li
2011/0117079 A1 5/2011 Benatuil et al.
2011/0117611 A1 5/2011 Dunican et al.
2011/0117617 A1 5/2011 Liu et al.
2011/0124073 A1 5/2011 Devroe et al.
2011/0125118 A1 5/2011 Lynch
2011/0135646 A1 6/2011 Bakaletz et al.
2011/0136759 A1 6/2011 Kahne et al.
2011/0142761 A1 6/2011 Wu et al.
2011/0152174 A1 6/2011 Foster et al.
2011/0152176 A1 6/2011 Horswill
2011/0159026 A1 6/2011 Bottje et al.
2011/0165063 A1 7/2011 Hsieh et al.
2011/0165066 A1 7/2011 Wu et al.
2011/0165660 A1 7/2011 Picataggio et al.
2011/0165661 A1 7/2011 Picataggio et al.
2011/0165680 A1 7/2011 Blattner et al.
2011/0166336 A1 7/2011 Gottesman et al.
2011/0171695 A1 7/2011 Bathe et al.
2011/0171727 A1 7/2011 Black, Jr.
2011/0177053 A1 7/2011 Foster et al.
2011/0189773 A1 8/2011 Altman et al.
2011/0189774 A1 8/2011 Mach et al.
2011/0190234 A1 8/2011 Nathan et al.
2011/0195090 A1 8/2011 Dimitrov
2011/0195423 A1 8/2011 Selinfreund et al.
2011/0201070 A1 8/2011 Soucaille et al.
2011/0201109 A1 8/2011 Zwaka et al.
2011/0206616 A1 8/2011 Ichtchenko et al.
2011/0207183 A1 8/2011 Herold et al.
2011/0207187 A1 8/2011 Tokuda et al.
2011/0212094 A1 9/2011 Ghayur et al.
2011/0217237 A1 9/2011 Chen et al.
2011/0223241 A1 9/2011 Tardi et al.
2011/0224416 A1 9/2011 Picataggio et al.
2011/0225663 A1 9/2011 Von Schaewen et al.
2011/0229959 A1 9/2011 Picataggio et al.
2011/0230523 A1 9/2011 Levy et al.
2011/0243980 A1 10/2011 Feldman et al.
2011/0243992 A1 10/2011 Kernodle
2011/0244529 A1 10/2011 Claes et al.
2011/0244575 A1 10/2011 Lipscomb et al.
2011/0245169 A1 10/2011 Brines et al.
2011/0250199 A1 10/2011 Fitzgerald et al.
2011/0251095 A1 10/2011 Levy
2011/0257080 A1 10/2011 Chai et al.
2011/0262347 A1 10/2011 Ruoslahti et al.
2011/0262474 A1 10/2011 Du et al.
2011/0262980 A1 10/2011 Soucaille et al.
2011/0263500 A1 10/2011 Hansel et al.
2011/0268661 A1 11/2011 Markiv et al.
2011/0268760 A1 11/2011 Telfer et al.
2011/0269201 A1 11/2011 Gray et al.
2011/0274719 A1 11/2011 Marshall
2011/0274721 A1 11/2011 Nabel et al.
2011/0275122 A1 11/2011 Min et al.
2011/0275585 A1 11/2011 Brahmbhatt et al.
2011/0277180 A1 11/2011 Romano
2011/0280800 A1 11/2011 Wu et al.
2011/0280830 A9 11/2011 Rosen et al.
2011/0281330 A1 11/2011 Sabbadini et al.
2011/0286916 A1 11/2011 Aste-Amezaga et al.
2011/0287037 A1 11/2011 Gentschev et al.
2011/0293608 A1 12/2011 Jaffee et al.
2011/0294170 A1 12/2011 Subbian et al.
2011/0300099 A1 12/2011 Debinski et al.
2011/0300176 A1 12/2011 Szalay et al.
2011/0300177 A1 12/2011 Gin et al.
2011/0305724 A1 12/2011 Paterson et al.
2011/0306611 A1 12/2011 Alekshun et al.
2011/0307978 A1 12/2011 Bogdanova et al.
2011/0318308 A1 12/2011 Ragolia
2011/0318316 A1 12/2011 Wong et al.
2011/0318317 A1 12/2011 Wong et al.
2011/0318349 A1 12/2011 Ghayur et al.
2011/0318357 A1 12/2011 O'Brien et al.
2012/0009194 A1 1/2012 Ferrone et al.
2012/0009196 A1 1/2012 Muerhoff et al.
2012/0009205 A1 1/2012 Gegg et al.
2012/0009627 A1 1/2012 Deng et al.
2012/0014941 A1 1/2012 Wu et al.
2012/0014957 A1 1/2012 Ghayur et al.
2012/0020883 A1 1/2012 Stritzker et al.
2012/0021517 A1 1/2012 Jin et al.
2012/0021985 A1 1/2012 Rosen et al.
2012/0027785 A1 2/2012 Dirienzo
2012/0028324 A1 2/2012 Buelter et al.
2012/0034160 A1 2/2012 Ghayur et al.
2012/0039985 A1 2/2012 de Muinck et al.
2012/0040414 A1 2/2012 Knight
2012/0040426 A1 2/2012 Sun et al.
2012/0042413 A1 2/2012 Albert et al.
2012/0045474 A1 2/2012 Motin et al.
2012/0058098 A1 3/2012 Foster et al.
2012/0058532 A1 3/2012 Buelter et al.
2012/0064062 A1 3/2012 Goguen et al.
2012/0064568 A1 3/2012 Hamilton
2012/0064572 A1 3/2012 Finlay et al.
2012/0070870 A1 3/2012 Way et al.
2012/0070881 A1 3/2012 Berka et al.
2012/0071545 A1 3/2012 Shapiro
2012/0076758 A1 3/2012 Diamond et al.
2012/0076803 A1 3/2012 Brophy et al.
2012/0077237 A1 3/2012 Picataggio et al.
2012/0077252 A1 3/2012 Picataggio et al.
2012/0083587 A1 4/2012 Gallo et al.
2012/0087858 A1 4/2012 Ghayur et al.
2012/0087946 A1 4/2012 Curtiss, III et al.
2012/0088314 A1 4/2012 Katanaev
2012/0093773 A1 4/2012 Li et al.
2012/0093805 A1 4/2012 Kubota
2012/0093868 A1 4/2012 Masignani et al.
2012/0094341 A1 4/2012 Burk et al.
2012/0094906 A1 4/2012 Guyon et al.
2012/0100140 A1 4/2012 Reyes et al.
2012/0100581 A1 4/2012 Gramatikova et al.
2012/0101027 A1 4/2012 Foster et al.
2012/0107360 A1 5/2012 Le Butt et al.
2012/0108521 A1 5/2012 Eggink et al.
2012/0108640 A1 5/2012 Hochman et al.
2012/0114652 A1 5/2012 Elvin et al.
2012/0121637 A1 5/2012 Granoff et al.
2012/0122762 A1 5/2012 Ruben et al.
2012/0122962 A1 5/2012 Han et al.
2012/0128594 A1 5/2012 Choy et al.
2012/0128624 A1 5/2012 Yu et al.
2012/0128718 A1 5/2012 Hassan et al.
2012/0135503 A1 5/2012 Sabbadini et al.
2012/0141415 A1 6/2012 Ballance et al.
2012/0141511 A1 6/2012 Foster et al.
2012/0142079 A1 6/2012 Sabbadini et al.
2012/0142080 A1 6/2012 Bermudes
2012/0142589 A1 6/2012 Brines et al.
2012/0142623 A1 6/2012 Lagunoff et al.
2012/0144509 A1 6/2012 Benghezal et al.
2012/0148601 A1 6/2012 Ulrich et al.
2012/0148615 A1 6/2012 Masignani et al.
2012/0149095 A1 6/2012 Kopecko et al.
2012/0156186 A1 6/2012 Foster et al.
2012/0156803 A1 6/2012 Evans et al.

(56) References Cited

U.S. PATENT DOCUMENTS

2012/0159674 A1 6/2012 Meade et al.
2012/0164687 A1 6/2012 Bereta et al.
2012/0164703 A1 6/2012 Yi et al.
2012/0171234 A1 7/2012 Wong et al.
2012/0177682 A1 7/2012 Marshall
2012/0184007 A1 7/2012 Picataggio et al.
2012/0184020 A1 7/2012 Picataggio et al.
2012/0189541 A1 7/2012 Wu
2012/0189572 A1 7/2012 Wei et al.
2012/0190011 A1 7/2012 Brummelkamp et al.
2012/0190089 A1 7/2012 Buelter et al.
2012/0195900 A1 8/2012 Ghayur et al.
2012/0195922 A1 8/2012 Lee
2012/0207735 A1 8/2012 Foster et al.
2012/0208181 A1 8/2012 Merighi et al.
2012/0210467 A1 8/2012 Barton et al.
2012/0213767 A1 8/2012 Wei et al.
2012/0219545 A1 8/2012 Ayuso et al.
2012/0220757 A1 8/2012 Christensen et al.
2012/0225453 A1* 9/2012 Withers, III ............ C12P 21/02 435/252.33
2012/0225454 A1 9/2012 Benghezal et al.
2012/0230976 A1 9/2012 Helmerhorst et al.
2012/0231538 A1 9/2012 Fernandez-Salas et al.
2012/0232012 A1 9/2012 Popel et al.
2012/0237491 A1 9/2012 Padmanabhan et al.
2012/0244600 A1 9/2012 Jin
2012/0244621 A1 9/2012 Weiss et al.
2012/0252074 A1 10/2012 Zhang et al.
2012/0252097 A1 10/2012 Rosenblum et al.
2012/0252099 A1 10/2012 Sabbadini et al.
2012/0253009 A1 10/2012 Walker
2012/0258108 A1 10/2012 Ghayur et al.
2012/0258521 A1 10/2012 Liu et al.
2012/0263722 A1 10/2012 Ghayur et al.
2012/0264686 A9 10/2012 Guyon et al.
2012/0264902 A1 10/2012 Lipscomb et al.
2012/0266328 A1 10/2012 Gray et al.
2012/0266329 A1 10/2012 Mathur et al.
2012/0271036 A1 10/2012 Smith et al.
2012/0275996 A1 11/2012 Hsieh
2012/0276010 A1 11/2012 Szalay et al.
2012/0276132 A1 11/2012 Feng et al.
2012/0276587 A1 11/2012 Beck et al.
2012/0276603 A1 11/2012 Beck et al.
2012/0277143 A1 11/2012 Jacobs et al.
2012/0282700 A1 11/2012 Lunder et al.
2012/0282701 A1 11/2012 Kopecko et al.
2012/0288901 A1 11/2012 Zelder et al.
2012/0301493 A1 11/2012 Brandariz Nunez et al.
2012/0301497 A1 11/2012 Yadava et al.
2012/0308484 A1 12/2012 Szalay et al.
2012/0308575 A1 12/2012 Guo et al.
2012/0308594 A1 12/2012 Sablon et al.
2012/0311745 A1 12/2012 Meade et al.
2012/0317681 A1 12/2012 Meade et al.
2012/0317682 A1 12/2012 Meade et al.
2012/0324606 A1 12/2012 Meade et al.
2012/0329150 A1 12/2012 Duke et al.
2012/0331589 A1 12/2012 Meade et al.
2012/0331590 A1 12/2012 Meade et al.
2013/0004416 A1 1/2013 Wu et al.
2013/0004537 A1 1/2013 Curtiss et al.
2013/0004998 A1 1/2013 Subbian et al.
2013/0004999 A1 1/2013 Reth et al.
2013/0007923 A1 1/2013 Meade et al.
2013/0011409 A1 1/2013 Shipp et al.
2013/0011421 A1 1/2013 Gin et al.
2013/0011874 A1 1/2013 Campbell et al.
2013/0017173 A1 1/2013 Nataro et al.
2013/0022539 A1 1/2013 Pilkington et al.
2013/0022578 A1 1/2013 Newman et al.
2013/0023472 A1 1/2013 Bristow
2013/0025006 A1 1/2013 Meade et al.
2013/0028901 A1 1/2013 Colonna et al.
2013/0028924 A1 1/2013 Ertl et al.
2013/0036520 A1 2/2013 Meade et al.
2013/0042374 A1 2/2013 Meade et al.
2013/0045184 A1 2/2013 Teitelbaum
2013/0052227 A1 2/2013 Gerke et al.
2013/0059318 A1 3/2013 Kaneko et al.
2013/0065274 A1 3/2013 Gerngross et al.
2013/0066035 A1 3/2013 Burgard et al.
2013/0071893 A1 3/2013 Lynch et al.
2013/0078254 A1 3/2013 Bakaletz et al.
2013/0078275 A1 3/2013 Tao
2013/0084304 A1 4/2013 Hargis et al.
2013/0089906 A1 4/2013 Beck et al.
2013/0095488 A1 4/2013 Bogdanova et al.
2013/0095566 A1 4/2013 Oltvai et al.
2013/0097729 A1 4/2013 Bonning et al.
2013/0101577 A9 4/2013 Wei et al.
2013/0102017 A1 4/2013 Pfaendler et al.
2013/0102530 A1 4/2013 Brines et al.
2013/0122043 A1 5/2013 Guimaraes et al.
2013/0122526 A1 5/2013 Foster et al.
2013/0122541 A1 5/2013 Lynch et al.
2013/0122553 A1 5/2013 Maertens et al.
2013/0122565 A1 5/2013 Pierce et al.
2013/0129713 A1 5/2013 Rescigno et al.
2013/0129737 A1 5/2013 Adderson et al.
2013/0129761 A1 5/2013 Garcia-Sastre et al.
2013/0130292 A1 5/2013 Szalay et al.
2013/0142937 A1 6/2013 Bathe et al.
2013/0149313 A1 6/2013 Gu et al.
2013/0150559 A1 6/2013 Colonna et al.
2013/0164257 A1 6/2013 Debinski et al.
2013/0164307 A1 6/2013 Markham
2013/0164317 A1 6/2013 Yousef et al.
2013/0164329 A1 6/2013 Rossomando et al.
2013/0164380 A1 6/2013 Durum et al.
2013/0164808 A1 6/2013 McAuliffe et al.
2013/0164809 A1 6/2013 Chotani et al.
2013/0171096 A1 7/2013 Hsieh et al.
2013/0171109 A1 7/2013 Helmerhorst et al.
2013/0171182 A1 7/2013 Whelan et al.
2013/0171190 A1 7/2013 Curtiss, III et al.
2013/0177555 A1 7/2013 Wilkinson et al.
2013/0183728 A1 7/2013 Botes et al.
2013/0189753 A1 7/2013 Pearlman et al.
2013/0190241 A1 7/2013 Wong et al.
2013/0190255 A1 7/2013 Wong et al.
2013/0196432 A1 8/2013 Poehlmann et al.
2013/0197194 A1 8/2013 Kaplan et al.
2013/0197203 A1 8/2013 Michon et al.
2013/0202557 A1 8/2013 Li et al.
2013/0202598 A1 8/2013 Benhar et al.
2013/0202623 A1 8/2013 Chomont et al.
2013/0203130 A1 8/2013 Wittmann et al.
2013/0203164 A1 8/2013 Rosen et al.
2013/0203657 A1 8/2013 Meade et al.
2013/0205416 A1 8/2013 Nash et al.
2013/0209405 A1 8/2013 Roy et al.
2013/0209407 A1 8/2013 Hamer
2013/0209499 A1 8/2013 Garcia-Sastre et al.
2013/0210073 A1 8/2013 Kwon et al.
2013/0210077 A1 8/2013 Brzezinski et al.
2013/0210121 A1 8/2013 Giacalone et al.
2013/0210149 A1 8/2013 Li
2013/0210747 A1 8/2013 Hamm-Alvarez et al.
2013/0211170 A1 8/2013 Amano et al.
2013/0216555 A1 8/2013 Nitsch et al.
2013/0216568 A1 8/2013 Maione et al.
2013/0217068 A1 8/2013 Parkot et al.
2013/0217145 A1 8/2013 Yoshimura et al.
2013/0219570 A1 8/2013 Lira et al.
2013/0224804 A1 8/2013 Knight
2013/0227741 A1 8/2013 Gray et al.
2013/0243747 A1 9/2013 Fima et al.
2013/0247254 A1 9/2013 Lira et al.
2013/0266585 A1 10/2013 Nitsch et al.
2013/0269057 A1 10/2013 Fosu-Nyarko et al.
2013/0273590 A1 10/2013 Oyler et al.
2013/0273613 A1 10/2013 Devroe et al.

(56) References Cited

U.S. PATENT DOCUMENTS

2013/0274187 A1 10/2013 Mogelsvang et al.
2013/0276168 A1 10/2013 Romaine et al.
2013/0280774 A1 10/2013 Blake et al.
2013/0287810 A1 10/2013 Mohamadzadeh et al.
2013/0295054 A1 11/2013 Huang et al.
2013/0295072 A1 11/2013 Fima et al.
2013/0295127 A1 11/2013 Prescott et al.
2013/0295616 A1 11/2013 Muramatsu et al.
2013/0295643 A1 11/2013 Foster et al.
2013/0310458 A1 11/2013 Eggeling et al.
2013/0316397 A1 11/2013 Airen et al.
2013/0316426 A1 11/2013 Burk et al.
2013/0318640 A1 11/2013 Oldenburg et al.
2013/0323801 A1 12/2013 Chilton et al.
2013/0330350 A1 12/2013 Dimasi
2013/0330709 A1 12/2013 Beatty et al.
2013/0330796 A1 12/2013 Beck et al.
2013/0330824 A1 12/2013 Li
2013/0337516 A1 12/2013 Herrema
2013/0337545 A1 12/2013 Sabbadini et al.
2013/0344033 A1 12/2013 Vergnolle et al.
2013/0345114 A1 12/2013 Williams et al.
2014/0004598 A1 1/2014 Picataggio et al.
2014/0005108 A1 1/2014 Bristow
2014/0010811 A1 1/2014 Ferrone et al.
2014/0010829 A1 1/2014 Bigner et al.
2014/0017765 A1 1/2014 Subbian et al.
2014/0024050 A1 1/2014 Yoshimura et al.
2014/0024820 A1 1/2014 Parkot et al.
2014/0031541 A1 1/2014 Heidtman et al.
2014/0037695 A1 2/2014 Yu
2014/0044748 A1 2/2014 Lee
2014/0045231 A1 2/2014 Lynch et al.
2014/0045261 A1 2/2014 Wang et al.
2014/0050693 A1 2/2014 Skerra et al.
2014/0051132 A1 2/2014 Samsonova et al.
2014/0051136 A1 2/2014 Liao et al.
2014/0056841 A1 2/2014 Vachon
2014/0057940 A1 2/2014 Mankowski et al.
2014/0072595 A1 3/2014 Benghezal et al.
2014/0073683 A1 3/2014 Han et al.
2014/0079701 A1 3/2014 Miller et al.
2014/0080201 A1 3/2014 Merighi et al.
2014/0086950 A1 3/2014 Pascual et al.
2014/0093521 A1 4/2014 Benatuil et al.
2014/0093528 A1 4/2014 Berkower
2014/0093534 A1 4/2014 Bottje et al.
2014/0093540 A1 4/2014 Wright et al.
2014/0093885 A1 4/2014 Hua et al.
2014/0093925 A1 4/2014 Guettler et al.
2014/0094404 A1 4/2014 Villaverde Corrales et al.
2014/0099670 A1 4/2014 Kostenuik et al.
2014/0099671 A1 4/2014 Wu et al.
2014/0105863 A1 4/2014 Vanden-Broucke et al.
2014/0112951 A1 4/2014 Tang et al.
2014/0113376 A1 4/2014 Sorek et al.
2014/0127216 A1 5/2014 Balraj et al.
2014/0127221 A1 5/2014 Bakaletz et al.
2014/0127765 A1 5/2014 Osterhout et al.
2014/0127780 A1 5/2014 Zhang et al.
2014/0134171 A1 5/2014 Ghayur et al.
2014/0134682 A1 5/2014 Wittmann et al.
2014/0134690 A1 5/2014 Yan et al.
2014/0141482 A1 5/2014 Pearlman et al.
2014/0148582 A1 5/2014 Gallo et al.
2014/0150134 A1 5/2014 Li et al.
2014/0154250 A1 6/2014 Thompson et al.
2014/0154252 A1 6/2014 Thompson et al.
2014/0154256 A1 6/2014 Wu et al.
2014/0154762 A1 6/2014 Duehring et al.
2014/0155343 A1 6/2014 Brahmbhatt et al.
2014/0155581 A1 6/2014 Gao et al.
2014/0161767 A1 6/2014 Leuschner et al.
2014/0161800 A1 6/2014 Blankenship et al.
2014/0162279 A1 6/2014 Ramseier et al.
2014/0162337 A1 6/2014 Chotani et al.
2014/0162952 A1 6/2014 Katagiri et al.
2014/0173774 A1 6/2014 Pareddy et al.
2014/0173780 A1 6/2014 Pareddy et al.
2014/0178341 A1 6/2014 Zhao et al.
2014/0182018 A1 6/2014 Lang et al.
2014/0186377 A1 7/2014 Gu et al.
2014/0186401 A1 7/2014 Diamond et al.
2014/0186884 A1 7/2014 Nunn, Jr. et al.
2014/0186902 A1 7/2014 Botes et al.
2014/0186904 A1 7/2014 Botes et al.
2014/0186913 A1 7/2014 Botes et al.
2014/0187491 A1 7/2014 Wilmen et al.
2014/0189896 A1 7/2014 Zhang et al.
2014/0193861 A1 7/2014 Botes et al.
2014/0193865 A1 7/2014 Botes et al.
2014/0194346 A1 7/2014 Aebi et al.
2014/0199306 A1 7/2014 Ghosh et al.
2014/0199737 A1 7/2014 Botes et al.
2014/0199742 A1 7/2014 Shibamoto
2014/0205538 A1 7/2014 Wei et al.
2014/0206064 A1 7/2014 Bayer et al.
2014/0206068 A1 7/2014 Claes et al.
2014/0206599 A1 7/2014 Baumann et al.
2014/0212396 A1 7/2014 Newman
2014/0212454 A1 7/2014 Pasmans et al.
2014/0212925 A1 7/2014 Wu et al.
2014/0219912 A1 8/2014 Ghayur et al.
2014/0220019 A1 8/2014 Ghayur et al.
2014/0220661 A1 8/2014 Bermudes
2014/0227286 A1 8/2014 Jaffee et al.
2014/0227291 A1 8/2014 Barghorn et al.
2014/0227294 A1 8/2014 Anderson et al.
2014/0227750 A1 8/2014 Picataggio et al.
2014/0234208 A1 8/2014 Ghayur et al.
2014/0234310 A1 8/2014 Shapiro
2014/0234363 A1 8/2014 Masignani et al.
2014/0242674 A1 8/2014 Subbian et al.
2014/0242704 A1 8/2014 Zelder et al.
2014/0248309 A1 9/2014 Kopecko et al.
2014/0248669 A1 9/2014 Marliere
2014/0248673 A1 9/2014 Botes et al.
2014/0255345 A1 9/2014 Grabstein et al.
2014/0255376 A1 9/2014 Johnson et al.
2014/0256922 A1 9/2014 David et al.
2014/0256960 A1 9/2014 Takagi et al.
2014/0271640 A1 9/2014 Bowdish et al.
2014/0273164 A1 9/2014 Liao et al.
2014/0273165 A1 9/2014 Liao et al.
2014/0287419 A1 9/2014 Althoff et al.
2014/0289906 A1 9/2014 Althoff et al.
2014/0294797 A1 10/2014 Foster et al.
2014/0294891 A1 10/2014 Szalay et al.
2014/0296480 A1 10/2014 Sanchez Garcia et al.
2014/0298499 A1 10/2014 Gray et al.
2014/0302078 A1 10/2014 Masignani et al.
2014/0302094 A1 10/2014 Titball et al.
2014/0308286 A1 10/2014 Ghayur et al.
2014/0322730 A1 10/2014 Chapman et al.
2014/0322779 A1 10/2014 Burgard et al.
2014/0322790 A1 10/2014 Sebastian et al.
2014/0328794 A1 11/2014 Rosen et al.
2014/0328849 A1 11/2014 Reif et al.
2014/0328875 A1 11/2014 Garcia-Sastre et al.
2014/0330032 A1 11/2014 Lynch et al.
2014/0335014 A1 11/2014 Ghayur et al.
2014/0335087 A1 11/2014 Buechler et al.
2014/0335564 A1 11/2014 Hsieh et al.
2014/0341943 A1 11/2014 Rikihisa
2014/0342405 A1 11/2014 Rosen et al.
2014/0342451 A1 11/2014 Kwon et al.
2014/0343267 A1 11/2014 Hsieh et al.
2014/0348817 A1 11/2014 Jiang et al.
2014/0348828 A1 11/2014 Foster et al.
2014/0356389 A1 12/2014 Masignani et al.
2014/0356916 A1 12/2014 Wittmann et al.
2014/0363847 A1 12/2014 Fujii et al.
2014/0369986 A1 12/2014 Padmanabhan et al.
2014/0370036 A1 12/2014 Shapiro

(56) References Cited

U.S. PATENT DOCUMENTS

| | | | |
|---|---|---|---|
| 2014/0371194 | A1 | 12/2014 | Seed et al. |
| 2014/0377752 | A1 | 12/2014 | Lee et al. |
| 2014/0377858 | A1 | 12/2014 | Wu et al. |
| 2014/0377860 | A1 | 12/2014 | Wu et al. |
| 2014/0378372 | A1 | 12/2014 | Mogelsvang et al. |
| 2015/0004665 | A1 | 1/2015 | Chotani et al. |
| 2015/0004705 | A1 | 1/2015 | Lu et al. |
| 2015/0010592 | A1 | 1/2015 | Wacker et al. |
| 2015/0017095 | A1 | 1/2015 | Ghayur et al. |
| 2015/0017138 | A1 | 1/2015 | Fruehauf et al. |
| 2015/0017204 | A1 | 1/2015 | Bermudes |
| 2015/0018522 | A1 | 1/2015 | Qasba et al. |
| 2015/0030573 | A1 | 1/2015 | Fruehauf et al. |
| 2015/0030584 | A1 | 1/2015 | Rummel |
| 2015/0030624 | A1 | 1/2015 | Armstrong et al. |
| 2015/0031658 | A1 | 1/2015 | Seed et al. |
| 2015/0037860 | A1 | 2/2015 | Botes et al. |
| 2015/0037861 | A1 | 2/2015 | Beck et al. |
| 2015/0044243 | A1 | 2/2015 | Wisniewski et al. |
| 2015/0044256 | A1 | 2/2015 | Dattwyler et al. |
| 2015/0044722 | A1 | 2/2015 | Tremblay et al. |
| 2015/0044755 | A1 | 2/2015 | Yocum et al. |
| 2015/0045535 | A1 | 2/2015 | Berka et al. |
| 2015/0050215 | A1 | 2/2015 | Novak et al. |
| 2015/0050308 | A1 | 2/2015 | Van Der Hoek |
| 2015/0056232 | A1 | 2/2015 | Roy |
| 2015/0056651 | A1 | 2/2015 | Lynch et al. |
| 2015/0056666 | A1 | 2/2015 | Reth et al. |
| 2015/0056684 | A1 | 2/2015 | Lipscomb et al. |
| 2015/0057191 | A1 | 2/2015 | Tissot et al. |
| 2015/0071904 | A1 | 3/2015 | Collins et al. |
| 2015/0071957 | A1 | 3/2015 | Kelly et al. |
| 2015/0072384 | A1 | 3/2015 | Lynch et al. |
| 2015/0079063 | A1 | 3/2015 | Fima et al. |
| 2015/0079654 | A1 | 3/2015 | Botes et al. |
| 2015/0086585 | A1 | 3/2015 | Gin et al. |
| 2015/0087035 | A1 | 3/2015 | Picataggio et al. |
| 2015/0093358 | A1 | 4/2015 | Fares et al. |
| 2015/0093387 | A1 | 4/2015 | Wu et al. |
| 2015/0098900 | A1 | 4/2015 | Ebens et al. |
| 2015/0099707 | A1 | 4/2015 | Pastan et al. |
| 2015/0104452 | A1 | 4/2015 | Ghayur et al. |
| 2015/0104514 | A1 | 4/2015 | Kaplan et al. |
| 2015/0110720 | A1 | 4/2015 | Markiv et al. |
| 2015/0110836 | A1 | 4/2015 | Glanville |
| 2015/0111262 | A1 | 4/2015 | Botes et al. |
| 2015/0112652 | A1 | 4/2015 | Palsson |
| 2015/0119354 | A1 | 4/2015 | Kahne et al. |
| 2015/0125849 | A1 | 5/2015 | Yeh et al. |
| 2015/0126445 | A1 | 5/2015 | Fares et al. |
| 2015/0132218 | A1 | 5/2015 | Asundi et al. |
| 2015/0132330 | A1 | 5/2015 | Garcia-Sastre et al. |
| 2015/0132368 | A1 | 5/2015 | Muro Galindo et al. |
| 2015/0133375 | A1 | 5/2015 | Mogelsvang et al. |
| 2015/0139940 | A1 | 5/2015 | Bermudez Humaran et al. |
| 2015/0140614 | A1 | 5/2015 | Reth et al. |
| 2015/0141331 | A1 | 5/2015 | Fares et al. |
| 2015/0141622 | A1 | 5/2015 | Alitalo et al. |
| 2015/0147343 | A1 | 5/2015 | Nitsch et al. |
| 2015/0148291 | A1 | 5/2015 | Fima et al. |
| 2015/0150959 | A1 | 6/2015 | Watnick |
| 2015/0152161 | A1 | 6/2015 | Reiter et al. |
| 2015/0153325 | A1 | 6/2015 | McNutt et al. |
| 2015/0153358 | A1 | 6/2015 | Ayuso et al. |
| 2015/0166594 | A1 | 6/2015 | Kahne et al. |
| 2015/0166661 | A1 | 6/2015 | Chen et al. |
| 2015/0166972 | A1 | 6/2015 | Dong et al. |
| 2015/0166975 | A1 | 6/2015 | Prakash et al. |
| 2015/0183867 | A1 | 7/2015 | Ghayur et al. |
| 2015/0184220 | A1 | 7/2015 | Sebastian et al. |
| 2015/0190496 | A1 | 7/2015 | Hargis et al. |
| 2015/0191691 | A1 | 7/2015 | Bisanz et al. |
| 2015/0197748 | A1 | 7/2015 | Liu et al. |
| 2015/0197775 | A1 | 7/2015 | Iida et al. |
| 2015/0202284 | A1 | 7/2015 | Dimitrov |
| 2015/0203557 | A1 | 7/2015 | Debinski et al. |
| 2015/0203578 | A1 | 7/2015 | Bebbington et al. |
| 2015/0203835 | A1 | 7/2015 | Nunn, Jr. et al. |
| 2015/0203854 | A1 | 7/2015 | Williams et al. |
| 2015/0211031 | A1 | 7/2015 | Lee et al. |
| 2015/0216954 | A1 | 8/2015 | Bottje et al. |
| 2015/0216965 | A1 | 8/2015 | Diamond et al. |
| 2015/0218231 | A1 | 8/2015 | Bakaletz et al. |
| 2015/0218254 | A1 | 8/2015 | Sabbadini et al. |
| 2015/0218261 | A1 | 8/2015 | Barghorn et al. |
| 2015/0218544 | A9 | 8/2015 | Jiang et al. |
| 2015/0218590 | A1 | 8/2015 | McAuliffe et al. |
| 2015/0225692 | A1 | 8/2015 | Bhatia et al. |
| 2015/0225732 | A1 | 8/2015 | Williams et al. |
| 2015/0225744 | A1 | 8/2015 | Beck et al. |
| 2015/0231207 | A1 | 8/2015 | Kaspar |
| 2015/0232550 | A1 | 8/2015 | Ghayur et al. |
| 2015/0232557 | A1 | 8/2015 | Tan et al. |
| 2015/0232861 | A1 | 8/2015 | Delisa et al. |
| 2015/0232903 | A1 | 8/2015 | HIidesaki et al. |
| 2015/0240226 | A1 | 8/2015 | Mathur et al. |
| 2015/0246137 | A1 | 9/2015 | Guo et al. |
| 2015/0247172 | A1 | 9/2015 | Herrema |
| 2015/0252097 | A1 | 9/2015 | Camphausen et al. |
| 2015/0258209 | A1 | 9/2015 | Benz et al. |
| 2015/0259389 | A9 | 9/2015 | Berka et al. |
| 2015/0259418 | A1 | 9/2015 | Barth et al. |
| 2015/0266939 | A1 | 9/2015 | Vogan et al. |
| 2015/0266977 | A1 | 9/2015 | Hsieh et al. |
| 2015/0267211 | A1 | 9/2015 | Botes et al. |
| 2015/0273045 | A1 | 10/2015 | Kolander et al. |
| 2015/0273048 | A1 | 10/2015 | Kang et al. |
| 2015/0275241 | A1 | 10/2015 | Herrema |
| 2015/0275242 | A1 | 10/2015 | Osterhout et al. |
| 2015/0284467 | A1 | 10/2015 | Lipp et al. |
| 2015/0284760 | A1 | 10/2015 | Schendzielorz et al. |
| 2015/0291667 | A1 | 10/2015 | Dirienzo |
| 2015/0307560 | A1 | 10/2015 | DeLisa et al. |
| 2015/0307576 | A1 | 10/2015 | Bowdish et al. |
| 2015/0307854 | A1 | 10/2015 | Botes et al. |
| 2015/0315283 | A1 | 11/2015 | Ghayur et al. |
| 2015/0329619 | A1 | 11/2015 | Rosen et al. |
| 2015/0329644 | A1 | 11/2015 | Shi et al. |
| 2015/0329882 | A1 | 11/2015 | Lee et al. |
| 2015/0335729 | A1 | 11/2015 | Garcia-Sastre et al. |
| 2015/0337053 | A1 | 11/2015 | McCarthy et al. |
| 2015/0337320 | A1 | 11/2015 | Devroe et al. |
| 2015/0337321 | A1 | 11/2015 | Mach et al. |
| 2015/0337340 | A1 | 11/2015 | Alvizo et al. |
| 2015/0344529 | A1 | 12/2015 | Yonemura et al. |
| 2015/0344838 | A1 | 12/2015 | Campbell et al. |
| 2015/0344862 | A1 | 12/2015 | Schellenberger et al. |
| 2015/0344894 | A1 | 12/2015 | Giacalone et al. |
| 2015/0344916 | A1 | 12/2015 | Lynch et al. |
| 2015/0351390 | A1 | 12/2015 | Castle et al. |
| 2015/0353911 | A1 | 12/2015 | Salas et al. |
| 2015/0355172 | A1 | 12/2015 | Kraus et al. |
| 2015/0361141 | A1 | 12/2015 | Buttigieg et al. |
| 2015/0361458 | A1 | 12/2015 | Botes et al. |
| 2015/0361459 | A1 | 12/2015 | Botes et al. |
| 2015/0361460 | A1 | 12/2015 | Botes et al. |
| 2015/0361462 | A1 | 12/2015 | Botes et al. |
| 2015/0361463 | A1 | 12/2015 | Botes et al. |
| 2015/0361464 | A1 | 12/2015 | Botes et al. |
| 2015/0361465 | A1 | 12/2015 | Botes et al. |
| 2015/0361466 | A1 | 12/2015 | Botes et al. |
| 2015/0361467 | A1 | 12/2015 | Botes et al. |
| 2015/0361468 | A1 | 12/2015 | Botes et al. |
| 2015/0362482 | A1 | 12/2015 | McNutt et al. |
| 2015/0366889 | A1 | 12/2015 | Brynildsen et al. |
| 2015/0368630 | A9 | 12/2015 | Fima et al. |
| 2016/0002672 | A1 | 1/2016 | Beck et al. |
| 2016/0010132 | A1 | 1/2016 | Subbian et al. |
| 2016/0017310 | A1 | 1/2016 | Nunn, Jr. et al. |
| 2016/0017339 | A1 | 1/2016 | Liao et al. |
| 2016/0024157 | A1 | 1/2016 | Masignani et al. |
| 2016/0032323 | A1 | 2/2016 | Beck et al. |
| 2016/0038581 | A1 | 2/2016 | Bielke et al. |
| 2016/0040139 | A1 | 2/2016 | Zhang et al. |

(56) References Cited

U.S. PATENT DOCUMENTS

| | | | | |
|---|---|---|---|---|
| 2016/0046675 | A1 | 2/2016 | Kwong et al. | |
| 2016/0058017 | A1 | 3/2016 | Lira et al. | |
| 2016/0060306 | A1 | 3/2016 | Lira et al. | |
| 2016/0060635 | A1 | 3/2016 | Liao et al. | |
| 2016/0060663 | A1 | 3/2016 | Grammann et al. | |
| 2016/0068831 | A1 | 3/2016 | Beck et al. | |
| 2016/0068882 | A1 | 3/2016 | Zhang et al. | |
| 2016/0097064 | A1 | 4/2016 | Zhang et al. | |
| 2016/0101168 | A1 | 4/2016 | Husseiny Elsayed et al. | |
| 2016/0106853 | A1 | 4/2016 | Hansel et al. | |
| 2016/0114025 | A1 | 4/2016 | Bottje et al. | |
| 2016/0122399 | A1 | 5/2016 | Frey et al. | |
| 2016/0130618 | A1 | 5/2016 | Hara et al. | |
| 2016/0138052 | A1 | 5/2016 | Mordaka | |
| 2016/0145657 | A1 | 5/2016 | Botes et al. | |
| 2016/0152957 | A1 | 6/2016 | Botes et al. | |
| 2016/0153012 | A1 | 6/2016 | Marliere | |
| 2016/0160245 | A1 | 6/2016 | Yocum et al. | |
| 2016/0160255 | A1 | 6/2016 | Botes et al. | |
| 2016/0168610 | A1 | 6/2016 | Conradie et al. | |
| 2016/0199328 | A1 | 7/2016 | Collins et al. | |
| 2016/0201097 | A1 | 7/2016 | Botes et al. | |
| 2016/0222362 | A1 | 8/2016 | Zhang et al. | |
| 2016/0222393 | A1 | 8/2016 | Bermudes | |
| 2016/0222420 | A1 | 8/2016 | Botes et al. | |
| 2016/0222425 | A1 | 8/2016 | Botes et al. | |
| 2016/0237452 | A1 | 8/2016 | Meade et al. | |
| 2016/0243210 | A1 | 8/2016 | O'Brien et al. | |
| 2016/0244489 | A1 | 8/2016 | Masignani et al. | |
| 2016/0244769 | A1 | 8/2016 | Xia et al. | |
| 2016/0251633 | A1 | 9/2016 | Muramatsu et al. | |
| 2016/0257975 | A1 | 9/2016 | Lynch et al. | |
| 2016/0272950 | A1 | 9/2016 | Corthals et al. | |
| 2016/0289278 | A1 | 10/2016 | Bakaletz et al. | |
| 2016/0289632 | A1 | 10/2016 | Gerke et al. | |
| 2016/0289776 | A1 | 10/2016 | Eggeling et al. | |
| 2016/0333053 | A1* | 11/2016 | Gombert | A61P 37/02 |
| 2016/0355803 | A1 | 12/2016 | Poma et al. | |
| 2016/0361429 | A1 | 12/2016 | Johnson et al. | |
| 2016/0369257 | A1 | 12/2016 | Foster et al. | |
| 2017/0029844 | A1 | 2/2017 | Ball et al. | |
| 2017/0049866 | A1 | 2/2017 | Sanders | |
| 2017/0051260 | A1 | 2/2017 | Bermudes et al. | |
| 2017/0151307 | A1* | 6/2017 | Mrsny | A61K 38/2066 |
| 2017/0157239 | A1 | 6/2017 | Bermudes | |
| 2017/0204407 | A1 | 7/2017 | Gilbert et al. | |
| 2017/0226496 | A1 | 8/2017 | Dong et al. | |
| 2017/0283450 | A1 | 10/2017 | Gin et al. | |
| 2017/0298381 | A1 | 10/2017 | Narva et al. | |
| 2017/0369538 | A1 | 12/2017 | Hey et al. | |
| 2017/0369539 | A1 | 12/2017 | Sheets et al. | |
| 2018/0002394 | A1 | 1/2018 | Debinski et al. | |
| 2018/0127734 | A1 | 5/2018 | Pavlik et al. | |
| 2018/0127771 | A1 | 5/2018 | Bonning et al. | |
| 2018/0208631 | A1 | 7/2018 | Baum et al. | |
| 2018/0244760 | A1 | 8/2018 | Feng et al. | |
| 2018/0271787 | A1 | 9/2018 | Tardi et al. | |
| 2018/0291395 | A1 | 10/2018 | Bowen et al. | |
| 2018/0319872 | A1 | 11/2018 | Feng et al. | |
| 2018/0362951 | A1 | 12/2018 | Foster et al. | |
| 2019/0017057 | A1 | 1/2019 | Bermudes | |
| 2019/0136216 | A1 | 5/2019 | Dong et al. | |
| 2019/0153057 | A1 | 5/2019 | Debinski et al. | |
| 2019/0153418 | A1 | 5/2019 | Dong et al. | |
| 2019/0183986 | A1 | 6/2019 | Sanders | |
| 2019/0239513 | A1 | 8/2019 | Bonning et al. | |
| 2019/0256834 | A1 | 8/2019 | Dong et al. | |
| 2019/0300869 | A1 | 10/2019 | Dong et al. | |
| 2019/0376079 | A1 | 12/2019 | Brummelkamp et al. | |

FOREIGN PATENT DOCUMENTS

| | | | |
|---|---|---|---|
| CA | 2224075 | | 12/1996 |
| CA | 2302866 | | 3/1999 |
| CA | 2386465 | | 4/2001 |
| CA | 2388045 | C | 4/2001 |
| CA | 2456055 | C | 2/2003 |
| CA | 2652538 | C | 11/2007 |
| EP | 0322237 | | 6/1989 |
| EP | 0338679 | | 10/1989 |
| EP | 0357208 | | 3/1990 |
| EP | 0400958 | | 12/1990 |
| EP | 0564121 | | 10/1993 |
| EP | 0833660 | | 4/1998 |
| EP | 1012232 | | 6/2000 |
| EP | 1068339 | | 1/2001 |
| EP | 1270730 | | 1/2003 |
| EP | 1402036 | | 3/2004 |
| EP | 1407052 | | 4/2004 |
| EP | 00195672 | | 9/2005 |
| EP | 1644048 | A2 | 4/2006 |
| EP | 1655370 | | 5/2006 |
| EP | 1689432 | B1 | 12/2009 |
| EP | 1786838 | B1 | 4/2010 |
| EP | 0873363 | B1 | 10/2010 |
| EP | 2611823 | | 7/2013 |
| EP | 2143437 | B1 | 8/2013 |
| EP | 2370107 | B1 | 8/2017 |
| JP | 2004536020 | A | 12/2004 |
| JP | 2006516089 | A | 6/2006 |
| JP | 2006516192 | A | 6/2006 |
| JP | 2013022091 | | 2/2013 |
| JP | 2016533174 | A | 10/2016 |
| KR | 20030029847 | A | 4/2003 |
| KR | 20040014392 | A | 2/2004 |
| KR | 20050004914 | A | 1/2005 |
| KR | 20050042082 | A | 5/2005 |
| KR | 20050103314 | A | 10/2005 |
| KR | 20060130038 | A | 12/2006 |
| KR | 101092730 | B1 | 12/2011 |
| KR | 20140089341 | A | 7/2014 |
| RU | 2319709 | C2 | 7/2014 |
| TW | 201708536 | A | 3/2017 |
| WO | WO1991000014 | | 1/1991 |
| WO | WO1991006317 | | 5/1991 |
| WO | WO 91/18099 | * | 11/1991 |
| WO | WO1992011361 | | 7/1992 |
| WO | WO1992015689 | | 9/1992 |
| WO | WO1995002048 | | 1/1995 |
| WO | WO1995005832 | | 3/1995 |
| WO | WO1995005835 | | 3/1995 |
| WO | WO1995009655 | | 4/1995 |
| WO | WO1996011277 | | 4/1996 |
| WO | WO1996014087 | | 5/1996 |
| WO | WO1996034631 | | 11/1996 |
| WO | WO1996038159 | | 12/1996 |
| WO | WO1996040238 | | 12/1996 |
| WO | WO1997008955 | | 3/1997 |
| WO | WO1997014782 | | 4/1997 |
| WO | WO1997018225 | | 5/1997 |
| WO | WO1997018837 | | 5/1997 |
| WO | WO1997019688 | | 6/1997 |
| WO | WO1997025061 | | 7/1997 |
| WO | WO1998033923 | | 8/1998 |
| WO | WO1998053854 | | 12/1998 |
| WO | WO1999010014 | | 3/1999 |
| WO | WO1999010485 | | 3/1999 |
| WO | WO1999013003 | | 3/1999 |
| WO | WO1999013053 | | 3/1999 |
| WO | WO1999052563 | | 10/1999 |
| WO | WO2000004919 | | 2/2000 |
| WO | WO2000009733 | | 2/2000 |
| WO | WO2000022110 | A2 | 2/2000 |
| WO | WO2000047222 | | 8/2000 |
| WO | WO2001014579 | | 3/2001 |
| WO | WO2001025397 | | 4/2001 |
| WO | WO2001025399 | A2 | 4/2001 |
| WO | WO2002020809 | | 3/2002 |
| WO | WO2002061113 | A9 | 8/2002 |
| WO | WO2002067983 | | 9/2002 |
| WO | WO2002070645 | | 9/2002 |
| WO | WO2002074336 | | 9/2002 |
| WO | WO2002083149 | | 10/2002 |
| WO | WO2002083214 | | 10/2002 |

(56) References Cited

FOREIGN PATENT DOCUMENTS

| | | | |
|---|---|---|---|
| WO | WO2002087494 | | 11/2002 |
| WO | WO 03014141 | * | 2/2003 |
| WO | WO2003014380 | | 2/2003 |
| WO | WO2003063593 | A1 | 2/2003 |
| WO | WO2004016281 | | 2/2004 |
| WO | WO2004016281 | A1 | 2/2004 |
| WO | WO2004043232 | A2 | 5/2004 |
| WO | WO2004076484 | | 9/2004 |
| WO | WO2004103404 | | 12/2004 |
| WO | WO2005005630 | | 1/2005 |
| WO | WO2005014618 | | 2/2005 |
| WO | WO2005018332 | | 3/2005 |
| WO | WO2005054477 | | 6/2005 |
| WO | WO2005065418 | A2 | 7/2005 |
| WO | WO2006010070 | | 1/2006 |
| WO | WO2006013441 | | 2/2006 |
| WO | WO2006017929 | | 2/2006 |
| WO | WO2006048344 | | 5/2006 |
| WO | WO2006073970 | A2 | 7/2006 |
| WO | WO2006103118 | | 10/2006 |
| WO | WO2006116545 | | 11/2006 |
| WO | WO2007048022 | A2 | 4/2007 |
| WO | WO2007083193 | | 7/2007 |
| WO | WO2008073148 | | 6/2008 |
| WO | WO2008089132 | A2 | 7/2008 |
| WO | WO2008091375 | | 7/2008 |
| WO | WO2008156702 | | 12/2008 |
| WO | WO2009006453 | | 1/2009 |
| WO | WO2009014650 | | 1/2009 |
| WO | WO2009021548 | | 2/2009 |
| WO | WO2009086116 | | 7/2009 |
| WO | WO2009111177 | | 9/2009 |
| WO | WO2009126189 | | 10/2009 |
| WO | WO2009139985 | | 11/2009 |
| WO | WO2009145956 | | 12/2009 |
| WO | WO2009150433 | | 12/2009 |
| WO | WO2009152480 | | 12/2009 |
| WO | WO2010027423 | | 3/2010 |
| WO | WO2010036391 | | 4/2010 |
| WO | WO2010057009 | | 5/2010 |
| WO | WO2010091294 | A2 | 8/2010 |
| WO | WO2011017137 | | 2/2011 |
| WO | WO2011086172 | | 7/2011 |
| WO | WO2012072806 | | 6/2012 |
| WO | WO2012104025 | | 8/2012 |
| WO | WO2012150269 | | 11/2012 |
| WO | WO2013022091 | | 2/2013 |
| WO | WO2013067185 | | 5/2013 |
| WO | WO 2013135748 | * | 6/2013 |

OTHER PUBLICATIONS

Boy et al, Sunflower Trypsin Inhibitor 1 Derivatives as Molecular Scaffolds for the Development of Novel Peptidic Radiopharmaceuticals, Mol Imaging Biol (2010) 12:377-385.*

Cheng and Allen, The use of single chain Fv as targeting agents for immunoliposomes: an update on immunoliposomal drugs for cancer treatment, Expert Opin Drug Deliv. Apr. 2010 ; 7(4): 461-478.*

GenBank: KP031494.1, Expression vector pXB300, complete sequence, Dec. 27, 2014.*

Long et a., Synthesis and Evaluation of the Sunflower Derived Trypsin Inhibitor as a Potent Inhibitor of the Type II Transmembrane Serine Protease, Matriptase, Bioorganic & Medicinal Chemistry Letters 11 (2001) 2515-2519.*

Kisker, Oliver, Shinya Onizuka, Jacqueline Banyard, Tomoko Komiyama, Christian M. Becker, Eike Gert Achilles, Carmen M. Barnes, Michael S. O'Reilly, Judah Folkman, and Steven R. Pirie-Shepherd. "Generation of multiple angiogenesis inhibitors by human pancreatic cancer." Cancer research 61, No. 19 (2001): 7298-7304.

* cited by examiner

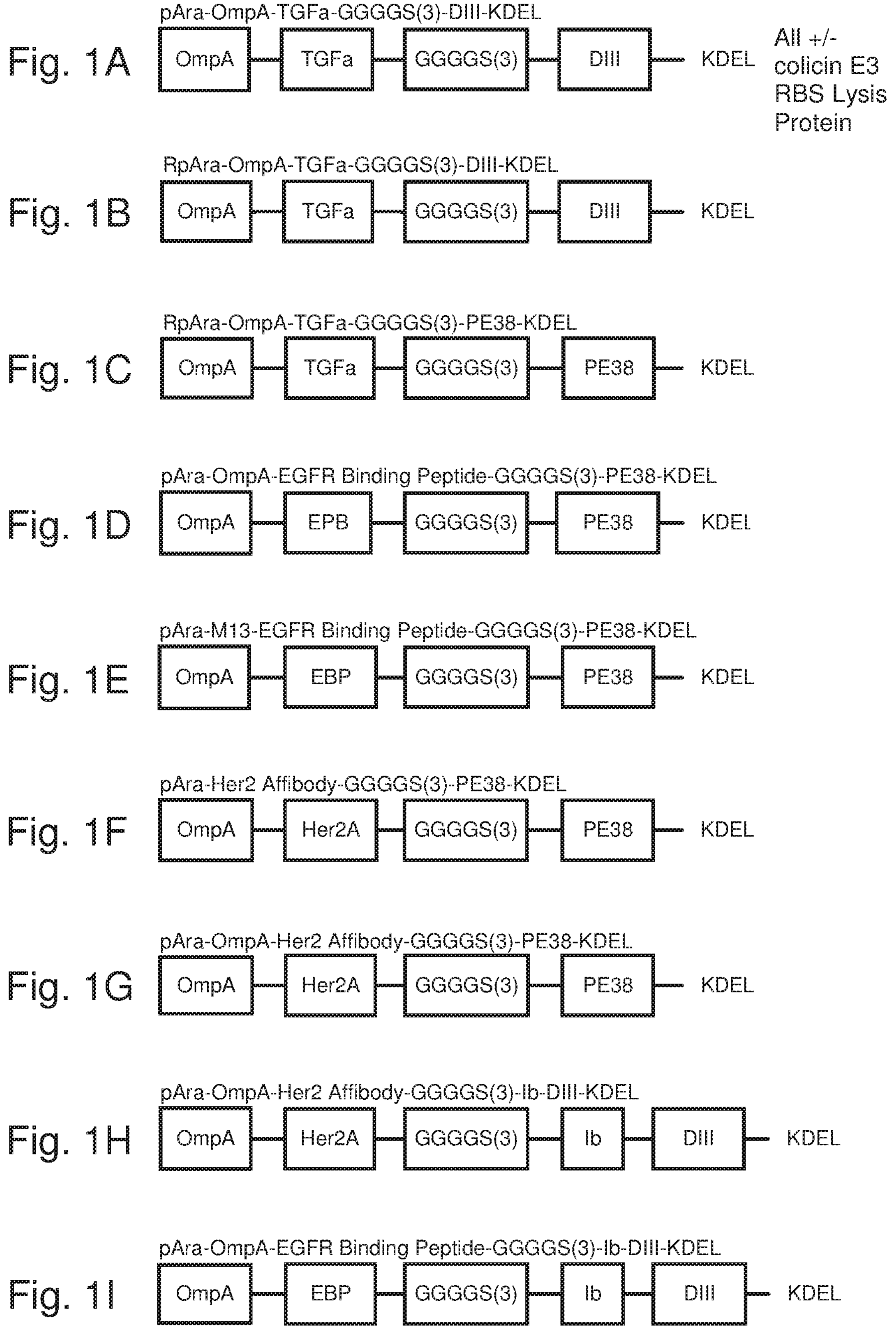
pAra-OmpA-TGFa-GGGGS(3)-DIII-KDEL
Fig. 1A
OmpA
TGFa
GGGGS(3)
DIII
KDEL
All +/- colicin E3 RBS Lysis Protein
RpAra-OmpA-TGFa-GGGGS(3)-DIII-KDEL
Fig. 1B
OmpA
TGFa
GGGGS(3)
DIII
KDEL
RpAra-OmpA-TGFa-GGGGS(3)-PE38-KDEL
Fig. 1C
OmpA
TGFa
GGGGS(3)
PE38
KDEL
pAra-OmpA-EGFR Binding Peptide-GGGGS(3)-PE38-KDEL
Fig. 1D
OmpA
EPB
GGGGS(3)
PE38
KDEL
pAra-M13-EGFR Binding Peptide-GGGGS(3)-PE38-KDEL
Fig. 1E
OmpA
EBP
GGGGS(3)
PE38
KDEL
pAra-Her2 Affibody-GGGGS(3)-PE38-KDEL
Fig. 1F
OmpA
Her2A
GGGGS(3)
PE38
KDEL
pAra-OmpA-Her2 Affibody-GGGGS(3)-PE38-KDEL
Fig. 1G
OmpA
Her2A
GGGGS(3)
PE38
KDEL
pAra-OmpA-Her2 Affibody-GGGGS(3)-Ib-DIII-KDEL
Fig. 1H
OmpA
Her2A
GGGGS(3)
Ib
DIII
KDEL
pAra-OmpA-EGFR Binding Peptide-GGGGS(3)-Ib-DIII-KDEL
Fig. 1I
OmpA
EBP
GGGGS(3)
Ib
DIII
KDEL NT: No Treatment EV 1: pAra-1

PBS: Phosphate Buffered Saline

1: Exotoxin A

2: TGFa-3GS-DIbDIIIKDEL

3: TGFa-3GS-DIbDIIIKDEL RBS Lysis

4: TGFa-3GS-DIbDIIIREDLK

EV 2: pAra-ME Stop

NT: No Treatment

EV 1: pAra-1

PBS: Phosphate Buffered Saline

5: TGFa-3GS-DIIIKDEL

6:TGFa-3GS-DIIIKDEL RBS Lysis

EV 2: pAra-ME Stop

SEQUENCE LISTING

<160> NUMBER OF SEQ ID NOS: 24

<210> SEQ ID NO 1
<211> LENGTH: 3789
<212> TYPE: DNA
<213> ORGANISM: Artificial Sequence
<220> FEATURE:
<223> OTHER INFORMATION: Modified TGF-alpha-GIII-KDEL

<400> SEQUENCE: 1

```
gggggcggcc gcaagaaacc aattgtccat attgcatcag acattgccgt cactgcgtct     60
tttactggct cttctcgcta accaaaccgg taaccccgct tattaaaagc attctgtaac    120
aaagcgggac caaagccatg acaaaaacgc gtaacaaaag tgtctataat cacggcagaa    180
aagtccacat tgattatttg cacggcgtca cactttgcta tgccatagca tttttatcca    240
taagattagc ggatcctacc tgacgctttt tatcgcaact ctctactgtt tctccatacc    300
cgtttttttg ggctagcgaa ttcgagctcg gtacccagga ggaattcacc atggctaaaa    360
agacagctat cgcgattgca gtggcactgg ctggtttcgc taccgtagcg caggcagctg    420
tggtgagcca ttttaacgat tgcccggata gccataccca gttttgcttt catggcacct    480
gccgctttct ggtgcaggaa gataaaccgg cgtgcgtgtg ccatagcggt tatgtgggcg    540
ctcgctgcga acatgcggat ctgctggccc atcaactagt gggcggtggt ggcagtggtg    600
gcggcggctc tggtggtggc gggtcccggg gtctgacctg cccggtcgcc gccggtgaat    660
gcgcgggccc ggcggacagc ggcgacgccc tgctggagcg caactatccc actggcgcgg    720
agttcctcgg cgacggcggc gacgtcagct tcagcacccg cggcacgcag aactggacgg    780
tggagcggct gctccaggcg caccgccaac tggaggagcg cggctatgtg ttcgtcggct    840
accacggcac cttcctcgaa gcggcgcaaa gcatcgtctt cggcggggtg cgcgcgcgca    900
gccaggacct cgacgcgatc tggcgcggtt tctatatcgc cggcgatccg gcgctggcct    960
acggctacgc ccaggaccag gaacccgacg cacgcggccg gatccgcaac ggtgccctgc   1020
tgcgggtcta tgtgccgcgc tcgagcctgc cgggcttcta ccgcaccagc ctgaccctgg   1080
ccgcgccgga ggcggcgggc gaggtcgaac ggctgatcgg ccatccgctg ccgctgcgcc   1140
tggacgccat caccggcccc gaggaggaag gcgggcgcct ggagaccatt ctcggctggc   1200
cgctggccga gcgcaccgtg gtgattccct cggcgatccc caccgacccg cgcaacgtcg   1260
gcggcgacct cgacccgtcc agcatccccg acaaggaaca ggcgatcagc gccctgccgg   1320
actacgccag ccagcccggc aaaccgccga aagatgaact gtaactcgag tagatctgta   1380
ctctagagtc gacctgcagg catgcaagct tggctgtttt ggcggatgag agaagatttt   1440
cagcctgata cagattaaat cagaacgcag aagcggtctg ataaaacaga atttgcctgg   1500
cggcagtagc gcggtggtcc cacctgaccc catgccgaac tcagaagtga aacgccgtag   1560
cgccgatggt agtgtggggt ctccccatgc gagagtaggg aactgccagg catcaaataa   1620
aacgaaaggc tcagtcgaaa gactgggcct ttcgttttat ctgttgtttg tcggtgaacg   1680
ctctcctgag taggacaaat ccgccgggag cggatttgaa cgttgcgaag caacggcccg   1740
```

-continued

```
gagggtggcg ggcaggacgc ccgccataaa ctgccaggca tcaaattaag cagaaggcca   1800

tcctgacgga tggccttttt gcgtttctac aaactctttt tgtttatttt tctaaataca   1860

ttcaaatatg tatccgctca tgagacaata accctgataa atgcttcaat aatattgaaa   1920

aaggaagagt atgagtattc aacatttccg tgtcgccctt attccctttt ttgcggcatt   1980

ttgccttcct gtttttgctc acccagaaac gctggtgaaa gtaaaagatg ctgaagatca   2040

gttgggtgca cgagtgggtt acatcgaact ggatctcaac agcggtaaga tccttgagag   2100

ttttcgcccc gaagaacgtt ttccaatgat gagcactttt aaagttctgc tatgtggcgc   2160

ggtattatcc cgtgttgacg ccgggcaaga gcaactcggt cgccgcatac actattctca   2220

gaatgacttg gttgagtact caccagtcac agaaaagcat cttacggatg gcatgacagt   2280

aagagaatta tgcagtgctg ccataaccat gagtgataac actgcggcca acttacttct   2340

gacaacgatc ggaggaccga aggagctaac cgcttttttg cacaacatgg gggatcatgt   2400

aactcgcctt gatcgttggg aaccggagct gaatgaagcc ataccaaacg acgagcgtga   2460

caccacgatg cctacagcaa tggcaacaac gttgcgcaaa ctattaactg gcgaactact   2520

tactctagct tcccggcaac aattaataga ctggatggag gcggataaag ttgcaggacc   2580

acttctgcgc tcggcccttc cggctggctg gtttattgct gataaatctg gagccggtga   2640

gcgtgggtct cgcggtatca ttgcagcact ggggccagat ggtaagccct cccgtatcgt   2700

agttatctac acgacgggga gtcaggcaac tatggatgaa cgaaatagac agatcgctga   2760

gataggtgcc tcactgatta agcattggta actgtcagac caagtttact catatatact   2820

ttagattgat ttaaaacttc atttttaatt taaaaggatc taggtgaaga tcctttttga   2880

taatctcatg accaaaatcc cttaacgtga gttttcgttc cactgagcgt cagaccccgt   2940

agaaaagatc aaaggatctt cttgagatcc tttttttctg cgcgtaatct gctgcttgca   3000

aacaaaaaaa ccaccgctac cagcggtggt ttgtttgccg gatcaagagc taccaactct   3060

ttttccgaag gtaactggct tcagcagagc gcagatacca aatactgtcc ttctagtgta   3120

gccgtagtta ggccaccact tcaagaactc tgtagcaccg cctacatacc tcgctctgct   3180

aatcctgtta ccagtggctg ctgccagtgg cgataagtcg tgtcttaccg ggttggactc   3240

aagacgatag ttaccggata aggcgcagcg gtcgggctga acggggggtt cgtgcacaca   3300

gcccagcttg gagcgaacga cctacaccga actgagatac ctacagcgtg agctatgaga   3360

aagcgccacg cttcccgaag ggagaaaggc ggacaggtat ccggtaagcg gcagggtcgg   3420

aacaggagag cgcacgaggg agcttccagg gggaaacgcc tggtatcttt atagtcctgt   3480

cgggtttcgc cacctctgac ttgagcgtcg atttttgtga tgctcgtcag gggggcggag   3540

cctatggaaa aacgccagca acgcggcctt tttacggttc ctggcctttt gctggccttt   3600

tgctcacatg ttctttcctg cgttatcccc tgattctgtg gataaccgta ttaccgcctt   3660

tgagtgagct gataccgctc gccgcagccg aacgaccgag cgcagcgagt cagtgagcga   3720

ggaagcggaa gagcgcctga tgcggtattt tctccttacg catctgtgcg gtatttcaca   3780

ccgcatatg                                                            3789
```

<210> SEQ ID NO 2
<211> LENGTH: 3938
<212> TYPE: DNA
<213> ORGANISM: Artificial Sequence
<220> FEATURE:
<223> OTHER INFORMATION: Modified TGF-alpha-GIII-KDEL

<400> SEQUENCE: 2
gggggcggcc gcaagaaacc aattgtccat attgcatcag acattgccgt cactgcgtct 60
tttactggct cttctcgcta accaaaccgg taaccccgct tattaaaagc attctgtaac 120
aaagcgggac caaagccatg acaaaaacgc gtaacaaaag tgtctataat cacggcagaa 180
aagtccacat tgattatttg cacggcgtca cactttgcta tgccatagca tttttatcca 240
taagattagc ggatcctacc tgacgctttt tatcgcaact ctctactgtt tctccatacc 300
cgtttttttg ggctagcgaa ttcgagctcg gtacccagga ggaattcacc atggctaaaa 360
agacagctat cgcgattgca gtggcactgg ctggtttcgc taccgtagcg caggcagctg 420
tggtgagcca ttttaacgat tgcccggata gccataccca gttttgcttt catggcacct 480
gccgctttct ggtgcaggaa gataaaccgg cgtgcgtgtg ccatagcggt tatgtgggcg 540
ctcgctgcga acatgcggat ctgctggccc atcaactagt gggcggtggt ggcagtggtg 600
gcggcggctc tggtggtggc gggtcccggg gtctgacctg cccggtcgcc gccggtgaat 660
gcgcgggccc ggcggacagc ggcgacgccc tgctggagcg caactatccc actggcgcgg 720
agttcctcgg cgacggcggc gacgtcagct tcagcacccg cggcacgcag aactggacgg 780
tggagcggct gctccaggcg caccgccaac tggaggagcg cggctatgtg ttcgtcggct 840
accacggcac cttcctcgaa gcggcgcaaa gcatcgtctt cggcggggtg cgcgcgcgca 900
gccaggacct cgacgcgatc tggcgcggtt tctatatcgc cggcgatccg gcgctggcct 960
acggctacgc ccaggaccag gaacccgacg cacgcggccg gatccgcaac ggtgccctgc 1020
tgcgggtcta tgtgccgcgc tcgagcctgc cgggcttcta ccgcaccagc ctgaccctgg 1080
ccgcgccgga ggcggcgggc gaggtcgaac ggctgatcgg ccatccgctg ccgctgcgcc 1140
tggacgccat caccggcccc gaggaggaag gcgggcgcct ggagaccatt ctcggctggc 1200
cgctggccga gcgcaccgtg gtgattccct cggcgatccc caccgacccg cgcaacgtcg 1260
gcggcgacct cgacccgtcc agcatccccg acaaggaaca ggcgatcagc gccctgccgg 1320
actacgccag ccagcccggc aaaccgccga aagatgaact gtaactcgag tagatctgta 1380
ctctagaaag gagtcgttat gaaaaaaata acagggatta ttttattgct tcttgcagtc 1440
attattctgt ctgcatgtca ggcaaactat atccgggatg ttcagggcgg gaccgtatct 1500
ccgtcatcaa cagctgaagt gaccggatta gcaacgcagt aactgcaggc atgcaagctt 1560
ggctgttttg gcggatgaga gaagattttc agcctgatac agattaaatc agaacgcaga 1620
agcggtctga taaaacagaa tttgcctggc ggcagtagcg cggtggtccc acctgacccc 1680
atgccgaact cagaagtgaa acgccgtagc gccgatggta gtgtggggtc tccccatgcg 1740
agagtaggga actgccaggc atcaaataaa acgaaaggct cagtcgaaag actgggcctt 1800
tcgttttatc tgttgtttgt cggtgaacgc tctcctgagt aggacaaatc cgccgggagc 1860
ggatttgaac gttgcgaagc aacggcccgg agggtggcgg gcaggacgcc cgccataaac 1920
tgccaggcat caaattaagc agaaggccat cctgacggat ggcctttttg cgtttctaca 1980
aactcttttt gtttattttt ctaaatacat tcaaatatgt atccgctcat gagacaataa 2040
ccctgataaa tgcttcaata atattgaaaa aggaagagta tgagtattca acatttccgt 2100
gtcgccctta ttcccttttt tgcggcattt tgccttcctg tttttgctca cccagaaacg 2160
ctggtgaaag taaaagatgc tgaagatcag ttgggtgcac gagtgggtta catcgaactg 2220
gatctcaaca gcggtaagat ccttgagagt tttcgccccg aagaacgttt tccaatgatg 2280
agcactttta aagttctgct atgtggcgcg gtattatccc gtgttgacgc cgggcaagag 2340

-continued

```
caactcggtc gccgcataca ctattctcag aatgacttgg ttgagtactc accagtcaca   2400

gaaaagcatc ttacggatgg catgacagta agagaattat gcagtgctgc cataaccatg   2460

agtgataaca ctgcggccaa cttacttctg acaacgatcg gaggaccgaa ggagctaacc   2520

gcttttttgc acaacatggg ggatcatgta actcgccttg atcgttggga accggagctg   2580

aatgaagcca taccaaacga cgagcgtgac accacgatgc ctacagcaat ggcaacaacg   2640

ttgcgcaaac tattaactgg cgaactactt actctagctt cccggcaaca attaatagac   2700

tggatggagg cggataaagt tgcaggacca cttctgcgct cggcccttcc ggctggctgg   2760

tttattgctg ataaatctgg agccggtgag cgtgggtctc gcggtatcat tgcagcactg   2820

gggccagatg gtaagccctc ccgtatcgta gttatctaca cgacggggag tcaggcaact   2880

atggatgaac gaaatagaca gatcgctgag ataggtgcct cactgattaa gcattggtaa   2940

ctgtcagacc aagtttactc atatatactt tagattgatt taaaacttca tttttaattt   3000

aaaaggatct aggtgaagat cctttttgat aatctcatga ccaaaatccc ttaacgtgag   3060

ttttcgttcc actgagcgtc agaccccgta gaaaagatca aaggatcttc ttgagatcct   3120

tttttctgc gcgtaatctg ctgcttgcaa acaaaaaaac caccgctacc agcggtggtt   3180

tgtttgccgg atcaagagct accaactctt tttccgaagg taactggctt cagcagagcg   3240

cagataccaa atactgtcct tctagtgtag ccgtagttag gccaccactt caagaactct   3300

gtagcaccgc ctacatacct cgctctgcta atcctgttac cagtggctgc tgccagtggc   3360

gataagtcgt gtcttaccgg gttggactca agacgatagt taccggataa ggcgcagcgg   3420

tcgggctgaa cggggggttc gtgcacacag cccagcttgg agcgaacgac ctacaccgaa   3480

ctgagatacc tacagcgtga gctatgagaa agcgccacgc ttcccgaagg gagaaaggcg   3540

gacaggtatc cggtaagcgg cagggtcgga acaggagagc gcacgaggga gcttccaggg   3600

ggaaacgcct ggtatcttta tagtcctgtc gggtttcgcc acctctgact tgagcgtcga   3660

tttttgtgat gctcgtcagg ggggcggagc ctatggaaaa acgccagcaa cgcggccttt   3720

ttacggttcc tggccttttg ctggcctttt gctcacatgt tctttcctgc gttatcccct   3780

gattctgtgg ataaccgtat taccgccttt gagtgagctg ataccgctcg ccgcagccga   3840

acgaccgagc gcagcgagtc agtgagcgag gaagcggaag agcgcctgat gcggtatttt   3900

ctccttacgc atctgtgcgg tatttcacac cgcatatg                          3938
```

<210> SEQ ID NO 3
<211> LENGTH: 3938
<212> TYPE: DNA
<213> ORGANISM: Artificial Sequence
<220> FEATURE:
<223> OTHER INFORMATION: arabinose inducible plasmid, with start codon at 351, stop codon at 1364, and the colicin E3 lysis protein from 1399 to 1542

<400> SEQUENCE: 3

```
gggggcggcc gcaagaaacc aattgtccat attgcatcag acattgccgt cactgcgtct     60

tttactggct cttctcgcta accaaaccgg taaccccgct tattaaaagc attctgtaac    120

aaagcgggac caaagccatg acaaaaacgc gtaacaaaag tgtctataat cacggcagaa    180

aagtccacat tgattatttg cacggcgtca cactttgcta tgccatagca tttttatcca    240

taagattagc ggatcctacc tgacgctttt tatcgcaact ctctactgtt tctccatacc    300

cgtttttttg ggctagcgaa ttcgagctcg gtacccagga ggaattcacc atggctaaaa    360
```

```
agacagctat cgcgattgca gtggcactgg ctggtttcgc taccgtagcg caggcagctg    420
tggtgagcca ttttaacgat tgcccggata gccataccca gttttgcttt catggcacct    480
gccgctttct ggtgcaggaa gataaaccgg cgtgcgtgtg ccatagcggt tatgtgggcg    540
ctcgctgcga acatgcggat ctgctggccc atcaactagt gggcggtggt ggcagtggtg    600
gcggcggctc tggtggtggc gggtcccggg gtctgacctg cccggtcgcc gccggtgaat    660
gcgcgggccc ggcggacagc ggcgacgccc tgctggagcg caactatccc actggcgcgg    720
agttcctcgg cgacggcggc gacgtcagct tcagcacccg cggcacgcag aactggacgg    780
tggagcggct gctccaggcg caccgccaac tggaggagcg cggctatgtg ttcgtcggct    840
accacggcac cttcctcgaa gcggcgcaaa gcatcgtctt cggcggggtg cgcgcgcgca    900
gccaggacct cgacgcgatc tggcgcggtt tctatatcgc cggcgatccg gcgctggcct    960
acggctacgc ccaggaccag gaacccgacg cacgcggccg gatccgcaac ggtgccctgc   1020
tgcgggtcta tgtgccgcgc tcgagcctgc cgggcttcta ccgcaccagc ctgaccctgg   1080
ccgcgccgga ggcggcgggc gaggtcgaac ggctgatcgg ccatccgctg ccgctgcgcc   1140
tggacgccat caccggcccc gaggaggaag gcgggcgcct ggagaccatt ctcggctggc   1200
cgctggccga gcgcaccgtg gtgattccct cggcgatccc caccgacccg cgcaacgtcg   1260
gcggcgacct cgacccgtcc agcatccccg acaaggaaca ggcgatcagc gccctgccgg   1320
actacgccag ccagcccggc aaaccgccga aagatgaact gtaactcgag tagatctgta   1380
ctctagaaag gagtcgttat gaaaaaaata acagggatta ttttattgct tcttgcagtc   1440
attattctgt ctgcatgtca ggcaaactat atccgggatg ttcagggcgg gaccgtatct   1500
ccgtcatcaa cagctgaagt gaccggatta gcaacgcagt aactgcaggc atgcaagctt   1560
ggctgttttg gcggatgaga gaagattttc agcctgatac agattaaatc agaacgcaga   1620
agcggtctga taaaacagaa tttgcctggc ggcagtagcg cggtggtccc acctgacccc   1680
atgccgaact cagaagtgaa acgccgtagc gccgatggta gtgtggggtc tccccatgcg   1740
agagtaggga actgccaggc atcaaataaa acgaaaggct cagtcgaaag actgggcctt   1800
tcgttttatc tgttgtttgt cggtgaacgc tctcctgagt aggacaaatc cgccgggagc   1860
ggatttgaac gttgcgaagc aacggcccgg agggtggcgg gcaggacgcc cgccataaac   1920
tgccaggcat caaattaagc agaaggccat cctgacggat ggcctttttg cgtttctaca   1980
aactcttttt gtttattttt ctaaatacat tcaaatatgt atccgctcat gagacaataa   2040
ccctgataaa tgcttcaata atattgaaaa aggaagagta tgagtattca acatttccgt   2100
gtcgccctta ttcccttttt tgcggcattt tgccttcctg tttttgctca cccagaaacg   2160
ctggtgaaag taaaagatgc tgaagatcag ttgggtgcac gagtgggtta catcgaactg   2220
gatctcaaca gcggtaagat ccttgagagt tttcgccccg aagaacgttt tccaatgatg   2280
agcactttta aagttctgct atgtggcgcg gtattatccc gtgttgacgc cgggcaagag   2340
caactcggtc gccgcataca ctattctcag aatgacttgg ttgagtactc accagtcaca   2400
gaaaagcatc ttacggatgg catgacagta agagaattat gcagtgctgc cataaccatg   2460
agtgataaca ctgcggccaa cttacttctg acaacgatcg gaggaccgaa ggagctaacc   2520
gcttttttgc acaacatggg ggatcatgta actcgccttg atcgttggga accggagctg   2580
aatgaagcca taccaaacga cgagcgtgac accacgatgc ctacagcaat ggcaacaacg   2640
ttgcgcaaac tattaactgg cgaactactt actctagctt cccggcaaca attaatagac   2700
tggatggagg cggataaagt tgcaggacca cttctgcgct cggcccttcc ggctggctgg   2760
```

-continued

```
tttattgctg ataaatctgg agccggtgag cgtgggtctc gcggtatcat tgcagcactg   2820

gggccagatg gtaagccctc ccgtatcgta gttatctaca cgacggggag tcaggcaact   2880

atggatgaac gaaatagaca gatcgctgag ataggtgcct cactgattaa gcattggtaa   2940

ctgtcagacc aagtttactc atatatactt tagattgatt taaaacttca tttttaattt   3000

aaaaggatct aggtgaagat cctttttgat aatctcatga ccaaaatccc ttaacgtgag   3060

ttttcgttcc actgagcgtc agaccccgta gaaaagatca aaggatcttc ttgagatcct   3120

tttttctgc gcgtaatctg ctgcttgcaa acaaaaaaac caccgctacc agcggtggtt   3180

tgtttgccgg atcaagagct accaactctt tttccgaagg taactggctt cagcagagcg   3240

cagataccaa atactgtcct tctagtgtag ccgtagttag gccaccactt caagaactct   3300

gtagcaccgc ctacatacct cgctctgcta atcctgttac cagtggctgc tgccagtggc   3360

gataagtcgt gtcttaccgg gttggactca agacgatagt taccggataa ggcgcagcgg   3420

tcgggctgaa cggggggttc gtgcacacag cccagcttgg agcgaacgac ctacaccgaa   3480

ctgagatacc tacagcgtga gctatgagaa agcgccacgc ttcccgaagg gagaaaggcg   3540

gacaggtatc cggtaagcgg cagggtcgga acaggagagc gcacgaggga gcttccaggg   3600

ggaaacgcct ggtatcttta tagtcctgtc gggtttcgcc acctctgact tgagcgtcga   3660

tttttgtgat gctcgtcagg ggggcggagc ctatggaaaa acgccagcaa cgcggccttt   3720

ttacggttcc tggccttttg ctggcctttt gctcacatgt tctttcctgc gttatcccct   3780

gattctgtgg ataaccgtat taccgccttt gagtgagctg ataccgctcg ccgcagccga   3840

acgaccgagc gcagcgagtc agtgagcgag gaagcggaag agcgcctgat gcggtatttt   3900

ctccttacgc atctgtgcgg tatttcacac cgcatatg                          3938


<210> SEQ ID NO 4
<211> LENGTH: 3711
<212> TYPE: DNA
<213> ORGANISM: Artificial Sequence
<220> FEATURE:
<223> OTHER INFORMATION: Modified TGF-alpha-GIII-KDEL

<400> SEQUENCE: 4

gggggcggcc gcaagaaacc aattgtccat attgcatcag acattgccgt cactgcgtct     60

tttactggct cttctcgcta accaaaccgg taaccccgct tattaaaagc attctgtaac    120

aaagcgggac caaagccatg acaaaaacgc gtaacaaaag tgtctataat cacggcagaa    180

aagtccacat tgattatttg cacggcgtca cactttgcta tgccatagca tttttatcca    240

taagattagc ggatcctacc tgacgctttt tatcgcaact ctctactgtt tctccatacc    300

cgttttttg ggctagcgaa ttcgagctcg gtacccagga ggaattcacc atggctaaaa    360

agacagctat cgcgattgca gtggcactgg ctggtttcgc taccgtagcg caggcagctg    420

tggtgagcca ttttaacgat tgcccggata gccataccca gttttgcttt catggcacct    480

gccgctttct ggtgcaggaa gataaaccgg cgtgcgtgtg ccatagcggt tatgtgggcg    540

ctcgctgcga acatgcggat ctgctggccc atcaactagt gggcggtggt ggcagtggtg    600

gcggcggctc tggtggtggc gggtcccggg gtactggcgc ggagttcctc ggcgacggcg    660

gcgacgtcag cttcagcacc cgcggcacgc agaactggac ggtggagcgg ctgctccagg    720

cgcaccgcca actggaggag cgcggctatg tgttcgtcgg ctaccacggc accttcctcg    780

aagcggcgca aagcatcgtc ttcggcgggg tgcgcgcgcg cagccaggac ctcgacgcga    840
```

-continued

```
tctggcgcgg tttctatatc gccggcgatc cggcgctggc ctacggctac gcccaggacc    900
aggaacccga cgcacgcggc cggatccgca acggtgccct gctgcgggtc tatgtgccgc    960
gctcgagcct gccgggcttc taccgcacca gcctgaccct ggccgcgccg gaggcggcgg   1020
gcgaggtcga acggctgatc ggccatccgc tgccgctgcg cctggacgcc atcaccggcc   1080
ccgaggagga aggcgggcgc ctggagacca ttctcggctg gccgctggcc gagcgcaccg   1140
tggtgattcc ctcggcgatc cccaccgacc cgcgcaacgt cggcggcgac ctcgacccgt   1200
ccagcatccc cgacaaggaa caggcgatca gcgccctgcc ggactacgcc agccagcccg   1260
gcaaaccgcc gaaagatgaa ctgtaactcg agtagatctg tactctagag tcgacctgca   1320
ggcatgcaag cttggctgtt ttggcggatg agagaagatt ttcagcctga tacagattaa   1380
atcagaacgc agaagcggtc tgataaaaca gaatttgcct ggcggcagta gcgcggtggt   1440
cccacctgac cccatgccga actcagaagt gaaacgccgt agcgccgatg gtagtgtggg   1500
gtctccccat gcgagagtag ggaactgcca ggcatcaaat aaaacgaaag gctcagtcga   1560
aagactgggc ctttcgtttt atctgttgtt tgtcggtgaa cgctctcctg agtaggacaa   1620
atccgccggg agcggatttg aacgttgcga agcaacggcc cggagggtgg cgggcaggac   1680
gcccgccata aactgccagg catcaaatta agcagaaggc catcctgacg gatggccttt   1740
ttgcgtttct acaaactctt tttgtttatt tttctaaata cattcaaata tgtatccgct   1800
catgagacaa taaccctgat aaatgcttca ataatattga aaaaggaaga gtatgagtat   1860
tcaacatttc cgtgtcgccc ttattccctt ttttgcggca ttttgccttc ctgtttttgc   1920
tcacccagaa acgctggtga aagtaaaaga tgctgaagat cagttgggtg cacgagtggg   1980
ttacatcgaa ctggatctca acagcggtaa gatccttgag agttttcgcc ccgaagaacg   2040
ttttccaatg atgagcactt ttaaagttct gctatgtggc gcggtattat cccgtgttga   2100
cgccgggcaa gagcaactcg gtcgccgcat acactattct cagaatgact tggttgagta   2160
ctcaccagtc acagaaaagc atcttacgga tggcatgaca gtaagagaat tatgcagtgc   2220
tgccataacc atgagtgata acactgcggc caacttactt ctgacaacga tcggaggacc   2280
gaaggagcta accgcttttt tgcacaacat gggggatcat gtaactcgcc ttgatcgttg   2340
ggaaccggag ctgaatgaag ccataccaaa cgacgagcgt gacaccacga tgcctacagc   2400
aatggcaaca acgttgcgca aactattaac tggcgaacta cttactctag cttcccggca   2460
acaattaata gactggatgg aggcggataa agttgcagga ccacttctgc gctcggccct   2520
tccggctggc tggtttattg ctgataaatc tggagccggt gagcgtgggt ctcgcggtat   2580
cattgcagca ctggggccag atggtaagcc ctcccgtatc gtagttatct acacgacggg   2640
gagtcaggca actatggatg aacgaaatag acagatcgct gagataggtg cctcactgat   2700
taagcattgg taactgtcag accaagttta ctcatatata ctttagattg atttaaaact   2760
tcatttttaa tttaaaagga tctaggtgaa gatccttttt gataatctca tgaccaaaat   2820
cccttaacgt gagttttcgt tccactgagc gtcagacccc gtagaaaaga tcaaaggatc   2880
ttcttgagat cctttttttc tgcgcgtaat ctgctgcttg caaacaaaaa aaccaccgct   2940
accagcggtg gtttgtttgc cggatcaaga gctaccaact ctttttccga aggtaactgg   3000
cttcagcaga gcgcagatac caaatactgt ccttctagtg tagccgtagt taggccacca   3060
cttcaagaac tctgtagcac cgcctacata cctcgctctg ctaatcctgt taccagtggc   3120
tgctgccagt ggcgataagt cgtgtcttac cgggttggac tcaagacgat agttaccgga   3180
taaggcgcag cggtcgggct gaacgggggg ttcgtgcaca cagcccagct tggagcgaac   3240
```

-continued gacctacacc gaactgagat acctacagcg tgagctatga gaaagcgcca cgcttcccga 3300
agggagaaag gcggacaggt atccggtaag cggcagggtc ggaacaggag agcgcacgag 3360
ggagcttcca gggggaaacg cctggtatct ttatagtcct gtcgggtttc gccacctctg 3420
acttgagcgt cgatttttgt gatgctcgtc aggggggcgg agcctatgga aaaacgccag 3480
caacgcggcc tttttacggt tcctggcctt ttgctggcct tttgctcaca tgttctttcc 3540
tgcgttatcc cctgattctg tggataaccg tattaccgcc tttgagtgag ctgataccgc 3600
tcgccgcagc cgaacgaccg agcgcagcga gtcagtgagc gaggaagcgg aagagcgcct 3660
gatgcggtat tttctcctta cgcatctgtg cggtatttca caccgcatat g 3711

<210> SEQ ID NO 5
<211> LENGTH: 4089
<212> TYPE: DNA
<213> ORGANISM: Artificial Sequence
<220> FEATURE:
<223> OTHER INFORMATION: arabinose inducible plasmid expressing the construct with start codon at 351 and stop codon at 1664

<400> SEQUENCE: 5
gggggcggcc gcaagaaacc aattgtccat attgcatcag acattgccgt cactgcgtct 60
tttactggct cttctcgcta accaaaccgg taaccccgct tattaaaagc attctgtaac 120
aaagcgggac caaagccatg acaaaaacgc gtaacaaaag tgtctataat cacggcagaa 180
aagtccacat tgattatttg cacggcgtca cactttgcta tgccatagca tttttatcca 240
taagattagc ggatcctacc tgacgctttt tatcgcaact ctctactgtt tctccatacc 300
cgtttttttg ggctagcgaa ttcgagctcg gtacccagga ggaattcacc atggctaaaa 360
agacagctat cgcgattgca gtggcactgg ctggtttcgc taccgtagcg caggcagctg 420
tggtgagcca ttttaacgat tgcccggata gccataccca gttttgcttt catggcacct 480
gccgctttct ggtgcaggaa gataaaccgg cgtgcgtgtg ccatagcggt tatgtgggcg 540
ctcgctgcga acatgcggat ctgctggccc atcaactagt gggcggtggt ggcagtggtg 600
gcggcggctc tggtggtggc gggtcccggg gtggcagcct ggccgcgctg accgcgcacc 660
aggcttgcca cctgccgctg gagactttca cccgtcatcg ccagccgcgc ggctgggaac 720
aactggagca gtgcggctat ccggtgcagc ggctggtcgc cctctacctg gcggcgcggc 780
tgtcgtggaa ccaggtcgac caggtgatcc gcaacgccct ggccagcccc ggcagcggcg 840
gcgacctggg cgaagcgatc cgcgagcagc cggagcaggc ccgtctggcc ctgaccctgg 900
ccgccgccga gagcgagcgc ttcgtccggc agggcaccgg caacgacgag gccggcgcgg 960
ccaacgcccc ggcggacagc ggcgacgccc tgctggagcg caactatccc actggcgcgg 1020
agttcctcgg cgacggcggc gacgtcagct tcagcacccg cggcacgcag aactggacgg 1080
tggagcggct gctccaggcg caccgccaac tggaggagcg cggctatgtg ttcgtcggct 1140
accacggcac cttcctcgaa gcggcgcaaa gcatcgtctt cggcggggtg cgcgcgcgca 1200
gccaggacct cgacgcgatc tggcgcggtt tctatatcgc cggcgatccg gcgctggcct 1260
acggctacgc ccaggaccag gaacccgacg cacgcggccg gatccgcaac ggtgccctgc 1320
tgcgggtcta tgtgccgcgc tcgagcctgc cgggcttcta ccgcaccagc ctgaccctgg 1380
ccgcgccgga ggcggcgggc gaggtcgaac ggctgatcgg ccatccgctg ccgctgcgcc 1440
tggacgccat caccggcccc gaggaggaag gcgggcgcct ggagaccatt ctcggctggc 1500
cgctggccga gcgcaccgtg gtgattccct cggcgatccc caccgacccg cgcaacgtcg 1560

```
gcggcgacct cgacccgtcc agcatccccg acaaggaaca ggcgatcagc gccctgccgg   1620
actacgccag ccagcccggc aaaccgccga aagatgaact gtaactcgag tagatctgta   1680
ctctagagtc gacctgcagg catgcaagct tggctgtttt ggcggatgag agaagatttt   1740
cagcctgata cagattaaat cagaacgcag aagcggtctg ataaaacaga atttgcctgg   1800
cggcagtagc gcggtggtcc cacctgaccc catgccgaac tcagaagtga aacgccgtag   1860
cgccgatggt agtgtggggt ctccccatgc gagagtaggg aactgccagg catcaaataa   1920
aacgaaaggc tcagtcgaaa gactgggcct ttcgttttat ctgttgtttg tcggtgaacg   1980
ctctcctgag taggacaaat ccgccgggag cggatttgaa cgttgcgaag caacggcccg   2040
gagggtggcg ggcaggacgc ccgccataaa ctgccaggca tcaaattaag cagaaggcca   2100
tcctgacgga tggccttttt gcgtttctac aaactctttt tgtttatttt tctaaataca   2160
ttcaaatatg tatccgctca tgagacaata accctgataa atgcttcaat aatattgaaa   2220
aaggaagagt atgagtattc aacatttccg tgtcgccctt attccctttt ttgcggcatt   2280
ttgccttcct gtttttgctc acccagaaac gctggtgaaa gtaaaagatg ctgaagatca   2340
gttgggtgca cgagtgggtt acatcgaact ggatctcaac agcggtaaga tccttgagag   2400
ttttcgcccc gaagaacgtt ttccaatgat gagcactttt aaagttctgc tatgtggcgc   2460
ggtattatcc cgtgttgacg ccgggcaaga gcaactcggt cgccgcatac actattctca   2520
gaatgacttg gttgagtact caccagtcac agaaaagcat cttacggatg gcatgacagt   2580
aagagaatta tgcagtgctg ccataaccat gagtgataac actgcggcca acttacttct   2640
gacaacgatc ggaggaccga aggagctaac cgcttttttg cacaacatgg gggatcatgt   2700
aactcgcctt gatcgttggg aaccggagct gaatgaagcc ataccaaacg acgagcgtga   2760
caccacgatg cctacagcaa tggcaacaac gttgcgcaaa ctattaactg gcgaactact   2820
tactctagct tcccggcaac aattaataga ctggatggag gcggataaag ttgcaggacc   2880
acttctgcgc tcggcccttc cggctggctg gtttattgct gataaatctg gagccggtga   2940
gcgtgggtct cgcggtatca ttgcagcact ggggccagat ggtaagccct cccgtatcgt   3000
agttatctac acgacgggga gtcaggcaac tatggatgaa cgaaatagac agatcgctga   3060
gataggtgcc tcactgatta agcattggta actgtcagac caagtttact catatatact   3120
ttagattgat ttaaaacttc atttttaatt taaaaggatc taggtgaaga tcctttttga   3180
taatctcatg accaaaatcc cttaacgtga gttttcgttc cactgagcgt cagaccccgt   3240
agaaaagatc aaaggatctt cttgagatcc tttttttctg cgcgtaatct gctgcttgca   3300
aacaaaaaaa ccaccgctac cagcggtggt ttgtttgccg gatcaagagc taccaactct   3360
ttttccgaag gtaactggct tcagcagagc gcagatacca aatactgtcc ttctagtgta   3420
gccgtagtta ggccaccact tcaagaactc tgtagcaccg cctacatacc tcgctctgct   3480
aatcctgtta ccagtggctg ctgccagtgg cgataagtcg tgtcttaccg ggttggactc   3540
aagacgatag ttaccggata aggcgcagcg gtcgggctga acggggggtt cgtgcacaca   3600
gcccagcttg gagcgaacga cctacaccga actgagatac ctacagcgtg agctatgaga   3660
aagcgccacg cttcccgaag ggagaaaggc ggacaggtat ccggtaagcg gcagggtcgg   3720
aacaggagag cgcacgaggg agcttccagg gggaaacgcc tggtatcttt atagtcctgt   3780
cgggtttcgc cacctctgac ttgagcgtcg atttttgtga tgctcgtcag gggggcggag   3840
cctatggaaa aacgccagca acgcggcctt tttacggttc ctggcctttt gctggccttt   3900
```

-continued tgctcacatg ttctttcctg cgttatcccc tgattctgtg gataaccgta ttaccgcctt 3960
tgagtgagct gataccgctc gccgcagccg aacgaccgag cgcagcgagt cagtgagcga 4020
ggaagcggaa gagcgcctga tgcggtattt tctccttacg catctgtgcg gtatttcaca 4080
ccgcatatg 4089

<210> SEQ ID NO 6
<211> LENGTH: 4238
<212> TYPE: DNA
<213> ORGANISM: Artificial Sequence
<220> FEATURE:
<223> OTHER INFORMATION: arabinose inducible plasmid expressing the construct with start codon at 351, a stop codon at 1664, and colicin E3 lysis protein from 1699 to 1842

<400> SEQUENCE: 6
gggggcggcc gcaagaaacc aattgtccat attgcatcag acattgccgt cactgcgtct 60
tttactggct cttctcgcta accaaaccgg taaccccgct tattaaaagc attctgtaac 120
aaagcgggac caaagccatg acaaaaacgc gtaacaaaag tgtctataat cacggcagaa 180
aagtccacat tgattatttg cacggcgtca cactttgcta tgccatagca tttttatcca 240
taagattagc ggatcctacc tgacgctttt tatcgcaact ctctactgtt tctccatacc 300
cgtttttttg ggctagcgaa ttcgagctcg gtacccagga ggaattcacc atggctaaaa 360
agacagctat cgcgattgca gtggcactgg ctggtttcgc taccgtagcg caggcagctg 420
tggtgagcca ttttaacgat tgcccggata gccataccca gttttgcttt catggcacct 480
gccgctttct ggtgcaggaa gataaaccgg cgtgcgtgtg ccatagcggt tatgtgggcg 540
ctcgctgcga acatgcggat ctgctggccc atcaactagt gggcggtggt ggcagtggtg 600
gcggcggctc tggtggtggc gggtcccggg gtggcagcct ggccgcgctg accgcgcacc 660
aggcttgcca cctgccgctg gagactttca cccgtcatcg ccagccgcgc ggctgggaac 720
aactggagca gtgcggctat ccggtgcagc ggctggtcgc cctctacctg gcggcgcggc 780
tgtcgtggaa ccaggtcgac caggtgatcc gcaacgccct ggccagcccc ggcagcggcg 840
gcgacctggg cgaagcgatc cgcgagcagc cggagcaggc ccgtctggcc ctgaccctgg 900
ccgccgccga gagcgagcgc ttcgtccggc agggcaccgg caacgacgag gccggcgcgg 960
ccaacgcccc ggcggacagc ggcgacgccc tgctggagcg caactatccc actggcgcgg 1020
agttcctcgg cgacggcggc gacgtcagct tcagcacccg cggcacgcag aactggacgg 1080
tggagcggct gctccaggcg caccgccaac tggaggagcg cggctatgtg ttcgtcggct 1140
accacggcac cttcctcgaa gcggcgcaaa gcatcgtctt cggcggggtg cgcgcgcgca 1200
gccaggacct cgacgcgatc tggcgcggtt tctatatcgc cggcgatccg gcgctggcct 1260
acggctacgc ccaggaccag gaacccgacg cacgcggccg gatccgcaac ggtgccctgc 1320
tgcgggtcta tgtgccgcgc tcgagcctgc cgggcttcta ccgcaccagc ctgaccctgg 1380
ccgcgccgga ggcggcgggc gaggtcgaac ggctgatcgg ccatccgctg ccgctgcgcc 1440
tggacgccat caccggcccc gaggaggaag gcgggcgcct ggagaccatt ctcggctggc 1500
cgctggccga gcgcaccgtg gtgattccct cggcgatccc caccgacccg cgcaacgtcg 1560
gcggcgacct cgacccgtcc agcatccccg acaaggaaca ggcgatcagc gccctgccgg 1620
actacgccag ccagcccggc aaaccgccga aagatgaact gtaactcgag tagatctgta 1680
ctctagaaag gagtcgttat gaaaaaaata acagggatta ttttattgct tcttgcagtc 1740
attattctgt ctgcatgtca ggcaaactat atccgggatg ttcagggcgg gaccgtatct 1800

```
ccgtcatcaa cagctgaagt gaccggatta gcaacgcagt aactgcaggc atgcaagctt   1860
ggctgttttg gcggatgaga gaagattttc agcctgatac agattaaatc agaacgcaga   1920
agcggtctga taaaacagaa tttgcctggc ggcagtagcg cggtggtccc acctgacccc   1980
atgccgaact cagaagtgaa acgccgtagc gccgatggta gtgtggggtc tccccatgcg   2040
agagtaggga actgccaggc atcaaataaa acgaaaggct cagtcgaaag actgggcctt   2100
tcgttttatc tgttgtttgt cggtgaacgc tctcctgagt aggacaaatc cgccgggagc   2160
ggatttgaac gttgcgaagc aacggcccgg agggtggcgg gcaggacgcc cgccataaac   2220
tgccaggcat caaattaagc agaaggccat cctgacggat ggcctttttg cgtttctaca   2280
aactcttttt gtttattttt ctaaatacat tcaaatatgt atccgctcat gagacaataa   2340
ccctgataaa tgcttcaata atattgaaaa aggaagagta tgagtattca acatttccgt   2400
gtcgccctta ttcccttttt tgcggcattt tgccttcctg tttttgctca cccagaaacg   2460
ctggtgaaag taaaagatgc tgaagatcag ttgggtgcac gagtgggtta catcgaactg   2520
gatctcaaca gcggtaagat ccttgagagt tttcgccccg aagaacgttt tccaatgatg   2580
agcactttta aagttctgct atgtggcgcg gtattatccc gtgttgacgc cgggcaagag   2640
caactcggtc gccgcataca ctattctcag aatgacttgg ttgagtactc accagtcaca   2700
gaaaagcatc ttacggatgg catgacagta agagaattat gcagtgctgc cataaccatg   2760
agtgataaca ctgcggccaa cttacttctg acaacgatcg gaggaccgaa ggagctaacc   2820
gcttttttgc acaacatggg ggatcatgta actcgccttg atcgttggga accggagctg   2880
aatgaagcca taccaaacga cgagcgtgac accacgatgc ctacagcaat ggcaacaacg   2940
ttgcgcaaac tattaactgg cgaactactt actctagctt cccggcaaca attaatagac   3000
tggatggagg cggataaagt tgcaggacca cttctgcgct cggcccttcc ggctggctgg   3060
tttattgctg ataaatctgg agccggtgag cgtgggtctc gcggtatcat tgcagcactg   3120
gggccagatg gtaagccctc ccgtatcgta gttatctaca cgacggggag tcaggcaact   3180
atggatgaac gaaatagaca gatcgctgag ataggtgcct cactgattaa gcattggtaa   3240
ctgtcagacc aagtttactc atatatactt tagattgatt taaaacttca tttttaattt   3300
aaaaggatct aggtgaagat cctttttgat aatctcatga ccaaaatccc ttaacgtgag   3360
ttttcgttcc actgagcgtc agaccccgta gaaaagatca aaggatcttc ttgagatcct   3420
ttttttctgc gcgtaatctg ctgcttgcaa acaaaaaaac caccgctacc agcggtggtt   3480
tgtttgccgg atcaagagct accaactctt tttccgaagg taactggctt cagcagagcg   3540
cagataccaa atactgtcct tctagtgtag ccgtagttag gccaccactt caagaactct   3600
gtagcaccgc ctacatacct cgctctgcta atcctgttac cagtggctgc tgccagtggc   3660
gataagtcgt gtcttaccgg gttggactca agacgatagt taccggataa ggcgcagcgg   3720
tcgggctgaa cggggggttc gtgcacacag cccagcttgg agcgaacgac ctacaccgaa   3780
ctgagatacc tacagcgtga gctatgagaa agcgccacgc ttcccgaagg gagaaaggcg   3840
gacaggtatc cggtaagcgg cagggtcgga acaggagagc gcacgaggga gcttccaggg   3900
ggaaacgcct ggtatcttta tagtcctgtc gggtttcgcc acctctgact tgagcgtcga   3960
tttttgtgat gctcgtcagg ggggcggagc ctatggaaaa acgccagcaa cgcggccttt   4020
ttacggttcc tggccttttg ctggcctttt gctcacatgt tctttcctgc gttatcccct   4080
gattctgtgg ataaccgtat taccgccttt gagtgagctg ataccgctcg ccgcagccga   4140
```

acgaccgagc gcagcgagtc agtgagcgag gaagcggaag agcgcctgat gcggtatttt 4200
ctccttacgc atctgtgcgg tatttcacac cgcatatg 4238

<210> SEQ ID NO 7
<211> LENGTH: 4770
<212> TYPE: DNA
<213> ORGANISM: Artificial Sequence
<220> FEATURE:
<223> OTHER INFORMATION: arabinose inducible plasmid expressing the construct with cldtB start codon at 351, stop codon at 1163, pltB start at 1197, stop at 1610, and pltA 1627-2355

<400> SEQUENCE: 7
gggggcggcc gcaagaaacc aattgtccat attgcatcag acattgccgt cactgcgtct 60
tttactggct cttctcgcta accaaaccgg taaccccgct tattaaaagc attctgtaac 120
aaagcgggac caaagccatg acaaaaacgc gtaacaaaag tgtctataat cacggcagaa 180
aagtccacat tgattatttg cacggcgtca cactttgcta tgccatagca tttttatcca 240
taagattagc ggatcctacc tgacgctttt tatcgcaact ctctactgtt tctccatacc 300
cgtttttttg ggctagcgaa ttcgagctcg gtacccagga ggaattcacc atggtcaaaa 360
aacctgtttt tttccttctg accatgatca tctgcagcta tatttctttt gcctgcgcta 420
atatcagtga ctacaaagtt atgacctgga atcttcaggg ctcttcagca tctacagaaa 480
gtaaatggaa tgtcaatgtc agacagcttt taagcggtac tgccggtgtg gatattctta 540
tggtacagga ggccggtgct gttcccacct cagcggttcc taccggacga catattcagc 600
cttttggagt gggtattccc attgatgaat acacctggaa tctcggaacc accagccgtc 660
aggatataag atatatctac tactcggcta ttgatgttgg agcacgccgt gttaatctgg 720
caatagtttc cagacaaaga gcggataatg tttatgtctt gcgtccgaca actgtcgcat 780
ctcgccccgt cattggcatc ggactgggta atgatgtttt tctgacagcg cacgcactgg 840
ctagtggagg tccggatgct gcagctattg tcagggttac cattaatttt tttagacaac 900
ctcagatgcg gcatttatcc tggtttcttg ccggggattt taatcgcagc ccagacagac 960
ttgaaaatga cctgatgact gagcatctgg aacgagttgt agccgtactc gcacctacag 1020
aacccacgca aattagcggt ggtattttag attatggggt cattgtcgat cgagcacctt 1080
attcacaaag ggtcgaagca ttacgtaatc cacaactcgc ttctgatcat tatcccgtag 1140 ccttttttggc acgaagctgt taatgatcta gataagtcga cgtacaggag agtagtatgt 1200
atataaataa gtttgtgcct gtttatacat tattaattct catttattct tttaatgcca 1260
gcgctgagtg gacaggagat aatacgaacg cctattactc agacgaagtt atcagtgaat 1320
tacatgttgg tcagatagat actagtcctt atttttgcat aaaaaacggt aaagctaacg 1380
gtagtggtac accagttgtt gcatgtgcgg tatcaaagca gagcatatgg gcgccctcct 1440
ttaaagaact tcttgatcag gcaagatatt tttacagtac agggcaatcc gtaaggattc 1500
atgttcaaaa aaatatctgg acctatccgc tttttgttaa taccttttca gcaaatgctc 1560
ttgtgggact atcatcgtgc agtgcgacac aatgctttgg acccaagtaa gaggggagaa 1620
gaaataatga aaaagttaat attcttaacc ttatctatag ttagctttaa taactatgct 1680
gtagattttg tgtatcgtgt ggactcaacc ccgccggacg ttatttttcg cgatgggttt 1740
tcactacttg ggtataaccg taactttcag caatttatta gtggaaggtc atgtagtggt 1800
ggaagtagtg acagtcgcta tattgcaaca acctcaagtg ttaatcaaac atatgctata 1860
gccagagcgt actattctcg ctcaacattc aaaggtaatt tatacagata tcagattcgt 1920

```
gcagataata atttctacag cttgctccca tccatcacct atctggaaac gcaaggtggt   1980
cactttaatg cttatgaaaa aacgatgatg cgattgcaaa gagagtatgt ttccacatta   2040
tctattttac ccgagaatat tcaaaaggcc gtggcgctag tttatgatag cgcaaccggt   2100
ctggtaaagg atggtgtaag cacaatgaat gccagttatt taggtttaag cactacgtct   2160
aatcctggtg tgataccttt tcttccggaa ccgcagacgt atacccaaca acgaattgat   2220
gcattcggcc cattaataag ttcatgcttt tcaataggta gcgtatgtca gtcacatcga   2280
gggcaaagag ctgacgtata caacatgtct tttatgatg caagacctgt aatagaactt   2340
atactttcta aataaatgaa acttacctat gttgccgcat gcaagctagc ttggctgttt   2400
tggcggatga gagaagattt tcagcctgat acagattaaa tcagaacgca gaagcggtct   2460
gataaaacag aatttgcctg gcggcagtag cgcggtggtc ccacctgacc ccatgccgaa   2520
ctcagaagtg aaacgccgta gcgccgatgg tagtgtgggg tctccccatg cgagagtagg   2580
gaactgccag gcatcaaata aaacgaaagg ctcagtcgaa agactgggcc tttcgtttta   2640
tctgttgttt gtcggtgaac gctctcctga gtaggacaaa tccgccggga gcggatttga   2700
acgttgcgaa gcaacggccc ggagggtggc gggcaggacg cccgccataa actgccaggc   2760
atcaaattaa gcagaaggcc atcctgacgg atggcctttt tgcgtttcta caaactcttt   2820
ttgtttattt ttctaaatac attcaaatat gtatccgctc atgagacaat aaccctgata   2880
aatgcttcaa taatattgaa aaaggaagag tatgagtatt caacatttcc gtgtcgccct   2940
tattcccttt tttgcggcat tttgccttcc tgtttttgct cacccagaaa cgctggtgaa   3000
agtaaaagat gctgaagatc agttgggtgc acgagtgggt tacatcgaac tggatctcaa   3060
cagcggtaag atccttgaga gttttcgccc cgaagaacgt tttccaatga tgagcacttt   3120
taaagttctg ctatgtggcg cggtattatc ccgtgttgac gccgggcaag agcaactcgg   3180
tcgccgcata cactattctc agaatgactt ggttgagtac tcaccagtca cagaaaagca   3240
tcttacggat ggcatgacag taagagaatt atgcagtgct gccataacca tgagtgataa   3300
cactgcggcc aacttacttc tgacaacgat cggaggaccg aaggagctaa ccgctttttt   3360
gcacaacatg ggggatcatg taactcgcct tgatcgttgg gaaccggagc tgaatgaagc   3420
cataccaaac gacgagcgtg acaccacgat gcctacagca atggcaacaa cgttgcgcaa   3480
actattaact ggcgaactac ttactctagc ttcccggcaa caattaatag actggatgga   3540
ggcggataaa gttgcaggac cacttctgcg ctcggccctt ccggctggct ggtttattgc   3600
tgataaatct ggagccggtg agcgtgggtc tcgcggtatc attgcagcac tggggccaga   3660
tggtaagccc tcccgtatcg tagttatcta cacgacgggg agtcaggcaa ctatggatga   3720
acgaaataga cagatcgctg agataggtgc ctcactgatt aagcattggt aactgtcaga   3780
ccaagtttac tcatatatac tttagattga tttaaaactt catttttaat ttaaaaggat   3840
ctaggtgaag atcctttttg ataatctcat gaccaaaatc ccttaacgtg agttttcgtt   3900
ccactgagcg tcagaccccg tagaaaagat caaaggatct tcttgagatc cttttttct   3960
gcgcgtaatc tgctgcttgc aaacaaaaaa accaccgcta ccagcggtgg tttgtttgcc   4020
ggatcaagag ctaccaactc tttttccgaa ggtaactggc ttcagcagag cgcagatacc   4080
aaatactgtc cttctagtgt agccgtagtt aggccaccac ttcaagaact ctgtagcacc   4140
gcctacatac ctcgctctgc taatcctgtt accagtggct gctgccagtg gcgataagtc   4200
gtgtcttacc gggttggact caagacgata gttaccggat aaggcgcagc ggtcgggctg   4260
```

-continued

```
aacggggggt tcgtgcacac agcccagctt ggagcgaacg acctacaccg aactgagata   4320

cctacagcgt gagctatgag aaagcgccac gcttcccgaa gggagaaagg cggacaggta   4380

tccggtaagc ggcagggtcg gaacaggaga gcgcacgagg gagcttccag ggggaaacgc   4440

ctggtatctt tatagtcctg tcgggtttcg ccacctctga cttgagcgtc gatttttgtg   4500

atgctcgtca ggggggcgga gcctatggaa aaacgccagc aacgcggcct ttttacggtt   4560

cctggccttt tgctggcctt ttgctcacat gttctttcct gcgttatccc ctgattctgt   4620

ggataaccgt attaccgcct ttgagtgagc tgataccgct cgccgcagcc gaacgaccga   4680

gcgcagcgag tcagtgagcg aggaagcgga agagcgcctg atgcggtatt ttctccttac   4740

gcatctgtgc ggtatttcac accgcatatg                                    4770


<210> SEQ ID NO 8
<211> LENGTH: 15
<212> TYPE: DNA
<213> ORGANISM: Artificial Sequence
<220> FEATURE:
<223> OTHER INFORMATION: Linker x3

<400> SEQUENCE: 8

ggggsggggs ggggs                                                      15


<210> SEQ ID NO 9
<211> LENGTH: 4851
<212> TYPE: DNA
<213> ORGANISM: Artificial Sequence
<220> FEATURE:
<223> OTHER INFORMATION: arabinose inducible plasmid with a cldtB start
      codon at 351 through codon at 1160 (without a stop), FLAG from
      1170-1193, and GGGGS(x3) from 1194-1238, pltB start at 1278 and
      stop at 1691 and pltA 1708-2436

<400> SEQUENCE: 9

gggggcggcc gcaagaaacc aattgtccat attgcatcag acattgccgt cactgcgtct     60

tttactggct cttctcgcta accaaaccgg taaccccgct tattaaaagc attctgtaac    120

aaagcgggac caaagccatg acaaaaacgc gtaacaaaag tgtctataat cacggcagaa    180

aagtccacat tgattatttg cacggcgtca cactttgcta tgccatagca tttttatcca    240

taagattagc ggatcctacc tgacgctttt tatcgcaact ctctactgtt tctccatacc    300

cgtttttttg ggctagcgaa ttcgagctcg gtacccagga ggaattcacc atggtcaaaa    360

aacctgtttt tttccttctg accatgatca tctgcagcta tatttctttt gcctgcgcta    420

atatcagtga ctacaaagtt atgacctgga atcttcaggg ctcttcagca tctacagaaa    480

gtaaatggaa tgtcaatgtc agacagcttt taagcggtac tgccggtgtg gatattctta    540

tggtacagga ggccggtgct gttcccacct cagcggttcc taccggacga catattcagc    600

cttttggagt gggtattccc attgatgaat acacctggaa tctcggaacc accagccgtc    660

aggatataag atatatctac tactcggcta ttgatgttgg agcacgccgt gttaatctgg    720

caatagtttc cagacaaaga gcggataatg tttatgtctt gcgtccgaca actgtcgcat    780

ctcgccccgt cattggcatc ggactgggta atgatgtttt tctgacagcg cacgcactgg    840

ctagtggagg tccggatgct gcagctattg tcagggttac cattaatttt tttagacaac    900

ctcagatgcg gcatttatcc tggtttcttg ccggggattt taatcgcagc ccagacagac    960

ttgaaaatga cctgatgact gagcatctgg aacgagttgt agccgtactc gcacctacag   1020

aacccacgca aattagcggt ggtattttag attatggggt cattgtcgat cgagcacctt   1080
```

-continued attcacaaag ggtcgaagca ttacgtaatc cacaactcgc ttctgatcat tatcccgtag 1140 ccttttggc acgaagctgt ataccaggtg attataaaga tgacgatgac aaaggcggtg 1200
gcggtagcgg cggtggcggt tctggcggtg gcggtagtaa gcttgggtct agataggtcg 1260
acgtacagga gagtagtatg tatataaata agtttgtgcc tgtttataca ttattaattc 1320
tcatttattc ttttaatgcc agcgctgagt ggacaggaga taatacgaac gcctattact 1380
cagacgaagt tatcagtgaa ttacatgttg gtcagataga tactagtcct tatttttgca 1440
taaaaacggt taaagctaac ggtagtggta caccagttgt tgcatgtgcg gtatcaaagc 1500
agagcatatg ggcgccctcc tttaaagaac ttcttgatca ggcaagatat ttttacagta 1560
cagggcaatc cgtaaggatt catgttcaaa aaaatatctg gacctatccg ctttttgtta 1620 atacctttc agcaaatgct cttgtgggac tatcatcgtg cagtgcgaca caatgctttg 1680
gacccaagta agaggggaga agaaataatg aaaaagttaa tattcttaac cttatctata 1740
gttagcttta ataactatgc tgtagatttt gtgtatcgtg tggactcaac cccgccggac 1800
gttatttttc gcgatgggtt ttcactactt gggtataacc gtaactttca gcaatttatt 1860
agtggaaggt catgtagtgg tggaagtagt gacagtcgct atattgcaac aacctcaagt 1920
gttaatcaaa catatgctat agccagagcg tactattctc gctcaacatt caaaggtaat 1980
ttatacagat atcagattcg tgcagataat aatttctaca gcttgctccc atccatcacc 2040
tatctggaaa cgcaaggtgg tcactttaat gcttatgaaa aaacgatgat gcgattgcaa 2100
agagagtatg tttccacatt atctatttta cccgagaata ttcaaaaggc cgtggcgcta 2160
gtttatgata gcgcaaccgg tctggtaaag gatggtgtaa gcacaatgaa tgccagttat 2220
ttaggtttaa gcactacgtc taatcctggt gtgatacctt ttcttccgga accgcagacg 2280
tatacccaac aacgaattga tgcattcggc ccattaataa gttcatgctt ttcaataggt 2340
agcgtatgtc agtcacatcg agggcaaaga gctgacgtat acaacatgtc tttttatgat 2400
gcaagacctg taatagaact tatactttct aaataaatga aacttaccta tgttgccgca 2460
tgcaagctag cttggctgtt ttggcggatg agagaagatt ttcagcctga tacagattaa 2520
atcagaacgc agaagcggtc tgataaaaca gaatttgcct ggcggcagta gcgcggtggt 2580
cccacctgac cccatgccga actcagaagt gaaacgccgt agcgccgatg gtagtgtggg 2640
gtctccccat gcgagagtag ggaactgcca ggcatcaaat aaaacgaaag gctcagtcga 2700
aagactgggc ctttcgtttt atctgttgtt tgtcggtgaa cgctctcctg agtaggacaa 2760
atccgccggg agcggatttg aacgttgcga agcaacggcc cggagggtgg cgggcaggac 2820
gcccgccata aactgccagg catcaaatta agcagaaggc catcctgacg gatggccttt 2880
ttgcgtttct acaaactctt tttgtttatt tttctaaata cattcaaata tgtatccgct 2940
catgagacaa taaccctgat aaatgcttca ataatattga aaaaggaaga gtatgagtat 3000
tcaacatttc cgtgtcgccc ttattccctt ttttgcggca ttttgccttc ctgtttttgc 3060
tcacccagaa acgctggtga aagtaaaaga tgctgaagat cagttgggtg cacgagtggg 3120
ttacatcgaa ctggatctca acagcggtaa gatccttgag agttttcgcc ccgaagaacg 3180
ttttccaatg atgagcactt ttaaagttct gctatgtggc gcggtattat cccgtgttga 3240
cgccgggcaa gagcaactcg gtcgccgcat acactattct cagaatgact tggttgagta 3300
ctcaccagtc acagaaaagc atcttacgga tggcatgaca gtaagagaat tatgcagtgc 3360
tgccataacc atgagtgata acactgcggc caacttactt ctgacaacga tcggaggacc 3420
gaaggagcta accgcttttt tgcacaacat gggggatcat gtaactcgcc ttgatcgttg 3480

```
ggaaccggag ctgaatgaag ccataccaaa cgacgagcgt gacaccacga tgcctacagc   3540

aatggcaaca acgttgcgca aactattaac tggcgaacta cttactctag cttcccggca   3600

acaattaata gactggatgg aggcggataa agttgcagga ccacttctgc gctcggccct   3660

tccggctggc tggtttattg ctgataaatc tggagccggt gagcgtgggt ctcgcggtat   3720

cattgcagca ctggggccag atggtaagcc ctcccgtatc gtagttatct acacgacggg   3780

gagtcaggca actatggatg aacgaaatag acagatcgct gagataggtg cctcactgat   3840

taagcattgg taactgtcag accaagttta ctcatatata ctttagattg atttaaaact   3900

tcatttttaa tttaaaagga tctaggtgaa gatccttttt gataatctca tgaccaaaat   3960

cccttaacgt gagttttcgt tccactgagc gtcagacccc gtagaaaaga tcaaaggatc   4020

ttcttgagat cctttttttc tgcgcgtaat ctgctgcttg caaacaaaaa aaccaccgct   4080

accagcggtg gtttgtttgc cggatcaaga gctaccaact ctttttccga aggtaactgg   4140

cttcagcaga gcgcagatac caaatactgt ccttctagtg tagccgtagt taggccacca   4200

cttcaagaac tctgtagcac cgcctacata cctcgctctg ctaatcctgt taccagtggc   4260

tgctgccagt ggcgataagt cgtgtcttac cgggttggac tcaagacgat agttaccgga   4320

taaggcgcag cggtcgggct gaacgggggg ttcgtgcaca cagcccagct tggagcgaac   4380

gacctacacc gaactgagat acctacagcg tgagctatga gaaagcgcca cgcttcccga   4440

agggagaaag gcggacaggt atccggtaag cggcagggtc ggaacaggag agcgcacgag   4500

ggagcttcca gggggaaacg cctggtatct ttatagtcct gtcgggtttc gccacctctg   4560

acttgagcgt cgatttttgt gatgctcgtc aggggggcgg agcctatgga aaaacgccag   4620

caacgcggcc tttttacggt tcctggcctt ttgctggcct tttgctcaca tgttctttcc   4680

tgcgttatcc cctgattctg tggataaccg tattaccgcc tttgagtgag ctgataccgc   4740

tcgccgcagc cgaacgaccg agcgcagcga gtcagtgagc gaggaagcgg aagagcgcct   4800

gatgcggtat tttctcctta cgcatctgtg cggtatttca caccgcatat g            4851
```

<210> SEQ ID NO 10
<211> LENGTH: 5250
<212> TYPE: DNA
<213> ORGANISM: Artificial Sequence
<220> FEATURE:
<223> OTHER INFORMATION: arabinose inducible plasmid expressing the TAT-apoptin construct as a cldtB fusion, with TAT-apoptin inserted in-frame within the HindIII and XbaI sites introduced into typhoid toxin cldtB, with the TAT-apoptin coding sequence from 1245-1646

<400> SEQUENCE: 10

```
gggggcggcc gcaagaaacc aattgtccat attgcatcag acattgccgt cactgcgtct     60

tttactggct cttctcgcta accaaaccgg taaccccgct tattaaaagc attctgtaac    120

aaagcgggac caaagccatg acaaaaaacgc gtaacaaaag tgtctataat cacggcagaa    180

aagtccacat tgattatttg cacggcgtca cactttgcta tgccatagca tttttatcca    240

taagattagc ggatcctacc tgacgctttt tatcgcaact ctctactgtt tctccatacc    300

cgtttttttg ggctagcgaa ttcgagctcg gtacccagga ggaattcacc atggtcaaaa    360

aacctgtttt tttccttctg accatgatca tctgcagcta tatttctttt gcctgcgcta    420

atatcagtga ctacaaagtt atgacctgga atcttcaggg ctcttcagca tctacagaaa    480

gtaaatggaa tgtcaatgtc agacagcttt taagcggtac tgccggtgtg gatattctta    540

tggtacagga ggccggtgct gttcccacct cagcggttcc taccggacga catattcagc    600
```

-continued

```
cttttggagt gggtattccc attgatgaat acacctggaa tctcggaacc accagccgtc    660
aggatataag atatatctac tactcggcta ttgatgttgg agcacgccgt gttaatctgg    720
caatagtttc cagacaaaga gcggataatg tttatgtctt gcgtccgaca actgtcgcat    780
ctcgccccgt cattggcatc ggactgggta atgatgtttt tctgacagcg cacgcactgg    840
ctagtggagg tccggatgct gcagctattg tcagggttac cattaatttt tttagacaac    900
ctcagatgcg gcatttatcc tggtttcttg ccggggattt taatcgcagc ccagacagac    960
ttgaaaatga cctgatgact gagcatctgg aacgagttgt agccgtactc gcacctacag   1020
aacccacgca aattagcggt ggtattttag attatggggt cattgtcgat cgagcacctt   1080
attcacaaag ggtcgaagca ttacgtaatc cacaactcgc ttctgatcat tatcccgtag   1140
ccttttggc acgaagctgt ataccaggtg attataaaga tgacgatgac aaaggcggtg   1200
gcggtagcgg cggtggcggt tctggcggtg gcggtagtaa gcttatggca tacggtcgca   1260
agaaacgtcg tcaacgccgc cgcatgaacg ccctgcaaga agacacgccg ccgggtccga   1320
gcacggtttt tcgtccgccg accagctctc gcccgctgga aacgccgcat tgccgtgaaa   1380
ttcgcatcgg cattgcaggt atcaccatta cgctgtctct gtgcggctgt gcaaacgcac   1440
gtgcaccgac cctgcgctcc gctacggcgg ataacagtga atccaccggt tttaaaaatg   1500
tgccggatct gcgtacggac cagccgaagc cgccgtcaaa aaagcgttcg tgtgacccga   1560
gcgaatatcg cgttagcgaa ctgaaagaat ctctgattac cacgaccccg tcccgtccgc   1620
gcaccgcaaa acgccgcatc cgtctgtcta gataggtcga cgtacaggag agtagtatgt   1680
atataaataa gtttgtgcct gtttatacat tattaattct catttattct tttaatgcca   1740
gcgctgagtg gacaggagat aatacgaacg cctattactc agacgaagtt atcagtgaat   1800
tacatgttgg tcagatagat actagtcctt atttttgcat aaaaacggtt aaagctaacg   1860
gtagtggtac accagttgtt gcatgtgcgg tatcaaagca gagcatatgg gcgccctcct   1920
ttaaagaact tcttgatcag gcaagatatt tttacagtac agggcaatcc gtaaggattc   1980
atgttcaaaa aaatatctgg acctatccgc tttttgttaa taccttttca gcaaatgctc   2040
ttgtgggact atcatcgtgc agtgcgacac aatgctttgg acccaagtaa gaggggagaa   2100
gaaataatga aaaagttaat attcttaacc ttatctatag ttagctttaa taactatgct   2160
gtagattttg tgtatcgtgt ggactcaacc ccgccggacg ttatttttcg cgatgggttt   2220
tcactacttg ggtataaccg taactttcag caatttatta gtggaaggtc atgtagtggt   2280
ggaagtagtg acagtcgcta tattgcaaca acctcaagtg ttaatcaaac atatgctata   2340
gccagagcgt actattctcg ctcaacattc aaaggtaatt tatacagata tcagattcgt   2400
gcagataata atttctacag cttgctccca tccatcacct atctggaaac gcaaggtggt   2460
cactttaatg cttatgaaaa aacgatgatg cgattgcaaa gagagtatgt ttccacatta   2520
tctattttac ccgagaatat tcaaaaggcc gtggcgctag tttatgatag cgcaaccggt   2580
ctggtaaagg atggtgtaag cacaatgaat gccagttatt taggtttaag cactacgtct   2640
aatcctggtg tgatacctt tcttccggaa ccgcagacgt atacccaaca acgaattgat   2700
gcattcggcc cattaataag ttcatgcttt tcaataggta gcgtatgtca gtcacatcga   2760
gggcaaagag ctgacgtata caacatgtct tttatgatg caagacctgt aatagaactt   2820
atactttcta aataaatgaa acttacctat gttgccgcat gcaagctagc ttggctgttt   2880
tggcggatga gagaagattt tcagcctgat acagattaaa tcagaacgca gaagcggtct   2940
```

-continued

```
gataaaacag aatttgcctg gcggcagtag cgcggtggtc ccacctgacc ccatgccgaa   3000
ctcagaagtg aaacgccgta gcgccgatgg tagtgtgggg tctccccatg cgagagtagg   3060
gaactgccag gcatcaaata aaacgaaagg ctcagtcgaa agactgggcc tttcgtttta   3120
tctgttgttt gtcggtgaac gctctcctga gtaggacaaa tccgccggga gcggatttga   3180
acgttgcgaa gcaacggccc ggagggtggc gggcaggacg cccgccataa actgccaggc   3240
atcaaattaa gcagaaggcc atcctgacgg atggcctttt tgcgtttcta caaactcttt   3300
ttgtttattt ttctaaatac attcaaatat gtatccgctc atgagacaat aaccctgata   3360
aatgcttcaa taatattgaa aaaggaagag tatgagtatt caacatttcc gtgtcgccct   3420
tattcccttt tttgcggcat tttgccttcc tgtttttgct cacccagaaa cgctggtgaa   3480
agtaaaagat gctgaagatc agttgggtgc acgagtgggt tacatcgaac tggatctcaa   3540
cagcggtaag atccttgaga gttttcgccc cgaagaacgt tttccaatga tgagcacttt   3600
taaagttctg ctatgtggcg cggtattatc ccgtgttgac gccgggcaag agcaactcgg   3660
tcgccgcata cactattctc agaatgactt ggttgagtac tcaccagtca cagaaaagca   3720
tcttacggat ggcatgacag taagagaatt atgcagtgct gccataacca tgagtgataa   3780
cactgcggcc aacttacttc tgacaacgat cggaggaccg aaggagctaa ccgctttttt   3840
gcacaacatg ggggatcatg taactcgcct tgatcgttgg gaaccggagc tgaatgaagc   3900
cataccaaac gacgagcgtg acaccacgat gcctacagca atggcaacaa cgttgcgcaa   3960
actattaact ggcgaactac ttactctagc ttcccggcaa caattaatag actggatgga   4020
ggcggataaa gttgcaggac cacttctgcg ctcggccctt ccggctggct ggtttattgc   4080
tgataaatct ggagccggtg agcgtgggtc tcgcggtatc attgcagcac tggggccaga   4140
tggtaagccc tcccgtatcg tagttatcta cacgacgggg agtcaggcaa ctatggatga   4200
acgaaataga cagatcgctg agataggtgc ctcactgatt aagcattggt aactgtcaga   4260
ccaagtttac tcatatatac tttagattga tttaaaactt catttttaat ttaaaaggat   4320
ctaggtgaag atcctttttg ataatctcat gaccaaaatc ccttaacgtg agttttcgtt   4380
ccactgagcg tcagaccccg tagaaaagat caaaggatct tcttgagatc cttttttttct   4440
gcgcgtaatc tgctgcttgc aaacaaaaaa accaccgcta ccagcggtgg tttgtttgcc   4500
ggatcaagag ctaccaactc tttttccgaa ggtaactggc ttcagcagag cgcagatacc   4560
aaatactgtc cttctagtgt agccgtagtt aggccaccac ttcaagaact ctgtagcacc   4620
gcctacatac ctcgctctgc taatcctgtt accagtggct gctgccagtg gcgataagtc   4680
gtgtcttacc gggttggact caagacgata gttaccggat aaggcgcagc ggtcgggctg   4740
aacggggggt tcgtgcacac agcccagctt ggagcgaacg acctacaccg aactgagata   4800
cctacagcgt gagctatgag aaagcgccac gcttcccgaa gggagaaagg cggacaggta   4860
tccggtaagc ggcagggtcg gaacaggaga gcgcacgagg gagcttccag ggggaaacgc   4920
ctggtatctt tatagtcctg tcgggtttcg ccacctctga cttgagcgtc gatttttgtg   4980
atgctcgtca ggggggcgga gcctatggaa aaacgccagc aacgcggcct ttttacggtt   5040
cctggccttt tgctggcctt ttgctcacat gttctttcct gcgttatccc ctgattctgt   5100
ggataaccgt attaccgcct ttgagtgagc tgataccgct cgccgcagcc gaacgaccga   5160
gcgcagcgag tcagtgagcg aggaagcgga agagcgcctg atgcggtatt ttctccttac   5220
gcatctgtgc ggtatttcac accgcatatg                                    5250
```

-continued

<210> SEQ ID NO 11
<211> LENGTH: 39
<212> TYPE: DNA
<213> ORGANISM: Artificial Sequence
<220> FEATURE:
<223> OTHER INFORMATION: paratyphi A NcoI_F1

<400> SEQUENCE: 11
tacgccatgg tcaaaaaacc tgttttttc cttctgacc 39

<210> SEQ ID NO 12
<211> LENGTH: 43
<212> TYPE: DNA
<213> ORGANISM: Artificial Sequence
<220> FEATURE:
<223> OTHER INFORMATION: PCR primer HindIII_Xbal Clal-R1

<400> SEQUENCE: 12
cgatccctct agacccaagc ttgtcactga tattagcgca ggc 43

<210> SEQ ID NO 13
<211> LENGTH: 49
<212> TYPE: DNA
<213> ORGANISM: Artificial Sequence
<220> FEATURE:
<223> OTHER INFORMATION: PCR primer HindIII_Xbal_Clal-F1

<400> SEQUENCE: 13
gcttgggtct agagggatcg attacaaagt tatgacctgg aatcttcag 49

<210> SEQ ID NO 14
<211> LENGTH: 39
<212> TYPE: DNA
<213> ORGANISM: Artificial Sequence
<220> FEATURE:
<223> OTHER INFORMATION: PCR primer cldtB_stop_Xbal_Sall-R1

<400> SEQUENCE: 14
gatcgtcgac ttatctagat cattaacagc ttcgtgcca 39

<210> SEQ ID NO 15
<211> LENGTH: 4794
<212> TYPE: DNA
<213> ORGANISM: Artificial Sequence
<220> FEATURE:
<223> OTHER INFORMATION: 13-350 = arabinose promoter; 351-1187 = cldtB;
1210-1213 =RBS pltB; 1221-1634 = pltB; 1651-2379 = pltA

<400> SEQUENCE: 15
gggggcggcc gcaagaaacc aattgtccat attgcatcag acattgccgt cactgcgtct 60
tttactggct cttctcgcta accaaaccgg taaccccgct tattaaaagc attctgtaac 120
aaagcgggac caaagccatg acaaaaacgc gtaacaaaag tgtctataat cacggcagaa 180
aagtccacat tgattatttg cacggcgtca cactttgcta tgccatagca tttttatcca 240
taagattagc ggatcctacc tgacgctttt tatcgcaact ctctactgtt tctccatacc 300
cgtttttttg ggctagcgaa ttcgagctcg gtacccagga ggaattcacc atggtcaaaa 360
aacctgtttt tttccttctg accatgatca tctgcagcta tatttctttt gcctgcgcta 420
atatcagtga caagcttggg tctagaggga tcgattacaa agttatgacc tggaatcttc 480
agggctcttc agcatctaca gaaagtaaat ggaatgtcaa tgtcagacag cttttaagcg 540
gtactgccgg tgtggatatt cttatggtac aggaggccgg tgctgttccc acctcagcgg 600
ttcctaccgg acgacatatt cagccttttg gagtgggtat tcccattgat gaatacacct 660

-continued

```
ggaatctcgg aaccaccagc cgtcaggata taagatatat ctactactcg gctattgatg    720
ttggagcacg ccgtgttaat ctggcaatag tttccagaca aagagcggat aatgtttatg    780
tcttgcgtcc gacaactgtc gcatctcgcc ccgtcattgg catcggactg ggtaatgatg    840
tttttctgac agcgcacgca ctggctagtg gaggtccgga tgctgcagct attgtcaggg    900
ttaccattaa tttttttaga caacctcaga tgcggcattt atcctggttt cttgccgggg    960
attttaatcg cagcccagac agacttgaaa atgacctgat gactgagcat ctggaacgag   1020
ttgtagccgt actcgcacct acagaaccca cgcaaattag cggtggtatt ttagattatg   1080
gggtcattgt cgatcgagca ccttattcac aaagggtcga agcattacgt aatccacaac   1140
tcgcttctga tcattatccc gtagcctttt tggcacgaag ctgttaatga tctagataag   1200
tcgacgtaca ggagagtagt atgtatataa ataagtttgt gcctgtttat acattattaa   1260
ttctcattta ttcttttaat gccagcgctg agtggacagg agataatacg aacgcctatt   1320
actcagacga agttatcagt gaattacatg ttggtcagat agatactagt ccttattttt   1380
gcataaaaac ggttaaagct aacggtagtg gtacaccagt tgttgcatgt gcggtatcaa   1440
agcagagcat atgggcgccc tcctttaaag aacttcttga tcaggcaaga tatttttaca   1500
gtacagggca atccgtaagg attcatgttc aaaaaaatat ctggacctat ccgctttttg   1560
ttaatacctt ttcagcaaat gctcttgtgg gactatcatc gtgcagtgcg acacaatgct   1620
ttggacccaa gtaagagggg agaagaaata atgaaaaagt taatattctt aaccttatct   1680
atagttagct ttaataacta tgctgtagat tttgtgtatc gtgtggactc aaccccgccg   1740
gacgttattt ttcgcgatgg gttttcacta cttgggtata accgtaactt tcagcaattt   1800
attagtggaa ggtcatgtag tggtggaagt agtgacagtc gctatattgc aacaacctca   1860
agtgttaatc aaacatatgc tatagccaga gcgtactatt ctcgctcaac attcaaaggt   1920
aatttataca gatatcagat tcgtgcagat aataatttct acagcttgct cccatccatc   1980
acctatctgg aaacgcaagg tggtcacttt aatgcttatg aaaaaacgat gatgcgattg   2040
caaagagagt atgtttccac attatctatt ttacccgaga atattcaaaa ggccgtggcg   2100
ctagtttatg atagcgcaac cggtctggta aaggatggtg taagcacaat gaatgccagt   2160
tatttaggtt taagcactac gtctaatcct ggtgtgatac cttttcttcc ggaaccgcag   2220
acgtataccc aacaacgaat tgatgcattc ggcccattaa taagttcatg cttttcaata   2280
ggtagcgtat gtcagtcaca tcgagggcaa agagctgacg tatacaacat gtctttttat   2340
gatgcaagac ctgtaataga acttatactt tctaaataaa tgaaacttac ctatgttgcc   2400
gcatgcaagc tagcttggct gttttggcgg atgagagaag attttcagcc tgatacagat   2460
taaatcagaa cgcagaagcg gtctgataaa acagaatttg cctggcggca gtagcgcggt   2520
ggtcccacct gaccccatgc cgaactcaga agtgaaacgc cgtagcgccg atggtagtgt   2580
ggggtctccc catgcgagag tagggaactg ccaggcatca aataaaacga aaggctcagt   2640
cgaaagactg ggcctttcgt tttatctgtt gtttgtcggt gaacgctctc ctgagtagga   2700
caaatccgcc gggagcggat ttgaacgttg cgaagcaacg gcccggaggg tggcgggcag   2760
gacgcccgcc ataaactgcc aggcatcaaa ttaagcagaa ggccatcctg acggatggcc   2820
tttttgcgtt tctacaaact ctttttgttt atttttctaa atacattcaa atatgtatcc   2880
gctcatgaga caataaccct gataaatgct tcaataatat tgaaaaagga agagtatgag   2940
tattcaacat ttccgtgtcg cccttattcc cttttttgcg gcattttgcc ttcctgtttt   3000
```

tgctcaccca gaaacgctgg tgaaagtaaa agatgctgaa gatcagttgg gtgcacgagt 3060
gggttacatc gaactggatc tcaacagcgg taagatcctt gagagttttc gccccgaaga 3120
acgttttcca atgatgagca cttttaaagt tctgctatgt ggcgcggtat tatcccgtgt 3180
tgacgccggg caagagcaac tcggtcgccg catacactat tctcagaatg acttggttga 3240
gtactcacca gtcacagaaa agcatcttac ggatggcatg acagtaagag aattatgcag 3300
tgctgccata accatgagtg ataacactgc ggccaactta cttctgacaa cgatcggagg 3360
accgaaggag ctaaccgctt ttttgcacaa catgggggat catgtaactc gccttgatcg 3420
ttgggaaccg gagctgaatg aagccatacc aaacgacgag cgtgacacca cgatgcctac 3480
agcaatggca acaacgttgc gcaaactatt aactggcgaa ctacttactc tagcttcccg 3540
gcaacaatta atagactgga tggaggcgga taaagttgca ggaccacttc tgcgctcggc 3600
ccttccggct ggctggttta ttgctgataa atctggagcc ggtgagcgtg ggtctcgcgg 3660
tatcattgca gcactggggc cagatggtaa gccctcccgt atcgtagtta tctacacgac 3720
ggggagtcag gcaactatgg atgaacgaaa tagacagatc gctgagatag gtgcctcact 3780
gattaagcat tggtaactgt cagaccaagt ttactcatat atactttaga ttgatttaaa 3840
acttcatttt taatttaaaa ggatctaggt gaagatcctt tttgataatc tcatgaccaa 3900
aatcccttaa cgtgagtttt cgttccactg agcgtcagac cccgtagaaa agatcaaagg 3960
atcttcttga gatccttttt ttctgcgcgt aatctgctgc ttgcaaacaa aaaaaccacc 4020
gctaccagcg gtggtttgtt tgccggatca agagctacca actctttttc cgaaggtaac 4080
tggcttcagc agagcgcaga taccaaatac tgtccttcta gtgtagccgt agttaggcca 4140
ccacttcaag aactctgtag caccgcctac atacctcgct ctgctaatcc tgttaccagt 4200
ggctgctgcc agtggcgata agtcgtgtct taccgggttg gactcaagac gatagttacc 4260
ggataaggcg cagcggtcgg gctgaacggg gggttcgtgc acacagccca gcttggagcg 4320
aacgacctac accgaactga gatacctaca gcgtgagcta tgagaaagcg ccacgcttcc 4380
cgaagggaga aaggcggaca ggtatccggt aagcggcagg gtcggaacag gagagcgcac 4440
gagggagctt ccagggggaa acgcctggta tctttatagt cctgtcgggt ttcgccacct 4500
ctgacttgag cgtcgatttt tgtgatgctc gtcagggggg cggagcctat ggaaaaacgc 4560
cagcaacgcg gcctttttac ggttcctggc cttttgctgg ccttttgctc acatgttctt 4620
tcctgcgtta tcccctgatt ctgtggataa ccgtattacc gcctttgagt gagctgatac 4680
cgctcgccgc agccgaacga ccgagcgcag cgagtcagtg agcgaggaag cggaagagcg 4740
cctgatgcgg tattttctcc ttacgcatct gtgcggtatt tcacaccgca tatg 4794

<210> SEQ ID NO 16
<211> LENGTH: 4902
<212> TYPE: DNA
<213> ORGANISM: Artificial Sequence
<220> FEATURE:
<223> OTHER INFORMATION: 13-350 = arabinose promoter; 351-1295 = cldtB; 1318-1321 =RBS pltB; 1329-1742 = pltB; 1759-2487 = pltA

<400> SEQUENCE: 16
gggggcggcc gcaagaaacc aattgtccat attgcatcag acattgccgt cactgcgtct 60
tttactggct cttctcgcta accaaaccgg taaccccgct tattaaaagc attctgtaac 120
aaagcgggac caaagccatg acaaaaacgc gtaacaaaag tgtctataat cacggcagaa 180
aagtccacat tgattatttg cacggcgtca cactttgcta tgccatagca tttttatcca 240

-continued

```
taagattagc ggatcctacc tgacgctttt tatcgcaact ctctactgtt tctccatacc    300
cgttttttttg ggctagcgaa ttcgagctcg gtacccagga ggaattcacc atggtcaaaa    360
aacctgtttt tttccttctg accatgatca tctgcagcta tatttctttt gcctgcgcta    420
atatcagtga caagcttggg tctagagact acaaagacca tgacggtgat tataaagatc    480
atgatatcga ctacaaagat gacgacgata aaggcggtgg cggatccggc ggtggcggtt    540
ctggcggtgg cggtagtatc gattacaaag ttatgacctg gaatcttcag ggctcttcag    600
catctacaga aagtaaatgg aatgtcaatg tcagacagct tttaagcggt actgccggtg    660
tggatattct tatggtacag gaggccggtg ctgttcccac ctcagcggtt cctaccggac    720
gacatattca gccttttgga gtgggtattc ccattgatga atacacctgg aatctcggaa    780
ccaccagccg tcaggatata agatatatct actactcggc tattgatgtt ggagcacgcc    840
gtgttaatct ggcaatagtt tccagacaaa gagcggataa tgtttatgtc ttgcgtccga    900
caactgtcgc atctcgcccc gtcattggca tcggactggg taatgatgtt tttctgacag    960
cgcacgcact ggctagtgga ggtccggatg ctgcagctat tgtcagggtt accattaatt   1020
tttttagaca acctcagatg cggcatttat cctggtttct tgccggggat tttaatcgca   1080
gcccagacag acttgaaaat gacctgatga ctgagcatct ggaacgagtt gtagccgtac   1140
tcgcacctac agaacccacg caaattagcg gtggtatttt agattatggg gtcattgtcg   1200
atcgagcacc ttattcacaa agggtcgaag cattacgtaa tccacaactc gcttctgatc   1260
attatcccgt agccttttttg gcacgaagct gttaatgatc tagataagtc gacgtacagg   1320
agagtagtat gtatataaat aagtttgtgc ctgtttatac attattaatt ctcatttatt   1380
cttttaatgc cagcgctgag tggacaggag ataatacgaa cgcctattac tcagacgaag   1440
ttatcagtga attacatgtt ggtcagatag atactagtcc ttatttttgc ataaaaaacgg   1500
ttaaagctaa cggtagtggt acaccagttg ttgcatgtgc ggtatcaaag cagagcatat   1560
gggcgccctc ctttaaagaa cttcttgatc aggcaagata tttttacagt acagggcaat   1620
ccgtaaggat tcatgttcaa aaaaatatct ggacctatcc gctttttgtt aatacctttt   1680
cagcaaatgc tcttgtggga ctatcatcgt gcagtgcgac acaatgcttt ggacccaagt   1740
aagaggggag aagaaataat gaaaaagtta atattcttaa ccttatctat agttagcttt   1800
aataactatg ctgtagattt tgtgtatcgt gtggactcaa ccccgccgga cgttattttt   1860
cgcgatgggt tttcactact tgggtataac cgtaactttc agcaatttat tagtggaagg   1920
tcatgtagtg gtggaagtag tgacagtcgc tatattgcaa caacctcaag tgttaatcaa   1980
acatatgcta tagccagagc gtactattct cgctcaacat tcaaaggtaa tttatacaga   2040
tatcagattc gtgcagataa taatttctac agcttgctcc catccatcac ctatctggaa   2100
acgcaaggtg gtcactttaa tgcttatgaa aaaacgatga tgcgattgca aagagagtat   2160
gtttccacat tatctatttt acccgagaat attcaaaagg ccgtggcgct agtttatgat   2220
agcgcaaccg gtctggtaaa ggatggtgta agcacaatga atgccagtta tttaggttta   2280
agcactacgt ctaatcctgg tgtgatacct ttttcttccgg aaccgcagac gtatacccaa   2340
caacgaattg atgcattcgg cccattaata agttcatgct tttcaatagg tagcgtatgt   2400
cagtcacatc gagggcaaag agctgacgta tacaacatgt ctttttatga tgcaagacct   2460
gtaatagaac ttatactttc taaataaatg aaacttacct atgttgccgc atgcaagcta   2520
gcttggctgt tttggcggat gagagaagat tttcagcctg atacagatta aatcagaacg   2580
cagaagcggt ctgataaaac agaatttgcc tggcggcagt agcgcggtgg tcccacctga   2640
```

```
ccccatgccg aactcagaag tgaaacgccg tagcgccgat ggtagtgtgg ggtctcccca   2700
tgcgagagta gggaactgcc aggcatcaaa taaaacgaaa ggctcagtcg aaagactggg   2760
cctttcgttt tatctgttgt ttgtcggtga acgctctcct gagtaggaca aatccgccgg   2820
gagcggattt gaacgttgcg aagcaacggc ccggagggtg gcgggcagga cgcccgccat   2880
aaactgccag gcatcaaatt aagcagaagg ccatcctgac ggatggcctt tttgcgtttc   2940
tacaaactct ttttgtttat ttttctaaat acattcaaat atgtatccgc tcatgagaca   3000
ataaccctga taaatgcttc aataatattg aaaaaggaag agtatgagta ttcaacattt   3060
ccgtgtcgcc cttattccct tttttgcggc attttgcctt cctgtttttg ctcacccaga   3120
aacgctggtg aaagtaaaag atgctgaaga tcagttgggt gcacgagtgg gttacatcga   3180
actggatctc aacagcggta agatccttga gagttttcgc cccgaagaac gttttccaat   3240
gatgagcact tttaaagttc tgctatgtgg cgcggtatta tcccgtgttg acgccgggca   3300
agagcaactc ggtcgccgca tacactattc tcagaatgac ttggttgagt actcaccagt   3360
cacagaaaag catcttacgg atggcatgac agtaagagaa ttatgcagtg ctgccataac   3420
catgagtgat aacactgcgg ccaacttact tctgacaacg atcggaggac cgaaggagct   3480
aaccgctttt ttgcacaaca tgggggatca tgtaactcgc cttgatcgtt gggaaccgga   3540
gctgaatgaa gccataccaa acgacgagcg tgacaccacg atgcctacag caatggcaac   3600
aacgttgcgc aaactattaa ctggcgaact acttactcta gcttcccggc aacaattaat   3660
agactggatg gaggcggata aagttgcagg accacttctg cgctcggccc ttccggctgg   3720
ctggtttatt gctgataaat ctggagccgg tgagcgtggg tctcgcggta tcattgcagc   3780
actggggcca gatggtaagc cctcccgtat cgtagttatc tacacgacgg ggagtcaggc   3840
aactatggat gaacgaaata gacagatcgc tgagataggt gcctcactga ttaagcattg   3900
gtaactgtca gaccaagttt actcatatat actttagatt gatttaaaac ttcattttta   3960
atttaaaagg atctaggtga agatcctttt tgataatctc atgaccaaaa tcccttaacg   4020
tgagttttcg ttccactgag cgtcagaccc cgtagaaaag atcaaaggat cttcttgaga   4080
tccttttttt ctgcgcgtaa tctgctgctt gcaaacaaaa aaaccaccgc taccagcggt   4140
ggtttgtttg ccggatcaag agctaccaac tctttttccg aaggtaactg gcttcagcag   4200
agcgcagata ccaaatactg tccttctagt gtagccgtag ttaggccacc acttcaagaa   4260
ctctgtagca ccgcctacat acctcgctct gctaatcctg ttaccagtgg ctgctgccag   4320
tggcgataag tcgtgtctta ccgggttgga ctcaagacga tagttaccgg ataaggcgca   4380
gcggtcgggc tgaacggggg gttcgtgcac acagcccagc ttggagcgaa cgacctacac   4440
cgaactgaga tacctacagc gtgagctatg agaaagcgcc acgcttcccg aagggagaaa   4500
ggcggacagg tatccggtaa gcggcagggt cggaacagga gagcgcacga gggagcttcc   4560
agggggaaac gcctggtatc tttatagtcc tgtcgggttt cgccacctct gacttgagcg   4620
tcgatttttg tgatgctcgt caggggggcg gagcctatgg aaaaacgcca gcaacgcggc   4680
ctttttacgg ttcctggcct tttgctggcc ttttgctcac atgttctttc ctgcgttatc   4740
ccctgattct gtggataacc gtattaccgc ctttgagtga gctgataccg ctcgccgcag   4800
ccgaacgacc gagcgcagcg agtcagtgag cgaggaagcg gaagagcgcc tgatgcggta   4860
ttttctcctt acgcatctgt gcggtatttc acaccgcata tg                       4902
```

<210> SEQ ID NO 17

-continued

<211> LENGTH: 3560
<212> TYPE: DNA
<213> ORGANISM: Artificial Sequence
<220> FEATURE:
<223> OTHER INFORMATION: tetracyclin-inducible YebF:SFTI, start codon begins at 724 and the stop codon ends at 1158

<400> SEQUENCE: 17
atatgggggc ggccgcctaa gacccacttt cacatttaag ttgtttttct aatccgcata 60
taatcaattc aaggccgaat aagaaggctg gctctgcacc ttggtgttca aataattcga 120
tagcttgtcg taataatgcc ggcatactat cagtagtagg tgtttccctt tcttctttag 180
cgacttgatg ctcttgatct tccaatacgc aacctaaagt aaaatgcccc acagcgctga 240
gtgcatataa tgcattctct agtgaaaaac cttgttggca taaaaaggct aattgatttt 300
cgagagtttc atactgtttt tctgtaggcc gtgtacctaa atgtactttt gctccatcgc 360
gatgacttag taaagcacat ctaaaacttt tagcgttatt acgtaaaaaa tcttgccagc 420
tttccccttc taaagggcaa aagtgagtat ggtgcctatc taacatctca atggctaagg 480
cgtcgagcaa agcccgctta tttttacat gccaatacaa tgtaggctgc tctacaccca 540
gtttctgggc gagtttacgg gtttttaaac cttcgattcc gacctcatta agcagctcta 600
atgcgctgtt aatcacttta cttttatcta atctggacat cataaattcc taatttttgt 660
tgacactcta tcattgatag agttatttta ccactcccta tcagtgatag agaaaagtga 720
accatggcta aaaaaagagg ggcgttttta gggctgttgt tggtttctgc ctgcgcatca 780
gttttcgctg ccaataatga aaccagcaag tcggtcactt tcccaaagtg tgaagatctg 840
gatgctgccg gaattgccgc gagcgtaaaa cgtgattatc aacaaaatcg cgtggcgcgt 900
tgggcagatg atcaaaaaat tgtcggtcag gccgatcccg tggcttgggt cagtttgcag 960
gacattcagg gtaaagatga taaatggtca gtaccgctaa ccgtgcgtgg taaaagtgcc 1020
gatattcatt accaggtcag cgtggactgc aaagcgggaa tggcggaata tcagcggcgt 1080
ctcgaggacg atgacgataa gggtaccctg aaaggccgct gcaccaaaag cattccgccg 1140 atttgcttc cggattagtc tagagtcgac ctgcaggcat gcaagcttgg ctgttttggc 1200
ggatgagaga agattttcag cctgatacag attaaatcag aacgcagaag cggtctgata 1260
aaacagaatt tgcctggcgg cagtagcgcg gtggtcccac ctgaccccat gccgaactca 1320
gaagtgaaac gccgtagcgc cgatggtagt gtggggtctc cccatgcgag agtagggaac 1380
tgccaggcat caaataaaac gaaaggctca gtcgaaagac tgggcctttc gttttatctg 1440
ttgtttgtcg gtgaacgctc tcctgagtag gacaaatccg ccgggagcgg atttgaacgt 1500
tgcgaagcaa cggcccggag ggtggcgggc aggacgcccg ccataaactg ccaggcatca 1560
aattaagcag aaggccatcc tgacggatgg cctttttgcg tttctacaaa ctctttttgt 1620
ttatttttct aaatacattc aaatatgtat ccgctcatga gacaataacc ctgataaatg 1680
cttcaataat attgaaaaag gaagagtatg agtattcaac atttccgtgt cgcccttatt 1740 ccctttttttg cggcattttg ccttcctgtt tttgctcacc cagaaacgct ggtgaaagta 1800
aaagatgctg aagatcagtt gggtgcacga gtgggttaca tcgaactgga tctcaacagc 1860
ggtaagatcc ttgagagttt tcgccccgaa gaacgttttc caatgatgag cacttttaaa 1920
gttctgctat gtggcgcggt attatcccgt gttgacgccg ggcaagagca actcggtcgc 1980
cgcatacact attctcagaa tgacttggtt gagtactcac cagtcacaga aaagcatctt 2040
acggatggca tgacagtaag agaattatgc agtgctgcca taaccatgag tgataacact 2100

-continued

```
gcggccaact tacttctgac aacgatcgga ggaccgaagg agctaaccgc ttttttgcac   2160

aacatggggg atcatgtaac tcgccttgat cgttgggaac cggagctgaa tgaagccata   2220

ccaaacgacg agcgtgacac cacgatgcct acagcaatgg caacaacgtt gcgcaaacta   2280

ttaactggcg aactacttac tctagcttcc cggcaacaat taatagactg gatggaggcg   2340

gataaagttg caggaccact tctgcgctcg gcccttccgg ctggctggtt tattgctgat   2400

aaatctggag ccggtgagcg tgggtctcgc ggtatcattg cagcactggg gccagatggt   2460

aagccctccc gtatcgtagt tatctacacg acggggagtc aggcaactat ggatgaacga   2520

aatagacaga tcgctgagat aggtgcctca ctgattaagc attggtaact gtcagaccaa   2580

gtttactcat atatacttta gattgattta aaacttcatt tttaatttaa aaggatctag   2640

gtgaagatcc tttttgataa tctcatgacc aaaatccctt aacgtgagtt ttcgttccac   2700

tgagcgtcag accccgtaga aaagatcaaa ggatcttctt gagatccttt ttttctgcgc   2760

gtaatctgct gcttgcaaac aaaaaaacca ccgctaccag cggtggtttg tttgccggat   2820

caagagctac caactctttt tccgaaggta actggcttca gcagagcgca gataccaaat   2880

actgtccttc tagtgtagcc gtagttaggc caccacttca agaactctgt agcaccgcct   2940

acatacctcg ctctgctaat cctgttacca gtggctgctg ccagtggcga taagtcgtgt   3000

cttaccgggt tggactcaag acgatagtta ccggataagg cgcagcggtc gggctgaacg   3060

gggggttcgt gcacacagcc cagcttggag cgaacgacct acaccgaact gagataccta   3120

cagcgtgagc tatgagaaag cgccacgctt cccgaaggga gaaaggcgga caggtatccg   3180

gtaagcggca gggtcggaac aggagagcgc acgagggagc ttccaggggg aaacgcctgg   3240

tatctttata gtcctgtcgg gtttcgccac ctctgacttg agcgtcgatt tttgtgatgc   3300

tcgtcagggg ggcggagcct atggaaaaac gccagcaacg cggccttttt acggttcctg   3360

gccttttgct ggccttttgc tcacatgttc tttcctgcgt tatcccctga ttctgtggat   3420

aaccgtatta ccgcctttga gtgagctgat accgctcgcc gcagccgaac gaccgagcgc   3480

agcgagtcag tgagcgagga agcggaagag cgcctgatgc ggtattttct ccttacgcat   3540

ctgtgcggta tttcacaccg                                               3560
```

<210> SEQ ID NO 18
<211> LENGTH: 3249
<212> TYPE: DNA
<213> ORGANISM: Artificial Sequence
<220> FEATURE:
<223> OTHER INFORMATION: tetracycline inducible OmpA:SFTI fusion, start codon begins at 725 and stop codon ends at 1008

<400> SEQUENCE: 18

```
catatggggg cggccgccta agacccactt tcacatttaa gttgtttttc taatccgcat     60

ataatcaatt caaggccgaa taagaaggct ggctctgcac cttggtgttc aaataattcg    120

atagcttgtc gtaataatgc cggcatacta tcagtagtag gtgtttccct ttcttcttta    180

gcgacttgat gctcttgatc ttccaatacg caacctaaag taaaatgccc cacagcgctg    240

agtgcatata atgcattctc tagtgaaaaa ccttgttggc ataaaaaggc taattgattt    300

tcgagagttt catactgttt ttctgtaggc cgtgtaccta aatgtacttt tgctccatcg    360

cgatgactta gtaaagcaca tctaaaactt ttagcgttat tacgtaaaaa atcttgccag    420

ctttcccctt ctaaagggca aaagtgagta tggtgcctat ctaacatctc aatggctaag    480

gcgtcgagca aagcccgctt atttttaca tgccaataca atgtaggctg ctctacaccc     540
```

-continued

```
agtttctggg cgagtttacg ggtttttaaa ccttcgattc cgacctcatt aagcagctct    600
aatgcgctgt taatcacttt acttttatct aatctggaca tcataaattc ctaatttttg    660
ttgacactct atcattgata gagttatttt accactccct atcagtgata gagaaaagtg    720
aaccatggct aaaaagacag ctatcgcgat tgcagtggca ctggctggtt tcgctaccgt    780
agcgcaggcc gctccgaaag atggccgctg caccaaaagc attccgccga tttgctttcc    840
ggattagtct agagtcgacc tgcaggcatg caagcttggc tgttttggcg gatgagagaa    900
gattttcagc ctgatacaga ttaaatcaga acgcagaagc ggtctgataa aacagaattt    960
gcctggcggc agtagcgcgg tggtcccacc tgaccccatg ccgaactcag aagtgaaacg   1020
ccgtagcgcc gatggtagtg tggggtctcc ccatgcgaga gtagggaact gccaggcatc   1080
aaataaaacg aaaggctcag tcgaaagact gggcctttcg ttttatctgt tgtttgtcgg   1140
tgaacgctct cctgagtagg acaaatccgc cgggagcgga tttgaacgtt gcgaagcaac   1200
ggcccggagg gtggcgggca ggacgcccgc cataaactgc caggcatcaa attaagcaga   1260
aggccatcct gacggatggc ctttttgcgt ttctacaaac tctttttgtt tatttttcta   1320
aatacattca aatatgtatc cgctcatgag acaataaccc tgataaatgc ttcaataata   1380
ttgaaaaagg aagagtatga gtattcaaca tttccgtgtc gcccttattc ccttttttgc   1440
ggcattttgc cttcctgttt ttgctcaccc agaaacgctg gtgaaagtaa aagatgctga   1500
agatcagttg ggtgcacgag tgggttacat cgaactggat ctcaacagcg gtaagatcct   1560
tgagagtttt cgccccgaag aacgttttcc aatgatgagc acttttaaag ttctgctatg   1620
tggcgcggta ttatcccgtg ttgacgccgg gcaagagcaa ctcggtcgcc gcatacacta   1680
ttctcagaat gacttggttg agtactcacc agtcacagaa aagcatctta cggatggcat   1740
gacagtaaga gaattatgca gtgctgccat aaccatgagt gataacactg cggccaactt   1800
acttctgaca acgatcggag gaccgaagga gctaaccgct tttttgcaca acatggggga   1860
tcatgtaact cgccttgatc gttgggaacc ggagctgaat gaagccatac caaacgacga   1920
gcgtgacacc acgatgccta cagcaatggc aacaacgttg cgcaaactat taactggcga   1980
actacttact ctagcttccc ggcaacaatt aatagactgg atggaggcgg ataaagttgc   2040
aggaccactt ctgcgctcgg cccttccggc tggctggttt attgctgata aatctggagc   2100
cggtgagcgt gggtctcgcg gtatcattgc agcactgggg ccagatggta agccctcccg   2160
tatcgtagtt atctacacga cggggagtca ggcaactatg gatgaacgaa atagacagat   2220
cgctgagata ggtgcctcac tgattaagca ttggtaactg tcagaccaag tttactcata   2280
tatactttag attgatttaa aacttcattt ttaatttaaa aggatctagg tgaagatcct   2340
ttttgataat ctcatgacca aaatccctta acgtgagttt tcgttccact gagcgtcaga   2400
ccccgtagaa aagatcaaag gatcttcttg agatcctttt tttctgcgcg taatctgctg   2460
cttgcaaaca aaaaaaccac cgctaccagc ggtggtttgt ttgccggatc aagagctacc   2520
aactcttttt ccgaaggtaa ctggcttcag cagagcgcag ataccaaata ctgtccttct   2580
agtgtagccg tagttaggcc accacttcaa gaactctgta gcaccgccta catacctcgc   2640
tctgctaatc ctgttaccag tggctgctgc cagtggcgat aagtcgtgtc ttaccgggtt   2700
ggactcaaga cgatagttac cggataaggc gcagcggtcg ggctgaacgg ggggttcgtg   2760
cacacagccc agcttggagc gaacgaccta caccgaactg agatacctac agcgtgagct   2820
atgagaaagc gccacgcttc ccgaagggag aaaggcggac aggtatccgg taagcggcag   2880
ggtcggaaca ggagagcgca cgagggagct tccaggggga aacgcctggt atctttatag   2940
```

-continued tcctgtcggg tttcgccacc tctgacttga gcgtcgattt ttgtgatgct cgtcaggggg 3000
gcggagccta tggaaaaacg ccagcaacgc ggccttttta cggttcctgg ccttttgctg 3060
gccttttgct cacatgttct ttcctgcgtt atcccctgat tctgtggata accgtattac 3120
cgcctttgag tgagctgata ccgctcgccg cagccgaacg accgagcgca gcgagtcagt 3180
gagcgaggaa gcggaagagc gcctgatgcg gtattttctc cttacgcatc tgtgcggtat 3240
ttcacaccg 3249

<210> SEQ ID NO 19
<211> LENGTH: 3398
<212> TYPE: DNA
<213> ORGANISM: Artificial Sequence
<220> FEATURE:
<223> OTHER INFORMATION: tetracycline inducible OmpA:SFTI fusion, start codon at 725, stop codon at 1008, followed by a Shine Delgarno sequence (RBS) and coding sequence for E3 Lysis sequence, start codon at 865, stop codon at 1008

<400> SEQUENCE: 19
catatggggg cggccgccta agacccactt tcacatttaa gttgtttttc taatccgcat 60
ataatcaatt caaggccgaa taagaaggct ggctctgcac cttggtgttc aaataattcg 120
atagcttgtc gtaataatgc cggcatacta tcagtagtag gtgtttccct ttcttcttta 180
gcgacttgat gctcttgatc ttccaatacg caacctaaag taaaatgccc cacagcgctg 240
agtgcatata atgcattctc tagtgaaaaa ccttgttggc ataaaaaggc taattgattt 300
tcgagagttt catactgttt ttctgtaggc cgtgtaccta aatgtacttt tgctccatcg 360
cgatgactta gtaaagcaca tctaaaactt ttagcgttat tacgtaaaaa atcttgccag 420
ctttcccctt ctaaagggca aaagtgagta tggtgcctat ctaacatctc aatggctaag 480
gcgtcgagca aagcccgctt atttttaca tgccaataca atgtaggctg ctctacaccc 540
agtttctggg cgagtttacg ggtttttaaa ccttcgattc cgacctcatt aagcagctct 600
aatgcgctgt taatcacttt acttttatct aatctggaca tcataaattc ctaatttttg 660
ttgacactct atcattgata gagttatttt accactccct atcagtgata gagaaaagtg 720
aaccatggct aaaaagacag ctatcgcgat tgcagtggca ctggctggtt tcgctaccgt 780
agcgcaggcc gctccgaaag atggccgctg caccaaaagc attccgccga tttgctttcc 840
ggattagtct agaaaggagt cgttatgaaa aaaataacag ggattatttt attgcttctt 900
gcagtcatta ttctgtctgc atgtcaggca aactatatcc gggatgttca gggcgggacc 960
gtatctccgt catcaacagc tgaagtgacc ggattagcaa cgcagtaact gcaggcatgc 1020
aagcttggct gttttggcgg atgagagaag attttcagcc tgatacagat taaatcagaa 1080
cgcagaagcg gtctgataaa acagaatttg cctggcggca gtagcgcggt ggtcccacct 1140
gaccccatgc cgaactcaga agtgaaacgc cgtagcgccg atggtagtgt ggggtctccc 1200
catgcgagag tagggaactg ccaggcatca aataaaacga aaggctcagt cgaaagactg 1260
ggcctttcgt tttatctgtt gtttgtcggt gaacgctctc ctgagtagga caaatccgcc 1320
gggagcggat ttgaacgttg cgaagcaacg gcccggaggg tggcgggcag gacgcccgcc 1380
ataaactgcc aggcatcaaa ttaagcagaa ggccatcctg acggatggcc tttttgcgtt 1440
tctacaaact ctttttgttt atttttctaa atacattcaa atatgtatcc gctcatgaga 1500
caataaccct gataaatgct tcaataatat tgaaaaagga agagtatgag tattcaacat 1560
ttccgtgtcg cccttattcc ctttttttgcg gcattttgcc ttcctgtttt tgctcaccca 1620
gaaacgctgg tgaaagtaaa agatgctgaa gatcagttgg gtgcacgagt gggttacatc 1680
gaactggatc tcaacagcgg taagatcctt gagagttttc gccccgaaga acgttttcca 1740
atgatgagca cttttaaagt tctgctatgt ggcgcggtat tatcccgtgt tgacgccggg 1800
caagagcaac tcggtcgccg catacactat tctcagaatg acttggttga gtactcacca 1860
gtcacagaaa agcatcttac ggatggcatg acagtaagag aattatgcag tgctgccata 1920
accatgagtg ataacactgc ggccaactta cttctgacaa cgatcggagg accgaaggag 1980
ctaaccgctt ttttgcacaa catgggggat catgtaactc gccttgatcg ttgggaaccg 2040
gagctgaatg aagccatacc aaacgacgag cgtgacacca cgatgcctac agcaatggca 2100
acaacgttgc gcaaactatt aactggcgaa ctacttactc tagcttcccg gcaacaatta 2160
atagactgga tggaggcgga taaagttgca ggaccacttc tgcgctcggc ccttccggct 2220
ggctggttta ttgctgataa atctggagcc ggtgagcgtg ggtctcgcgg tatcattgca 2280
gcactggggc cagatggtaa gccctcccgt atcgtagtta tctacacgac ggggagtcag 2340
gcaactatgg atgaacgaaa tagacagatc gctgagatag gtgcctcact gattaagcat 2400
tggtaactgt cagaccaagt ttactcatat atactttaga ttgatttaaa acttcatttt 2460
taatttaaaa ggatctaggt gaagatcctt tttgataatc tcatgaccaa aatcccttaa 2520
cgtgagtttt cgttccactg agcgtcagac cccgtagaaa agatcaaagg atcttcttga 2580
gatccttttt ttctgcgcgt aatctgctgc ttgcaaacaa aaaaaccacc gctaccagcg 2640
gtggtttgtt tgccggatca agagctacca actctttttc cgaaggtaac tggcttcagc 2700
agagcgcaga taccaaatac tgtccttcta gtgtagccgt agttaggcca ccacttcaag 2760
aactctgtag caccgcctac atacctcgct ctgctaatcc tgttaccagt ggctgctgcc 2820
agtggcgata agtcgtgtct taccgggttg gactcaagac gatagttacc ggataaggcg 2880
cagcggtcgg gctgaacggg gggttcgtgc acacagccca gcttggagcg aacgacctac 2940
accgaactga gatacctaca gcgtgagcta tgagaaagcg ccacgcttcc cgaagggaga 3000
aaggcggaca ggtatccggt aagcggcagg gtcggaacag gagagcgcac gagggagctt 3060
ccagggggaa acgcctggta tctttatagt cctgtcgggt ttcgccacct ctgacttgag 3120
cgtcgatttt tgtgatgctc gtcagggggg cggagcctat ggaaaaacgc cagcaacgcg 3180
gcctttttac ggttcctggc cttttgctgg ccttttgctc acatgttctt tcctgcgtta 3240
tcccctgatt ctgtggataa ccgtattacc gcctttgagt gagctgatac cgctcgccgc 3300
agccgaacga ccgagcgcag cgagtcagtg agcgaggaag cggaagagcg cctgatgcgg 3360
tattttctcc ttacgcatct gtgcggtatt tcacaccg 3398

<210> SEQ ID NO 20
<211> LENGTH: 11
<212> TYPE: PRT
<213> ORGANISM: Artificial Sequence
<220> FEATURE:
<223> OTHER INFORMATION: HIV TAT protein amino acids 47-57

<400> SEQUENCE: 20

Tyr Gly Arg Lys Lys Arg Arg Gln Arg Arg Arg
1 5 10

<210> SEQ ID NO 21
<211> LENGTH: 9
<212> TYPE: PRT
<213> ORGANISM: Artificial Sequence -continued

```
<220> FEATURE:
<223> OTHER INFORMATION: lymphoid tissue targeting peptide

<400> SEQUENCE: 21

Cys Ala Tyr His Arg Leu Arg Arg Cys
1               5


<210> SEQ ID NO 22
<211> LENGTH: 12
<212> TYPE: PRT
<213> ORGANISM: Artificial Sequence
<220> FEATURE:
<223> OTHER INFORMATION: Peptide from Clostridium

<400> SEQUENCE: 22

Cys Gln Thr Ile Asp Gly Lys Lys Tyr Tyr Phe Asn
1               5                   10


<210> SEQ ID NO 23
<211> LENGTH: 5
<212> TYPE: PRT
<213> ORGANISM: Artificial Sequence
<220> FEATURE:
<223> OTHER INFORMATION: native C-terminal signal of ToxA sequence

<400> SEQUENCE: 23

Arg Glu Asp Leu Lys
1               5


<210> SEQ ID NO 24
<211> LENGTH: 5
<212> TYPE: PRT
<213> ORGANISM: Artificial Sequence
<220> FEATURE:
<223> OTHER INFORMATION: portion of linker peptide

<400> SEQUENCE: 24

Gly Gly Gly Gly Ser
1               5
```

CHIMERIC PROTEIN TOXINS FOR EXPRESSION BY THERAPEUTIC BACTERIA

CROSS REFERENCE TO RELATED APPLICATIONS

The present application is a Divisional of U.S. patent application Ser. No. 15/151,194, filed May 10, 2016, now U.S. Pat. No. 10,676,723, issued Jun. 9, 2020, which is a non-provisional of U.S. Provisional Patent Application 62/159,645, filed May 11, 2015, entitled "IMPROVED CHIMERIC PROTEIN TOXINS FOR EXPRESSION BY THERAPEUTIC BACTERIA", naming Dr. David Bermudes and Mr. David Quintero as inventors, the entirety of which are expressly incorporated herein by reference in its entirety.

This specification incorporates by reference the sequence listing dated Jul. 24, 2023, named "Magna-212-1-rev1_ST25.txt" and comprising 82,005 bytes.

STATEMENT OF GOVERNMENT RIGHTS

This invention was made with government support under 1SC3GM098207 awarded by The National Institutes of Health. The government has certain rights in the invention.

BACKGROUND

Field of the Invention

This invention is generally in the field of therapeutic delivery systems including bacteria, and systems and methods for providing chimeric proteins efficiently targeted to cancer cells.

Description of the Prior Art

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application.

Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57:4537-4544; Low et al., 1999, Lipid A mutant *salmonella* with suppressed virulence and TNF-alpha induction retain tumor-targeting in vivo, Nature Biotechnol. 17:37-41). However, the primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella typhimurium* to patients with metastatic melanoma, J. Clin, Oncol. 20:142-152; Meir et al., 2001, Phase 1 trial of a live, attenuated *Salmonella typhimurium* (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10:737-744) is that no significant antitumor activity has been observed, even in patients where the bacteria was documented to target the tumor. One method of increasing the ability of the bacteria to kill tumor cells is to engineer the bacteria to express conventional bacterial toxins (e.g., WO 2009/126189, WO 03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849, 8,241,623, 8,524,220 8,771,669, 8,524,220, each of which is expressly incorporated herein by reference).

Use of protein toxins for treatment of various disorders including inflammation, autoimmunity, neurological disorders and cancer has long-suffered from off-target toxicity. Enhancing toxin specificity, which offers the potential to eliminate side effect, has been achieved by several different means, such as attachment of a specific antibodies or peptide ligand (e.g., *Pseudomonas* exotoxin A (PE-ToxA) antibody conjugate, known as an immunotoxin), or a ligand targeted to a surface molecule of the target cell. Based upon the binding specificity of the attached antibody or ligand moiety for a specific target, enhanced specificity of the target is achieved.

Other toxins have been engineered to achieve specificity based upon their sight of activation. For example, proaerolysin requires proteolytic activation to become the cytotoxic protein aerolysin. Substitution of the natural protease cleavage site for a tumor-specific protease cleavage site (e.g., that of the prostate specific antigen (PSA) protease or urokinase) results in a toxin selectively activated within tumors (Denmeade et al. WO 03/018611 and Denmeade et al. U.S. Pat. No. 7,635,682), specifically incorporated by reference herein. Another similar activation system has utilized ubiquitin fusion, coupled with a hydrolysable tumor protease (e.g., PSA) sequence and a toxin (e.g., saporin), as described by Tschrniuk et al. 2005 (Construction of tumor-specific toxins using ubiquitin fusion technique, Molecular Therapy 11:196-204), also specifically incorporated by reference herein. However, while some specificity is engendered and thus these activated protein types are useful in the present technology as modified herein, in these types of engineered toxins, off-target toxicity can occur. In the case of the *Pseudomonas* immunotoxin, several dose-limiting toxicities have been identified. Vascular leakage syndrome (VLS) is associated with hypoalbuminemia, edema, weight gain, hypotension and occasional dyspnea, which is suggested to occur by immunotoxin-mediated endothelial cell injury (Baluna et al., 2000, Exp. Cell Res. 258:417-424), resulting in a dose-limiting toxicity. Renal injury has occurred in some patients treated with immunotoxins, which may be due to micro-aggregates of the immunotoxin (Frankel et al., 2001, Blood 98: 722a). Liver damage from immunotoxins is a frequent occurrence that is believed to be multifactorial (Frankel, 2002, Clinical Cancer Research 8:942-944). To date, antibodies linked to proteinaceous toxins have limited success clinically.

Recently developed approaches to delivery of therapeutic molecules (U.S. Pat. Nos. 8,241,623; 8,524,220; 8,771,669; and 8,524,220) have coupled a protease sensitive therapeutic molecule with co-expression of protease inhibitors, expressly incorporated by reference herein.

Use of secreted proteins in live bacterial vectors has been demonstrated by several authors. Holland et al. (U.S. Pat. No. 5,143,830) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37:87-98). Those limitations include the amount of protein secreted and the ability of the protein fused to it to interfere with secretion. Improvements of the type I secretion system have been demonstrated by Sugamata and Shiba (2005 Applied and Environmental Micobiology 71:656-662) using a modified hlyB, and by Gupta and Lee (2008 Biotechnology and Bioengineering, 101:967-974) by addition of rare codons to the hlyA gene, each of which is expressly incorporated by reference in their entirety herein. Fusion to the gene ClyA (Galen et al., 2004, Infection and Immunity, 72:7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96:129-154, expressly incorporated by reference in its entirety herein). The autotransporter surface display has been described by Berthet et al., WO/2002/070645, expressly incorporated by reference herein. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68:692-744; Jose, 2006 Applied Microbiol. Biotechnol. 69:607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5:22). For example, Veiga et al. (2003 Journal of Bacteriology 185:5585-5590 and Klauser et al., 1990 EMBO Journal 9:1991-1999) demonstrated hybrid proteins containing the β-autotransporter domain of the immunoglobulin A (IgA) protease of Nisseria gonorrhea. Fusions to flagellar proteins have been demonstrated. The peptide, usually of 15 to 36 amino acids in length, is inserted into the central, hypervariable region of the FliC gene such as that from *Salmonella* muenchen (Verma et al. 1995 Vaccine 13:235-24; Wu et al., 1989 Proc. Natl. Acad. Sci. USA 86:4726-4730; Cuadro et al., 2004 Infect. Immun. 72:2810-2816; Newton et al., 1995, Res. Microbiol. 146: 203-216, expressly incorporated by reference in their entirety herein). Multihybrid FliC insertions of up to 302 amino acids have also been prepared (Tanskanen et al. 2000, Appl. Env. Microbiol. 66:4152-4156, expressly incorporated by reference in its entirety herein). Trimerization of antigens can be achieved using the T4 fibritin foldon trimerization sequence (Wei et al. 2008 J. Virology 82:6200-6208) and VASP tetramerization domains (Kühnel et al., 2004 PNAS 101:17027-17032), expressly incorporated by reference in their entirety herein. The multimerization domains are used to create, bi-specific, tri-specific, and quatra-specific targeting agents, whereby each individual agent is expressed with a multimerization tag, each of which may have the same or separate targeting peptide, such that following expression, surface display, secretion and/or release, they form multimers with multiple targeting domains.

SUMMARY OF THE INVENTION

Modified Therapeutic Molecules

The present technology, according to various embodiments, consists of known and/or novel chimeric proteins, or combinations of proteins, that are expressed, secreted, surface displayed and/or released by bacteria and result in anticancer activity or have direct inhibitory or cytotoxic anti-neoplastic activity, including activity against cancer stem cells and/or cancer mesenchymal stromal cells, and may optionally include the combination with secreted protease inhibitors. The bacterial delivery vector may be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intrathecally (intrathecal), by inhaler or nasal spray) or to the mucosal system through oral, nasal, pulmonary intravessically, enema or suppository administration where they are able to undergo limited replication, express, surface display, secrete and/or release the anti-cancer inhibitory proteins or a combination thereof, and thereby provide a therapeutic benefit by reducing or eliminating the disease, malignancy and/or neoplasia.

The present technology, according to various embodiments, further consists of modified forms of toxins with improved secretion, surface display and/or release by the bacteria, and/or modifications that improve the overall activity and/or specificity of the toxin. Such toxins may be further co-expressed with protease inhibitors as previously described (See, U.S. Pat. Nos. 8,241,623; 8,524,220; 8,771,669; 8,524,220).

Toxins, therapeutic cytokines and other molecules, homologues or fragments thereof useful in conjunction with the present technology, according to various embodiments, includes small lytic peptides, larger lytic peptides, pore-forming toxins, protein inhibitors, extracellular DNases, intracellular DNases, apoptosis inducing peptides, cytokines, prodrug converting enzymes, metabolite destroying enzymes, ribonucleases, antibody inactivating toxins and other anticancer peptides. In a preferred embodiment, the toxins include those that are naturally secreted, released and/or surface displayed, or heterologously secreted, released and/or surface displayed, and that can be modified uniquely to suit the delivery by a bacterium and may be further engineered to have the tumor, lymphoma, leukemic bone marrow or proximity-selective targeting system described herein, including but not limited to the proteins azurin, carboxyesterase Est55 (a prodrug-converting enzyme from *Geobacillus* that activates CPT-11 to SN-38), thiaminase (e.g., from *Bacillus*), methionase (methioninase), asparaginase, tryptophanase, apoptin, Torquetnovirus (TTV) derived apoptosis-inducing protein TAIP and with gyrovirus VP3 bax, bim, p53, BAK, BH3 peptide (BCL2 homology domain 3), cytochrome C, thrombospondin, platlet factor 4 (PF4) peptide, *Bacillus* sp. cytolysins, *Bacillus* sp. nheABC toxins, cytolethal distending toxins (cldt) including those cldts from *Haemophilus, Aggregatibacter, Salmonella, Escherichia, Shigella, Campylobacter, Helicobacter*, Hahella and *Yersinia*, typhoid toxins (pertussis like toxin) (pltAB), pertussis toxin, cldt: plt hybrids, actAB, cytotoxic nectrotic factor (cnf), dermonecrotic factor (dnf), shiga toxins and shiga-like toxins, bacteriocins, (colicins and microcins; Hen and Jack, Chapter 13 Microcins, in Kastin (ed), 2006, Handbook of Biologically Active Peptides, Academic Press; Nes et al., Chapter 17, The nonlantibiotic heat-stable bacteriocins in gram-positive bacteria, in Kastin (ed), 2006, Handbook of Biologically Active Peptides, Academic Press; Sharma et al., Chapter 18 in Kastin (ed), 2006, Handbook of Biologically Active Peptides, Academic Press)

including membrane depolarizing (or pore-forming), DNases (including colicin DNase, Staphylococcal Nuclease A: OmpA fusions (Takahara et al., 1985 J. Biol. Chem 260:2670-2674), *Serratia marcescens* DNase (Clegg and Allen, 1985, FEMS Microbiology Letters 27:257-262; *Vibrio* DNase Newland et al., 1985 Infect Immun 47:691-696) or other bacterial DNase), RNAases RNases, and tRNases, including but not limited colicin A, colicin D, colicin E5, colicin E492, microcin M24, colE1, colE2, colE3, colE5 colE7, coleE8, colE9, col-Ia, colicin N and colicin B, membrane lytic peptides from *Staphylococcus* (listed below) and sea anemones, P15 peptide and other TGF-beta mimics, repeat in toxin (RTX) family members (together with the necessary acylation and secretion genes) including *Actinobacillus* leukotoxins, a leukotoxin: *E. coli* HlyA hybrid, *E. coli* HlyA hemolysin, *Bordetella* adenylate cyclase toxin, heat stable enterotoxins from *E. coli* and *Vibrio* sp. (Dubreuil 2006, Chapter 48*, Escherichia coli, Vibrio* and *Yersinia* species heat stable enterotoxins, Alouf and Popoff (eds), 2006, Comprehensive Sourcebook of Bacterial Protein Toxins, Third Edition, Academic Press), autotransporter toxins including but not limited to IgA protease, picU espC, and sat, *Staphylococcus* protein A, *Clostridium* enterotoxin, *Clostridium difficile* toxin A, scorpion chlorotoxin, aerolysin, subtilase, cereolysin, *Staphylococcus* leukotoxins (e.g. LukF-PV, LukF-R, LukF-I, LukM, HlgB) and the other, to class S (e.g. LukS-PV, LukS-R, LukS-I, HlgA, HlgC). Best known are the toxins produced by *S. aureus*: γ-haemolysins, HlgA/HlgB and HlgC/HlgB and leukocidin Panton-Valentine, LukS-PV/LukF-PV (Luk-PV, PVL)) TRAIL, fasL, IL-18, CCL-21, human cytokine LIGHT, agglutinins (*Maackia amurensis*, wheat germ, *Datura stramonium, Lycopersicon* (tomato) plant lectin, leukoagglutinin (L-PHA, *Helix pomatia*) saporin, ricin, pertussus toxin, and porB, as well as other toxins and peptides (Kastin (ed), 2006, Handbook of Biologically Active Peptides, Academic Press; Alouf and Popoff (eds), 2006, Comprehensive Sourcebook of Bacterial Protein Toxins, Third Edition, Academic Press; each of which is expressly incorporated by reference in their entirety herein). Metabolite toxins such as the Chromobacterium violacium dipsepeptides (Shigeatsu et al., 1994, FR901228, a novel antitumor bicyclic depsipeptide produced by Chromobacterium *violaceum* No. 968. II. Structure determination. J Antibiot (Tokyo) 47 (3): 311-4) or those from *Serratia* are also of use in the present technology.

The chimeras may be further modified by addition of one or more multimerization domains, such as the T4 foldon trimerization domain (Meier et al., 2004, Journal of Molecular Biology, 344:1051-1069; Bhardwaj et al., Protein Sci. 2008 17:1475-1485) or tetramerization domains such as VASP (Kühnel et al., 2004 PNAS 101:17027-17032). Chimeric toxins may be further modified by the addition of known cell penetrating (ferry) peptide which further improves their entry into target cells. Cell penetrating peptides include those derived from the human immunodeficiency virus (HIV) TAT protein amino acids 47-57 (YGRKKRRQRRR SEQ ID NO.: 020) and used in fusion proteins (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexalysine, hexaarginine or “Chariot” (Active Motif, Carlsbad, Calif.; U.S. Pat. No. 6,841,535). Nuclear localization signals (NLSs) may also be added, including but not limited to that from herpes simplex virus thymidine kinase, the SV40 large T antigen monopartite NLS, or the nucleoplamin bipartite NLS or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13:495-508; Backendor et al., 2008, Apoptin: Therapeutic potential of an early sensor of carcinogenic transformation, Ann Rev Pharmacol Toxicol 48:143-69).

Expression of wild type *Pseudomonas* exotoxin A has been previously described (U.S. Pat. Nos. 6,962,696; 7,452,531; 8,241,623; Swofford C A et al. 2014. Identification of *Staphylococcus aureus* α-hemolysin as a protein drug that is secreted by anticancer bacteria and rapidly kills cancer cells. Biotechnol Bioeng. 111:1233-45). Regarding chimeric *Pseudomonas* exotoxin A (ToxA), numerous forms have been generated and shown to be effective at killing tumor cells in vitro and in murine cancer models (TGF-α-GIII-KDEL (Kihara and I. Pastan 1994 Small Chimeric Toxins Containing Only Transforming Growth Factor α and Domain III of *Pseudomonas* Exotoxin with Good Antitumor Activity in Mice. Cancer Res 1994:54:5154-5159; TGF α-PE38; Kreitman et al., 1992, Properties of Chimeric Toxins with Two Recognition Domains: Interleukin 6 and Transforming Growth Factor α at Different Locations in *Pseudomonas* Exotoxin. Bioconjugate Chem. 1992, 3, 63-68; Kreitman et al., Recombinant immunotoxins containing anti-Tac (Fv) and derivatives of *Pseudomonas* exotoxin produce complete regression in mice of an interleukin 2 receptor-expressing human carcinoma. Blood 1994, 83, 426-434; Zielenski 2009, Affitoxin-A Novel Recombinant, HER2-Specific, Anti-Cancer Agent for Targeted Therapy of HER2-Positive Tumors. J Immunother. 32:817-825). However, these investigators did not use a live bacterial vector to deliver the chimeric agent, and purified the agent from bacteria that were killed and lysed, generally requiring the biochemical manipulation of “refolding” of an inactively produced agent in the form of an inclusion body to produce the active form. The process of refolding an inactive inclusion body is not facilitated by live bacteria, and thus cannot be effective when delivered by a live bacterium expressing such a cancer therapeutic protein. Proteins produced in a “soluble” form, while not requiring refolding, likewise are ineffective because they do not get out of the cell. The present technology, according to various embodiments, uses, alone or in combination, ToxA domain Ib containing at least 2 available cysteines for cysteine bonds, flexible linkers, colicin lysis protein and/or signal sequences that result in functional ToxA chimeric proteins that are expressed, secreted, surface displayed and/or released by the bacteria and have the ability to kill cancer cells in the absence of biochemical manipulation.

Regarding use of tumor-targeted bacteria expressing wild type cytolethal distending toxin and chimeras including those with apoptin, there have been several earlier descriptions (U.S. Pat. Nos. 6,962,696; 7,452,531; 8,241,623; 8,524,220; 8,623,350; 8,771,669). Cytolethal distending toxins (CLDTs) comprise a family of heterotrimeric holotoxins produced by bacteria that are internalized into mammalian cells and translocated into the nucleus. CLDTs are known to occur in a number of bacterial genera including *Haemophilus, Aggregatibacter, Salmonella, Escherichia, Shigella, Campylobacter, Helicobacter*, Hahella and *Yersinia* (Gargi et al., 2012 Bacterial toxin modulation of the eukaryotic cell cycle: are all cytolethal distending toxins created equally? Frontiers in Cellular and Infection Microbiol. 2:124. doi: 10.3389/fcimb.2012.00124), however CLDT does not exist in the VNP20009 strain of *Salmonella* used in human clinical studies (Toso et al. 2002. Phase I Study of the Intravenous Administration of Attenuated *Salmonella typhimurium* to Patients With Metastatic Melanoma. J. Clin. Oncol. 20, 142-152; Low et al., 2004, Construction of VNP20009, a novel, genetically stable antibiotic sensitive strain of tumor-targeting *Salmonella* for parentral administration in humans. Methods Mol Med 90:47-60).

Depending upon both the specific CLDT and the mammalian cells type, different effects have been documented. All CLDTs have homology to exonuclease III and several have been directly shown to exhibit DNase activity in vitro (Ewell and Dreyfus 2000 DNase I homologous residues in CdtB are critical for cytolethal distending toxin-mediated cell cycle arrest. Mol Microbiol 37, 952-963; Lara-Tejero and Galán, 2000 A bacterial toxin that controls cell cycle progression as a deoxyribonuclease I-like protein. Science 290, 354-357), which is believed to be the primary effect of the toxin. The DNase activity results in double-stranded DNA breaks that activates the cell's DNA damage response and interrupts the cell cycle at G2M. Non hematopoietic cells tend to enlarge, hence part of the toxin name distending, and in many cases the cells subsequently undergo apoptosis. In hematopoietic cells apoptosis is more rapidly produced (Jinadasa et al., 2011, Cytolethal distending toxin: a conserved bacterial genotoxin that blocks cell cycle progression, leading to apoptosis of a broad range of mammalian cell lineages. Microbiology 157:1851-1875; Gargi et al., 2012).

Most of the CLDTs are organized in a unidirectional operon of cldtA, cldtB and cldtC genes, where the cldtB encodes the active subcomponent, and cldtA and cldtC encode peptides that are involved in cell binding and translocation. In *Salmonella* however, the genes exist as a bidirectional operon consisting of cldtB together with a two pertussis like toxin subunits oriented in the opposite direction, pltA and pltB, as well as sty and ttsA, also in opposing directions, that are reported to be required for secretion of the toxin (Hodak and Galan 2013 A *Salmonella Typhi* homologue of bacteriophage muramidase controls typhoid toxin secretion. EMBO Reports 14:95-102). However, in the present technology, according to various embodiments, the presence of sty and ttsA are not required for secretion of the active toxin when the operon is reorganized into a unidirectional operon of cldtB, pltB and pltA.

Translocation of *E. coli* CLDTs to the nucleus, which constitutes the target location for the endonuclease activity, requires the presence of a nuclear localization signal (NLS). In *Escherichia coli* CLDT-II for example, the NLS is bipartite and located at the C-terminus (McSweeney and Dreyfus, 2004). Nishikubo et al., 2003 identified an NLS occurring in the 48-124 amino acid region in *Actinobacillus actinomycetemcomitans.*

Apoptins are a family of viral genes that were first discovered in chicken anemia virus. Apoptin is the product of the VP3 gene that is involved in lymphoidal atrophy and anemia in infected chickens (Peñaloza et al., 2014 Apoptins: selective anticancer agents, Trends in Molecular Medicine 20:519-528; Los et al., 2009 Apoptin, a tumor selective killer, Biochimica et Biophysica Acta 1793:1335-1342). Apoptin was subsequently found to selectively induce apoptosis in cancer cells (Danen-Van Oorschot et al., 1997 Apoptin induces apoptosis in human transformed and malignant cells but not in normal cells. Proc. Natl. Acad. Sci. USA 94:5843-5847). Apoptin shares similarity with Torquetnovirus (TTV) derived apoptosis-inducing protein TAIP and with gyrovirus VP3. Apoptin consists of several different domains including a leucine rich sequence (LRS) which is involved in binding to the promyelocytic leukemia (PML) protein of nuclei and in apoptin multimerization, an SRC homology 3 (SH3) binding domain with is part of a bipartite nuclear localization signal (NLS), a nuclear export sequence (NES) that promotes egress of apoptin from normal cell nuclei, a set of threonines of which T108 must be phosphorylated for full apoptin activity, the C-terminal portion of the bipartite NLS and an anaphase promoting complex/cyclosome 1 (APC/C1) binding domain that consists of approximately one third of the C-terminus.

The present technology, according to various embodiments, consists of a modified *Salmonella* CLDT operon and forms of cytolethal distending toxins that are chimeric with apoptin and other peptide moieties including peptide linkers that improve activity and peptide blocking moieties that must be specifically cleaved to activate the protein. The present technology, according to various embodiments, uses deletions in the CLDT nuclear localization signals which are then complemented by N- or C-terminal fusions with apoptin, or apoptin fragments, which supply its nuclear localization signal in trans as a fusion peptide.

The types of cancers or neoplasias to which the present technology is directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas. Specific types of cancers include acute lymphoblastic leukemia, acute myeloid leukemia, adrenocortical carcinoma adrenocortical carcinoma, adult (primary) liver cancer, adult acute myeloid leukemia, AIDS-related cancers, AIDS-related lymphoma, anal cancer, appendix cancer, astrocytomas, astrocytomas (childhood), basal cell carcinoma, bile duct cancer, bladder cancer, bone cancer, brain stem glioma, brain tumor, breast cancer (female), breast cancer (male), bronchial tumors, Burkitt's lymphoma, carcinoid tumor, carcinoma of unknown primary site, central nervous system atypical teratoid/rhabdoid tumor, central nervous system embryonal tumors, central nervous system lymphoma, central nervous system tumors, cervical cancer, childhood acute myeloma, childhood multiple myeloma/plasma cell neoplasm, chordoma, chronic lymphocytic leukemia, chronic myelogenous leukemia, chronic myeloid leukemia, chronic myeloproliferative disorders, colon cancer, colorectal cancer, craniopharyngioma, cutaneous T-cell lymphoma, embryonal tumors, endometrial cancer, endometrial uterine sarcoma, ependymoblastoma, ependymoma, esophageal cancer, Ewing sarcoma family of tumors, extracranial germ cell tumor, extragonadal germ cell tumor, extrahepatic bile duct cancer, extrahepatic gallbladder cancer, eye cancer, gallbladder cancer, gastric (stomach) cancer, gastrointestinal carcinoma, gastrointestinal carcinoid tumor, gastrointestinal stromal cell tumor, gastrointestinal stromal tumor (gist), germ cell tumor, glioma, hairy cell leukemia, head and neck cancer, hepatocellular (liver) cancer, histiocytosis, Hodgkin lymphoma, hypopharyngeal cancer, intraocular (eye) melanoma, intraocular melanoma, islet cell tumors, Kaposi sarcoma, kidney (renal cell) cancer, kidney cancer, Langerhans cell, Langerhans cell histiocytosis, laryngeal cancer, leukemia, lip and oral cavity cancer, lip and oropharyngeal cancer, liver cancer (metastatic), lung cancer (primary), macroglobulinemia, medulloblastoma, medulloepithelioma, melanoma, Merkel cell carcinoma, mesothelioma, metastatic squamous neck cancer with occult primary, metastatic stomach (gastric) cancer, mouth cancer, multiple endocrine neoplasia syndrome, multiple myeloproliferative disorders, mycosis fungoides, myelodysplastic syndromes, myelodysplastic/myeloproliferative diseases, myelogenous leukemia, nasal cavity and paranasal sinus cancer, nasopharyngeal cancer, nervous system atypical teratoid/rhabdoid tumor, neuroblastoma, non-Hodgkin lymphoma, non-small cell lung cancer, oral cancer, oral cavity cancer, osteosarcoma and malignant fibrous histiocytoma, osteosarcoma and malignant fibrous histiocytoma of bone, ovarian cancer, ovarian epithelial cancer, ovarian germ cell tumor, ovarian gestational trophoblastic tumor, ovarian low malignant potential tumor, pancreatic cancer, papillomatosis, paranasal sinus and nasal cavity cancer, parathyroid cancer, penile cancer, pharyngeal cancer, pineal parenchymal tumors, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, primary cervical cancer, primary hepatocellular (liver) cancer, prostate cancer, rectal cancer, renal cell (kidney) cancer, renal pelvis and ureter, respiratory tract carcinoma involving the nut gene on chromosome 15, retinoblastoma, rhabdomyosarcoma, salivary gland cancer, sarcoma, skin cancer (Basal cell carcinoma), Sézary syndrome, skin cancer (nonmelanoma), skin carcinoma, small cell lung cancer, small cell lymphoma, small intestine cancer, soft tissue sarcoma, spinal cord tumors, squamous cell carcinoma, squamous neck cancer with occult primary, stomach (gastric) cancer, supratentorial primitive neuroectodermal tumors and pineoblastoma, T-cell lymphoma, teratoid/rhabdoid tumor (childhood), testicular cancer, throat cancer, thymoma and thymic carcinoma, thyroid cancer, transitional cell cancer, transitional cell cancer of the renal pelvis and ureter, trophoblastic tumor (gestational), unknown primary site, ureter and renal pelvis, urethral cancer, uterine cancer, uterine sarcoma, vaginal cancer, vulvar cancer, Waldenström macroglobulinemia, Waldenström malignant fibrous histiocytoma of bone and osteosarcoma, and Wilms tumor.

The therapeutic agent can be a chimera consisting of a peptide or protein, toxin, chimeric toxin, cytokine, antibody, bispecific antibody including single chain antibodies, camel antibodies and nanobodies chemokine, prodrug converting enzyme or metabolite-degrading enzyme such as thiaminase, methionase (methioninase, L-methionine γ-lyase) or asperaginase. In a preferred embodiment the therapeutic agent is a toxin, or modified toxin.

The chimeras may be further modified by addition of one or more multimerization domains, such as the T4 foldon trimerization domain (Meier et al., 2004, Journal of Molecular Biology, 344:1051-1069; Bhardwaj et al., Protein Sci. 2008 17:1475-1485) or tetramerization domains such as VASP (Kühnel et al., 2004 PNAS 101:17027-17032). Chimeric toxins may be further modified by the addition of known cell penetrating (ferry) peptide which further improves their entry into target cells. Cell penetrating peptides include those derived from the HIV TAT protein (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexalysine, hexaarginine or "Chariot" (Active Motif, Carlsbad, CA; U.S. Pat. No. 6,841,535). Nuclear localization signals (NLSs) may also be added, including but not limited to that from herpes simplex virus thymidine kinase, the SV40 large T antigen monopartite NLS, or the nucleoplasmin bipartite NLS or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13:495-508; Backendor et al., 2008, Apoptin: Therapeutic potential of an early sensor of carcinogenic transformation, Ann Rev Pharmacol Toxicol 48:143-69).

The chimeric proteins may have one or more additional features or protein domains known to those skilled in the art which are designed to be active or catalytic domains that result in the death of the cell, allow or facilitate them being secreted or released by autolytic peptides such as those associated with colicins or bacteriophage release peptides have targeting peptides that direct them to the target cells, and protease cleavage sites for activation (e.g., release from parent peptide), and thioredoxin or glutathione S-transferase (GST) fusions that improve solubility.

The present technology also provides in accordance with some embodiments, unique chimeric modifications of the above listed toxins that contain specific combinations of components resulting in secretion by selective anti-tumor activity. The technology also provides extracellular protease sensitivity (deactivation) that may include the addition of protease cleavage sites and may be co-expressed with a protease inhibitor. The chimeric proteins may have one or more additional features or protein domains known to those skilled in the art which are designed to 1) be active or catalytic domains that result in the death of the cell or make them susceptible to other known anticancer agents, 2) allow or facilitate them being secreted or released by autolytic peptides such as colicin release peptides, 3) membrane protein transduction (ferry) peptides, 4) autotransporter domains, 5) have targeting peptides that direct them to the target cells, and 6) protease cleavage sites for activation (e.g., release from parent peptide). However, the specific organization and combination of these domains is unique and specific to the technology.

Small lytic peptides (less than 50 amino acids) are used to construct chimeric proteins for more than one purpose. The chimeric proteins containing lytic peptides may be directly cytotoxic for the cancer cells, and/or other cells of the tumor including the tumor matrix cells and immune cells which may diminish the effects of the bacteria by eliminating them. Furthermore, the lytic peptides are useful in chimeric proteins for affecting release from the endosome. Small lytic peptides have been used in the experimental treatment of cancer. However, it is evident that most, if not all, of the commonly used antitumor small lytic peptides have strong antibacterial activity, and thus are not compatible with delivery by a bacterium (see Table 1 of Leschner and Hansel, 2004 Current Pharmaceutical Design 10:2299-2310, the entirety of which is expressly incorporated herein by reference). Small lytic peptides useful in the technology, according to various embodiments, are those derived from Staphaloccus *aureus, S. epidermidis* and related species, including the phenol-soluble modulin (PSM) peptides and delta-lysin (Wang et al., 2007 Nature Medicine 13:1510-1514, expressly incorporated herein by reference). Larger lytic peptides that may be used includes the actinoporins from sea anemones or other coelenterates, such as SrcI, FraC equinatoxin-II and sticholysin-II (Anderluh and Macek 2002, Toxicon 40:111-124). The selection of the lytic peptide depends upon the primary purpose of the construct, which may be used in combination with other constructs providing other anticancer features. Construct designed to be directly cytotoxic to cells employ the more cytotoxic peptides, particularly PSM-α-3 and actinoporins. Constructs which are designed to use the lytic peptide to affect escape from the endosome use the peptides with the lower level of cytotoxicity, such as PSM-alpha-1, PSM-α-2 or delta-lysin.

Promoters, i.e., genetic regulatory elements that control the expression of the genes encoding the therapeutic molecules described above that are useful in the present technology, according to various embodiments, include constitutive and inducible promoters. A preferred constitutive promoter is that from the vector pTrc99a (Promega). Preferred inducible promoters include the tetracycline inducible promoter (TET promoter), SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the PepT promoter (Bermudes et al., WO 01/25397), the arabinose inducible promoter (AraBAD) (Lossner et al., 2007, Cell Microbiol. 9:1529-1537; WO/2006/048344) the salicylate (aspirin) derivatives inducible promoter (Royo et al., 2007, Nature Methods 4:937-942; WO/2005/054477), a tumor-specific promoter (Arrach et al., 2008, Cancer Research 68:4827-4832; WO/2009/152480) or a quorum-sensing (autoinduction) promoter Anerson et al., 2006 Environmentally controlled invasion of cancer cells by engineered bacteria, J. Mol. Biol. 355:619-627.

A single promoter may be used to drive the expression of more than one gene, such as a protease sensitive toxin and a protease inhibitor. The genes may be part of a single synthetic operon (polycistronic), or may be separate, monocystronic constructs, with separate individual promoters of the same type used to drive the expression of their respective genes. The promoters may also be of different types, with different genes expressed by different constitutive or inducible promoters. Use of two separate inducible promoter for more than one cytotoxin or other effector type peptide allows, when sufficient X-ray, tetracycline, arabinose or salicylic acid is administered following administration of the bacterial vector, their expression to occur simultaneously, sequentially, or alternatingly (i.e., repeated).

OBJECTS OF THE INVENTION

The present technology provides, according to one embodiment, live attenuated therapeutic bacterial strains that express one or more therapeutic molecules. The technology, according to various embodiments, relates specifically to certain modified forms of chimeric toxins especially suitable for expression by tumor-targeted bacteria. In a preferred embodiment, the modified toxin is derived from *Pseudomonas* exotoxin A (ToxA). In another preferred embodiment, the toxin is derived from cytolethal distending toxin. In a more preferred embodiment, the cytolethal distending toxin is derived from *Salmonella* paratyphi A, *Salmonella typhi* or *Salmonella bongori*. In particular, the technology, according to various embodiments, relates to live attenuated tumor-targeted bacterial strains that may include *Salmonella* sp., group B *Streptococcus* or *Listeria* vectoring chimeric anti-tumor toxins to an individual to elicit a therapeutic response against cancer. Another aspect of the technology relates to live attenuated tumor-targeted bacterial strains that may include *Salmonella*, group B *Streptococcus* or *Listeria* vectoring chimeric anti-tumor toxin molecules to an individual to elicit a therapeutic response against cancer including cancer stem cells. The toxins may also be targeted to tumor matrix cells, and/or immune cells. In another embodiment of the technology, *Salmonella* strains including *Salmonella* paratyphi A, *Salmonella typhi* or *Salmonella bongori* which contain endogenous cytolethal distending toxins may, when suitably attenuated, be used as vectors for delivery of cytolethal distending toxin. In order to achieve inducible control, the endogenous reporter is replaced with an inducible promoter by homologous recombination. In another embodiment, a chimeric secreted protease inhibitor is used alone or in combination with the chimeric toxins.

Whereas the prior strains of *Salmonella* studied in human clinical trials used either no heterologous antitumor protein (i.e., VNP20009) or an antitumor protein located within the cytoplasm of the bacterium (i.e., cytosine deaminase expressed by TAPET-CD), or secreted proteins (Bermudes et al., WO 2001/025397) the technology, according to various embodiments, provides, according to some embodiments, methods and compositions comprising bacterial vectors that express, secrete, surface display and/or release protease inhibitors that protect co-expressed protease sensitive antitumor molecules that are also secreted, surface displayed and/or released into the tumor, lymphoma-containing lymph node, leukemic bone lumen, or proximally or topically on a carcinoma or precancerous lesion for the treatment of the neoplasia.

The primary characteristic of the bacteria of the technology, according to various embodiments, is the enhanced effect of the effector molecule such as a toxin, lytic peptide etc. relative to the parental strain of bacteria. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more protease inhibitors under the same conditions. A second characteristic of the bacteria of the technology, according to various embodiments, is that they carry novel chimeric proteins that improve their function compared to other chimeric protein expression systems. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

The bacteria according to a preferred embodiment of the present technology, according to various embodiments, include those modified to have little or no ability to undergo bacterial conjugation, limiting incoming and outgoing exchange of genetic material, whereas the prior art fails to limit exchange of genetic material. In addition, certain of the therapeutic molecules have co-transmission requirements (e.g., colicin proteins and colicin immunity) that are distal (i.e., genetically dissected and separated) to the therapeutic molecule location further limiting known forms of genetic exchange.

Aspects of the present technology also provide novel chimeric bacterial toxins particularly suited for expression by gram-negative bacteria. The toxins may have added targeting ligands that render them selectively cytotoxic for tumor cells, tumor stem cells and/or matrix and tumor-infiltrating immune cells. The technology also provides means to determine optimal toxin combinations which are preferably additive or more preferably synergistic. The technology also provides means to determine the optimal combination of protein toxin with conventional cancer chemotherapeutics, liposomal agents or biologics, including immunosuppressive anti-complement agents (e.g., anti-C5B). Accordingly, administration to an individual, of a live *Salmonella* bacterial vector, in accordance with an aspect of the present technology, that is genetically engineered to express one or more protease inhibitors as described herein co-expressed with one or more cytotoxic proteins has the ability to establish a population in the tumor, kill tumor cells, tumor stem cells as well as tumor matrix and immune infiltrating cells, resulting in a therapeutic benefit.

A preferred composition will contain, for example, a sufficient amount of live bacteria expressing the targeted cytotoxin(s) or effector proteins/peptides to produce a therapeutic response in the patient. Accordingly, the attenuated *Salmonella* strains described herein are both safe and useful as live bacterial vectors that can be systemically or orally administered to an individual to provide therapeutic benefit for the treatment of cancer.

Although not wishing to be bound by any particular mechanism, an effective antitumor response in humans by administration of genetically engineered, attenuated strains of *Salmonella* strains as described herein may be due to the ability of such mutant strains to persist within the tumor, lymphoma or leukemic bone marrow and to supply their own nutrient needs by killing tumor cells, tumor matrix and or immune infiltrating cells and further expanding the zone of the tumor that they occupy. Bacterial strains useful in accordance with a preferred aspect of the technology may carry the ability to produce a therapeutic molecule expressing plasmid or chromosomally integrated cassette that encodes and directs expression of one or more therapeutic molecules together with optionally one or more protease inhibitors, as described herein. The protease inhibitors serve to prevent the destruction of the therapeutic molecule while within the tumor. The protease inhibitor may also have an anticlotting effect, wherein a blood clot may prevent spread of the bacteria throughout the tumor. The protease inhibitor may also have direct or indirect anticancer effects through the inhibition of proteases that participate in the spread of cancerous cells. If the cytotoxin and protease inhibitor diffuse outside of the tumor, lymph node, bone lumen, proximity to a carcinoma or other neoplasia-localized distribution, they fall below the protease inhibitory concentration, no longer inhibit proteolysis of the cytotoxins or effector genes, and are then inactivated. Thus the protease inhibitor system both increases activity and provides tumor specificity.

The serovars of *S. enterica* that may be used as the attenuated bacterium of the live compositions described in accordance with various embodiments herein include, without limitation, *Salmonella enterica* serovar *Typhimurium* ("*S. typhimurium*"), *Salmonella* montevideo, *Salmonella enterica* serovar *Typhi* ("*S. typhi*"), *Salmonella enterica* serovar Paratyphi A ("S. paratyphi A"), *Salmonella enterica* serovar Paratyphi B ("S. paratyphi B"), *Salmonella enterica* serovar Paratyphi C ("S. paratyphi C"), *Salmonella enterica* serovar Hadar ("S. hadar"), *Salmonella enterica* serovar *Enteriditis* ("*S. enteriditis*"), *Salmonella enterica* serovar Kentucky ("S. kentucky"), *Salmonella enterica* serovar *Infantis* ("*S. infantis*"), *Salmonella enterica* serovar Pullorum ("*S. pullorum*"), *Salmonella enterica* serovar *Gallinarum* ("*S. gallinarum*"), *Salmonella enterica* serovar Muenchen ("S. muenchen"), *Salmonella enterica* serovar Anaturn ("S. anatum"), *Salmonella enterica* serovar Dublin ("S. dublin"), *Salmonella enterica* serovar Derby ("S. derby"), *Salmonella enterica* serovar *Choleraesuis* var. Kunzendorf ("*S. cholerae* kunzendorf), and *Salmonella enterica* serovar Minnesota (*S. minnesota*). A preferred serotype for the treatment of bone marrow related diseases is S. dublin. In another embodiment of the technology, *Salmonella* strains including *Salmonella* paratyphi A, *Salmonella typhi* or *Salmonella bongori* which contain endogenous cytolethal distending toxins, may, when suitably attenuated, be used as vectors for delivery of cytolethal distending toxin. In order to achieve inducible control, the endogenous reporter is replaced with an inducible promoter by homologous recombination.

By way of example, live bacteria in accordance with aspects of the technology include known strains of *S. enterica* serovar *Typhimurium* (*S. typhimurium*) and *S. enterica* serovar *Typhi* (*S. typhi*) which are further modified as provided by the technology to form vectors for the prevention and/or treatment of neoplasia. Such Strains include Ty21a, CMV906, CMV908, CMV906-htr, CMV908-htr, Ty800, aroA-/serC-, holavax, M01ZH09, VNP20009. These strains contain defined mutations within specific serotypes of bacteria. The technology also includes the use of these same mutational combinations contained within alternate serotypes or strains in order to avoid immune reactions which may occur in subsequent administrations. In a preferred embodiment, S. *Typhimurium*, S. montevideo, and *S. typhi* which have non-overlapping O-antigen presentation (e.g., *S. typhimurium* is O-1, 4, 5, 12 and *S. typhi* is Vi, S. montevideo is O-6, 7) may be used. Thus, for example, *S. typhimurium* is a suitable serotype for a first injection and another serotype such as *S. typhi* or S. montevideo are used for a second injection and third injections. Likewise, the flagellar antigens are also selected for non-overlapping antigenicity between different injections. The flagellar antigen may be H1 or H2 or no flagellar antigen, which, when combined with the three different O-antigen serotypes, provides three completely different antigenic profiles.

Novel strains of *Salmonella* are also encompassed that are, for example, attenuated in virulence by mutations in a variety of metabolic and structural genes. The technology therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is a combinations of other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, met, cys, pur, purA, purB, purI, purF, leu, ilv, arg, lys, zwf, aroA, aroB, aroC, aroD, serC, gua, cadA, rfc, rjb, rfa, ompR, msbB, pfkAB, crr, glk, ptsG, ptsHI, manXYZ and combinations thereof. The strain may also contain a mutation known as "Suwwan", which is an approximately 100 kB deletion between two IS200 elements. The strain may also carry a defective thioredoxin gene (trxA-; which may be used in combination with a TrxA fusion), a defective glutathione oxidoreductase (gor-) and optionally, overexpress a protein disulfide bond isomerase (DsbA). The strain may also be engineered to express invasion and/or escape genes tlyA, tlyC patI and pld from *Rickettsia*, whereby the bacteria exhibit enhanced invasion and/or escape from the phagolysosome (Witworth et al., 2005, Infect. Immun. 73:6668-6673), thereby enhancing the activity of the effector genes described below. The strain may also be engineered to be deleted in an avirulence (anti-virulence) gene, such as zirTS, grvA and/or pcgL, or express the *E. coli* lac repressor, which is also an avirulence gene in order to compensate for over-attenuation. The strain may also express SlyA, a known transcriptional activator. In a preferred embodiment, the *Salmonella* strains are msbB mutants (msbB-). In a more preferred embodiment, the strains are msbB- and Suwwan. In a more preferred embodiment the strains are msbB-, Suwwan and zwf-. Zwf has recently been shown to provide resistance to CO2, acidic pH and osmolarity (Karsten et al., 2009, BMC Microbiology August 18; 9:170). Use of the msbB zwf genetic combination is also particularly preferred for use in combination with administered carbogen (an oxygen carbon dioxide mixture that may enhance delivery of therapeutic agents to a tumor). In a more preferred embodiment, the strains are msbB-, Suwwan, zwf- and trxA-. In a most preferred embodiment, the strains are msbB-, Suwwan, zwf-, trxA- and gor-.

The technology also encompasses according to a preferred embodiment, gram-positive bacteria. Preferred bacteria of the technology are group B *Streptococcus* including S. agalaciae, and *Listeria* species including *L. monocytogenes*. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336; Geertsma and Poolman, 2007, High-throughput cloning and expression in recalcitrant bacteria, Nature Methods 4:705-707; Prudhomme et al., 2006, Antibiotic stress induces genetic transformability in the human pathogen *Streptococcus pneumoniae*, Science 313:89-92; WO/2009/139985 Methods and materials for gastrointestinal delivery of a pathogen toxin binding agent; van Asseldonk, M et al. 1990, Cloning of usp45, a gene encoding a secreted protein from *Lactococcus lactis* subsp. *lactis* MG1363 Gene 95, 15-160; Kim et al., J Appl Microbiol. 2008 June; 104 (6): 1636-43. Epub 2008 Feb. 19. Display of heterologous proteins on the surface of *Lactococcus lactis* using the H and W domain of PrtB from *Lactobacillus* delburueckii subsp. *bulgaricus* as an anchoring matrix; Lee et al., 1999, Characterization of *Enterococcus faecalis* alkaline phosphatase and use in identifying *Streptococcus agalactiae* secreted proteins, J. Bacteriol 181 (18): 5790-9.) are required and substituted as needed.

Mutational backgrounds of *Listeria* vectors include those previously isolated, including the delta-actA strain 142 (Wallecha et al., 2009, Construction and characterization of an attenuated Listera *monocytogenes* strain for clinical use in cancer immunotherapy, Clin Vaccine Immunol 16:96-103), the double D-alanine (D-ala) strain described by Jiang et al., 2007, Vaccine 16:7470-7479, Yoshimura et al., 2006, Cancer Research 66:1096-1104, Lenz et al., 2008, Clinical and Vaccine Immunology 15:1414-1419, Roberts et al., 2005, Definition of genetically distinct attenuation mechanisms in naturally virulent *Listeria* moncyogenes by comparative cell culture and molecular characterization, Appl. Environ. Microbiol 71:3900-3910, the actA, prfA strain by Yan et al., Infect Immun 76:3439-3450, and those described by Portnoy et al., EP1513924 and Portnoy et al., WO/2003/102168.

Mutational backgrounds of the group B *Streptococcus, S. agalactiae*, include wild type (no mutations), of any of the nine serotypes that depend on the immunologic reactivity of the polysaccharide capsule and among nine serotypes, preferably types Ia, Ib, II, III, and V capable of being invasive in humans. The strain may be deleted in the beta-hemolysin/cytolysin (beta-H/C), including any member of the cly operon, preferably the clyE gene, or the CspA protease associated with virulence (Shelver and Bryan, 2008, J Bacteriol. 136:129-134), or the hyaluronate lyse C5a peptidase CAMP factor, oligopeptidase (Liu and Nizet 2004, Frontiers in Biosci 9:1794-1802; Doran and Nizet 2004, Mol Microbiol 54:23-31; Herbert et al., 2004, Curr Opin Infect Dis 17:225-229). The strains may further have mutations in metabolic genes pur, *purA*, aroA, aroB, aroC, aroD, pgi (glucose-6-phosphate isomerase), fructose-1,6-bisphosphatase, ptsH, ptsI, and/or one or more amino acid transporters and/or amino acid permeases. In a preferred embodiment, the strain is clyE deficient.

Other bacterial strains are also encompassed, including non-pathogenic bacteria of the gut such as *E. coli* strains, *Bacteroides, Bifidobacterium* and *Bacillus*, attenuated pathogenic strains of *E. coli* including enteropathogenic and uropathogenic isolates, *Enterococcus* sp. and *Serratia* sp. as well as attenuated *Shigella* sp., *Yersinia* sp., *Streptococcus* sp. and *Listeria* sp.

Bacteria of low pathogenic potential to humans such as *Clostridium* spp. and attenuated *Clostridium* spp., *Proteus mirabilis*, insect pathogenic Xenorhabdus sp., *Photorhabdus* sp. and human wound *Photorhabdus* (Xenorhabdus) are also encompassed. Probiotic strains of bacteria are also encompassed, including *Lactobacillus* sp., *Lactococcus* sp., *Leuconostoc* sp., *Pediococcus* sp., *Streptococcus* sp., *Streptococcus agalactiae, Lactococcus* sp., *Bacillus* sp., *Bacillus* natto, *Bifidobacterium* sp., *Bacteroides* sp., and *Escherichia coli* such as the 1917 Nissel strain.

The technology also provides, according to one embodiment, a process for preparing genetically stable therapeutic bacterial strains comprising genetically engineering the therapeutic genes of interest into a bacterially codon optimized expression sequence within a bacterial plasmid expression vector, endogenous virulence (VIR) plasmid (of *Salmonella* sp.), or chromosomal localization expression vector for any of the deleted genes or IS200 genes, defective phage or intergenic regions within the strain and further containing engineered restriction endonuclease sites such that the bacterially codon optimized expression gene contains subcomponents which are easily and rapidly exchangeable, and the bacterial strains so produced. Administration of the strain to the patient is therapeutic for the treatment of cancer.

The present technology provides, for example, and without limitation, live bacterial compositions that are genetically engineered to express one or more protease inhibitors combined with antitumor effector molecules for the treatment of cancers or neoplasias.

According to various embodiments, the technology provides pharmaceutical compositions comprising pharmaceutically acceptable carriers and one or more bacterial mutants. The technology also provides pharmaceutical compositions comprising pharmaceutically acceptable carriers and one or more bacterial mutants comprising nucleotide sequences encoding one or more therapeutic molecules. The pharmaceutical compositions of the technology may be used in accordance with the methods of the technology for the prophylaxis or treatment of neoplastic disease. Preferably, the bacterial mutants are attenuated by introducing one or more mutations in one or more genes in the lipopolysaccharide (LPS) biosynthetic pathway (for gram-negative bacteria), and optionally one or more mutations to auxotrophy for one or more nutrients or metabolites.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is chimeric toxin.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is a molecule with direct anti-cancer lytic capability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cancer cytotoxic or inhibitory ability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cellular activity against other cells of a tumor, including neutrophils, macrophages, T-cells, stromal cells, endothelial cells (tumor vasculature) and/or cancer stem cells.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules co-expressed with a protease inhibitor.

In a specific embodiment, a pharmaceutical composition comprises a pharmaceutically acceptable carrier and one or more attenuated bacterial mutants, wherein the bacterial mutants are a *Salmonella* sp. In another specific embodiment, a pharmaceutical composition comprises a pharmaceutically acceptable carrier and one or more attenuated stress-resistant gram-negative bacterial mutants, wherein the attenuated stress-resistant gram-negative bacterial mutants are a *Salmonella* sp., and the attenuated stress-resistant gram-negative bacterial mutants comprise one or more nucleic acid molecules encoding one or more therapeutic molecules, prodrug converting enzymes, metabolite degrading enzymes, lytic peptides, DNases or anti-cancer peptides.

In another specific embodiment, a pharmaceutical composition comprises a pharmaceutically acceptable carrier and one or more attenuated gram-positive bacterial mutants, wherein the attenuated gram-positive bacterial mutants are a *Streptococcus* sp., and the attenuated gram-positive bacterial mutants comprise one or more nucleic acid molecules encoding one or more therapeutic molecules, prodrug converting enzymes, metabolite degrading enzyme, lytic peptides, DNases or anti-cancer peptides.

In a specific embodiment, a pharmaceutical composition comprises a pharmaceutically acceptable carrier and one or more attenuated bacterial mutants, wherein the bacterial mutants are a *Listeria* sp. In another specific embodiment, a pharmaceutical composition comprises a pharmaceutically acceptable carrier and one or more attenuated bacterial mutants, wherein the attenuated gram-positive bacterial mutants are a *Listeria* sp., and the attenuated gram-positive bacterial mutants comprise one or more nucleic acid molecules encoding one or more therapeutic molecules, prodrug converting enzymes, metabolite degrading enzyme, lytic peptides, DNases or anti-cancer peptides.

The present technology, according to various embodiments, encompasses treatment protocols that provide a better therapeutic effect than current existing anticancer therapies. In particular, the present technology provides methods for prophylaxis or treatment of neoplastic diseases in a subject comprising administering to said subject and one or more bacterial mutants. The present technology also provides methods for the prophylaxis or treatment of neoplastic diseases in a subject comprising administering to said subject one or more bacterial mutants, wherein said bacterial mutants comprise one or more nucleic acid molecules encoding one or more therapeutic molecules together with one or more protease inhibitors.

The methods of the present technology, according to various embodiments, permit lower dosages and/or less frequent dosing of the bacterial mutants to be administered to a subject for prophylaxis or treatment of neoplastic disease to achieve a therapeutically effective amount of one or more therapeutic molecules. In a preferred embodiment, the genetically modified bacteria are used in animals, including humans, dogs, cats, and/or horses for protection or treatment against neoplastic diseases.

Accordingly, when administered to an individual, a live *Salmonella, Listeria* or *Streptococcus* bacterial vector or therapeutic, in accordance with the present technology, that is genetically engineered to express one or more anti-neoplastic molecules or molecules against other cells within the neoplastic milieu, optionally in combination with a protease inhibitor, and have improved efficacy due to improved surface display, secretion and/or released of the modified chimeric therapeutic proteins and/or enhanced binding to the target receptor resulting enhanced therapeutic activity against a neoplastic tissue including solid tumors, lymphomas and leukemias.

It is therefore an object to provide a genetic construct which causes a live host bacterium to express a peptide selected from the group consisting of at least one of: (a) a reorganized polycistronic cytolethal distending toxin fusion expressed or secreted in an absence of sty and ttsa, (b) a modified chimeric cytolethal distending toxin:apoptin fusion expressed or secreted in an absence of in an absence of sty and ttsa, and (c) a functionally active modified chimeric *Pseudomonas* ToxA therapeutic molecule. The genetic construct or bacterium may be provided in a pharmaceutically acceptable dosage form, suitable for administration to a human or animal, without causing significant morbidity. The peptide may act as an antineoplastic agent, and the bacterium may be trophic for diseased or malignant growths. The dosage form may be oral, enteral, parenteral, intravenous, per anus, topical, or inhaled, for example. The peptide may comprise a combination of at least one secretion signal, a linker, and domain Ib.

A pharmaceutically effective dosage form may comprise between about $10^5$ to $10^{12}$ live bacteria, within a lyophilized medium for oral administration. In some embodiments, about $10^9$ live bacteria are administered.

The live host bacterium may have antineoplastic activity against lymphoma, or solid tumors.

The peptide may be, for example, the modified chimeric cytolethal distending toxin:apoptin fusion with antineoplastic activity, having deletions of at least one cytolethal distending toxin nuclear localization signal. The peptide may also comprise an N-terminal fusion, e.g., of the modified chimeric cytolethal distending toxin:apoptin fusion.

Another object of the technology provides a chimeric protease inhibitor comprising YebF fused to sunflower trypsin inhibitor, adapted to inhibit at least one serine protease. The chimeric protease inhibitor may be formed by genetically engineered bacteria, wherein the genetically engineered bacteria secretes the YebF fused to sunflower trypsin inhibitor. The chimeric protease inhibitor may be provided in combination with a host bacteria and a genetically engineered construct which encodes the chimeric protease inhibitor, wherein the host bacteria secretes the chimeric protease inhibitor and the chimeric protease inhibitor inhibits at least one serine protease.

A further object provides a method for treating neoplastic tumor cells within a living organism, comprising: administering to a human or animal a live genetically engineered bacterium expressing peptide selected from the group consisting of at least one of: (a) a reorganized polycistronic cytolethal distending toxin fusion with antineoplastic activity expressed or secreted in an absence of sty and ttsa, (b) a modified chimeric cytolethal distending toxin:apoptin fusion with antineoplastic activity expressed or secreted in an absence of in an absence of sty and ttsa, and (c) a functionally active modified chimeric *Pseudomonas* ToxA therapeutic molecule with antineoplastic activity, wherein said peptide is secreted or released by said bacterium in a functionally active form. According to one embodiment of the method, the live genetically bacterium is allowed to colonize at least one tissue of the human or animal after administration, and the human or animal is treated with at least one systemic antibiotic to which the live genetically engineered bacterium is sensitive. The antibiotic may be narrow spectrum, and indeed, may comprise a composition not generally toxic to other bacteria or animal cells.

BRIEF DESCRIPTION OF THE DRAWINGS

FIGS. 1A-1I shows a comparison of modified ToxA chimeras.

DETAILED DESCRIPTION OF THE INVENTION

Figure 2A:
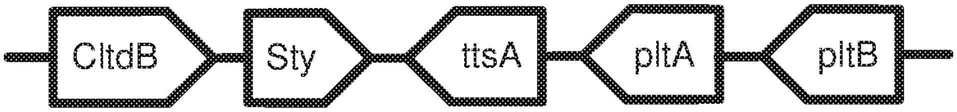
FIGS. 2A-2E show C-terminal modified cldt from *Salmonella* paratyphi A.

The present technology provides, according to various embodiments, live attenuated therapeutic bacterial strains that express one or more therapeutic with improved expression, secretion, surface display and/or release and/or have improved binding and anticancer cell activity that results in improved therapeutic efficacy. In particular, one aspect of the technology relates to live attenuated tumor-targeted bacterial strains that may include *Salmonella, Streptococcus* or *Listeria* vectoring novel chimeric anti-tumor toxins to an individual to elicit a therapeutic response against cancer. The types of cancer may generally include solid tumors, carcinomas, leukemias, lymphomas and multiple myelomas. Another aspect of the technology relates to live attenuated tumor-targeted bacterial strains that may include *Salmonella, Streptococcus, Clostridium* and *Listeria* that encode anti-neoplastic molecules to an individual to elicit a therapeutic response against cancers including cancer stem cells, immune infiltrating cells and or tumor matrix cells.

For reasons of clarity, the detailed description is divided into the following subsections: targeting ligands; chimeric bacterial toxins; and secreted protease inhibitors.

Targeting Ligands

Targeting ligands have specificity for the target cell and are used to both confer specificity to chimeric proteins, and to direct attachment and/or internalization into the target cell. The ligands are known ligands or may be novel ligands isolated through standard means such as phage display (Barbass III et al., 2004, Phage Display, A Laboratory Manual, Cold Spring Harbor Press) including the use of commercially available kits (Ph.D-7 Phage Display Library Kit, New England Biolabs, Ipswich, MA; Li et al., 2006. Molecular addresses of tumors: selection by in vivo phage display. Arch Immunol Ther Exp 54:177-181,). The ligands of various aspects of the present technology are peptides that can be expressed as fusions with other bacterially-expressed proteins. The peptides may be further modified, as for gastrin and bombesin, in being amidated by a peptidylglycine-alpha-amidating monoxygenase or C-terminal amidating enzyme, which is co-expressed in the bacteria that use these peptides using standard molecular genetic techniques. Examples of targeting peptides are shown in Bermudes U.S. Pat. No. 8,524,220 Table 4, incorporated by reference herein. These ligands and their targets include TGF-α (EGFR), HAVDI and INPISGQ and dimeric versions (N-cadherin of prostate), DUP-1 peptide (prostate cancer), laminin-411 binding peptides (brain neovasculature), pertussis toxin S3 subunit (cancer cells), DARPINS (e.g., H10, HER2), affibody against Her2 (Zielenski, R., Lyakhov, I., Jacobs, A., Chertov, O., Kramer-Marek, G., Francella, N., Stephen, A., Fisher, R., Blumenthal, R., and Capala, J. Affitoxin-A Novel Recombinant, HER2-Specific, Anti-Cancer Agent for Targeted Therapy of HER2-Positive Tumors. J Immunother. 2009 October; 32 (8): 817-825) luteinizing hormone-releasing hormone (LHRH receptor), IL2 (IL2R), EGF and EGF receptor related peptide (EGFR), tissue factor (TfR), IL4 (IL4R), IL134 (IL13R), GM-CSF (GM-CSFR), CAYHRLRRC SEQ ID NO.: 021 (lymphoid tissue; AML), A33 antigen binding peptide (A33) CLTA-4/CD152 melanoma, CD19 binding peptides/Bpep (alpha (v) beta (6) integrin (αvβ6), non-Hodgkin lymphoma, chronic lymphocytic leukemia (CLL) and acute lymphocytic leukemia (ALL)), CD20 binding peptides (CD20, B-cell malignancies), CD22 binding peptides (B lymphocytes, hairy cell leukemia), CD25 binding peptides (chemotherapy-resistant human leukemia stem cells), TRU-015 (CD-20), CD30 binding peptides (CD-30 Hodgkin's lymphoma), CD32 binding peptides (chemotherapy resistant human leukemia stem cells), CD33 binding peptides (CD-33 AML myleodysplastic cells MDS)), CD37 binding peptides (leukemia and lymphoma), CD40 binding peptides (CD40 multiple myeloma, non-Hodgkin lymphoma, chronic lymphocytic leukemia (CLL), Hodgkin lymphoma and acute lymphoblastic leukemia (ALL), diffuse large B-cell lymphoma, refractory non-Hodgkin lymphoma, including follicular lymphoma), CD52 (CLL), CD55 (CD55R), CD70 (hematological malignancies, non-Hodgkin's lymphoma), CD123 binding peptides (AML), RGD peptides (tumor cells and tumor endothelium), nanobodies derived from camels and llamas (camelids), including humanized nanobodies and VHH recognition domains (cancer), bombesin (gastrin releasing peptide receptor), gastrin releasing peptide (gastrin releasing peptide receptor), somatostatin octapeptide RC-121 (colon cancer), vasoactive intestinal peptide (tumor cell membranes), PTHrP (parathyroid hormone receptor G-protein coupled receptor), mesothelin binding peptides (mesothelin), CA125/MUC16 (mesothelin), heat stable enterotoxin (HST) (guanylyl cyclase C), GM-CSF (AML), vitronectin (Alfa (V) Beta (3) integrin), gastrin (gastrin receptor), CQTIDGKKYYFN SEQ ID NO.: 022 peptide from *Clostridium*, affibody against HER3, DARPIN against HER2, TGFα, EGF, EGFR-binding peptides and other, non-limiting, peptides. In preferred embodiments, the peptides are affibody against HER2, H10 DARPIN against HER2, TGFα, EGF, EGFR-binding peptides.

FIGS. 1A-1I show a comparison of modified ToxA chimeras. Optionally, the colicin E3 lysis protein with a separate ribosomal binding site may be added to any of the constructs.

FIG. 1A shows a chimera containing an OmpA secretion signal, TGF α targeting domain, a GGGGS (x3) (i.e., GGGGSGGGGSGGGGS, SEQ ID NO.: 008 linker, ToxA domain Ib (containing cysteine bonding), ToxA domain III, followed optionally by KDEL retrograde trafficking signal; without KDEL the native signal REDLK SEQ ID NO.: 023).

FIG. 1B shows a chimera containing an OmpA secretion signal, TGFα targeting domain, a GGGGS (x3), SEQ ID NO.: 008 linker), ToxA domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1C shows a chimera containing an OmpA secretion signal, TGFα targeting domain, a GGGGS (x3), SEQ ID NO.: 008 linker, ToxA PE38 (contains Domain II, partial Ib (A365-380 amino acids) domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1D shows a chimera containing an OmpA secretion signal, EGF binding peptide (EGB), a GGGGS (x3), SEQ ID NO.: 008 linker, ToxA PE38 (contains Domain II, partial Ib (A365-380 amino acids) domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1E shows a chimera containing an M13 pIII secretion signal, EGF binding peptide (EGB), a GGGGS (x3), SEQ ID NO.: 008 linker, ToxA PE38 (contains Domain II, partial Ib (4365-380 amino acids) domain III followed optionally by KDEL retrograde trafficking signal; without KDEL the native signal REDLK SEQ ID NO.: 023. Optionally, the colicin E3 lysis protein with a separate ribosomal binding site may be added.

FIG. 1F shows a chimera containing an OmpA secretion signal, Her2 affibody binding, a GGGGS SEQ ID NO.: 024 linker, ToxA PE38 (contains Domain II, partial Ib (Δ365-380 amino acids) domain III followed optionally by KDEL retrograde trafficking signal; without KDEL the native signal REDLK SEQ ID NO.: 023.

FIG. 1G shows a chimera containing an OmpA secretion signal, Her2 affibody binding, a GGGGS (x3), SEQ ID NO.: 008 linker, ToxA PE38 (contains Domain II, partial Ib (A365-380 amino acids) domain III followed optionally by KDEL retrograde trafficking signal; without KDEL the native signal REDLK SEQ ID NO.: 023.

FIG. 1H shows a chimera containing an OmpA secretion signal, Her2 affibody, a GGGGS (x3) linker, ToxA domain Ib (containing cysteine bonding), ToxA domain III followed optionally by KDEL retrograde trafficking signal; without KDEL the native signal REDLK SEQ ID NO.: 023.

FIG. 1I shows a chimera containing an OmpA secretion signal, EGFR binding peptide, a GGGGS (x3), SEQ ID NO.: 008 linker, ToxA domain Ib (containing cysteine bonding), ToxA domain III followed optionally by KDEL retrograde trafficking signal; without KDEL the native signal REDLK SEQ ID NO.: 023.

Chimeric Bacterial Toxins

Chimeric toxins are toxins that may contain combinations of elements including targeting peptides, flexible linkers, disulfide bonding, lytic peptides, nuclear localization signals, blocking peptides, protease cleavage (deactivation or activation) sites, N- or C-terminal secretion signals, autotransporter constructs, used to adapt the proteins to be expressed, secreted, surface displayed and/or released by bacteria to provide therapeutic molecules that are effective in treating neoplastic cells, stromal cells, neoplastic stem cells as well as immune infiltrating cells. Targeting to a particular cell type uses the appropriate ligand described above or from other known sources. Toxin activity is determined using standard methods known to those skilled in the art such as Aktories (ed) 1997 (Bacterial Toxins, Tools In Cell Biology and Pharmacology, Laboratory Companion, Chapman & Hall).

FIGS. 2A-2D show C-terminal fusions of modified cldt from *Salmonella* paratyphi A.

FIG. 2A shows the *Salmonella* typhoid toxin cytolethal distending toxin subunit B (cldtB) together with sty, ttsA, pltA and pltB. The entire operon is with cldtB and sty under control of an inducible promoter such as the arabinose inducible promoter, with pltB, pltA and ttsA under control of their upstream region.

Figure 2B:
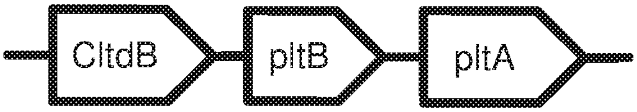

FIG. 2B shows the *Salmonella* typhoid toxin cytolethal distending toxin subunit B (cldtB) together with pltB and pltA as a single artificial operon under control of an inducible promoter, and the genes sty and ttsA removed.

Figure 2C:
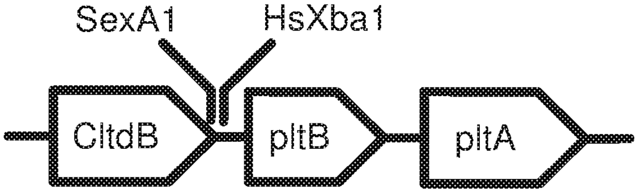

FIG. 2C shows the cldtB, pltB and pltA artificial operon with an in frame fusion of the restriction enzymes SexAl, HindIII and Xbal followed by a stop codon.

Figure 2D:
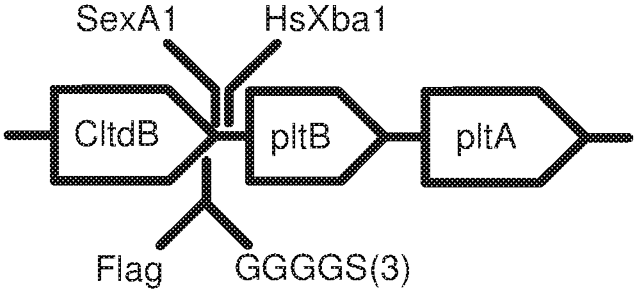

FIG. 2D shows the cldtB, pltB and pltA artificial operon with SexAl, HindIII and Xbal with the FLAG epitope and a GGGGS (x3), SEQ ID NO.: 008 linker inserted in the SexAl and HindIII sites.

Figure 2E:
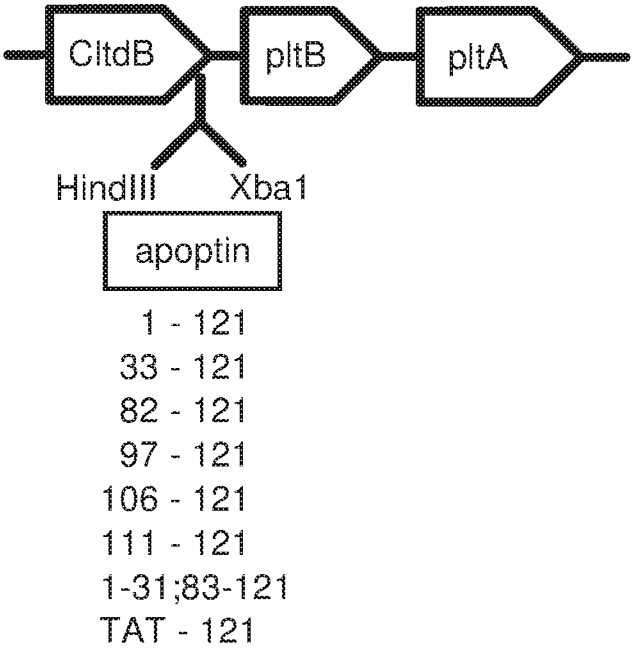

FIG. 2E shows the cldtB, pltB and pltA artificial operon with SexAl, HindIII and Xbal with the FLAG epitope and a GGGGS (x3), SEQ ID NO.: 008 linker inserted in the SexAl and HindIII sites and apoptin fragments inserted in-frame into the HindIII and Xbal sites. The apoptin and/or apoptin fragments can consist of 1) apoptin 1-121, 2) apoptin 33-121, 3) apoptin 82-121, 4) apoptin 97-121, 5) apoptin 106-121, 6) apoptin 111-121 or 7) apoptin 1-31 linked ot 83-121 or 8) TAT-apoptin.

Chimeric ToxA Forms Secreted by Bacteria.

Cytotoxic forms of ToxA that can be secreted by bacteria have targeting ligands. Previous ToxA conjugates were not adapted for secretion by bacteria in an active form. For example, TGFα-GIII-KDEL (Kihara and Pastan 1994, Small Chimeric Toxins Containing Only Transforming Growth Factor α and Domain III of *Pseudomonas* Exotoxin with Good Antitumor Activity in Mice. Cancer Res 1994: 54:5154-5159) had a TGFα α-PE38 which has a deletion of amino acids 365-380 of domain I (Kreitman et al., 1992, Properties of Chimeric Toxins with Two Recognition Domains: Interleukin 6 and Transforming Growth Factor α at Different Locations in *Pseudomonas* Exotoxin. Bioconjugate Chem. 3, 63-68) have no signal peptide, only a single GGGGS SEQ ID NO.: 024 linker with 10 amino acids upstream of DIII, compared to the present version (FIGS. 1A-1I). PE38-KDEL (Kreitman et al., 1994, Recombinant immunotoxins containing anti-Tac (Fv) and derivatives of *Pseudomonas* exotoxin produce complete regression in mice of an interleukin 2 receptor-expressing human carcinoma. Blood 1994, 83, 426-434) uses anti-Tac (Fv) as binding ligand rather than those we describe here. Similarly, the Affitoxin (Zielenski et al., 2009, Affitoxin-A Novel Recombinant, HER2-Specific, Anti-Cancer Agent for Targeted Therapy of HER2-Positive Tumors. J Immunother 32:817-825) has no signal peptide and only a short flexible linker. The forms of ToxA shown in FIGS. 1A-1I and described in the examples with targeting moieties supply the necessary components for secreted by bacteria and are cytotoxic for cancer cells.

FIGS. 3A-3D show N-terminal fusions of modified cldt from *Salmonella* paratyphi A.

Figure 3A:
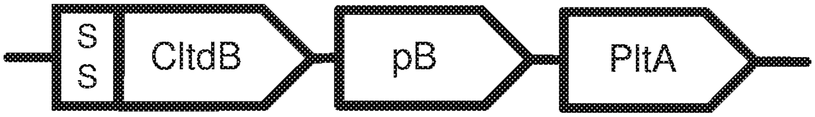
FIG. 3A-3D show N-terminal modified cldt from *Salmonella* paratyphi A.

FIG. 3A shows the *Salmonella* typhoid toxin cytolethal distending toxin subunit B (cldtB) together with pltB and pltA as a single artificial operon under control of an inducible promoter, and the genes sty and ttsA removed. The presence and relative location of an N-terminal signal sequence (SS) is shown.

Figure 3B:
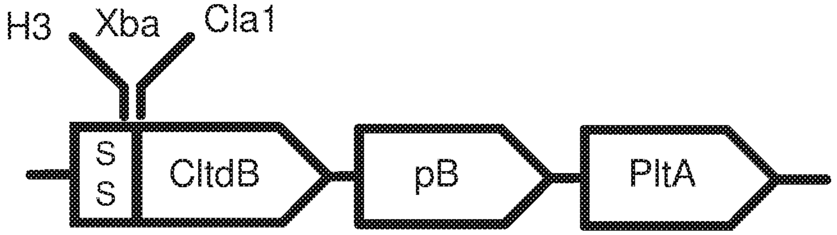

FIG. 3B shows the cldtB, pltB and pltA artificial operon with an in frame fusion of the restriction enzymes HindIII, Xbal and Clal inserted after the signal sequence.

Figure 3C:
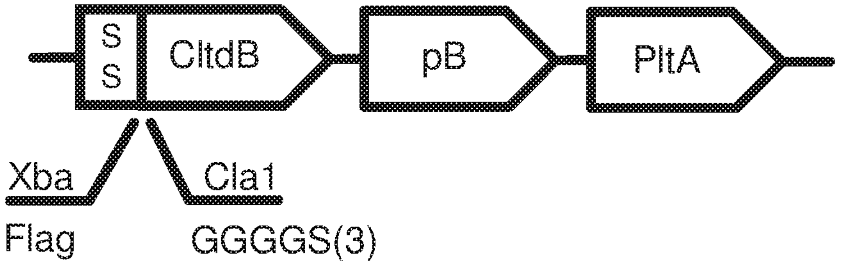

FIG. 3C shows the cldtB, pltB and pltA artificial operon with HindIII, Xbal and Clal with the FLAG epitope and a GGGGS (x3), SEQ ID NO.: 008 linker inserted in the Xbal and Clal sites.

Figure 3D:
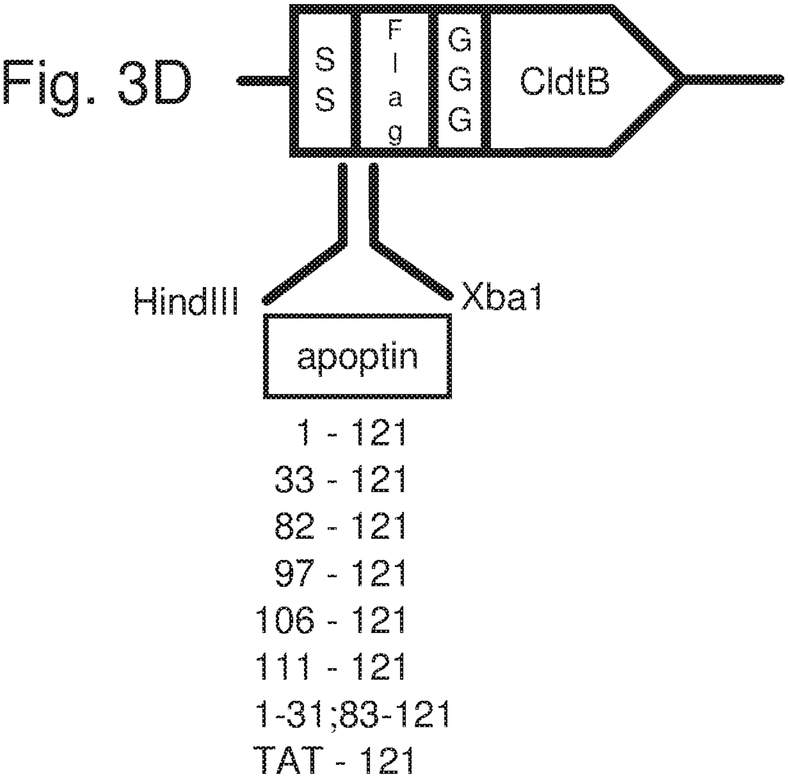

FIG. 3D shows the cldtB, pltB and pltA artificial operon with the FLAG epitope and a GGGGS (x3), SEQ ID NO.: 008 linker inserted in the Xbal and Clal sites and apoptin fragments inserted in-frame into the HindIII and Xbal sites. The apoptin and/or apoptin fragments can consist of 1) apoptin 1-121, 2) apoptin 33-121, 3) apoptin 82-121, 4) apoptin 97-121, 5) apoptin 106-121, 6) apoptin 111-121 or 7) apoptin 1-31 linked to 83-121 or 8) TAT-apoptin.

Chimeric Cvtolethal Distending Toxins.

Cytolethal distending toxins (cldt) including those cldts from *Haemophilus, Aggregatibacter, Salmonella, Escherichia, Shigella, Campylobacter, Helicobacter*, Hahella and *Yersinia*, typhoid toxins (pertussis like toxin) (pltAB), pertussis toxin, cldt: plt hybrids are three component toxins of these bacteria. Cldt is an endonuclease toxin and has a nuclear localization signal on the B subunit. Chimeric toxins are provided that utilize N-terminal or C-terminal fusions to apoptin, a canary virus protein that has a tumor-specific nuclear localization signal, and a normal (non-transformed) cell nuclear export signal (FIGS. 2A-4D). The present technology, according to one embodiment, consists of a modified *Salmonella* CLDT operon and forms of cytolethal distending toxins that are chimeric with apoptin and other peptide moieties including peptide linkers that improve activity and peptide blocking moieties that must be specifically cleaved to activate the protein.

The present technology, according to one embodiment. uses deletions in the CLDT nuclear localization signals which are then complemented by N- or C-terminal fusions with apoptin, or apoptin fragments, which supply its nuclear localization signal in trans as a fusion peptide.

The cytolethal distending toxin B and chimeric cltdB may be expressed as a polycistronic construct consisting of cldtABC. The cytolethal distending toxin B and chimeric cltdB may be expressed as a polycistronic construct consisting containing the typhoid pertussis-like toxin (plt) AB genes. However, in the present technology, according to one embodiment, the presence of sty and ttsA are not required for secretion of the active toxin when the operon is reorganized into a unidirectional operon of cldtB, pltB and pltA.

Overall improvement is defined as an increase in effect, such as the ability to kill neoplastic cells in vitro by the bacteria, or inhibit or reduce the volume or cell number of a solid tumor, carcinoma, lymphoma or leukemia in vivo following administration with the bacteria expressing a therapeutic molecule, with and without the protease inhibitor. The effect of the protein therapeutic activity is determined using standard techniques and assays known to those skilled in the art. The contribution of the therapeutic protein and protease inhibitors is determined individually and in combination. Additivity, synergy or antagonism may be determined using the median effect analysis (Chou and Talaly 1981 Eur. J. Biochem. 115:207-216) or other standard methods.

FIGS. 4A-4D show nuclear localization signal (NLS) modified partially or completely cldt from *Salmonella* paratyphi A.

Figure 4A:
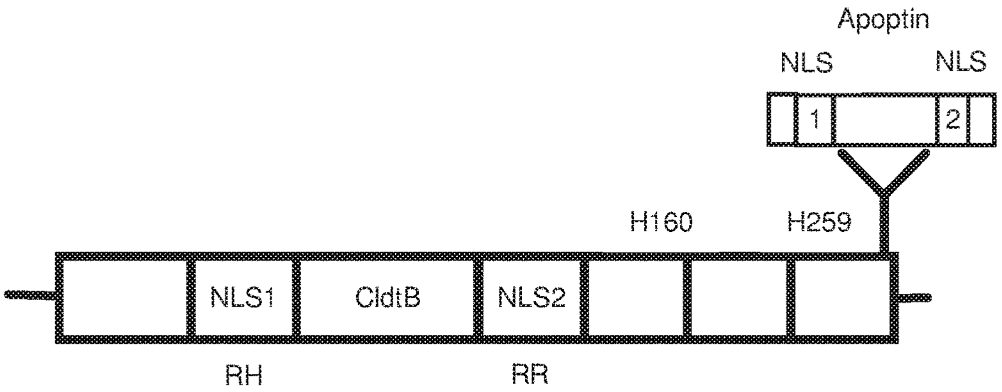
FIGS. 4A-4D show nuclear localization signal (NLS) modified cldt from *Salmonella* paratyphi A.

FIG. 4A shows inactivated *Salmonella* paratyphi A typhoid toxin as a delivery mechanism for peptide fusions. The *Salmonella* typhoid toxin cldtB is inactivated by site-directed mutagenesis of the known active sites such as H160Q and/or H259Q. Fusions to the inactivated form retain the secretion and delivery to the cytosol and allow transport to the nucleus.

Figure 4B:
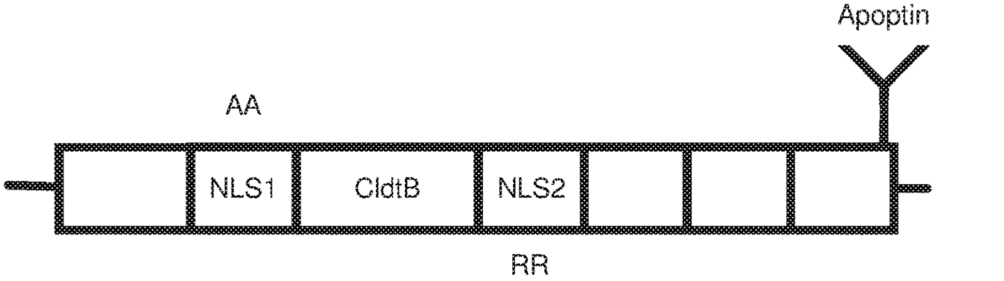

FIG. 4B shows inactivated *Salmonella* paratyphi A typhoid toxin nuclear localization signals (NLS1) enhancing dependence on apoptin NLSs and/or nuclear export as a mode of tumor cell-specific delivery of an active cldtB.

Figure 4C:
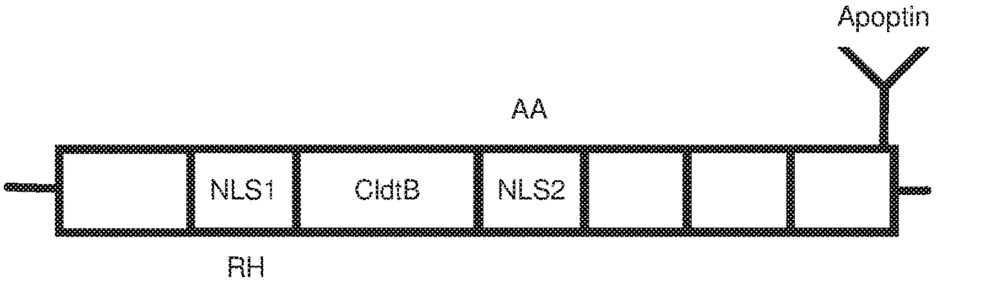

FIG. 4C shows inactivation of NLS2 and

Figure 4D:
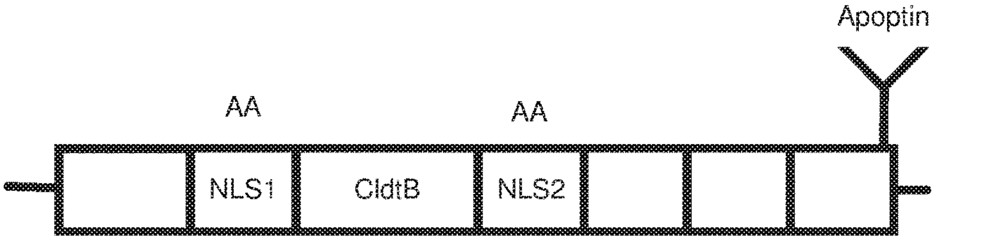

FIG. 4D shows both portions of the cldtB bipartite nuclear localization signals can be altered from charged (basic) e.g., arginines and/or histidines to polar serines or threonines.

Secreted Protease Inhibitors

A chimeric protease inhibitor secreted by *Escherichia coli* with the potential for use in biofuel fermentations and therapeutic bacteria is provided.

There is growing interest in the use of live bacteria targeting solid tumors as an alternative to or in conjunction with standard chemotherapy and radiation treatment. These bacteria can be engineered to secrete bacterial derived cytotoxins, such as *Pseudomonas aeruginosa* exotoxin A, directly to the site of the tumor (Forbes, 2010 and Swofford et al, 2014). Therapeutic bacteria expressing and secreting cytotoxins that are tumor cell specific may enhance tumor destruction and spare healthy adjacent tissues (Siegal et al, 1989). Bacteria expressing protease inhibitors specific for proteases associated with metastasis is an innovative approach to cancer therapeutics. Co-expression of a tumor specific cytotoxin and a protease inhibitor may enhance the stability of the toxin by protecting it in the highly proteolytic environment of the tumor while confining the cancer.

From a bio-industrial standpoint, fermentations which are sensitive to bacterial contaminations, especially those due to proteolytic strains such as *Lactobacillus* sp., may benefit from protease inhibition. Bacteria and fungi secreting protease inhibitors offer a potential augmentation to extracellular fermentations such as cellulosic ones used in the production of biofuels where microbial contaminations reduce production efficiency.

Protease inhibitor-secreting bacteria have an ability to protect extracellular proteins from proteolytic destruction by trypsin, utilizing exotoxin A in cytotoxicity studies and α-amylase as a model industrial extracellular fermentation enzyme.

FIGS. 5A-5D show results of a secreted protease inhibition assay for detection of bacterial secreted protease inhibitors, using the method of Quintero and Bermudes (2014. A culture-based method for determining the production of secreted protease inhibitors. J. Micro. Methods. 100, 105-110).

Figure 5A:
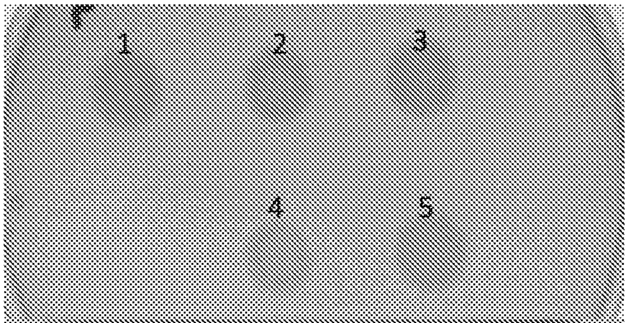
FIGS. 5A-5D show a secreted protease inhibition assay.

FIG. 5A shows growth pattern of *E. coli* harboring 1) pTet-1 (EV), 2) pTetOmpA-SFTI, 3) pTetTxA-SFTI, 4) pTetOmpA-SFTI-RBS Lys, 5) pTetTxA-SFTI-RBS Lys on BCG 0.5% Casein induced with 1 μg/mL anhydrotetraclyine HCl after 24 hours at 37° C.

Figure 5B:
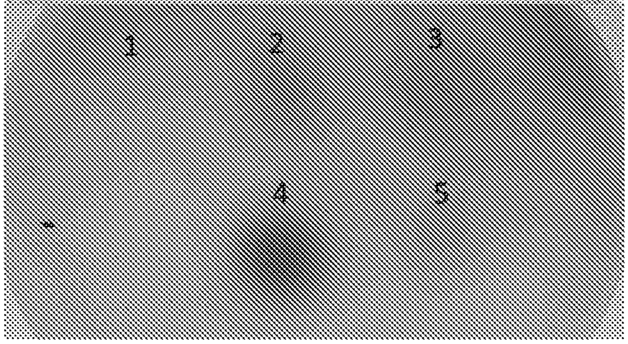

FIG. 5B shows staining pattern of protected protein, using the method of Quintero and Bermudes (2014. A culture-based method for determining the production of secreted protease inhibitors. J. Micro. Methods. 100, 105-110).

Figure 5C:
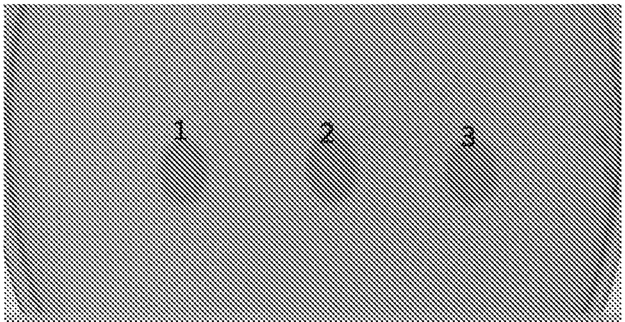

FIG. 5C shows growth of *E. coli* harboring 1) pTet-1 (EV), 2) pTetYebF, 3) pTetYebF-SFTI, on BCG 0.5% Casein with 1 mg/mL anhydrotetraclyine HCl after 24 hours at 37° C.

Figure 5D:
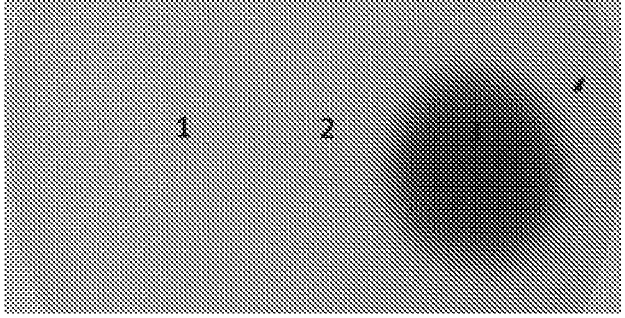

FIG. 5D shows a staining pattern of protected protein.

Figure 6:
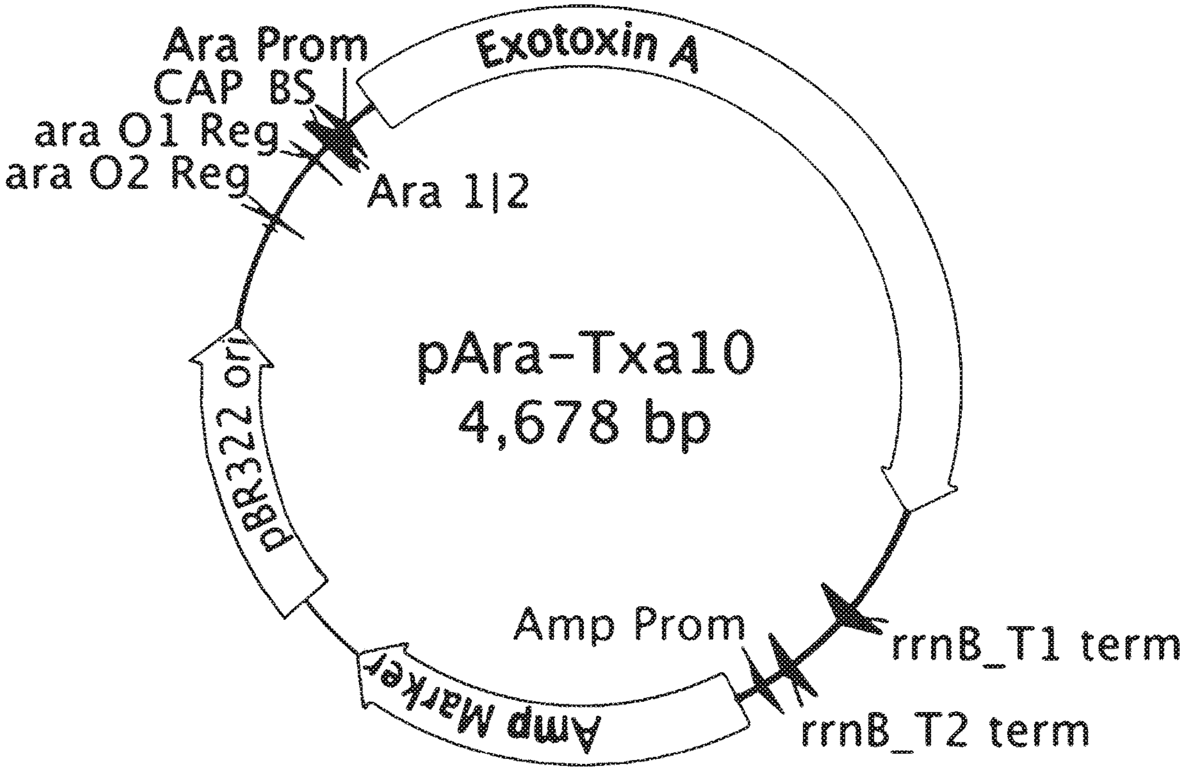
FIG. 6 shows a pAra-Txa10 4,678 bp plasmid.

FIG. 6 shows the gene encoding exotoxin A, which was amplified from *Pseudomonas aeruginosa* str. PA103 in a colony PCR and ligated to pAra-1 to create pAra-Txa10. The plasmids were electroporated into *Salmonella typhimurium* str. JR501 and induced with 0.1% arabinose. Filter sterile supernatant was diluted 2-fold in PBS. MDA-MB-468 breast cancer cells were plated at 2.5×103 cells in DMEM with 10% FBS and allowed to adhere to a 96-well plate for 24 hours. Bacterial supernatant or PBS was delivered to the cell culture to 10% and allowed to incubate for an additional 72 hours.

The sunflower trypsin inhibitor (SFTI), a 14 amino acid cyclic peptide was chosen for its small size and ability to inhibit matriptase, a tumor associated protease over-expressed in cancers of the breast, ovaries, prostate and liver. (Cai et al, 2011). SFTI was fused to the secretion signal peptides derived from the outer membrane protein OmpA and the secreted cytotoxin exotoxin A and evaluated for its ability to be secreted extracellularly and to inhibit degradation of a protein substrate. These constructs were coupled with the pColE3 lysis protein, which activates phospholipase and outer-membrane porins to facilitate secretion. SFTI was also fused to YebF, which is known to accumulate in the extracellular milieu of select proteobacteria.

Therefore, it can be seen that SFTI can be secreted in low amounts when fused to a type II secretion signal peptide. Co-expression of pColE3 lysis protein with the fusions enhances secretion when the OmpA signal is utilized, but not the Exotoxin A signal. This may be due to ineffective cleavage of the latter in the periplasm. Fusion of SFTI to YebF demonstrated high protease inhibition both in solid and liquid culture media. The protective effect of YebF-SFTI is shown by conducting an in vitro digest of Exotoxin A followed by a cytotoxity assay, which demonstrated sustained toxin activity. An in vitro digest of amylase followed by DNS assay showed only slight inhibition of trypsin by YebF-SFTI for unknown reasons.

Figure 7A:
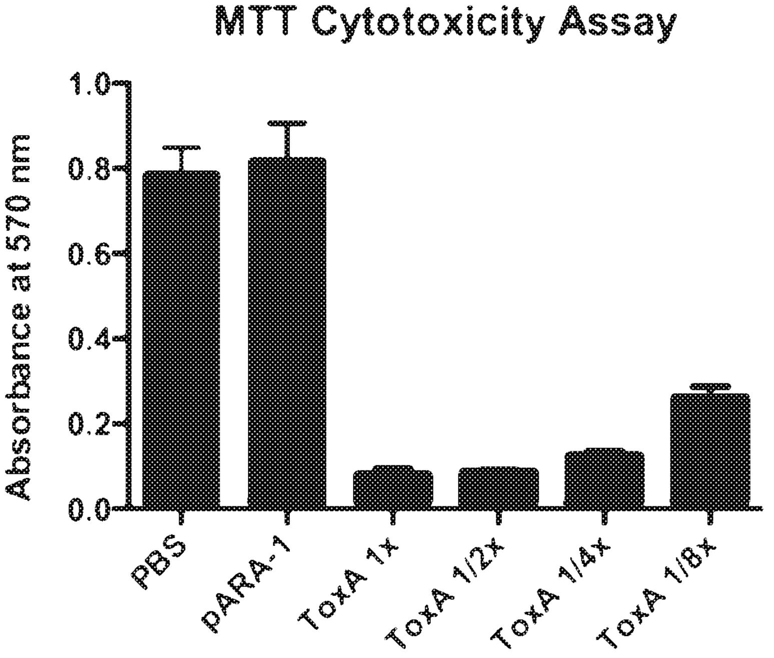
FIGS. 7A and 7B show results of MTT cytotoxicity (anticancer cell killing) assay of protease challenge/protease inhibitors.

FIG. 7A shows cytotoxicity (anticancer cell killing) protease challenge/protease inhibitor assay results, in in particular protection of extracellular ToxA from trypsin by YebF-SFTI assessed by cell killing. MDA-MB-468 breast cancer cells assessed by MTT after supernatants from *S. typhimurium* harboring pAra-1 was mixed with supernatants from *E. coli* harboring pTet-1 (EV), pTetYebF, or pTetYebf-SFTI then delivered to the cell culture. A 1:4 (vol:vol) mixture of supernatant containing exotoxin A and either YebF or YebF-SFTI was prepared and delivered to the cell culture. A seven hour in vitro digest (IVD) at 37° C. utilizing trypsin at a final concentration of 0.1 mg/ml containing exotoxin A and either YebF or YebF-SFTI (1:4) was conducted to test if the secreted protein maintained measurable activity.

Figure 7B:
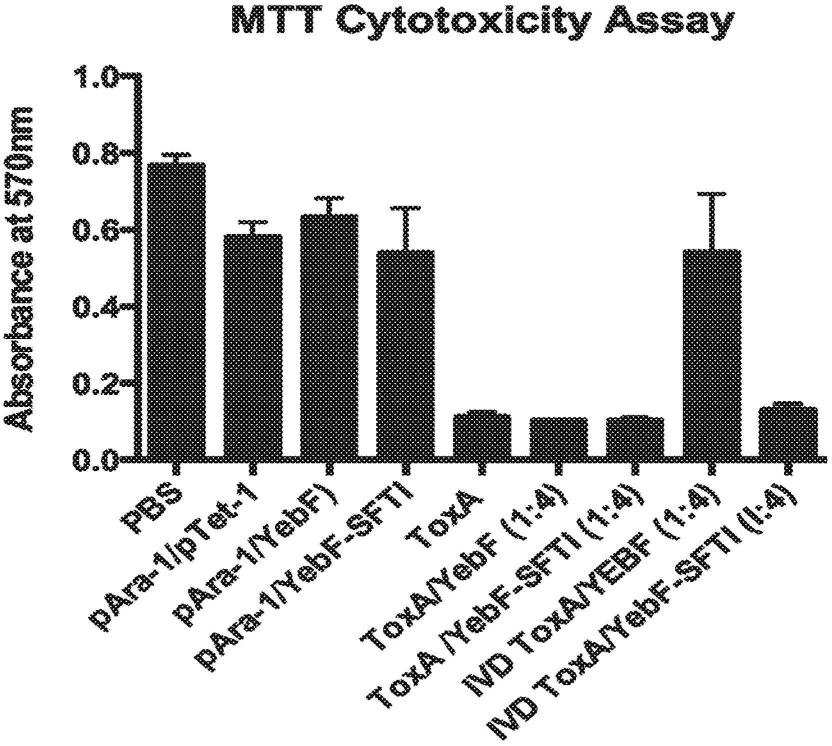

FIG. 7B shows protection of extracellular ToxA from trypsin by YebF-SFTI assessed by cell killing. MDA-MB-468 breast cancer cells were plated as above, and assessed by MTT after Supernatants from *S. typhimurium* harboring pAra-1 was mixed with supernatants from *E. coli* harboring pTet-1 (EV), pTetYebF, or pTetYebf-SFTI then delivered to the cell culture. A 1:4 (vol:vol) mixture of supernatant containing exotoxin A and either YebF or YebF-SFTI was prepared and delivered to the cell culture. A seven hour in vitro digest (IVD) at 37° C. utilizing trypsin at a final concentration of 0.1 mg/ml containing exotoxin A and either YebF or YebF-SFTI (1:4) was conducted to test if the secreted protein maintained measurable activity.

See: Forbes, N. S., 2010. Engineering the perfect (bacterial) cancer therapy. Nature Reviews Cancer 10, 785-794; Swofford, C., St. Jean, A. T., Panteli, J. T., Brentzel, Z. J., Forbes, N. S. 2014. Identification of *Staphylococcus aureus* α-hemolysin as a Protein Drug that is Secreted by Anticancer Bacteria and Rapidly kills Cancer Cells. Biotech. Bioeng. 111, 1233-1245; Siegall, C., Yong-Hua, X., Vijay, K. C., Sankar, A., Fitzgerald, D., and Pastin, I. 1989. Cytotoxic activities of a fusion protein comprised of TGFα and *Pseudomonas* exotoxin. FASEB. J. 3, 2547-2652; Quintero, D. and Bermudes, D. 2014. A culture-based method for determining the production of secreted protease inhibitors. J. Micro. Methods. 100, 105-110.

See also Examples 12-14.

Figure 8A:
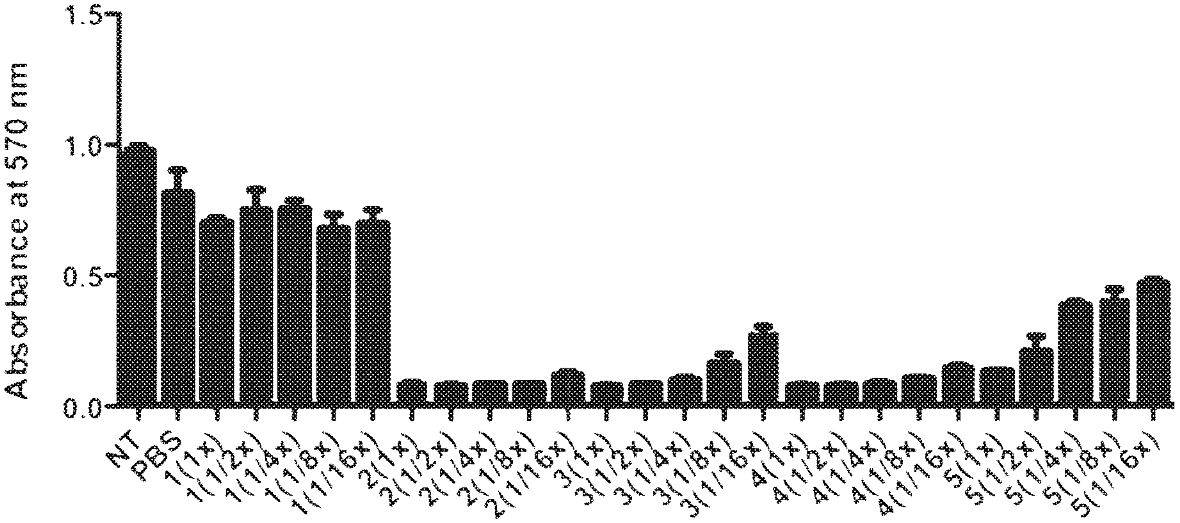
FIGS. 8A and 8B show results of a cytotoxicity (anticancer cell killing) assay of cytolethal distending toxin and cytolethal distending toxin:apoptin fusions.
Figure 8B:
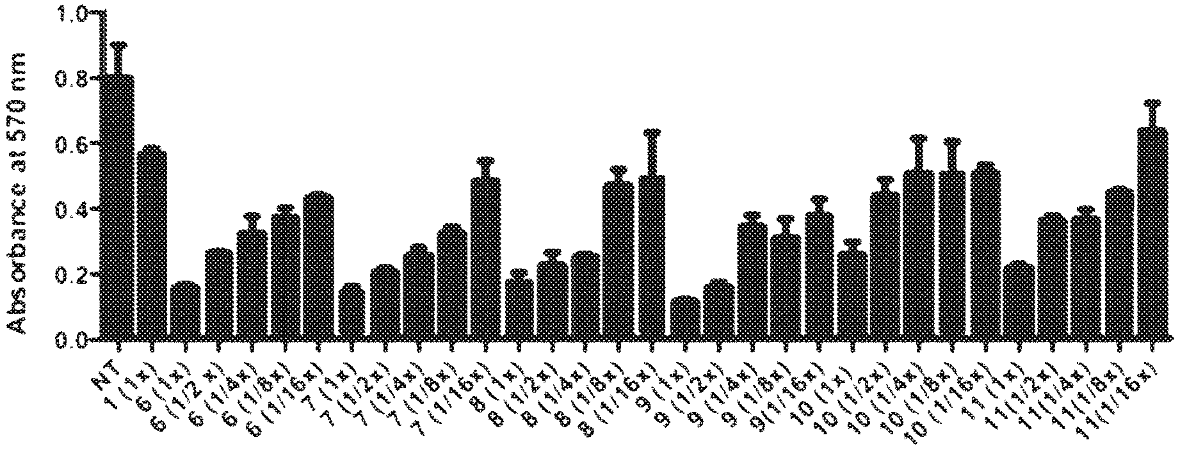

FIGS. 8A and 8B show results of a cytotoxicity (anticancer cell killing) assay of *Salmonella* paratyphi A cytolethal distending toxin and cytolethal distending toxin:apoptin fusions toward MDA-MB-468 breast cancer cells.

NT: no treatment.

PBS: phosphate buffered saline.

1: treatment with 10 μL of a bacterial culture supernatant carrying an empty vector plasmid into a 100 μL tissue culture wells, with dilutions of 1, 1/2, 1/4, 1/8 and 1/16.

2: the cloned wild type S. paratyphi A cytolethal distending operon (as shown in FIGS. 2A-2E), with dilutions of 1/2, 1/4, 1/8 and 1/16.

3: the reorganized polycistronic S. paratyphi A cytolethal distending operon containing a polylinker in cldtB C-terminus with dilutions of 1/2, 1/4, 1/8, and 1/16.

4: the reorganized polycistronic S. paratyphi A cytolethal distending operon without a polylinker in cldtB C-terminus with dilutions of 1/2 1/4 1/8 and 1/16. Absorbance at 570 nm indicates the relative number of live cells.

5: the reorganized polycistronic S. paratyphi A cytolethal distending operon containing a polylinker in cldtB C-terminus and a flexible linker GGGGS (3) SEQ ID NO.: 008 with dilutions of 1/2, 1/4, 1/8, and 1/16.

6: the reorganized polycistronic S. paratyphi A cytolethal distending operon containing a polylinker in cldtB C-terminus and a fusion of apoptin 1-121 with dilutions of 1/2, 1/4, 1/8, and 1/16.

7: the reorganized polycistronic S. paratyphi A cytolethal distending operon containing a polylinker in cldtB C-terminus and a fusion of apoptin 82-121 with dilutions of 1/2, 1/4, 1/8 and 1/16.

8: the reorganized polycistronic S. paratyphi A cytolethal distending operon containing a polylinker in cldtB C-terminus and a fusion of apoptin 111-121 with dilutions of 1/2, 1/4, 1/8 and 1/16.

9: the reorganized polycistronic S. paratyphi A cytolethal distending operon containing a polylinker in cldtB C-terminus and a fusion of apoptin 97-121 with dilutions of 1/2, 1/4, 1/8 and 1/16.

10: the reorganized polycistronic S. paratyphi A cytolethal distending operon containing a polylinker in cldtB C-terminus and a fusion of apoptin 33-121 with dilutions of 1/2, 1/4, 1/8 and 1/16.

11: the reorganized polycistronic S. paratyphi A cytolethal distending operon containing a polylinker in cldtB C-terminus and a fusion of TAT: apoptin 1-121 with dilutions of 1/2, 1/4, 1/8 and 1/16.

Figure 9:
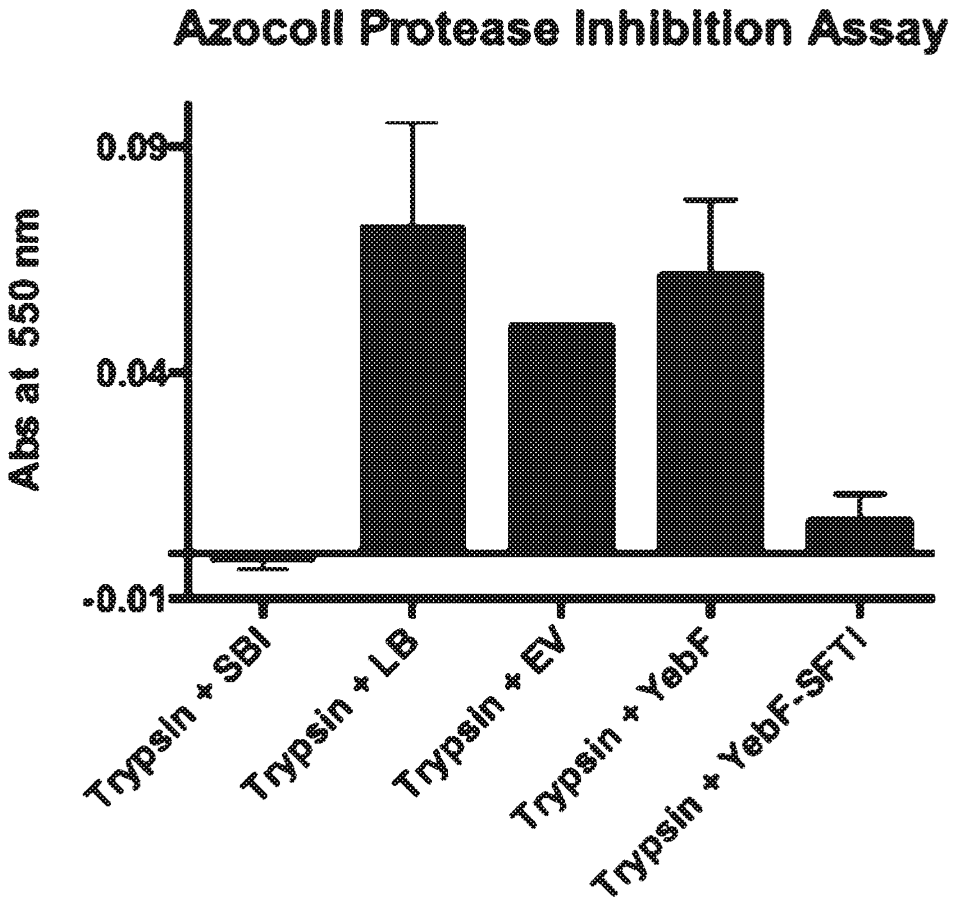
FIG. 9 shows results of an Azocoll protease inhibition assay.

FIG. 9 shows results of an assay using Azo dye impregnated collagen (Azocoll) protease substrate. *E. coli* harboring pTet-1 (EV), pTetYebF, or pTetYebF-SFTI, were induced overnight. 500 μL of filter sterile supernatant was incubated with 10 mL of 6.25 mg/mL trypsin solution for 1 hour at room temperature to allow binding. Soybean inhibitor (SBI) and LB served as controls. After equilibration, 400 mL of a 1.5 mg/mL Azocoll suspension was mixed with each sample and incubated at 37° C. for a 2 hour digestion. Proteolytic degradation of Azocoll was measured with a spectrophotometer at Abs 550 nm. After subtracting background, the absorbance values were plotted using Prism version 6.

Figure 10A:
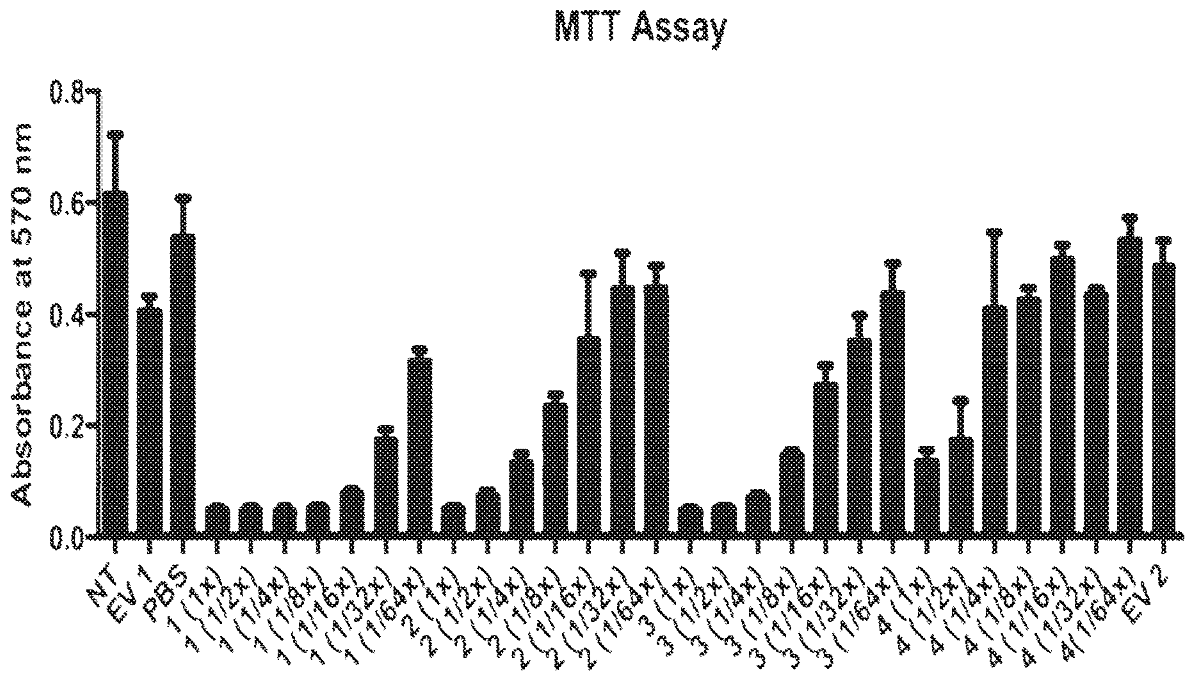
FIGS. 10A and 10B show a cytotoxicity (anticancer cell killing) assay of Exotoxin A (ToxA) and chimeric TGFα-ToxA fusions.
Figure 10B:
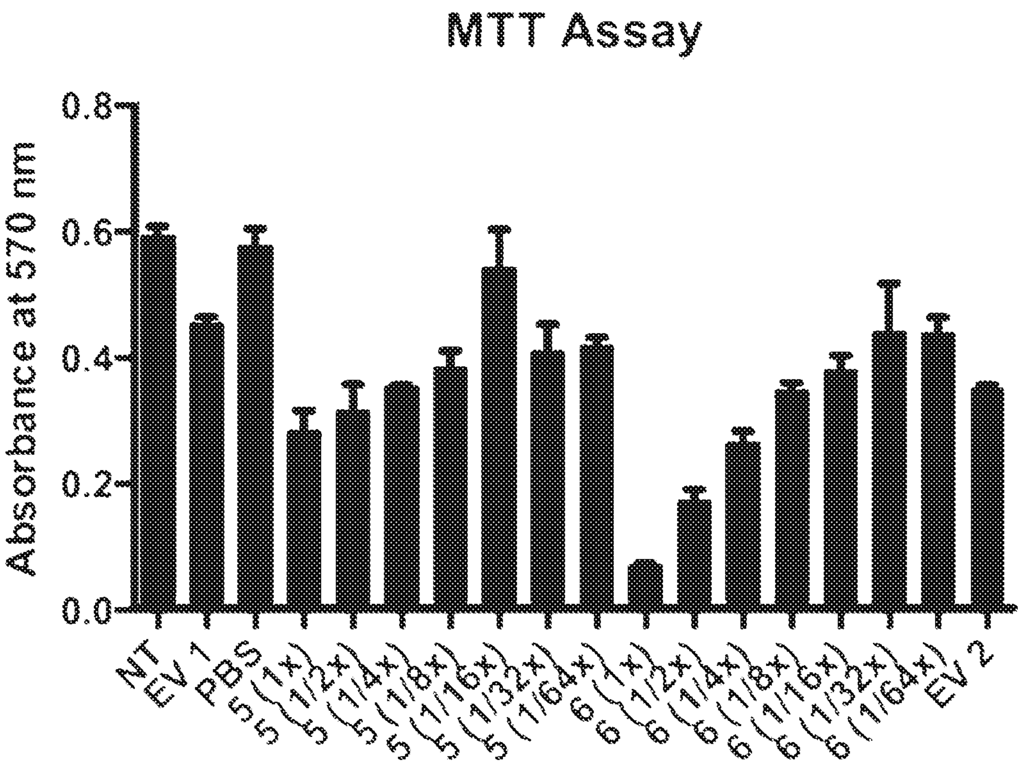

FIGS. 10A and 10B show the cytotoxicity of *Pseudomonas aeruginosa* Exotoxin A (ToxA) and chimeric derivatives toward MDA-MB-468 breast cancer cells.

FIG. 10A:

NT: no treatment. PBS, phosphate buffered saline.

EV 1: treatment with 10 μL of a bacterial culture supernatant carrying an empty vector plasmid into a 100 μL tissue culture wells.

1: the cloned wild type *Pseudomonas aeruginosa* Exotoxin A (ToxA) with dilutions of 1, 1/2, 1/4, 1/8, 1/16, 1/32, 1/64.

2: A chimeric toxin composed of N-terminal TGFα fused to domains Ib and III of ToxA with a C-terminal KDEL sequence with dilutions of 1, 1/2, 1/4, 1/8, 1/16, 1/32, 1/64.

3: A chimeric toxin composed of N-terminal TGFα fused to domains Ib and III of ToxA with a C-terminal KDEL sequence co-expressed with the RBS E3 Lysis protein with dilutions of 1, 1/2, 1/4, 1/8, 1/16, 1/32, 1/64.

4: A chimeric toxin composed of N-terminal TGFα fused to domains Ib and III of ToxA with the native C-terminal REDLK SEQ ID NO.: 023 ToxA sequence with dilutions of 1, 1/2, 1/4, 1/8, 1/16, 1/32, 1/64.

EV 2: empty vector plasmid.

FIG. 10B:

NT: no treatment. PBS, phosphate buffered saline.

EV 1: treatment with 10 μL of a bacterial culture supernatant carrying an empty vector plasmid into a 100 μL tissue culture wells.

1: the cloned wild type *Pseudomonas aeruginosa* Exotoxin A (ToxA) with dilutions of 1, 1/2, 1/4, 1/8, 1/16, 1/32, 1/64.

2: A chimeric toxin composed of N-terminal TGFα fused to domain III of ToxA with a C-terminal KDEL sequence with dilutions of 1, 1/2, 1/4, 1/8, 1/16, 1/32, 1/64.

3: A chimeric toxin composed of N-terminal TGFα fused to domain III of ToxA with a C-terminal KDEL sequence co-expressed with the RBS E3 Lysis protein with dilutions of 1, 1/2, 1/4, 1/8, 1/16, 1/32, 1/64.

4: A chimeric toxin composed of N-terminal TGFα fused to domains Ib and III of ToxA with the native C-terminal REDLK SEQ ID NO.: 023 ToxA sequence with dilutions of 1, 1/2, 1/4, 1/8, 1/16, 1/32, 1/64.

EV 2: empty vector plasmid.

Figure 11A:
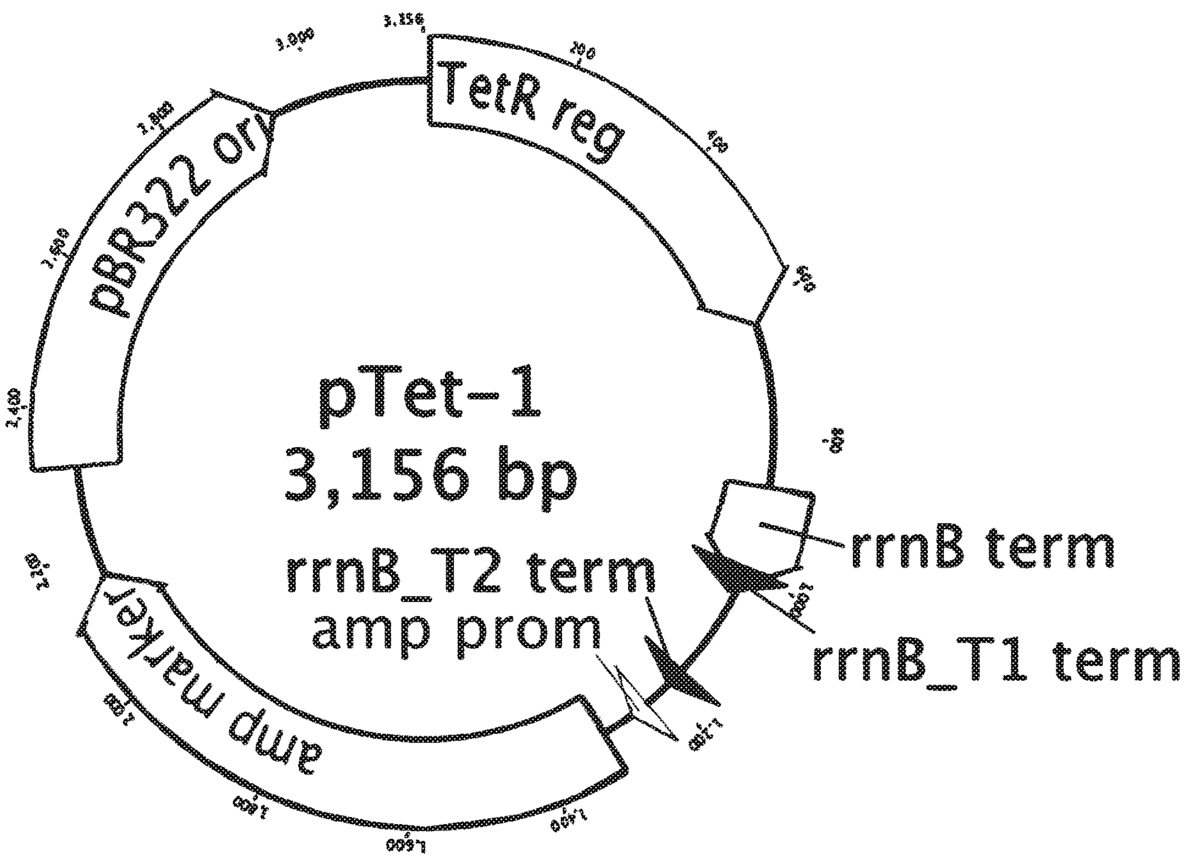
FIGS. 11A and 11B shows a pTet-1 3,156 plasmid, and pTet-1 under tetracycline controlled transcriptional activation.
Figure 11B:
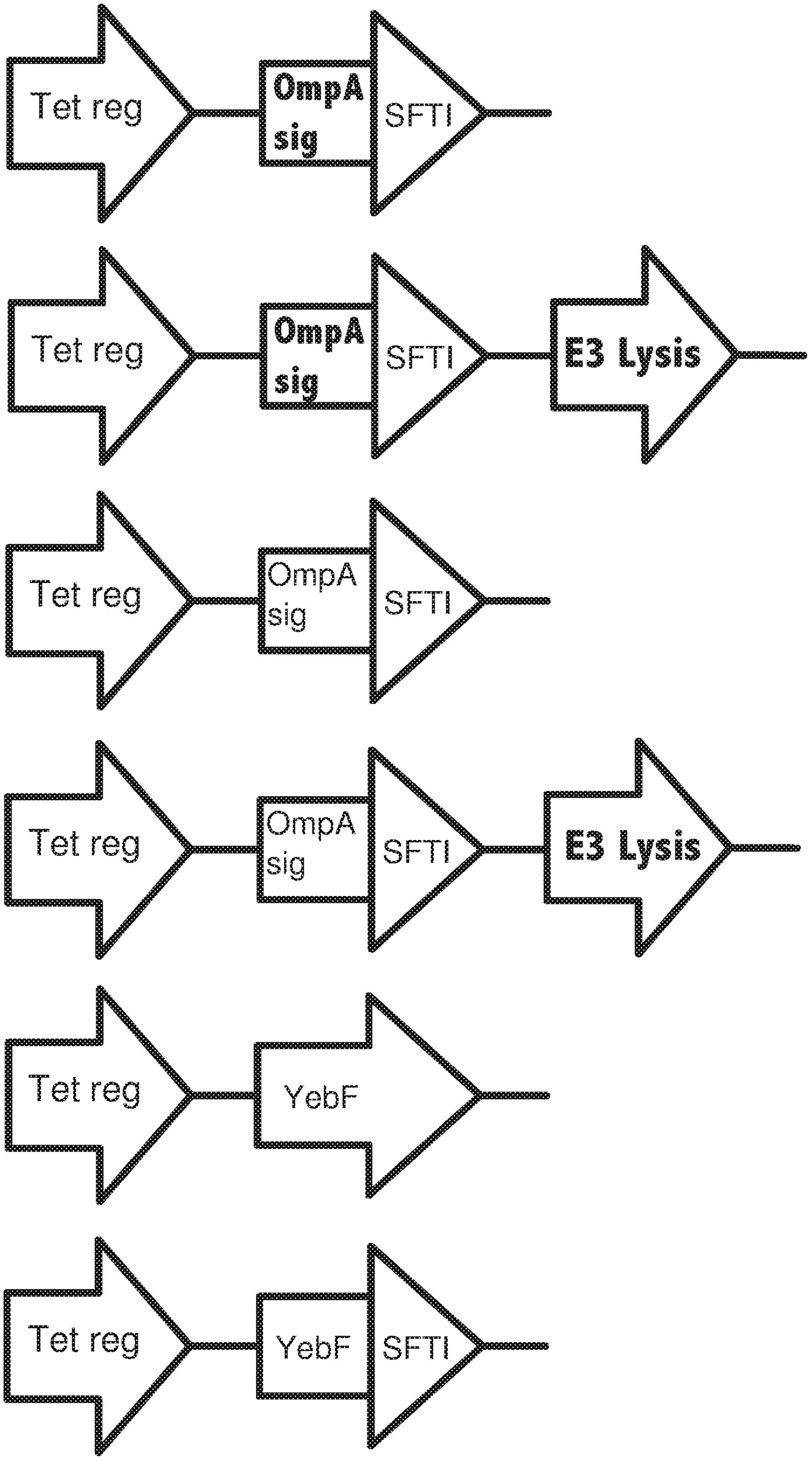

FIGS. 11A and 11B show pTet-1 under tetracycline controlled transcriptional activation (FIG. 11A), and insertion sequences downstream from the tetracycline repressor sequence (FIG. 11B). The sunflower trypsin inhibitor DNA sequence was fused to the signal peptide sequences derived from OmpA and Exotoxin A and ligated to pTet-1. The pColE3 lysis sequence, including its Shine-Delgarno sequence was cloned into pTetOmpA-SFTI and pTetTxA-SFTI. The YebF sequence was cloned into pTet-1 to create pTet-YebF. The SFTI sequence was fused in frame with YebF to produce pTetYebF-SFTI. All constructs were verified by sequencing then transformed into electrocompetent *E. coli* str. JW2197-1 lacking the periplasmic trypsin inhibitor, ecotin.

Figure 12:
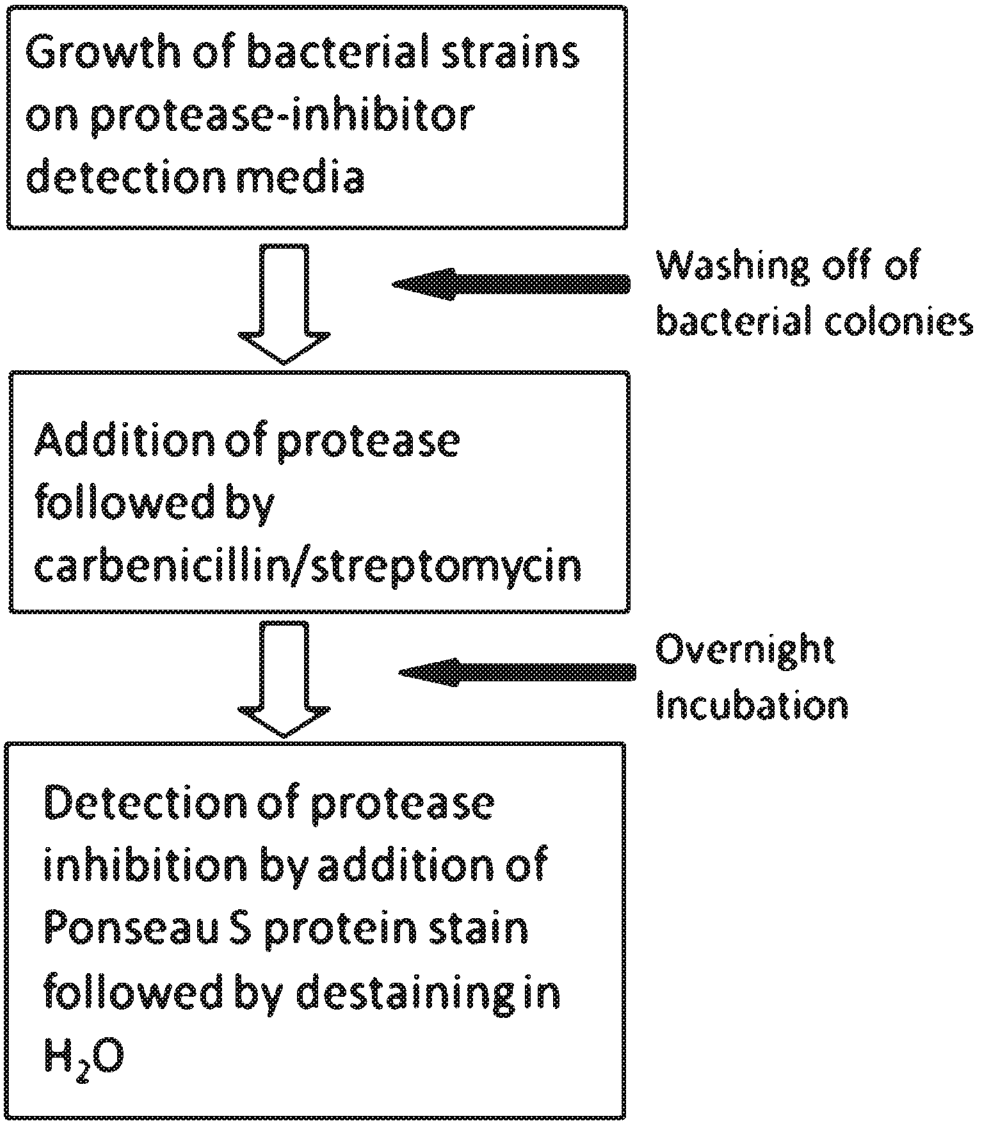
FIG. 12 shows a flowchart of a method for detection of protease inhibitory activity on protein based plates.

FIG. 12 shows a flowchart of a method for detection of protease inhibitory activity on protein based plates.

Figure 13:
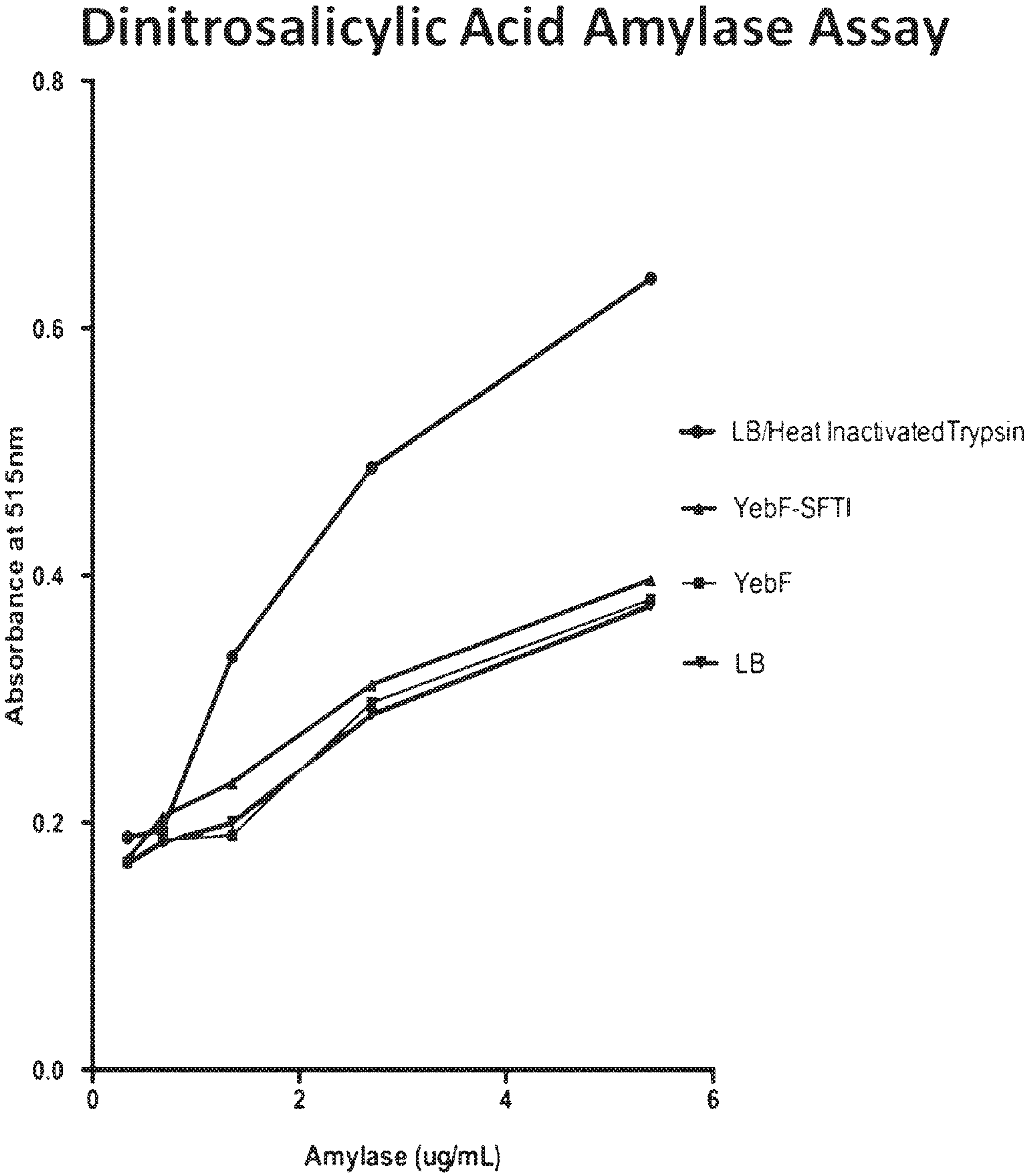
FIG. 13 shows Dinitrosalicylic Acid (DNS) assay for the detection of reducing sugars produced by active amylase under a trypsin challenge.

FIG. 13 shows Dinitrosalicylic Acid (DNS) assay for the detection of reducing sugars produced by active amylase under a trypsin challenge. 200 mL of the YebF and YebF-SFTI supernatants or LB was mixed with 10 mL of a 1.25 mg/mL trypsin solution and allowed to equilibrate for 30 minutes. Heat inactivated trypsin served as a control. 10 mL amylase at 1 mg/mL was considered a 1× concentration and two-fold dilutions to 1/16× were conducted. The amylase was then added to the mixtures and incubated at 37° C. for five hours to allow digestion. 100 mL of 1% starch solution was then added and the reaction allowed to proceed for fifteen minutes. DNS was added and the mixture was boiled for 5 minutes, diluted with 500 mL H2O, and absorbance was read at 515 nm.

EXAMPLES

In order to more fully illustrate the technology, the following examples are provided.

Example 1

A *Salmonella* expression vector.

Inducible expression vectors for *E. coli* and *Salmonella*, such as arabinose inducible expression vectors, are widely available and known to those skilled in the art. By way of example, an expression vector typically contains a promoter which functions to generate an mRNA from the DNA, such as an inducible arabinose promoter with a functional ribosomal binding site (RBS) an initiation codon (ATG) and suitable cloning sites for operable insertion of the functional DNA encoding the effector proteins described below into the vector, followed by a transcriptional termination site, plasmid origin of replication, and an antibiotic resistance factor that allows selection for the plasmid. Vectors that lack antibiotic resistance such as asd (-) balanced lethal vectors (Galan et al., 1990 cloning and characterization of the asd gene of *Salmonella Typhimurium*: use in stable maintenance of recombinant *Salmonella* vaccine strains, Gene 94:29-35) may also be used, or insertion into the chromosome.

Example 2

Modified TGFα-GIII-KDEL (A. Kihara and I. Pastan. Small Chimeric Toxins Containing Only Transforming Growth Factor α and Domain III of *Pseudomonas* Exotoxin with Good Antitumor Activity in Mice. Cancer Res 1994: 54:5154-5159). A modified form with an added OmpA signal sequence, extended flexible linker and presence of domain lb with enhanced activity functionally expressed, secreted, surface displayed and/or released is shown in FIG. 1A. The construct contains an OmpA secretion signal, TGFα targeting domain, a GGGGS (x3) SEQ ID NO.: 008 linker, ToxA domain Ib (containing cysteine bonding), ToxA domain III followed by, optionally KDEL retrograde trafficking signal; without KDEL the native signal REDLK SEQ ID NO.: 023 is used. The complete sequence of the arabinose inducible plasmid capable of expressing the construct with a start codon at 351 and a stop codon at 1364 is:

SEQ ID NO.: 001

```
gggGGCGGCCGCaagaaaccaattgtccatattgcatcagacattgccgt
cactgcgtcttttactggctcttctcgctaaccaaaccggtaaccccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcatttttatccataagattagc
ggatcctacctgacgctttttatcgcaactctctactgtttctccatacc
```

-continued

```
cgtttttttgggctagcgaattcgagctCGGTACCCAGGAGGAATTCACC
ATGGCTAAAAAGACAGCTATCGCGATTGCAGTGGCACTGGCTGGTTTCGC
TACCGTAGCGCAGGCAGctGTGGTGAGCCATTTTAACGATTGCCCGGATA
GCCATACCCAGTTTTGCTTTCATGGCACCTGCCGCTTTCTGGTGCAGGAA
GATAAACCGGCGTGCGTGTGCCATAGCGGTTATGTGGGCGCTCGCTGCGA
ACATGCGGATCTGCTGGCCCATCAACTAGTGGGCGGTGGTGGCAGTGGTG
GCGGCGGCTCTGGTGGTGGCGGGTCCCGGGGTctgacctgcccggtcgcc
gccggtgaatgcgcgggcccggcggacagcggcgacgccctgctggagcg
caactatcccactggcgcggagttcctcggcgacggcggcgacgtcagct
tcagcacccgcggcacgcagaactggacggtggagcggctgctccaggcg
caccgccaactggaggagcgcggctatgtgttcgtcggctaccacggcac
cttcctcgaagcggcgcaaagcatcgtcttcggcggggtgcgcgcgcgca
gccaggacctcgacgcgatctggcgcggtttctatatcgccggcgatccg
gcgctggcctacggctacgcccaggaccaggaacccgacgcacgcggccg
gatccgcaacggtgccctgctgcgggtctatgtgccgcgctcgagcctgc
cgggcttctaccgcaccagcctgaccctggccgcgccggaggcggcgggc
gaggtcgaacggctgatcggccatccgctgccgctgcgcctggacgccat
caccggccccgaggaggaaggcgggcgcctggagaccattctcggctggc
cgctggccgagcgcaccgtggtgattccctcggcgatccccaccgacccg
cgcaacgtcggcggcgacctcgacccgtccagcatccccgacaaggaaca
ggcgatcagcgccctgccggactacgccagccagcccggcaaaccgccga
aagatgaactgtaaCTCGAGTagatctgtactCTAGAGTCGACCTGCAGG
CATGCAAGCTTGGCTGTTTTGGCGGATGAGAGAAGATTTTCAGCCTGATA
CAGATTAAATCAGAACGCAGAAGCGGTCTGATAAAACAGAATTTGCCTGG
CGGCAGTAGCGCGGTGGTCCCACCTGACCCCATGCCGAACTCAGAAGTGA
AACGCCGTAGCGCCGATGGTAGTGTGGGGTCTCCCCATGCGAGAGTAGGG
AACTGCCAGGCATCAAATAAAACGAAAGGCTCAGTCGAAAGACTGGGCCT
TTCGTTTTATCTGTTGTTTGTCGGTGAACGCTCTCCTGAGTAGGACAAAT
CCGCCGGGAGCGGATTTGAACGTTGCGAAGCAACGGCCCGGAGGGTGGCG
GGCAGGACGCCCGCCATAAACTGCCAGGCATCAAATTAAGCAGAAGGCCA
TCCTGACGGATGGCCTTTTTGCGTTTCTACAAACTCTTTTTGTTTATTTT
TCTAAATACATTCAAATATGTATCCGCTCATGAGACAATAACCCTGATAA
ATGCTTCAATAATATTGAAAAAGGAAGAGTATGAGTATTCAACATTTCCG
TGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAG
TTTTCGCCCCGAAGAACGTTTTCCAATGATGAGCACTTTTAAAGTTCTGC
TATGTGGCGCGGTATTATCCCGTGTTGACGCCGGGCAAGAGCAACTCGGT
CGCCGCATACACTATTCTCAGAATGACTTGGTTGAGTACTCACCAGTCAC
AGAAAAGCATCTTACGGATGGCATGACAGTAAGAGAATTATGCAGTGCTG
```

-continued

CCATAACCATGAGTGATAACACTGCGGCCAACTTACTTCTGACAACGATC
GGAGGACCGAAGGAGCTAACCGCTTTTTTGCACAACATGGGGGATCATGT
AACTCGCCTTGATCGTTGGGAACCGGAGCTGAATGAAGCCATACCAAACG
ACGAGCGTGACACCACGATGCCTACAGCAATGGCAACAACGTTGCGCAAA
CTATTAACTGGCGAACTACTTACTCTAGCTTCCCGGCAACAATTAATAGA
CTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCT
CGCGGTATCATTGCAGCACTGGGGCCAGATGGTAAGCCCTCCCGTATCGT
AGTTATCTACACGACGGGGAGTCAGGCAACTATGGATGAACGAAATAGAC
AGATCGCTGAGATAGGTGCCTCACTGATTAAGCATTGGTAACTGTCAGAC
CAAGTTTACTCATATATACTTTAGATTGATTTAAAACTTCATTTTTAATT
TAAAAGGATCTAGGTGAAGATCCTTTTTGATAATCTCATGACCAAAATCC
CTTAACGTGAGTTTTCGTTCCACTGAGCGTCAGACCCCGTAGAAAAGATC
AAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGC
TACCAACTCTTTTTCCGAAGGTAACTGGCTTCAGCAGAGCGCAGATACCA
AATACTGTCCTTCTAGTGTAGCCGTAGTTAGGCCACCACTTCAAGAACTC
TGTAGCACCGCCTACATACCTCGCTCTGCTAATCCTGTTACCAGTGGCTG
CTGCCAGTGGCGATAAGTCGTGTCTTACCGGGTTGGACTCAAGACGATAG
TTACCGGATAAGGCGCAGCGGTCGGGCTGAACGGGGGGTTCGTGCACACA
GCCCAGCTTGGAGCGAACGACCTACACCGAACTGAGATACCTACAGCGTG
AGCTATGAGAAAGCGCCACGCTTCCCGAAGGGAGAAAGGCGGACAGGTAT
CCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGAC
TTGAGCGTCGATTTTTGTGATGCTCGTCAGGGGGGCGGAGCCTATGGAAA
AACGCCAGCAACGCGGCCTTTTTACGGTTCCTGGCCTTTTGCTGGCCTTT
TGCTCACATGTTCTTTCCTGCGTTATCCCCTGATTCTGTGGATAACCGTA
TTACCGCCTTTGAGTGAGCTGATACCGCTCGCCGCAGCCGAACGACCGAG
CGCAGCGAGTCAGTGAGCGAGGAAGCGGAAGAGCGCCTGATGCGGTATTT
TCTCCTTACGCATCTGTGCGGTATTTCACACCGCATATG

The complete sequence of the arabinose inducible plasmid capable of expressing the construct with a start codon at 351 and a stop codon at 1364 together with the colicin E3 lysis protein from 1399 to 1542 is:

SEQ ID NO.: 002 gggGGCGGCCGCaagaaaccaattgtccatattgcatcagacattgccgt
cactgcgtcttttactggctcttctcgctaaccaaaccggtaaccccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcattttttatccataagattagc
ggatcctacctgacgctttttatcgcaactctctactgtttctccatacc
cgtttttttgggctagcgaattcgagctCGGTACCCAGGAGGAATTCACC
ATGGCTAAAAAGACAGCTATCGCGATTGCAGTGGCACTGGCTGGTTTCGC
TACCGTAGCGCAGGCAGctGTGGTGAGCCATTTTAACGATTGCCCGGATA
GCCATACCCAGTTTTGCTTTCATGGCACCTGCCGCTTTCTGGTGCAGGAA
GATAAACCGGCGTGCGTGTGCCATAGCGGTTATGTGGGCGCTCGCTGCGA
ACATGCGGATCTGCTGGCCCATCAACTAGTGGGCGGTGGTGGCAGTGGTG
GCGGCGGCTCTGGTGGTGGCGGGTCCCGGGGTctgacctgcccggtcgcc
gccggtgaatgcgcgggcccggcggacagcggcgacgccctgctggagcg
caactatcccactggcgcggagttcctcggcgacggcggcgacgtcagct
tcagcacccgcggcacgcagaactggacggtggagcggctgctccaggcg
caccgccaactggaggagcgcggctatgtgttcgtcggctaccacggcac
cttcctcgaagcggcgcaaagcatcgtcttcggcggggtgcgcgcgcgca
gccaggacctcgacgcgatctggcgcggtttctatatcgccggcgatccg
gcgctggcctacggctacgcccaggaccaggaacccgacgcacgcggccg
gatccgcaacggtgccctgctgcgggtctatgtgccgcgctcgagcctgc
cgggcttctaccgcaccagcctgaccctggccgcgccggaggcggcgggc
gaggtcgaacggctgatcggccatccgctgccgctgcgcctggacgccat
caccggccccgaggaggaaggcgggcgcctggagaccattctcggctggc
cgctggccgagcgcaccgtggtgattccctcggcgatccccaccgacccg
cgcaacgtcggcggcgacctcgacccgtccagcatccccgacaaggaaca
ggcgatcagcgccctgccggactacgccagccagcccggcaaaccgccga
aagatgaactgtaaCTCGAGTagatctgtactCTAGAAAGGAGTCGTTAT
GAAAAAAATAACAGGGATTATTTTATTGCTTCTTGCAGTCATTATTCTGT
CTGCATGTCAGGCAAACTATATCCGGGATGTTCAGGGCGGGACCGTATCT
CCGTCATCAACAGCTGAAGTGACCGGATTAGCAACGCAGTAACTGCAGGC
ATGCAAGCTTGGCTGTTTTGGCGGATGAGAGAAGATTTTCAGCCTGATAC
AGATTAAATCAGAACGCAGAAGCGGTCTGATAAAACAGAATTTGCCTGGC
GGCAGTAGCGCGGTGGTCCCACCTGACCCCATGCCGAACTCAGAAGTGAA
ACGCCGTAGCGCCGATGGTAGTGTGGGGTCTCCCCATGCGAGAGTAGGGA
ACTGCCAGGCATCAAATAAAACGAAAGGCTCAGTCGAAAGACTGGGCCTT
TCGTTTTATCTGTTGTTTGTCGGTGAACGCTCTCCTGAGTAGGACAAATC
CGCCGGGAGCGGATTTGAACGTTGCGAAGCAACGGCCCGGAGGGTGGCGG
GCAGGACGCCCGCCATAAACTGCCAGGCATCAAATTAAGCAGAAGGCCAT
CCTGACGGATGGCCTTTTTGCGTTTCTACAAACTCTTTTTGTTTATTTTT
CTAAATACATTCAAATATGTATCCGCTCATGAGACAATAACCCTGATAAA
TGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCAC
GAGTGGGTTACATCGAACTGGATCTCAACAGCGGTAAGATCCTTGAGAGT
TTTCGCCCCGAAGAACGTTTTCCAATGATGAGCACTTTTAAAGTTCTGCT
ATGTGGCGCGGTATTATCCCGTGTTGACGCCGGGCAAGAGCAACTCGGTC -continued

```
GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTACAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCTGATGCGGTATTTT

CTCCTTACGCATCTGTGCGGTATTTCACACCGCATATG
```

Example 3

Modified TGFα-GIII-KDEL (A. Kihara and I. Pastan. Small Chimeric Toxins Containing Only Transforming Growth Factor α and Domain III of *Pseudomonas* Exotoxin with Good Antitumor Activity in Mice. Cancer Res 1994: 54:5154-5159). A modified form with an added OmpA signal sequence and extended flexible linker with enhanced activity functionally expressed, secreted, surface displayed and/or released is shown in FIG. 1B. The construct contains an OmpA secretion signal, TGFα targeting domain, a GGGGS (x3), SEQ ID NO.: 008 linker, ToxA domain III followed by, optionally KDEL retrograde trafficking signal; without KDEL the native signal REDLK SEQ ID NO.: 023 is used. The complete sequence of the arabinose inducible plasmid capable of expressing the construct with a start codon at 351 and a stop codon at 1286 is:

SEQ ID NO.: 003

```
gggGGCGGCCGCaagaaaccaattgtccatattgcatcagacattgccg

tcactgcgtcttttactggctcttctcgctaaccaaaccggtaaccccg

cttattaaaagcattctgtaacaaagcgggaccaaagccatgacaaaaa

cgcgtaacaaaagtgtctataatcacggcagaaaagtccacattgatta

tttgcacggcgtcacactttgctatgccatagcatttttatccataaga

ttagcggatcctacctgacgctttttatcgcaactctctactgtttctc

catacccgtttttttgggctagcgaattcgagctCGGTACCCAGGAGGA

ATTCACCATGGCTAAAAAGACAGCTATCGCGATTGCAGTGGCACTGGCT

GGTTTCGCTACCGTAGCGCAGGCAGctGTGGTGAGCCATTTTAACGATT

GCCCGGATAGCCATACCCAGTTTTGCTTTCATGGCACCTGCCGCTTTCT

GGTGCAGGAAGATAAACCGGCGTGCGTGTGCCATAGCGGTTATGTGGGC

GCTCGCTGCGAACATGCGGATCTGCTGGCCCATCAACTAGTGGGCGGTG

GTGGCAGTGGTGGCGGCGGCTCTGGTGGTGGCGGGTCCCGGGGTactgg

cgcggagttcctcggcgacggcggcgacgtcagcttcagcacccgcggc

acgcagaactggacggtggagcggctgctccaggcgcaccgccaactgg

aggagcgcggctatgtgttcgtcggctaccacggcaccttcctcgaagc

ggcgcaaagcatcgtcttcggcggggtgcgcgcgcgcagccaggacctc

gacgcgatctggcgcggtttctatatcgccggcgatccggcgctggcct

acggctacgcccaggaccaggaacccgacgcacgcggccggatccgcaa

cggtgccctgctgcgggtctatgtgccgcgctcgagcctgccgggcttc

taccgcaccagcctgaccctggccgcgccggaggcggcgggcgaggtcg

aacggctgatcggccatccgctgccgctgcgcctggacgccatcaccgg

ccccgaggaggaaggcgggcgcctggagaccattctcggctggccgctg

gccgagcgcaccgtggtgattccctcggcgatccccaccgacccgcgca

acgtcggcggcgacctcgacccgtccagcatccccgacaaggaacaggc

gatcagcgccctgccggactacgccagccagcccggcaaaccgccgaaa

gatgaactgtaaCTCGAGTagatctgtactCTAGAGTCGACCTGCAGGC

ATGCAAGCTTGGCTGTTTTGGCGGATGAGAGAAGATTTTCAGCCTGATA

CAGATTAAATCAGAACGCAGAAGCGGTCTGATAAAACAGAATTTGCCTG

GCGGCAGTAGCGCGGTGGTCCCACCTGACCCCATGCCGAACTCAGAAGT

GAAACGCCGTAGCGCCGATGGTAGTGTGGGGTCTCCCCATGCGAGAGTA

GGGAACTGCCAGGCATCAAATAAAACGAAAGGCTCAGTCGAAAGACTGG

GCCTTTCGTTTTATCTGTTGTTTGTCGGTGAACGCTCTCCTGAGTAGGA

CAAATCCGCCGGGAGCGGATTTGAACGTTGCGAAGCAACGGCCCGGAGG

GTGGCGGGCAGGACGCCCGCCATAAACTGCCAGGCATCAAATTAAGCAG

AAGGCCATCCTGACGGATGGCCTTTTTGCGTTTCTACAAACTCTTTTTG

TTTATTTTTCTAAATACATTCAAATATGTATCCGCTCATGAGACAATAA

CCCTGATAAATGCTTCAATAATATTGAAAAAGGAAGAGTATGAGTATTC
```

-continued

AACATTTCCGTGTCGCCCTTATTCCCTTTTTTGCGGCATTTTGCCTTCC
TGTTTTTGCTCACCCAGAAACGCTGGTGAAAGTAAAAGATGCTGAAGAT
CAGTTGGGTGCACGAGTGGGTTACATCGAACTGGATCTCAACAGCGGTA
AGATCCTTGAGAGTTTTCGCCCCGAAGAACGTTTTCCAATGATGAGCAC
TTTTAAAGTTCTGCTATGTGGCGCGGTATTATCCCGTGTTGACGCCGGG
CAAGAGCAACTCGGTCGCCGCATACACTATTCTCAGAATGACTTGGTTG
AGTACTCACCAGTCACAGAAAAGCATCTTACGGATGGCATGACAGTAAG
AGAATTATGCAGTGCTGCCATAACCATGAGTGATAACACTGCGGCCAAC
TTACTTCTGACAACGATCGGAGGACCGAAGGAGCTAACCGCTTTTTTGC
ACAACATGGGGGATCATGTAACTCGCCTTGATCGTTGGGAACCGGAGCT
GAATGAAGCCATACCAAACGACGAGCGTGACACCACGATGCCTACAGCA
ATGGCAACAACGTTGCGCAAACTATTAACTGGCGAACTACTTACTCTAGC
TTCCCGGCAACAATTAATAGACTGGATGGAGGCGGATAAAGTTGCAGGAC
CACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAA
CTATGGATGAACGAAATAGACAGATCGCTGAGATAGGTGCCTCACTGATT
AAGCATTGGTAACTGTCAGACCAAGTTTACTCATATATACTTTAGATTGA
TTTAAAACTTCATTTTTAATTTAAAAGGATCTAGGTGAAGATCCTTTTTG
ATAATCTCATGACCAAAATCCCTTAACGTGAGTTTTCGTTCCACTGAGCG
TCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGC
TTCAGCAGAGCGCAGATACCAAATACTGTCCTTCTAGTGTAGCCGTAGTT
AGGCCACCACTTCAAGAACTCTGTAGCACCGCCTACATACCTCGCTCTGC
TAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTG
AACGGGGGGTTCGTGCACACAGCCCAGCTTGGAGCGAACGACCTACACCG
AACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGA
GCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCC
CTGATTCTGTGGATAACCGTATTACCGCCTTTGAGTGAGCTGATACCGCT
CGCCGCAGCCGAACGACCGAGCGCAGCGAGTCAGTGAGCGAGGAAGCGGA
AGAGCGCCTGATGCGGTATTTTCTCCTTACGCATCTGTGCGGTATTTCAC
ACCGCATATG

The complete sequence of the arabinose inducible plasmid capable of expressing the construct with a start codon at 351 and a stop codon at 1286 together with the colicin E3 lysis protein from 1321 to 1464 is:

SEQ ID NO.: 004 gggGGCGGCCGCaagaaaccaattgtccatattgcatcagacattgccg
tcactgcgtcttttactggctcttctcgctaaccaaaccggtaaccccg
cttattaaaagcattctgtaacaaagcgggaccaaagccatgacaaaaa
cgcgtaacaaaagtgtctataatcacggcagaaaagtccacattgatta
tttgcacggcgtcacactttgctatgccatagcatttttatccataaga
ttagcggatcctacctgacgctttttatcgcaactctctactgtttctc
catacccgtttttttgggctagcgaattcgagctCGGTACCCAGGAGGA
ATTCACCATGGCTAAAAAGACAGCTATCGCGATTGCAGTGGCACTGGCT
GGTTTCGCTACCGTAGCGCAGGCAGctGTGGTGAGCCATTTTAACGATT
GCCCGGATAGCCATACCCAGTTTTGCTTTCATGGCACCTGCCGCTTTCT
GGTGCAGGAAGATAAACCGGCGTGCGTGTGCCATAGCGGTTATGTGGGC
GCTCGCTGCGAACATGCGGATCTGCTGGCCCATCAACTAGTGGGCGGTG
GTGGCAGTGGTGGCGGCGGCTCTGGTGGTGGCGGGTCCCGGGGTctgac
ctgcccggtcgccgccggtgaatgcgcgggcccggcggacagcggcgac
gccctgctggagcgcaactatcccactggcgcggagttcctcggcgacg
gcggcgacgtcagcttcagcacccgcggcacgcagaactggacggtgga
gcggctgctccaggcgcaccgccaactggaggagcgcggctatgtgttc
gtcggctaccacggcaccttcctcgaagcggcgcaaagcatcgtcttcg
gcggggtgcgcgcgcgcagccaggacctcgacgcgatctggcgcggttt
ctatatcgccggcgatccggcgctggcctacggctacgcccaggaccag
gaacccgacgcacgcggccggatccgcaacggtgccctgctgcgggtct
atgtgccgcgctcgagcctgccgggcttctaccgcaccagcctgaccct
ggccgcgccggaggcggcgggcgaggtcgaacggctgatcggccatccg
ctgccgctgcgcctggacgccatcaccggccccgaggaggaaggcgggc
gcctggagaccattctcggctggccgctggccgagcgcaccgtggtgat
tccctcggcgatccccaccgacccgcgcaacgtcggcggcgacctcgac
ccgtccagcatccccgacaaggaacaggcgatcagcgccctgccggact
acgccagccagcccggcaaaccgccgaaagatgaactgtaaCTCGAGTa
gatctgtactCTAGAAAGGAGTCGTTATGAAAAAAATAACAGGGATTAT
TTTATTGCTTCTTGCAGTCATTATTCTGTCTGCATGTCAGGCAAACTAT
ATCCGGGATGTTCAGGGCGGGACCGTATCTCCGTCATCAACAGCTGAAG
TGACCGGATTAGCAACGCAGTAACTGCAGGCATGCAAGCTTGGCTGTTT
TGGCGGATGAGAGAAGATTTTCAGCCTGATACAGATTAAATCAGAACGC
AGAAGCGGTCTGATAAAACAGAATTTGCCTGGCGGCAGTAGCGCGGTGG
TCCCACCTGACCCCATGCCGAACTCAGAAGTGAAACGCCGTAGCGCCGA
TGGTAGTGTGGGGTCTCCCCATGCGAGAGTAGGGAACTGCCAGGCATCA
AATAAAACGAAAGGCTCAGTCGAAAGACTGGGCCTTTCGTTTTATCTGT
TGTTTGTCGGTGAACGCTCTCCTGAGTAGGACAAATCCGCCGGGAGCGG
ATTTGAACGTTGCGAAGCAACGGCCCGGAGGGTGGCGGGCAGGACGCCC
GCCATAAACTGCCAGGCATCAAATTAAGCAGAAGGCCATCCTGACGGAT -continued

```
GGCCTTTTTGCGTTTCTACAAACTCTTTTTGTTTATTTTTCTAAATACA

TTCAAATATGTATCCGCTCATGAGACAATAACCCTGATAAATGCTTCAA

TAATATTGAAAAAGGAAGAGTATGAGTATTCAACATTTCCGTGTCGCCC

TTATTCCCTTTTTTGCGGCATTTTGCCTTCCTGTTTTTGCTCACCCAGA

AACGCTGGTGAAAGTAAAAGATGCTGAAGATCAGTTGGGTGCACGAGTG

GGTTACATCGAACTGGATCTCAACAGCGGTAAGATCCTTGAGAGTTTTC

GCCCCGAAGAACGTTTTCCAATGATGAGCACTTTTAAAGTTCTGCTAT

GTGGCGCGGTATTATCCCGTGTTGACGCCGGGCAAGAGCAACTCGGTCGC

CGCATACACTATTCTCAGAATGACTTGGTTGAGTACTCACCAGTCACAGA

AAAGCATCTTACGGATGGCATGACAGTAAGAGAATTATGCAGTGCTGCCA

TAACCATGAGTGATAACACTGCGGCCAACTTACTTCTGACAACGATCGGA

GGACCGAAGGAGCTAACCGCTTTTTTGCACAACATGGGGGATCATGTAAC

TCGCCTTGATCGTTGGGAACCGGAGCTGAATGAAGCCATACCAAACGACG

AGCGTGACACCACGATGCCTACAGCAATGGCAACAACGTTGCGCAAACTA

TTAACTGGCGAACTACTTACTCTAGCTTCCCGGCAACAATTAATAGACTG

GATGGAGGCGGATAAAGTTGCAGGACCACTTCTGCGCTCGGCCCTTCCGG

CTGGCTGGTTTATTGCTGATAAATCTGGAGCCGGTGAGCGTGGGTCTCGC

GGTATCATTGCAGCACTGGGGCCAGATGGTAAGCCCTCCCGTATCGTAGT

TATCTACACGACGGGGAGTCAGGCAACTATGGATGAACGAAATAGACAGA

TCGCTGAGATAGGTGCCTCACTGATTAAGCATTGGTAACTGTCAGACCAA

GTTTACTCATATATACTTTAGATTGATTTAAAACTTCATTTTTAATTTAA

AAGGATCTAGGTGAAGATCCTTTTTGATAATCTCATGACCAAAATCCCTT

AACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAAC

AAAAAAACCACCGCTACCAGCGGTGGTTTGTTTGCCGGATCAAGAGCTAC

CAACTCTTTTTCCGAAGGTAACTGGCTTCAGCAGAGCGCAGATACCAAAT

ACTGTCCTTCTAGTGTAGCCGTAGTTAGGCCACCACTTCAAGAACTCTGT

AGCACCGCCTACATACCTCGCTCTGCTAATCCTGTTACCAGTGGCTGCTG

CCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCC

CAGCTTGGAGCGAACGACCTACACCGAACTGAGATACCTACAGCGTGAGC

TATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGG

AAACGCCTGGTATCTTTATAGTCCTGTCGGGTTTCGCCACCTCTGACTTG

AGCGTCGATTTTTGTGATGCTCGTCAGGGGGGCGGAGCCTATGGAAAAAC

GCCAGCAACGCGGCCTTTTTACGGTTCCTGGCCTTTTGCTGGCCTTTTGC

TCACATGTTCTTTCCTGCGTTATCCCCTGATTCTGTGGATAACCGTATTA

CCGCCTTTGAGTGAGCTGATACCGCTCGCCGCAGCCGAACGACCGAGCGC

AGCGAGTCAGTGAGCGAGGAAGCGGAAGAGCGCCTGATGCGGTATTTTCT

CCTTACGCATCTGTGCGGTATTTCACACCGCATATG
```

Example 4

Modified TGFα-PE38 (Kreitman, R. J., Siegall, C. B., Chaudhary, V. K, Fitzgerald, D. J., and Pastan. I. Properties of Chimeric Toxins with Two Recognition Domains: Interleukin 6 and Transforming Growth Factor α at Different Locations in *Pseudomonas* Exotoxin. Bioconjugate Chem. 1992, 3, 63-68.)

The original form of this product represents a deletion of amino acids 365-380 of ToxA domain I. The modified form is a chimera containing an OmpA secretion signal, TGFα targeting domain, a GGGGS (x3), SEQ ID NO.: 008 linker, ToxA PE38 (contains Domain II, partial Ib (A365-380 amino acids) domain III followed by, optionally KDEL retrograde trafficking signal; without KDEL the native signal REDLK SEQ ID NO.: 023 is used. Optionally, the colicin E3 lysis protein with a separate ribosomal binding site may be added. The modified form with an added extended flexible linker with enhanced activity functionally expressed, secreted, surface displayed and/or released is shown in FIG. 1C. The complete sequence of the arabinose inducible plasmid capable of expressing the construct with a start codon at 351 and a stop codon at 1664 is:

SEQ ID NO.: 005

```
gggGGCGGCCGCaagaaaccaattgtccatattgcatcagacattgccg

tcactgcgtcttttactggctcttctcgctaaccaaaccggtaaccccg

cttattaaaagcattctgtaacaaagcgggaccaaagccatgacaaaaa

cgcgtaacaaaagtgtctataatcacggcagaaaagtccacattgatta

tttgcacggcgtcacactttgctatgccatagcatttttatccataaga

ttagcggatcctacctgacgctttttatcgcaactctctactgtttctc

catacccgtttttttgggctagcgaattcgagctCGGTACCCAGGAGGA

ATTCACCATGGCTAAAAAGACAGCTATCGCGATTGCAGTGGCACTGGCT

GGTTTCGCTACCGTAGCGCAGGCAGctGTGGTGAGCCATTTTAACGATT

GCCCGGATAGCCATACCCAGTTTTGCTTTCATGGCACCTGCCGCTTTCT

GGTGCAGGAAGATAAACCGGCGTGCGTGTGCCATAGCGGTTATGTGGGC

GCTCGCTGCGAACATGCGGATCTGCTGGCCCATCAACTAGTGGGCGGTG

GTGGCAGTGGTGGCGGCGGCTCTGGTGGTGGCGGGTCCCggggtggcag

cctggccgcgctgaccgcgcaccaggcttgccacctgccgctggagact

ttcacccgtcatcgccagccgcgcggctgggaacaactggagcagtgcg

gctatccggtgcagcggctggtcgccctctacctggcggcgcggctgtc

gtggaaccaggtcgaccaggtgatccgcaacgccctggccagccccggc

agcggcggcgacctgggcgaagcgatccgcgagcagccggagcaggccc

gtctggccctgaccctggccgccgccgagagcgagcgcttcgtccggca

gggcaccggcaacgacgaggccggcgcggccaacgccccggcggacagc

ggcgacgccctgctggagcgcaactatcccactggcgcggagttcctcg

gcgacggcggcgacgtcagcttcagcacccgcggcacgcagaactggac

ggtggagcggctgctccaggcgcaccgccaactggaggagcgcggctat

gtgttcgtcggctaccacggcaccttcctcgaagcggcgcaaagcatcg

tcttcggcggggtgcgcgcgcgcagccaggacctcgacgcgatctggcg
```

-continued cggtttctatatcgccggcgatccggcgctggcctacggctacgcccag gaccaggaacccgacgcacgcggccggatccgcaacggtgccctgctgc gggtctatgtgccgcgctcgagcctgccgggcttctaccgcaccagcct gaccctggccgcgccggaggcggcgggcgaggtcgaacggctgatcggc catccgctgccgctgcgcctggacgccatcaccggccccgaggaggaag gcgggcgcctggagaccattctcggctggccgctggccgagcgcaccgt ggtgattccctcggcgatccccaccgacccgcgcaacgtcggcggcgac ctcgacccgtccagcatccccgacaaggaacaggcgatcagcgccctgc cggactacgccagccagcccggcaaaccgccgaaagatgaactgtaaCT CGAGTagatctgtactCTAGAGTCGACCTGCAGGCATGCAAGCTTGGCT

GTTTTGGCGGATGAGAGAAGATTTTCAGCCTGATACAGATTAAATCAGA

ACGCAGAAGCGGTCTGATAAAACAGAATTTGCCTGGCGGCAGTAGCGCG

GTGGTCCCACCTGACCCCATGCCGAACTCAGAAGTGAAACGCCGTAGCG

CCGATGGTAGTGTGGGGTCTCCCCATGCGAGAGTAGGGAACTGCCAGGC

ATCAAATAAAACGAAAGGCTCAGTCGAAAGACTGGGCCTTTCGTTTTAT

CTGTTGTTTGTCGGTGAACGCTCTCCTGAGTAGGACAAATCCGCCGGGA

GCGGATTTGAACGTTGCGAAGCAACGGCCCGGAGGGTGGCGGGCAGGAC

GCCCGCCATAAACTGCCAGGCATCAAATTAAGCAGAAGGCCATCCTGAC

GGATGGCCTTTTTGCGTTTCTACAAACTCTTTTTGTTTATTTTTCTAAA

TACATTCAAATATGTATCCGCTCATGAGACAATAACCCTGATAAATGCT

TCAATAATATTGAAAAAGGAAGAGTATGAGTATTCAACATTTCCGTGTC

GCCCTTATTCCCTTTTTTGCGGCATTTTGCCTTCCTGTTTTTGCTCACC

CAGAAACGCTGGTGAAAGTAAAAGATGCTGAAGATCAGTTGGGTGCACGA

GTGGGTTACATCGAACTGGATCTCAACAGCGGTAAGATCCTTGAGAGTTT

TCGCCCCGAAGAACGTTTTCCAATGATGAGCACTTTTAAAGTTCTGCTAT

GTGGCGCGGTATTATCCCGTGTTGACGCCGGGCAAGAGCAACTCGGTCGC

CGCATACACTATTCTCAGAATGACTTGGTTGAGTACTCACCAGTCACAGA

AAAGCATCTTACGGATGGCATGACAGTAAGAGAATTATGCAGTGCTGCCA

TAACCATGAGTGATAACACTGCGGCCAACTTACTTCTGACAACGATCGGA

GGACCGAAGGAGCTAACCGCTTTTTTGCACAACATGGGGGATCATGTAAC

TCGCCTTGATCGTTGGGAACCGGAGCTGAATGAAGCCATACCAAACGACG

AGCGTGACACCACGATGCCTACAGCAATGGCAACAACGTTGCGCAAACTA

TTAACTGGCGAACTACTTACTCTAGCTTCCCGGCAACAATTAATAGACTG

GATGGAGGCGGATAAAGTTGCAGGACCACTTCTGCGCTCGGCCCTTCCGG

CTGGCTGGTTTATTGCTGATAAATCTGGAGCCGGTGAGCGTGGGTCTCGC

GGTATCATTGCAGCACTGGGGCCAGATGGTAAGCCCTCCCGTATCGTAGT

TATCTACACGACGGGGAGTCAGGCAACTATGGATGAACGAAATAGACAGA

TCGCTGAGATAGGTGCCTCACTGATTAAGCATTGGTAACTGTCAGACCAA

GTTTACTCATATATACTTTAGATTGATTTAAAACTTCATTTTTAATTTAA

AAGGATCTAGGTGAAGATCCTTTTTGATAATCTCATGACCAAAATCCCTT

AACGTGAGTTTTCGTTCCACTGAGCGTCAGACCCCGTAGAAAAGATCAAA

-continued

GGATCTTCTTGAGATCCTTTTTTTCTGCGCGTAATCTGCTGCTTGCAAAC

AAAAAAACCACCGCTACCAGCGGTGGTTTGTTTGCCGGATCAAGAGCTAC

CAACTCTTTTTCCGAAGGTAACTGGCTTCAGCAGAGCGCAGATACCAAAT

ACTGTCCTTCTAGTGTAGCCGTAGTTAGGCCACCACTTCAAGAACTCTGT

AGCACCGCCTACATACCTCGCTCTGCTAATCCTGTTACCAGTGGCTGCTG

CCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCC

CAGCTTGGAGCGAACGACCTACACCGAACTGAGATACCTACAGCGTGAGC

TATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGG

AAACGCCTGGTATCTTTATAGTCCTGTCGGGTTTCGCCACCTCTGACTTG

AGCGTCGATTTTTGTGATGCTCGTCAGGGGGGGGAGCCTATGGAAAAAC

GCCAGCAACGCGGCCTTTTTACGGTTCCTGGCCTTTTGCTGGCCTTTTGC

TCACATGTTCTTTCCTGCGTTATCCCCTGATTCTGTGGATAACCGTATTA

CCGCCTTTGAGTGAGCTGATACCGCTCGCCGCAGCCGAACGACCGAGCGC

AGCGAGTCAGTGAGCGAGGAAGCGGAAGAGCGCCTGATGCGGTATTTTCT

CCTTACGCATCTGTGCGGTATTTCACACCGCATATG

The complete sequence of the arabinose inducible plasmid capable of expressing the construct with a start codon at 351 and a stop codon at 1664 together with the colicin E3 lysis protein from 1699 to 1842 is:

SEQ ID NO.: 006 gggGGCGGCCGCaagaaaccaattgtccatattgcatcagacattgccg tcactgcgtcttttactggctcttctcgctaaccaaaccggtaaccccg cttattaaaagcattctgtaacaaagcgggaccaaagccatgacaaaaa cgcgtaacaaaagtgtctataatcacggcagaaaagtccacattgatta tttgcacggcgtcacactttgctatgccatagcatttttatccataaga ttagcggatcctacctgacgctttttatcgcaactctctactgtttctc catacccgtttttttgggctagcgaattcgagctCGGTACCCAGGAGGA

ATTCACCATGGCTAAAAAGACAGCTATCGCGATTGCAGTGGCACTGGCT

GGTTTCGCTACCGTAGCGCAGGCAGctGTGGTGAGCCATTTTAACGATT

GCCCGGATAGCCATACCCAGTTTTGCTTTCATGGCACCTGCCGCTTTCT

GGTGCAGGAAGATAAACCGGCGTGCGTGTGCCATAGCGGTTATGTGGGC

GCTCGCTGCGAACATGCGGATCTGCTGGCCCATCAACTAGTGGGCGGTG

GTGGCAGTGGTGGCGGCGGCTCTGGTGGTGGCGGGTCCCgggggcagc ctggccgcgctgaccgcgcaccaggcttgccacctgccgctggagactt tcacccgtcatcgccagccgcgcggctgggaacaactggagcagtgcgg ctatccggtgcagcggctggtcgccctctacctggcggcgcggctgtcg tggaaccaggtcgaccaggtgatccgcaacgccctggccagccccggca gcggcggcgacctgggcgaagcgatccgcgagcagccggagcaggcccg tctggccctgaccctggccgccgccgagagcgagcgcttcgtccggcag -continued

```
ggcaccggcaacgacgaggccggcgcggccaacgccccggcggacagcg
gcgacgccctgctggagcgcaactatcccactggcgcggagttcctcgg
cgacggcggcgacgtcagcttcagcacccgcggcacgcagaactggacg
gtggagcggctgctccaggcgcaccgccaactggaggagcgcggctatg
tgttcgtcggctaccacggcaccttcctcgaagcggcgcaaagcatcgt
cttcggcggggtgcgcgcgcgcagccaggacctcgacgcgatctggcgc
ggtttctatatcgccggcgatccggcgctggcctacggctacgcccagg
accaggaacccgacgcacgcggccggatccgcaacggtgccctgctgcg
ggtctatgtgccgcgctcgagcctgccgggcttctaccgcaccagcctg
accctggccgcgccggaggcggcgggcgaggtcgaacggctgatcggcc
atccgctgccgctgcgcctggacgccatcaccggccccgaggaggaagg
cgggcgcctggagaccattctcggctggccgctggccgagcgcaccgtg
gtgattccctcggcgatccccaccgacccgcgcaacgtcggcggcgacc
tcgacccgtccagcatccccgacaaggaacaggcgatcagcgccctgcc
ggactacgccagccagcccggcaaaccgccgaaagatgaactgtaaCTC
GAGTagatctgtactCTAGAAAGGAGTCGTTATGAAAAAAATAACAGGG
ATTATTTTATTGCTTCTTGCAGTCATTATTCTGTCTGCATGTCAGGCAA
ACTATATCCGGGATGTTCAGGGCGGGACCGTATCTCCGTCATCAACAGC
TGAAGTGACCGGATTAGCAACGCAGTAACTGCAGGCATGCAAGCTTGGC
TGTTTTGGCGGATGAGAGAAGATTTTCAGCCTGATACAGATTAAATCAG
AACGCAGAAGCGGTCTGATAAAACAGAATTTGCCTGGCGGCAGTAGCGC
GGTGGTCCCACCTGACCCCATGCCGAACTCAGAAGTGAAACGCCGTAGC
GCCGATGGTAGTGTGGGGTCTCCCCATGCGAGAGTAGGGAACTGCCAGG
CATCAAATAAAACGAAAGGCTCAGTCGAAAGACTGGGCCTTTCGTTTTA
TCTGTTGTTTGTCGGTGAACGCTCTCCTGAGTAGGACAAATCCGCCGGG
AGCGGATTTGAACGTTGCGAAGCAACGGCCCGGAGGGTGGCGGGCAGGA
CGCCCGCCATAAACTGCCAGGCATCAAATTAAGCAGAAGGCCATCCTGA
CGGATGGCCTTTTTGCGTTTCTACAAACTCTTTTTGTTTATTTTTCTAA
ATACATTCAAATATGTATCCGCTCATGAGACAATAACCCTGATAAATGC
TTCAATAATATTGAAAAAGGAAGAGTATGAGTATTCAACATTTCCGTGT
CGCCCTTATTCCCTTTTTTGCGGCATTTTGCCTTCCTGTTTTTGCTCAC
CCAGAAACGCTGGTGAAAGTAAAAGATGCTGAAGATCAGTTGGGTGCACG
AGTGGGTTACATCGAACTGGATCTCAACAGCGGTAAGATCCTTGAGAGTT
TTCGCCCCGAAGAACGTTTTCCAATGATGAGCACTTTTAAAGTTCTGCTA
TGTGGCGCGGTATTATCCCGTGTTGACGCCGGGCAAGAGCAACTCGGTCG
CCGCATACACTATTCTCAGAATGACTTGGTTGAGTACTCACCAGTCACAG
AAAAGCATCTTACGGATGGCATGACAGTAAGAGAATTATGCAGTGCTGCC
ATAACCATGAGTGATAACACTGCGGCCAACTTACTTCTGACAACGATCGG
AGGACCGAAGGAGCTAACCGCTTTTTTGCACAACATGGGGGATCATGTAA
CTCGCCTTGATCGTTGGGAACCGGAGCTGAATGAAGCCATACCAAACGAC
GAGCGTGACACCACGATGCCTACAGCAATGGCAACAACGTTGCGCAAACT
```

-continued

```
ATTAACTGGCGAACTACTTACTCTAGCTTCCCGGCAACAATTAATAGACT
GGATGGAGGCGGATAAAGTTGCAGGACCACTTCTGCGCTCGGCCCTTCCG
GCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAG
TTATCTACACGACGGGGAGTCAGGCAACTATGGATGAACGAAATAGACAG
ATCGCTGAGATAGGTGCCTCACTGATTAAGCATTGGTAACTGTCAGACCA
AGTTTACTCATATATACTTTAGATTGATTTAAAACTTCATTTTTAATTTA
AAAGGATCTAGGTGAAGATCCTTTTTGATAATCTCATGACCAAAATCCCT
TAACGTGAGTTTTCGTTCCACTGAGCGTCAGACCCCGTAGAAAAGATCAA
AGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAA
TACTGTCCTTCTAGTGTAGCCGTAGTTAGGCCACCACTTCAAGAACTCTG
TAGCACCGCCTACATACCTCGCTCTGCTAATCCTGTTACCAGTGGCTGCT
GCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGC
CCAGCTTGGAGCGAACGACCTACACCGAACTGAGATACCTACAGCGTGAG
CTATGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAA
CGCCAGCAACGCGGCCTTTTTACGGTTCCTGGCCTTTTGCTGGCCTTTTG
CTCACATGTTCTTTCCTGCGTTATCCCCTGATTCTGTGGATAACCGTATT
ACCGCCTTTGAGTGAGCTGATACCGCTCGCCGCAGCCGAACGACCGAGCG
CAGCGAGTCAGTGAGCGAGGAAGCGGAAGAGCGCCTGATGCGGTATTTTC
TCCTTACGCATCTGTGCGGTATTTCACACCGCATATG
```

Example 5

An artificial typhoid toxin operon lacking sty and ttsA.

An artificial, inducible typhoid toxin operon lacking sty and ttsA as shown in FIG. 2B, is generated by multiple PCR and restriction endonuclease cloning steps known to those skilled in the art. The operon is capable of being induced with an inducing agent, in the present instance, arabinose. As compared with FIG. 1B, the artificial operon lacks the sty and ttsA genes. The complete sequence of the arabinose inducible plasmid capable of expressing the construct with a cldtB start codon at 351 and a stop codon at 1163, pltB start at 1197 and stop at 1610 and pltA 1627-2355:

SEQ ID NO.: 007

```
gggGGCGGCCGCaagaaaccaattgtccatattgcatcagacattgccg
tcactgcgtcttttactggctcttctcgctaaccaaaccggtaaccccg
cttattaaaagcattctgtaacaaagcgggaccaaagccatgacaaaaa
cgcgtaacaaaagtgtctataatcacggcagaaaagtccacattgatta
```

-continued tttgcacggcgtcacactttgctatgccatagcatttttatccataaga ttagcggatcctacctgacgctttttatcgcaactctctactgtttctc catacccgtttttttgggctagcgaattcgagctcggtacccaggagga attcaCCATGGTCAAAAACCTGTTTTTTTCCTTCTGACCATGATCATC

TGCAGCTATATTTCTTTTGCCTGCGCTAATATCAGTGACTACAAAGTTA

TGACCTGGAATCTTCAGGGCTCTTCAGCATCTACAGAAAGTAAATGGAA

TGTCAATGTCAGACAGCTTTTAAGCGGTACTGCCGGTGTGGATATTCTT

ATGGTACAGGAGGCCGGTGCTGTTCCCACCTCAGCGGTTCCTACCGGAC

GACATATTCAGCCTTTTGGAGTGGGTATTCCCATTGATGAATACACCTG

GAATCTCGGAACCACCAGCCGTCAGGATATAAGATATATCTACTACTCG

GCTATTGATGTTGGAGCACGCCGTGTTAATCTGGCAATAGTTTCCAGAC

AAAGAGCGGATAATGTTTATGTCTTGCGTCCGACAACTGTCGCATCTCG

CCCCGTCATTGGCATCGGACTGGGTAATGATGTTTTTCTGACAGCGCAC

GCACTGGCTAGTGGAGGTCCGGATGCTGCAGCTATTGTCAGGGTTACCA

TTAATTTTTTTAGACAACCTCAGATGCGGCATTTATCCTGGTTTCTTGC

CGGGGATTTTAATCGCAGCCCAGACAGACTTGAAAATGACCTGATGACT

GAGCATCTGGAACGAGTTGTAGCCGTACTCGCACCTACAGAACCCACGC

AAATTAGCGGTGGTATTTTAGATTATGGGGTCATTGTCGATCGAGCACC

TTATTCACAAAGGGTCGAAGCATTACGTAATCCACAACTCGCTTCTGAT

CATTATCCCGTAGCCTTTTTGGCACGAAGCTGTTAAtgaTCTAGATAAG

TCGACgtacAGGAgagtagtATGTATATAAATAAGTTTGTGCCTGTTTA

TACATTATTAATTCTCATTTATTCTTTTAATGCCAGCGCTGAGTGGACA

GGAGATAATACGAACGCCTATTACTCAGACGAAGTTATCAGTGAATTAC

ATGTTGGTCAGATAGATACTAGTCCTTATTTTTGCATAAAAACGGTTAA

AGCTAACGGTAGTGGTACACCAGTTGTTGCATGTGCGGTATCAAAGCAG

AGCATATGGGCGCCCTCCTTTAAAGAACTTCTTGATCAGGCAAGATATT

TTTACAGTACAGGGCAATCCGTAAGGATTCATGTTCAAAAAAATATCTG

GACCTATCCGCTTTTTGTTAATACCTTTTCAGCAAATGCTCTTGTGGGA

CTATCATCGTGCAGTGCGACACAATGCTTTGGACCCAAGTAAgagggga gaagaaataATGAAAAAGTTAATATTCTTAACCTTATCTATAGTTAGCT

TTAATAACTATGCTGTAGATTTTGTGTATCGTGTGGACTCAACCCCGCC

GGACGTTATTTTTCGCGATGGGTTTTCACTACTTGGGTATAACCGTAAC

TTTCAGCAATTTATTAGTGGAAGGTCATGTAGTGGTGGAAGTAGTGACA

GTCGCTATATTGCAACAACCTCAAGTGTTAATCAAACATATGCTATAGC

CAGAGCGTACTATTCTCGCTCAACATTCAAAGGTAATTTATACAGATAT

CAGATTCGTGCAGATAATAATTTCTACAGCTTGCTCCCATCCATCACCT

ATCTGGAAACGCAAGGTGGTCACTTTAATGCTTATGAAAAAACGATGAT

GCGATTGCAAAGAGAGTATGTTTCCACATTATCTATTTTACCCGAGAAT

ATTCAAAAGGCCGTGGCGCTAGTTTATGATAGCGCAACCGGTCTGGTAA

AGGATGGTGTAAGCACAATGAATGCCAGTTATTTAGGTTTAAGCACTAC

-continued

GTCTAATCCTGGTGTGATACCTTTTCTTCCGGAACCGCAGACGTATACC

CAACAACGAATTGATGCATTCGGCCCATTAATAAGTTCATGCTTTTCAA

TAGGTAGCGTATGTCAGTCACATCGAGGGCAAAGAGCTGACGTATACAA

CATGTCTTTTTATGATGCAAGACCTGTAATAGAACTTATACTTTCTAAA

TAAatgaaacttacctatgttgccGCATGCAAGCTAGCTTGGCTGTTTTG

GCGGATGAGAGAAGATTTTCAGCCTGATACAGATTAAATCAGAACGCAGA

AGCGGTCTGATAAAACAGAATTTGCCTGGCGGCAGTAGCGCGGTGGTCCC

ACCTGACCCCATGCCGAACTCAGAAGTGAAACGCCGTAGCGCCGATGGTA

GTGTGGGGTCTCCCCATGCGAGAGTAGGGAACTGCCAGGCATCAAATAAA

ACGAAAGGCTCAGTCGAAAGACTGGGCCTTTCGTTTTATCTGTTGTTTGT

CGGTGAACGCTCTCCTGAGTAGGACAAATCCGCCGGGAGCGGATTTGAAC

GTTGCGAAGCAACGGCCCGGAGGGTGGCGGGCAGGACGCCCGCCATAAAC

TGCCAGGCATCAAATTAAGCAGAAGGCCATCCTGACGGATGGCCTTTTTG

CGTTTCTACAAACTCTTTTTGTTTATTTTTCTAAATACATTCAAATATGT

ATCCGCTCATGAGACAATAACCCTGATAAATGCTTCAATAATATTGAAAA

AGGAAGAGTATGAGTATTCAACATTTCCGTGTCGCCCTTATTCCCTTTTT

TGCGGCATTTTGCCTTCCTGTTTTTGCTCACCCAGAAACGCTGGTGAAAG

TAAAAGATGCTGAAGATCAGTTGGGTGCACGAGTGGGTTACATCGAACTG

GATCTCAACAGCGGTAAGATCCTTGAGAGTTTTCGCCCCGAAGAACGTTT

TCCAATGATGAGCACTTTTAAAGTTCTGCTATGTGGCGCGGTATTATCCC

GTGTTGACGCCGGGCAAGAGCAACTCGGTCGCCGCATACACTATTCTCAG

AATGACTTGGTTGAGTACTCACCAGTCACAGAAAAGCATCTTACGGATGG

CATGACAGTAAGAGAATTATGCAGTGCTGCCATAACCATGAGTGATAACA

CTGCGGCCAACTTACTTCTGACAACGATCGGAGGACCGAAGGAGCTAACC

GCTTTTTTGCACAACATGGGGGATCATGTAACTCGCCTTGATCGTTGGGA

ACCGGAGCTGAATGAAGCCATACCAAACGACGAGCGTGACACCACGATGC

CTACAGCAATGGCAACAACGTTGCGCAAACTATTAACTGGCGAACTACTT

ACTCTAGCTTCCCGGCAACAATTAATAGACTGGATGGAGGCGGATAAAGT

TGCAGGACCACTTCTGCGCTCGGCCCTTCCGGCTGGCTGGTTTATTGCTG

ATAAATCTGGAGCCGGTGAGCGTGGGTCTCGCGGTATCATTGCAGCACTG

GGGCCAGATGGTAAGCCCTCCCGTATCGTAGTTATCTACACGACGGGGAG

TCAGGCAACTATGGATGAACGAAATAGACAGATCGCTGAGATAGGTGCCT

CACTGATTAAGCATTGGTAACTGTCAGACCAAGTTTACTCATATATACTT

TAGATTGATTTAAAACTTCATTTTTAATTTAAAAGGATCTAGGTGAAGAT

CCTTTTTGATAATCTCATGACCAAAATCCCTTAACGTGAGTTTTCGTTCC

ACTGAGCGTCAGACCCCGTAGAAAAGATCAAAGGATCTTCTTGAGATCCT

TTTTTTCTGCGCGTAATCTGCTGCTTGCAAACAAAAAAACCACCGCTACC

AGCGGTGGTTTGTTTGCCGGATCAAGAGCTACCAACTCTTTTTCCGAAGG

TAACTGGCTTCAGCAGAGCGCAGATACCAAATACTGTCCTTCTAGTGTAG

CCGTAGTTAGGCCACCACTTCAAGAACTCTGTAGCACCGCCTACATACCT

CGCTCTGCTAATCCTGTTACCAGTGGCTGCTGCCAGTGGCGATAAGTCGT

-continued

GTCTTACCGGGTTGGACTCAAGACGATAGTTACCGGATAAGGCGCAGCGG

TCGGGCTGAACGGGGGGTTCGTGCACACAGCCCAGCTTGGAGCGAACGAC

CTACACCGAACTGAGATACCTACAGCGTGAGCTATGAGAAAGCGCCACGC

TTCCCGAAGGGAGAAAGGCGGACAGGTATCCGGTAAGCGGCAGGGTCGGA

ACAGGAGAGCGCACGAGGGAGCTTCCAGGGGGAAACGCCTGGTATCTTTA

TAGTCCTGTCGGGTTTCGCCACCTCTGACTTGAGCGTCGATTTTTGTGAT

GCTCGTCAGGGGGGCGGAGCCTATGGAAAAACGCCAGCAACGCGGCCTTT

TTACGGTTCCTGGCCTTTTGCTGGCCTTTTGCTCACATGTTCTTTCCTGC

GTTATCCCCTGATTCTGTGGATAACCGTATTACCGCCTTTGAGTGAGCTG

ATACCGCTCGCCGCAGCCGAACGACCGAGCGCAGCGAGTCAGTGAGCGAG

GAAGCGGAAGAGCGCCTGATGCGGTATTTTCTCCTTACGCATCTGTGCGG

TATTTCACACCGCATATG

Example 6

An artificial typhoid toxin operon lacking sty and ttsA with introduced cloning sites FLAG epitope and GGGGS (x3) SEQ ID NO.: 008 linker at the C-terminus of cldtB.

An artificial, inducible typhoid toxin operon lacking sty and ttsA and containing introduced cloning sites FLAG epitope and GGGGS (x3) SEQ ID NO.: 008 linker at the C-terminus as shown in FIG. 2D, is generated by multiple overlapping PCR and restriction endonuclease cloning steps and synthetic biology known to those skilled in the art. The operon is capable of being induced with an inducing agent, in the present instance, arabinose. As compared with FIG. 2B, the artificial operon now contains an artificial, in-frame restriction endonuclease linker containing SexAl, HindIII and Xbal the FLAG epitope and a GGGGS (x3) SEQ ID NO.: 008 flexible linker. The complete sequence of the arabinose inducible plasmid capable of expressing the construct with a cldtB start codon at 351 through codon at 1160 (without a stop), FLAG from 1170-1193, and GGGGS (x3) SEQ ID NO.: 008 from 1194-1238, pltB start at 1278 and stop at 1691 and pltA 1708-2436:

SEQ ID NO.: 009 gggGGCGGCCGCaagaaaccaattgtccatattgcatcagacattgccgt cactgcgtcttttactggctcttctcgctaaccaaaccggtaaccccgct tattaaaagcattctgtaacaaagcgggaccaaagccatgacaaaaacgc gtaacaaaagtgtctataatcacggcagaaaagtccacattgattatttg cacggcgtcacactttgctatgccatagcatttttatccataagattagc ggatcctacctgacgctttttatcgcaactctctactgtttctccatacc cgtttttttgggctagcgaattcgagctcggtacccaggaggaattcaCC atgGTCaaaaaacctgtttttttccttctgaccatgatcatctgcagcta tatttcttttgcctgcgctaatatcagtgactacaaagttatgacctgga atcttcagggctcttcagcatctacagaaagtaaatggaatgtcaatgtc agacagcttttaagcggtactgccggtgtggatattcttatggtacagga ggccggtgctgttcccacctcagcggttcctaccggacgacatattcagc -continued cttttggagtgggtattcccattgatgaatacacctggaatctcggaacc accagccgtcaggatataagatatatctactactcggctattgatgttgg agcacgccgtgttaatctggcaatagtttccagacaaagagcggataatg tttatgtcttgcgtccgacaactgtcgcatctcgccccgtcattggcatc ggactgggtaatgatgtttttctgacagcgcacgcactggctagtggagg tccggatgctgcagctattgtcagggttaccattaatttttttagacaac ctcagatgcggcatttatcctggtttcttgccggggattttaatcgcagc ccagacagacttgaaaatgacctgatgactgagcatctggaacgagttgt agccgtactcgcacctacagaacccacgcaaattagcggtggtattttag attatggggtcattgtcgatcgagcaccttattcacaaagggtcgaagca ttacgtaatccacaactcgcttctgatcattatcccgtagcctttttggc acgaagctgtaTAccaggtgattataaagatgacgatgacaaaggcggtg gcggtagcggcggtggcggttctggcggtggcggtagtaagcttGGGtct agaTAGgtcgacgtacAGGAgagtagtATGTATATAAATAAGTTTGTGCC

TGTTTATACATTATTAATTCTCATTTATTCTTTTAATGCCAGCGCTGAGT

GGACAGGAGATAATACGAACGCCTATTACTCAGACGAAGTTATCAGTGAA

TTACATGTTGGTCAGATAGATACTAGTCCTTATTTTTGCATAAAAACGGT

TAAAGCTAACGGTAGTGGTACACCAGTTGTTGCATGTGCGGTATCAAAGC

AGAGCATATGGGCGCCCTCCTTTAAAGAACTTCTTGATCAGGCAAGATAT

TTTTACAGTACAGGGCAATCCGTAAGGATTCATGTTCAAAAAAATATCTG

GACCTATCCGCTTTTTGTTAATACCTTTTCAGCAAATGCTCTTGTGGGAC

TATCATCGTGCAGTGCGACACAATGCTTTGGACCCAAGTAAgaggggaga agaaataATGAAAAAGTTAATATTCTTAACCTTATCTATAGTTAGCTTTA

ATAACTATGCTGTAGATTTTGTGTATCGTGTGGACTCAACCCCGCCGGAC

GTTATTTTTCGCGATGGGTTTTCACTACTTGGGTATAACCGTAACTTTCA

GCAATTTATTAGTGGAAGGTCATGTAGTGGTGGAAGTAGTGACAGTCGCT

ATATTGCAACAACCTCAAGTGTTAATCAAACATATGCTATAGCCAGAGCG

TACTATTCTCGCTCAACATTCAAAGGTAATTTATACAGATATCAGATTCG

TGCAGATAATAATTTCTACAGCTTGCTCCCATCCATCACCTATCTGGAAA

CGCAAGGTGGTCACTTTAATGCTTATGAAAAAACGATGATGCGATTGCAA

AGAGAGTATGTTTCCACATTATCTATTTTACCCGAGAATATTCAAAAGGC

CGTGGCGCTAGTTTATGATAGCGCAACCGGTCTGGTAAAGGATGGTGTAA

GCACAATGAATGCCAGTTATTTAGGTTTAAGCACTACGTCTAATCCTGGT

GTGATACCTTTTCTTCCGGAACCGCAGACGTATACCCAACAACGAATTGA

TGCATTCGGCCCATTAATAAGTTCATGCTTTTCAATAGGTAGCGTATGTC

AGTCACATCGAGGGCAAAGAGCTGACGTATACAACATGTCTTTTTATGAT

GCAAGACCTGTAATAGAACTTATACTTTCTAAATAAatgaaacttaccta tgttgccGCATGCAAGCTAGCTTGGCTGTTTTGGCGGATGAGAGAAGATT

TTCAGCCTGATACAGATTAAATCAGAACGCAGAAGCGGTCTGATAAAACA

GAATTTGCCTGGCGGCAGTAGCGCGGTGGTCCCACCTGACCCCATGCCGA

ACTCAGAAGTGAAACGCCGTAGCGCCGATGGTAGTGTGGGGTCTCCCCAT

-continued

```
GCGAGAGTAGGGAACTGCCAGGCATCAAATAAAACGAAAGGCTCAGTCGA

AAGACTGGGCCTTTCGTTTTATCTGTTGTTTGTCGGTGAACGCTCTCCTG

AGTAGGACAAATCCGCCGGGAGCGGATTTGAACGTTGCGAAGCAACGGCC

CGGAGGGTGGCGGGCAGGACGCCCGCCATAAACTGCCAGGCATCAAATTA

AGCAGAAGGCCATCCTGACGGATGGCCTTTTTGCGTTTCTACAAACTCTT

TTTGTTTATTTTTCTAAATACATTCAAATATGTATCCGCTCATGAGACAA

TAACCCTGATAAATGCTTCAATAATATTGAAAAAGGAAGAGTATGAGTAT

TCAACATTTCCGTGTCGCCCTTATTCCCTTTTTTGCGGCATTTTGCCTTC

CTGTTTTTGCTCACCCAGAAACGCTGGTGAAAGTAAAAGATGCTGAAGAT

CAGTTGGGTGCACGAGTGGGTTACATCGAACTGGATCTCAACAGCGGTAA

GATCCTTGAGAGTTTTCGCCCCGAAGAACGTTTTCCAATGATGAGCACTT

TTAAAGTTCTGCTATGTGGCGCGGTATTATCCCGTGTTGACGCCGGGCAA

GAGCAACTCGGTCGCCGCATACACTATTCTCAGAATGACTTGGTTGAGTA

CTCACCAGTCACAGAAAAGCATCTTACGGATGGCATGACAGTAAGAGAAT

TATGCAGTGCTGCCATAACCATGAGTGATAACACTGCGGCCAACTTACTT

CTGACAACGATCGGAGGACCGAAGGAGCTAACCGCTTTTTTGCACAACAT

GGGGGATCATGTAACTCGCCTTGATCGTTGGGAACCGGAGCTGAATGAAG

CCATACCAAACGACGAGCGTGACACCACGATGCCTACAGCAATGGCAACA

ACGTTGCGCAAACTATTAACTGGCGAACTACTTACTCTAGCTTCCCGGCA

ACAATTAATAGACTGGATGGAGGCGGATAAAGTTGCAGGACCACTTCTGC

GCTCGGCCCTTCCGGCTGGCTGGTTTATTGCTGATAAATCTGGAGCCGGT

GAGCGTGGGTCTCGCGGTATCATTGCAGCACTGGGGCCAGATGGTAAGCC

CTCCCGTATCGTAGTTATCTACACGACGGGGAGTCAGGCAACTATGGATG

AACGAAATAGACAGATCGCTGAGATAGGTGCCTCACTGATTAAGCATTGG

TAACTGTCAGACCAAGTTTACTCATATATACTTTAGATTGATTTAAAACT

TCATTTTTAATTTAAAAGGATCTAGGTGAAGATCCTTTTTGATAATCTCA

TGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAAT

CTGCTGCTTGCAAACAAAAAAACCACCGCTACCAGCGGTGGTTTGTTTGC

CGGATCAAGAGCTACCAACTCTTTTTCCGAAGGTAACTGGCTTCAGCAGA

GCGCAGATACCAAATACTGTCCTTCTAGTGTAGCCGTAGTTAGGCCACCA

CTTCAAGAACTCTGTAGCACCGCCTACATACCTCGCTCTGCTAATCCTGT

TACCAGTGGCTGCTGCCAGTGGCGATAAGTCGTGTCTTACCGGGTTGGAC

TCAAGACGATAGTTACCGGATAAGGCGCAGCGGTCGGGCTGAACGGGGGG

TTCGTGCACACAGCCCAGCTTGGAGCGAACGACCTACACCGAACTGAGAT

ACCTACAGCGTGAGCTATGAGAAAGCGCCACGCTTCCCGAAGGGAGAAAG

GCGGACAGGTATCCGGTAAGCGGCAGGGTCGGAACAGGAGAGCGCACGAG

GGAGCTTCCAGGGGGAAACGCCTGGTATCTTTATAGTCCTGTCGGGTTTC

GCCACCTCTGACTTGAGCGTCGATTTTTGTGATGCTCGTCAGGGGGGCGG

AGCCTATGGAAAAACGCCAGCAACGCGGCCTTTTTACGGTTCCTGGCCTT

TTGCTGGCCTTTTGCTCACATGTTCTTTCCTGCGTTATCCCCTGATTCTG

TGGATAACCGTATTACCGCCTTTGAGTGAGCTGATACCGCTCGCCGCAGC

CGAACGACCGAGCGCAGCGAGTCAGTGAGCGAGGAAGCGGAAGAGCGCCT

GATGCGGTATTTTCTCCTTACGCATCTGTGCGGTATTTCACACCGCATAT

G
```

Example 7

Apoptin C-terminal fusions with typhoid toxin cldtB.

An artificial, inducible typhoid toxin operon lacking sty and ttsA and containing introduced FLAG epitope, GGGGS (x3) SEQ ID NO.: 008 linker and HindIII and Xbal is used to insert apoptin, TAT-apoptin, and apoptin fragments as shown in FIG. 2E as generated by PCR and restriction endonuclease-based cloning methods and synthetic biology known to those skilled in the art. Fragments consisting of either 1) apoptin 1-121, 2) apoptin 33-121, 3) apoptin 82-121, 4) apoptin 97-121, 5) apoptin 106-121, 6) apoptin 111-121 or 7) apoptin 1-31 linked to 83-121. By way of example complete sequence of the arabinose inducible plasmid capable of expressing the TAT-apoptin construct as a cldtB fusion, with TAT-apoptin inserted in-frame within the HindIII and Xbal sites introduced into typhoid toxin cldtB, with the TAT-apoptin coding sequence from 1245-1646:

```
                                                SEQ ID NO.: 010
gggGGCGGCCGCaagaaaccaattgtccatattgcatcagacattgccgtc

actgcgtcttttactggctcttctcgctaaccaaaccggtaaccccgctt

attaaaagcattctgtaacaaagcgggaccaaagccatgacaaaaacgcg

taacaaaagtgtctataatcacggcagaaaagtccacattgattatttgc

acggcgtcacactttgctatgccatagcattttttatccataagattagcg

gatcctacctgacgctttttatcgcaactctctactgtttctccataccc

gtttttttgggctagcgaattcgagctcggtacccaggaggaattcaCCa

tgGTCaaaaaacctgtttttttccttctgaccatgatcatctgcagctat

atttcttttgcctgcgctaatatcagtgactacaaagttatgacctggaa

tcttcagggctcttcagcatctacagaaagtaaatggaatgtcaatgtca

gacagcttttaagcggtactgccggtgtggatattcttatggtacaggag

gccggtgctgttcccacctcagcggttcctaccggacgacatattcagcc

ttttggagtgggtattcccattgatgaatacacctggaatctcggaacca

ccagccgtcaggatataagatatatctactactcggctattgatgttgga

gcacgccgtgttaatctggcaatagtttccagacaaagagcggataatgt

ttatgtcttgcgtccgacaactgtcgcatctcgccccgtcattggcatcg

gactgggtaatgatgtttttctgacagcgcacgcactggctagtggaggt

ccggatgctgcagctattgtcagggttaccattaatttttttagacaacc

tcagatgcggcatttatcctggtttcttgccggggattttaatcgcagcc

cagacagacttgaaaatgacctgatgactgagcatctggaacgagttgta

gccgtactcgcacctacagaacccacgcaaattagcggtggtattttaga

ttatggggtcattgtcgatcgagcaccttattcacaaagggtcgaagcat
```

-continued tacgtaatccacaactcgcttctgatcattatcccgtagcctttttggca cgaagctgtaTAccaggtgattataaagatgacgatgacaaaggcggtgg cggtagcggcggtggcggttctggcggtggcggtagtaagcttATGGCAT

ACGGTCGCAAGAAACGTCGTCAACGCCGCCGCATGAACGCCCTGCAAGAA

GACACGCCGCCGGGTCCGAGCACGGTTTTTCGTCCGCCGACCAGCTCTCG

CCCGCTGGAAACGCCGCATTGCCGTGAAATTCGCATCGGCATTGCAGGTA

TCACCATTACGCTGTCTCTGTGCGGCTGTGCAAACGCACGTGCACCGACC

CTGCGCTCCGCTACGGCGGATAACAGTGAATCCACCGGTTTTAAAAATGT

GCCGGATCTGCGTACGGACCAGCCGAAGCCGCCGTCAAAAAAGCGTTCGT

GTGACCCGAGCGAATATCGCGTTAGCGAACTGAAAGAATCTCTGATTACC

ACGACCCCGTCCCGTCCGCGCACCGCaaaACGCCGCATCCGTCTGTCTAG

ATAGGtcgacgtacAGGAgagtagtATGTATATAAATAAGTTTGTGCCTG

TTTATACATTATTAATTCTCATTTATTCTTTTAATGCCAGCGCTGAGTGG

ACAGGAGATAATACGAACGCCTATTACTCAGACGAAGTTATCAGTGAATT

ACATGTTGGTCAGATAGATACTAGTCCTTATTTTTGCATAAAAACGGTTA

AAGCTAACGGTAGTGGTACACCAGTTGTTGCATGTGCGGTATCAAAGCAG

AGCATATGGGCGCCCTCCTTTAAAGAACTTCTTGATCAGGCAAGATATTT

TTACAGTACAGGGCAATCCGTAAGGATTCATGTTCAAAAAAATATCTGGA

CCTATCCGCTTTTTGTTAATACCTTTTCAGCAAATGCTCTTGTGGGACTA

TCATCGTGCAGTGCGACACAATGCTTTGGACCCAAGTAAgaggggagaag aaataATGAAAAAGTTAATATTCTTAACCTTATCTATAGTTAGCTTTAAT

AACTATGCTGTAGATTTTGTGTATCGTGTGGACTCAACCCCGCCGGACGT

TATTTTTCGCGATGGGTTTTCACTACTTGGGTATAACCGTAACTTTCAGC

AATTTATTAGTGGAAGGTCATGTAGTGGTGGAAGTAGTGACAGTCGCTAT

ATTGCAACAACCTCAAGTGTTAATCAAACATATGCTATAGCCAGAGCGTA

CTATTCTCGCTCAACATTCAAAGGTAATTTATACAGATATCAGATTCGTG

CAGATAATAATTTCTACAGCTTGCTCCCATCCATCACCTATCTGGAAACG

CAAGGTGGTCACTTTAATGCTTATGAAAAAACGATGATGCGATTGCAAAG

AGAGTATGTTTCCACATTATCTATTTTACCCGAGAATATTCAAAAGGCCG

TGGCGCTAGTTTATGATAGCGCAACCGGTCTGGTAAAGGATGGTGTAAGC

ACAATGAATGCCAGTTATTTAGGTTTAAGCACTACGTCTAATCCTGGTGT

GATACCTTTTCTTCCGGAACCGCAGACGTATACCCAACAACGAATTGATG

CATTCGGCCCATTAATAAGTTCATGCTTTTCAATAGGTAGCGTATGTCAG

TCACATCGAGGGCAAAGAGCTGACGTATACAACATGTCTTTTTATGATGC

AAGACCTGTAATAGAACTTATACTTTCTAAATAAatgaaacttacctatg ttgccGCATGCAAGCTAGCTTGGCTGTTTTGGCGGATGAGAGAAGATTTT

CAGCCTGATACAGATTAAATCAGAACGCAGAAGCGGTCTGATAAAACAGA

ATTTGCCTGGCGGCAGTAGCGCGGTGGTCCCACCTGACCCCATGCCGAAC

TCAGAAGTGAAACGCCGTAGCGCCGATGGTAGTGTGGGGTCTCCCCATGC

GAGAGTAGGGAACTGCCAGGCATCAAATAAAACGAAAGGCTCAGTCGAAA

GACTGGGCCTTTCGTTTTATCTGTTGTTTGTCGGTGAACGCTCTCCTGAG

-continued

TAGGACAAATCCGCCGGGAGCGGATTTGAACGTTGCGAAGCAACGGCCCG

GAGGGTGGCGGGCAGGACGCCCGCCATAAACTGCCAGGCATCAAATTAAG

CAGAAGGCCATCCTGACGGATGGCCTTTTTGCGTTTCTACAAACTCTTTT

TGTTTATTTTTCTAAATACATTCAAATATGTATCCGCTCATGAGACAATA

ACCCTGATAAATGCTTCAATAATATTGAAAAAGGAAGAGTATGAGTATTC

AACATTTCCGTGTCGCCCTTATTCCCTTTTTTGCGGCATTTTGCCTTCCT

GTTTTTGCTCACCCAGAAACGCTGGTGAAAGTAAAAGATGCTGAAGATCA

GTTGGGTGCACGAGTGGGTTACATCGAACTGGATCTCAACAGCGGTAAGA

TCCTTGAGAGTTTTCGCCCCGAAGAACGTTTTCCAATGATGAGCACTTTT

AAAGTTCTGCTATGTGGCGCGGTATTATCCCGTGTTGACGCCGGGCAAGA

GCAACTCGGTCGCCGCATACACTATTCTCAGAATGACTTGGTTGAGTACT

CACCAGTCACAGAAAAGCATCTTACGGATGGCATGACAGTAAGAGAATTA

TGCAGTGCTGCCATAACCATGAGTGATAACACTGCGGCCAACTTACTTCT

GACAACGATCGGAGGACCGAAGGAGCTAACCGCTTTTTTGCACAACATGG

GGGATCATGTAACTCGCCTTGATCGTTGGGAACCGGAGCTGAATGAAGCC

ATACCAAACGACGAGCGTGACACCACGATGCCTACAGCAATGGCAACAAC

GTTGCGCAAACTATTAACTGGCGAACTACTTACTCTAGCTTCCCGGCAAC

AATTAATAGACTGGATGGAGGCGGATAAAGTTGCAGGACCACTTCTGCGC

TCGGCCCTTCCGGCTGGCTGGTTTATTGCTGATAAATCTGGAGCCGGTGA

GCGTGGGTCTCGCGGTATCATTGCAGCACTGGGGCCAGATGGTAAGCCCT

CCCGTATCGTAGTTATCTACACGACGGGGAGTCAGGCAACTATGGATGAA

CGAAATAGACAGATCGCTGAGATAGGTGCCTCACTGATTAAGCATTGGTA

ACTGTCAGACCAAGTTTACTCATATATACTTTAGATTGATTTAAAACTTC

ATTTTTAATTTAAAAGGATCTAGGTGAAGATCCTTTTTGATAATCTCATG

ACCAAAATCCCTTAACGTGAGTTTTCGTTCCACTGAGCGTCAGACCCCGT

AGAAAAGATCAAAGGATCTTCTTGAGATCCTTTTTTTCTGCGCGTAATCT

GCTGCTTGCAAACAAAAAAACCACCGCTACCAGCGGTGGTTTGTTTGCCG

GATCAAGAGCTACCAACTCTTTTTCCGAAGGTAACTGGCTTCAGCAGAGC

GCAGATACCAAATACTGTCCTTCTAGTGTAGCCGTAGTTAGGCCACCACT

TCAAGAACTCTGTAGCACCGCCTACATACCTCGCTCTGCTAATCCTGTTA

CCAGTGGCTGCTGCCAGTGGCGATAAGTCGTGTCTTACCGGGTTGGACTC

AAGACGATAGTTACCGGATAAGGCGCAGCGGTCGGGCTGAACGGGGGGTT

CGTGCACACAGCCCAGCTTGGAGCGAACGACCTACACCGAACTGAGATAC

CTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGG

AGCTTCCAGGGGGAAACGCCTGGTATCTTTATAGTCCTGTCGGGTTTCGC

CACCTCTGACTTGAGCGTCGATTTTTGTGATGCTCGTCAGGGGGGCGGAG

CCTATGGAAAAACGCCAGCAACGCGGCCTTTTTACGGTTCCTGGCCTTTT

GCTGGCCTTTTGCTCACATGTTCTTTCCTGCGTTATCCCCTGATTCTGTG

GATAACCGTATTACCGCCTTTGAGTGAGCTGATACCGCTCGCCGCAGCCG

-continued

```
AACGACCGAGCGCAGCGAGTCAGTGAGCGAGGAAGCGGAAGAGCGCCTGA

TGCGGTATTTTCTCCTTACGCATCTGTGCGGTATTTCACACCGCATATG
```

Example 8

N-terminal fusions with typhoid toxin cldtB.

An artificial, inducible typhoid toxin operon lacking sty and ttsA and containing introduced FLAG epitope, GGGGS (x3) SEQ ID NO.: 008 linker and HindIII and XbaI is used to insert functional peptides in frame (e.g., apoptin, TAT-apoptin, and apoptin fragments) as shown in FIG. 3B as generated by PCR and restriction endonuclease-based cloning methods and synthetic biology known to those skilled in the art. For example, two separate PCR primer sets that generate N-terminal restriction sites (HindIII (H3) XbaI and ClaI) for cloning typhoid/paratyphoid cldtB are paratyphi A NcoI_F1:
5'-TACGCCATGGT-CAAAAAACCTGTTTTTTCCTTCTGACC-3'
SEQ ID NO.: 011 and
HindIII_XbaI ClaI-R1:
5'-CGATCCCTCTAGACCCAAGCTTGTCACTGAT-ATTAGCGCAGGC-3'
SEQ ID NO.: 012 (set 1) and
HindIII_XbaI_ClaI-F1:
5'-GCTTGGGTCTAGAGGGATCGATTACAAAGT-TATGACCTGGAATCTTCAG-3'
SEQ ID NO.: 013 and
cldtB_stop_XbaI_SalI-R1:
5'-GATCGTCGACTTATCTAGATCAT-TAACAGCTTCGTGCCA-3'
SEQ ID NO.: 014 (set 2).

The two sets are used for separate PCRs (for example, using the DNA of FIG. 2B as a template) followed by overlapping PCR and cloning into the NcoI and XbaI restriction endonuclease sites (13-350=arabinose promoter; 351-1187=cldtB; 1210-1213=RBS pltB; 1221-1634=pltB; 1651-2379=pltA).

SEQ ID NO.: 015

```
gggGGCGGCCGCaagaaaccaattgtccatattgcatcagacattgccgt

cactgcgtcttttactggctcttctcgctaaccaaaccggtaaccccgct

tattaaaagcattctgtaacaaagcgggaccaaagccatgacaaaaacgc

gtaacaaaagtgtctataatcacggcagaaaagtccacattgattatttg

cacggcgtcacactttgctatgccatagcatttttatccataagattagc

ggatcctacctgacgctttttatcgcaactctctactgtttctccatacc

cgtttttttgggctagcgaattcgagctcggtacccaggaggaattcaCC

ATGGTCAAAAAACCTGTTTTTTTCCTTCTGACCATGATCATCTGCAGCTA

TATTTCTTTTGCCTGCGCTAATATCAGTGACaagcttgggtctagaggga

tcgatTACAAAGTTATGACCTGGAATCTTCAGGGCTCTTCAGCATCTACA

GAAAGTAAATGGAATGTCAATGTCAGACAGCTTTTAAGCGGTACTGCCGG

TGTGGATATTCTTATGGTACAGGAGGCCGGTGCTGTTCCCACCTCAGCGG

TTCCTACCGGACGACATATTCAGCCTTTTGGAGTGGGTATTCCCATTGAT

GAATACACCTGGAATCTCGGAACCACCAGCCGTCAGGATATAAGATATAT

CTACTACTCGGCTATTGATGTTGGAGCACGCCGTGTTAATCTGGCAATAG
```

-continued

```
TTTCCAGACAAAGAGCGGATAATGTTTATGTCTTGCGTCCGACAACTGTC

GCATCTCGCCCCGTCATTGGCATCGGACTGGGTAATGATGTTTTTCTGAC

AGCGCACGCACTGGCTAGTGGAGGTCCGGATGCTGCAGCTATTGTCAGGG

TTACCATTAATTTTTTTAGACAACCTCAGATGCGGCATTTATCCTGGTTT

CTTGCCGGGGATTTTAATCGCAGCCCAGACAGACTTGAAAATGACCTGAT

GACTGAGCATCTGGAACGAGTTGTAGCCGTACTCGCACCTACAGAACCCA

CGCAAATTAGCGGTGGTATTTTAGATTATGGGGTCATTGTCGATCGAGCA

CCTTATTCACAAAGGGTCGAAGCATTACGTAATCCACAACTCGCTTCTGA

TCATTATCCCGTAGCCTTTTTGGCACGAAGCTGTTAAtgaTCTAGATAAG

TCGACgtacAGGAgagtagtATGTATATAAATAAGTTTGTGCCTGTTTAT

ACATTATTAATTCTCATTTATTCTTTTAATGCCAGCGCTGAGTGGACAGG

AGATAATACGAACGCCTATTACTCAGACGAAGTTATCAGTGAATTACATG

TTGGTCAGATAGATACTAGTCCTTATTTTTGCATAAAAACGGTTAAAGCT

AACGGTAGTGGTACACCAGTTGTTGCATGTGCGGTATCAAAGCAGAGCAT

ATGGGCGCCCTCCTTTAAAGAACTTCTTGATCAGGCAAGATATTTTTACA

GTACAGGGCAATCCGTAAGGATTCATGTTCAAAAAAATATCTGGACCTAT

CCGCTTTTTGTTAATACCTTTTCAGCAAATGCTCTTGTGGGACTATCATC

GTGCAGTGCGACACAATGCTTTGGACCCAAGTAAgaggggagaagaaata

ATGAAAAAGTTAATATTCTTAACCTTATCTATAGTTAGCTTTAATAACTA

TGCTGTAGATTTTGTGTATCGTGTGGACTCAACCCCGCCGGACGTTATTT

TTCGCGATGGGTTTTCACTACTTGGGTATAACCGTAACTTTCAGCAATTT

ATTAGTGGAAGGTCATGTAGTGGTGGAAGTAGTGACAGTCGCTATATTGC

AACAACCTCAAGTGTTAATCAAACATATGCTATAGCCAGAGCGTACTATT

CTCGCTCAACATTCAAAGGTAATTTATACAGATATCAGATTCGTGCAGAT

AATAATTTCTACAGCTTGCTCCCATCCATCACCTATCTGGAAACGCAAGG

TGGTCACTTTAATGCTTATGAAAAAACGATGATGCGATTGCAAAGAGAGT

ATGTTTCCACATTATCTATTTTACCCGAGAATATTCAAAAGGCCGTGGCG

CTAGTTTATGATAGCGCAACCGGTCTGGTAAAGGATGGTGTAAGCACAAT

GAATGCCAGTTATTTAGGTTTAAGCACTACGTCTAATCCTGGTGTGATAC

CTTTTCTTCCGGAACCGCAGACGTATACCCAACAACGAATTGATGCATTC

GGCCCATTAATAAGTTCATGCTTTTCAATAGGTAGCGTATGTCAGTCACA

TCGAGGGCAAAGAGCTGACGTATACAACATGTCTTTTTATGATGCAAGAC

CTGTAATAGAACTTATACTTTCTAAATAAatgaaacttacctatgttgcc

GCATGCAAGCTAGCTTGGCTGTTTTGGCGGATGAGAGAAGATTTTCAGCC

TGATACAGATTAAATCAGAACGCAGAAGCGGTCTGATAAAACAGAATTTG

CCTGGCGGCAGTAGCGCGGTGGTCCCACCTGACCCCATGCCGAACTCAGA

AGTGAAACGCCGTAGCGCCGATGGTAGTGTGGGGTCTCCCCATGCGAGAG

TAGGGAACTGCCAGGCATCAAATAAAACGAAAGGCTCAGTCGAAAGACTG

GGCCTTTCGTTTTATCTGTTGTTTGTCGGTGAACGCTCTCCTGAGTAGGA

CAAATCCGCCGGGAGCGGATTTGAACGTTGCGAAGCAACGGCCCGGAGGG
```

-continued

```
TGGCGGGCAGGACGCCCGCCATAAACTGCCAGGCATCAAATTAAGCAGAA
GGCCATCCTGACGGATGGCCTTTTTGCGTTTCTACAAACTCTTTTTGTTT
ATTTTTCTAAATACATTCAAATATGTATCCGCTCATGAGACAATAACCCT
GATAAATGCTTCAATAATATTGAAAAAGGAAGAGTATGAGTATTCAACAT
TTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGG
GTGCACGAGTGGGTTACATCGAACTGGATCTCAACAGCGGTAAGATCCTT
GAGAGTTTTCGCCCCGAAGAACGTTTTCCAATGATGAGCACTTTTAAAGT
TCTGCTATGTGGCGCGGTATTATCCCGTGTTGACGCCGGGCAAGAGCAAC
TCGGTCGCCGCATACACTATTCTCAGAATGACTTGGTTGAGTACTCACCA
GTCACAGAAAAGCATCTTACGGATGGCATGACAGTAAGAGAATTATGCAG
TGCTGCCATAACCATGAGTGATAACACTGCGGCCAACTTACTTCTGACAA
CGATCGGAGGACCGAAGGAGCTAACCGCTTTTTTGCACAACATGGGGGAT
CATGTAACTCGCCTTGATCGTTGGGAACCGGAGCTGAATGAAGCCATACC
AAACGACGAGCGTGACACCACGATGCCTACAGCAATGGCAACAACGTTGC
GCAAACTATTAACTGGCGAACTACTTACTCTAGCTTCCCGGCAACAATTA
ATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGT
ATCGTAGTTATCTACACGACGGGGAGTCAGGCAACTATGGATGAACGAAA
TAGACAGATCGCTGAGATAGGTGCCTCACTGATTAAGCATTGGTAACTGT
CAGACCAAGTTTACTCATATATACTTTAGATTGATTTAAAACTTCATTTT
TAATTTAAAAGGATCTAGGTGAAGATCCTTTTTGATAATCTCATGACCAA
AATCCCTTAACGTGAGTTTTCGTTCCACTGAGCGTCAGACCCCGTAGAAA
AGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGA
TACCAAATACTGTCCTTCTAGTGTAGCCGTAGTTAGGCCACCACTTCAAG
AACTCTGTAGCACCGCCTACATACCTCGCTCTGCTAATCCTGTTACCAGT
GGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGC
ACACAGCCCAGCTTGGAGCGAACGACCTACACCGAACTGAGATACCTACA
GCGTGAGCTATGAGAAAGCGCCACGCTTCCCGAAGGGAGAAAGGCGGACA
GGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTAT
GGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAA
CCGTATTACCGCCTTTGAGTGAGCTGATACCGCTCGCCGCAGCCGAACGA
CCGAGCGCAGCGAGTCAGTGAGCGAGGAAGCGGAAGAGCGCCTGATGCGG
TATTTTCTCCTTACGCATCTGTGCGGTATTTCACACCGCATATG
```

Example 9

N-terminal fusions with typhoid toxin cldtB containing a 3XFLAG epitope and a flexible linker.

The artificial, inducible typhoid toxin operon lacking sty and ttsA and containing introduced HindIII (H3) Xbal and Clal of Example 8 is used to insert an in-frame 3XFLAG epitope (for immune identification and/or purification) and a flexible linker (GGGGS (x3), SEQ ID NO.: 008 as shown in FIG. 3C as generated by PCR and restriction endonuclease-based cloning methods and synthetic biology known to those skilled in the art (13-350=arabinose promoter; 351-1295=cldtB; 1318-1321=RBS pltB; 1329-1742=pltB; 1759-2487=pltA).

SEQ ID NO.: 016

```
gggGGCGGCCGCaagaaaccaattgtccatattgcatcagacattgccgt
cactgcgtcttttactggctcttctcgctaaccaaaccggtaaccccgct
tattaaaagcattctgtaacaaagcgggaccaaagccatgacaaaaacgc
gtaacaaaagtgtctataatcacggcagaaaagtccacattgattatttg
cacggcgtcacactttgctatgccatagcattttttatccataagattagc
ggatcctacctgacgctttttatcgcaactctctactgtttctccatacc
cgtttttttgggctagcgaattcgagctcggtacccaggaggaattcaCC
ATGGTCAAAAAACCTGTTTTTTTCCTTCTGACCATGATCATCTGCAGCTA
TATTTCTTTTGCCTGCGCTAATATCAGTGACaagcttgggtctagagact
acaaagaccatgacggtgattataaagatcatgatatcgactacaaagat
gacgacgataaaGGCGGTGGCGGATCCGGCGGTGGCGGTTCTGGCGGTGG
CGGTAGTatcgatTACAAAGTTATGACCTGGAATCTTCAGGGCTCTTCAG
CATCTACAGAAAGTAAATGGAATGTCAATGTCAGACAGCTTTTAAGCGGT
ACTGCCGGTGTGGATATTCTTATGGTACAGGAGGCCGGTGCTGTTCCCAC
CTCAGCGGTTCCTACCGGACGACATATTCAGCCTTTTGGAGTGGGTATTC
CCATTGATGAATACACCTGGAATCTCGGAACCACCAGCCGTCAGGATATA
AGATATATCTACTACTCGGCTATTGATGTTGGAGCACGCCGTGTTAATCT
GGCAATAGTTTCCAGACAAAGAGCGGATAATGTTTATGTCTTGCGTCCGA
CAACTGTCGCATCTCGCCCCGTCATTGGCATCGGACTGGGTAATGATGTT
TTTCTGACAGCGCACGCACTGGCTAGTGGAGGTCCGGATGCTGCAGCTAT
TGTCAGGGTTACCATTAATTTTTTTAGACAACCTCAGATGCGGCATTTAT
CCTGGTTTCTTGCCGGGGATTTTAATCGCAGCCCAGACAGACTTGAAAAT
GACCTGATGACTGAGCATCTGGAACGAGTTGTAGCCGTACTCGCACCTAC
AGAACCCACGCAAATTAGCGGTGGTATTTTAGATTATGGGGTCATTGTCG
ATCGAGCACCTTATTCACAAAGGGTCGAAGCATTACGTAATCCACAACTC
GCTTCTGATCATTATCCCGTAGCCTTTTTGGCACGAAGCTGTTAAtgaTC
TAGATAAGTCGACgtacAGGAgagtagtATGTATATAAATAAGTTTGTGC
CTGTTTATACATTATTAATTCTCATTTATTCTTTTAATGCCAGCGCTGAG
TGGACAGGAGATAATACGAACGCCTATTACTCAGACGAAGTTATCAGTGA
ATTACATGTTGGTCAGATAGATACTAGTCCTTATTTTTGCATAAAAACGG
TTAAAGCTAACGGTAGTGGTACACCAGTTGTTGCATGTGCGGTATCAAAG
```

-continued

```
CAGAGCATATGGGCGCCCTCCTTTAAAGAACTTCTTGATCAGGCAAGATA
TTTTTACAGTACAGGGCAATCCGTAAGGATTCATGTTCAAAAAAATATCT
GGACCTATCCGCTTTTTGTTAATACCTTTTCAGCAAATGCTCTTGTGGGA
CTATCATCGTGCAGTGCGACACAATGCTTTGGACCCAAGTAAgaggggag
aagaaataATGAAAAAGTTAATATTCTTAACCTTATCTATAGTTAGCTTT
AATAACTATGCTGTAGATTTTGTGTATCGTGTGGACTCAACCCCGCCGGA
CGTTATTTTTCGCGATGGGTTTTCACTACTTGGGTATAACCGTAACTTTC
AGCAATTTATTAGTGGAAGGTCATGTAGTGGTGGAAGTAGTGACAGTCGC
TATATTGCAACAACCTCAAGTGTTAATCAAACATATGCTATAGCCAGAGC
GTACTATTCTCGCTCAACATTCAAAGGTAATTTATACAGATATCAGATTC
GTGCAGATAATAATTTCTACAGCTTGCTCCCATCCATCACCTATCTGGAA
ACGCAAGGTGGTCACTTTAATGCTTATGAAAAAACGATGATGCGATTGCA
AAGAGAGTATGTTTCCACATTATCTATTTTACCCGAGAATATTCAAAAGG
CCGTGGCGCTAGTTTATGATAGCGCAACCGGTCTGGTAAAGGATGGTGTA
AGCACAATGAATGCCAGTTATTTAGGTTTAAGCACTACGTCTAATCCTGG
TGTGATACCTTTTCTTCCGGAACCGCAGACGTATACCCAACAACGAATTG
ATGCATTCGGCCCATTAATAAGTTCATGCTTTTCAATAGGTAGCGTATGT
CAGTCACATCGAGGGCAAAGAGCTGACGTATACAACATGTCTTTTTATGA
TGCAAGACCTGTAATAGAACTTATACTTTCTAAATAAatgaaacttacct
atgttgccGCATGCAAGCTAGCTTGGCTGTTTTGGCGGATGAGAGAAGAT
TTTCAGCCTGATACAGATTAAATCAGAACGCAGAAGCGGTCTGATAAAAC
AGAATTTGCCTGGCGGCAGTAGCGCGGTGGTCCCACCTGACCCCATGCCG
AACTCAGAAGTGAAACGCCGTAGCGCCGATGGTAGTGTGGGGTCTCCCCA
TGCGAGAGTAGGGAACTGCCAGGCATCAAATAAAACGAAAGGCTCAGTCG
AAAGACTGGGCCTTTCGTTTTATCTGTTGTTTGTCGGTGAACGCTCTCCT
GAGTAGGACAAATCCGCCGGGAGCGGATTTGAACGTTGCGAAGCAACGGC
CCGGAGGGTGGCGGGCAGGACGCCCGCCATAAACTGCCAGGCATCAAATT
AAGCAGAAGGCCATCCTGACGGATGGCCTTTTTGCGTTTCTACAAACTCT
TTTTGTTTATTTTTCTAAATACATTCAAATATGTATCCGCTCATGAGACA
ATAACCCTGATAAATGCTTCAATAATATTGAAAAAGGAAGAGTATGAGTA
TTCAACATTTCCGTGTCGCCCTTATTCCCTTTTTTGCGGCATTTTGCCTT
CCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTA
AGATCCTTGAGAGTTTTCGCCCCGAAGAACGTTTTCCAATGATGAGCACT
TTTAAAGTTCTGCTATGTGGCGCGGTATTATCCCGTGTTGACGCCGGGCA
AGAGCAACTCGGTCGCCGCATACACTATTCTCAGAATGACTTGGTTGAGT
ACTCACCAGTCACAGAAAAGCATCTTACGGATGGCATGACAGTAAGAGAA
TTATGCAGTGCTGCCATAACCATGAGTGATAACACTGCGGCCAACTTACT
TCTGACAACGATCGGAGGACCGAAGGAGCTAACCGCTTTTTTGCACAACA
TGGGGGATCATGTAACTCGCCTTGATCGTTGGGAACCGGAGCTGAATGAA
```

-continued

```
GCCATACCAAACGACGAGCGTGACACCACGATGCCTACAGCAATGGCAAC
AACGTTGCGCAAACTATTAACTGGCGAACTACTTACTCTAGCTTCCCGGC
AACAATTAATAGACTGGATGGAGGCGGATAAAGTTGCAGGACCACTTCTG
CGCTCGGCCCTTCCGGCTGGCTGGTTTATTGCTGATAAATCTGGAGCCGG
TGAGCGTGGGTCTCGCGGTATCATTGCAGCACTGGGGCCAGATGGTAAGC
CCTCCCGTATCGTAGTTATCTACACGACGGGGAGTCAGGCAACTATGGAT
GAACGAAATAGACAGATCGCTGAGATAGGTGCCTCACTGATTAAGCATTG
GTAACTGTCAGACCAAGTTTACTCATATATACTTTAGATTGATTTAAAAC
TTCATTTTTAATTTAAAAGGATCTAGGTGAAGATCCTTTTTGATAATCTC
ATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAA
TCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACC
ACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGG
GTTCGTGCACACAGCCCAGCTTGGAGCGAACGACCTACACCGAACTGAGA
TACCTACAGCGTGAGCTATGAGAAAGCGCCACGCTTCCCGAAGGGAGAAA
GGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGGCG
GAGCCTATGGAAAAACGCCAGCAACGCGGCCTTTTTACGGTTCCTGGCCT
TTTGCTGGCCTTTTGCTCACATGTTCTTTCCTGCGTTATCCCCTGATTCT
GTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCC
TGATGCGGTATTTTCTCCTTACGCATCTGTGCGGTATTTCACACCGCATA
TG
```

Functional in-frame peptide fragments such as those consisting of either 1) apoptin 1-121, 2) apoptin 33-121, 3) apoptin 82-121, 4) apoptin 97-121, 5) apoptin 106-121, 6) apoptin 111-121 or 7) apoptin 1-31 linked to 83-121 are further constructed by PCR and restriction endonuclease-based cloning methods and synthetic biology known to those skilled in the art as shown in FIG. 3D.

Example 10

Cytotoxicity of the cloned S. paratyphi cytolethal distending toxin wild type and reorganized operon with an inserted polylinker, and apoptin fusions. Cytotoxicity of *Salmonella* paratyphi A Cytolethal distending toxin toward MDA-MB-468 breast cancer cells is conducted using methods known to those skilled in the art and is measured by the MTT assay where absorbance at 570 nm indicates the relative number of live cells. (FIGS. 8A and 8B). By comparing no treatment control and a bacterial culture supernatant carrying an empty vector plasmid into a 100 μL tissue culture well control with a the reorganized polycistronic S. paratyphi A cytolethal distending operon containing a polylinker in cldtB C-terminus with dilutions of 1/2, 1/4, 1/8, and 1/16 and the reorganized polycistronic S. paratyphi A cytolethal distending operon without a polylinker in cldtB C-terminus, the ability of the CLDT is demonstrated, and the ability to secrete CLDT from the reorganized operon lacking sty and ttsA is demonstrated, as well as the ability to accommodate a polylinker.

Example 11

C-terminal fusions with typhoid toxin cldtB and a modified apoptin wherein the phosphorylation site T108 and the two adjacent threonines 106 and 107 are mutated to alanines does not alter cytotoxicity. The mutations are made by methods known to those skilled in the art. Modification of the phosphorylation sites abrogates the activity of apoptin. The resulting cytotoxicity test shows that there was no change in cytotoxicity, therefore, the cldtB: apoptin fusion does not acquire cell killing ability from the apoptin.

Example 12

A chimeric YebF: SFTI. The chimeric sunflower trypsin inhibitor: YebF fusion is made by methods known to those skilled in the art. The complete sequence of a tetracycline-inducible YebF: SFTI the start codon begins at 724 and the stop codon ends at 1158 is given by:

SEQ ID NO.: 017

```
ATATGGGGGCGGCCGCCTAAGACCCACTTTCACATTTAAGTTGTTTTTCT
AATCCGCATATAATCAATTCAAGGCCGAATAAGAAGGCTGGCTCTGCACC
TTGGTGTTCAAATAATTCGATAGCTTGTCGTAATAATGCCGGCATACTAT
CAGTAGTAGGTGTTTCCCTTTCTTCTTTAGCGACTTGATGCTCTTGATCT
TCCAATACGCAACCTAAAGTAAAATGCCCCACAGCGCTGAGTGCATATAA
TGCATTCTCTAGTGAAAAACCTTGTTGGCATAAAAAGGCTAATTGATTTT
CGAGAGTTTCATACTGTTTTTCTGTAGGCCGTGTACCTAAATGTACTTTT
GCTCCATCGCGATGACTTAGTAAAGCACATCTAAAACTTTTAGCGTTATT
ACGTAAAAAATCTTGCCAGCTTTCCCCTTCTAAAGGGCAAAAGTGAGTAT
GGTGCCTATCTAACATCTCAATGGCTAAGGCGTCGAGCAAAGCCCGCTTA
TTTTTTACATGCCAATACAATGTAGGCTGCTCTACACCCAGTTTCTGGGC
GAGTTTACGGGTTTTTAAACCTTCGATTCCGACCTCATTAAGCAGCTCTA
ATGCGCTGTTAATCACTTTACTTTTATCTAATCTGGACATCATAAATTCC
TAATTTTTGTTGACACTCTATCATTGATAGAGTTATTTTACCACTCCCTA
TCAGTGATAGAGAAAAGTGAACCatggctaaaaaaagaggggcgtttta
gggctgttgttggtttctgcctgcgcatcagttttcgctgccaataatga
aaccagcaagtcggtcactttcccaaagtgtgaagatctggatgctgccg
gaattgccgcgagcgtaaaacgtgattatcaacaaaatcgcgtggcgcgt
tgggcagatgatcaaaaaattgtcggtcaggccgatcccgtggcttgggt
cagtttgcaggacattcagggtaaagatgataaatggtcagtaccgctaa
ccgtgcgtggtaaaagtgccgatattcattaccaggtcagcgtggactgc
aaagcgggaatggcggaatatcagcggcgtCTCGAGGACGATGACGATAA
```

-continued

```
GGGTACCCTGAAAGGCCGCTGCACCAAAAGCATTCCGCCGATTTGCTTTC
CGGATTAGTCTAGAGTCGACCTGCAGGCATGCAAGCTTGGCTGTTTTGGC
GGATGAGAGAAGATTTTCAGCCTGATACAGATTAAATCAGAACGCAGAAG
CGGTCTGATAAAACAGAATTTGCCTGGCGGCAGTAGCGCGGTGGTCCCAC
CTGACCCCATGCCGAACTCAGAAGTGAAACGCCGTAGCGCCGATGGTAGT
GTGGGGTCTCCCCATGCGAGAGTAGGGAACTGCCAGGCATCAAATAAAAC
GAAAGGCTCAGTCGAAAGACTGGGCCTTTCGTTTTATCTGTTGTTTGTCG
GTGAACGCTCTCCTGAGTAGGACAAATCCGCCGGGAGCGGATTTGAACGT
TGCGAAGCAACGGCCCGGAGGGTGGCGGGCAGGACGCCCGCCATAAACTG
CCAGGCATCAAATTAAGCAGAAGGCCATCCTGACGGATGGCCTTTTTGCG
TTTCTACAAACTCTTTTTGTTTATTTTTCTAAATACATTCAAATATGTAT
CCGCTCATGAGACAATAACCCTGATAAATGCTTCAATAATATTGAAAAAG
GAAGAGTATGAGTATTCAACATTTCCGTGTCGCCCTTATTCCCTTTTTTG
CGGCATTTTGCCTTCCTGTTTTTGCTCACCCAGAAACGCTGGTGAAAGTA
AAAGATGCTGAAGATCAGTTGGGTGCACGAGTGGGTTACATCGAACTGGA
TCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGT
GTTGACGCCGGGCAAGAGCAACTCGGTCGCCGCATACACTATTCTCAGAA
TGACTTGGTTGAGTACTCACCAGTCACAGAAAAGCATCTTACGGATGGCA
TGACAGTAAGAGAATTATGCAGTGCTGCCATAACCATGAGTGATAACACT
GCGGCCAACTTACTTCTGACAACGATCGGAGGACCGAAGGAGCTAACCGC
TTTTTTGCACAACATGGGGGATCATGTAACTCGCCTTGATCGTTGGGAAC
CGGAGCTGAATGAAGCCATACCAAACGACGAGCGTGACACCACGATGCCT
ACAGCAATGGCAACAACGTTGCGCAAACTATTAACTGGCGAACTACTTAC
TCTAGCTTCCCGGCAACAATTAATAGACTGGATGGAGGCGGATAAAGTTG
CAGGACCACTTCTGCGCTCGGCCCTTCCGGCTGGCTGGTTTATTGCTGAT
AAATCTGGAGCCGGTGAGCGTGGGTCTCGCGGTATCATTGCAGCACTGGG
GCCAGATGGTAAGCCCTCCCGTATCGTAGTTATCTACACGACGGGGAGTC
AGGCAACTATGGATGAACGAAATAGACAGATCGCTGAGATAGGTGCCTCA
CTGATTAAGCATTGGTAACTGTCAGACCAAGTTTACTCATATATACTTTA
GATTGATTTAAAACTTCATTTTTAATTTAAAAGGATCTAGGTGAAGATCC
TTTTTGATAATCTCATGACCAAAATCCCTTAACGTGAGTTTTCGTTCCAC
TGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTA
ACTGGCTTCAGCAGAGCGCAGATACCAAATACTGTCCTTCTAGTGTAGCC
GTAGTTAGGCCACCACTTCAAGAACTCTGTAGCACCGCCTACATACCTCG
CTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTC
GGGCTGAACGGGGGGTTCGTGCACACAGCCCAGCTTGGAGCGAACGACCT
ACACCGAACTGAGATACCTACAGCGTGAGCTATGAGAAAGCGCCACGCTT
```

-continued

CCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGC
TCGTCAGGGGGGCGGAGCCTATGGAAAAACGCCAGCAACGCGGCCTTTTT
ACGGTTCCTGGCCTTTTGCTGGCCTTTTGCTCACATGTTCTTTCCTGCGT
TATCCCCTGATTCTGTGGATAACCGTATTACCGCCTTTGAGTGAGCTGAT
ACCGCTCGCCGCAGCCGAACGACCGAGCGCAGCGAGTCAGTGAGCGAGGA
AGCGGAAGAGCGCCTGATGCGGTATTTTCTCCTTACGCATCTGTGCGGTA
TTTCACACCG

Example 13

A chimeric OmpA: SFTI. The chimeric sunflower trypsin inhibitor: OmpA fusion is made by methods known to those skilled in the art. The complete sequence of a tetracycline inducible OmpA: SFTI fusion of which the coding sequence begins with an ATG start codon begins at 725 and the TAG stop codon ends at 1008 that can be inserted into an expression vector is given by:

SEQ ID NO.: 018

CATATGGGGGCGGCCGCCTAAGACCCACTTTCACATTTAAGTTGTTTTTC
TAATCCGCATATAATCAATTCAAGGCCGAATAAGAAGGCTGGCTCTGCAC
CTTGGTGTTCAAATAATTCGATAGCTTGTCGTAATAATGCCGGCATACTA
TCAGTAGTAGGTGTTTCCCTTTCTTCTTTAGCGACTTGATGCTCTTGATC
TTCCAATACGCAACCTAAAGTAAAATGCCCCACAGCGCTGAGTGCATATA
ATGCATTCTCTAGTGAAAAACCTTGTTGGCATAAAAAGGCTAATTGATTT
TCGAGAGTTTCATACTGTTTTTCTGTAGGCCGTGTACCTAAATGTACTTT
TGCTCCATCGCGATGACTTAGTAAAGCACATCTAAAACTTTTAGCGTTAT
TACGTAAAAAATCTTGCCAGCTTTCCCCTTCTAAAGGGCAAAAGTGAGTA
TGGTGCCTATCTAACATCTCAATGGCTAAGGCGTCGAGCAAAGCCCGCTT
ATTTTTTACATGCCAATACAATGTAGGCTGCTCTACACCCAGTTTCTGGG
CGAGTTTACGGGTTTTTAAACCTTCGATTCCGACCTCATTAAGCAGCTCT
AATGCGCTGTTAATCACTTTACTTTTATCTAATCTGGACATCATAAATTC
CTAATTTTTGTTGACACTCTATCATTGATAGAGTTATTTTACCACTCCCT
ATCAGTGATAGAGAAAAGTGAACCATGGCTAAAAAGACAGCTATCGCGAT
TGCAGTGGCACTGGCTGGTTTCGCTACCGTAGCGCAGGCCGCTCCGAAAG
ATGGCCGCTGCACCAAAAGCATTCCGCCGATTTGCTTTCCGGATTAGTCT
AGAGTCGACCTGCAGGCATGCAAGCTTGGCTGTTTTGGCGGATGAGAGAA
GATTTTCAGCCTGATACAGATTAAATCAGAACGCAGAAGCGGTCTGATAA
AACAGAATTTGCCTGGCGGCAGTAGCGCGGTGGTCCCACCTGACCCCATG
CCGAACTCAGAAGTGAAACGCCGTAGCGCCGATGGTAGTGTGGGGTCTCC
CCATGCGAGAGTAGGGAACTGCCAGGCATCAAATAAAACGAAAGGCTCAG
TCGAAAGACTGGGCCTTTCGTTTTATCTGTTGTTTGTCGGTGAACGCTCT

-continued

CCTGAGTAGGACAAATCCGCCGGGAGCGGATTTGAACGTTGCGAAGCAAC
GGCCCGGAGGGTGGCGGGCAGGACGCCCGCCATAAACTGCCAGGCATCAA
ATTAAGCAGAAGGCCATCCTGACGGATGGCCTTTTTGCGTTTCTACAAAC
TCTTTTTGTTTATTTTTCTAAATACATTCAAATATGTATCCGCTCATGAG
ACAATAACCCTGATAAATGCTTCAATAATATTGAAAAAGGAAGAGTATGA
GTATTCAACATTTCCGTGTCGCCCTTATTCCCTTTTTTGCGGCATTTTGC
CTTCCTGTTTTTGCTCACCCAGAAACGCTGGTGAAAGTAAAAGATGCTGA
AGATCAGTTGGGTGCACGAGTGGGTTACATCGAACTGGATCTCAACAGCG
GTAAGATCCTTGAGAGTTTTCGCCCCGAAGAACGTTTTCCAATGATGAGC
ACTTTTAAAGTTCTGCTATGTGGCGCGGTATTATCCCGTGTTGACGCCGG
GCAAGAGCAACTCGGTCGCCGCATACACTATTCTCAGAATGACTTGGTTG
AGTACTCACCAGTCACAGAAAAGCATCTTACGGATGGCATGACAGTAAGA
GAATTATGCAGTGCTGCCATAACCATGAGTGATAACACTGCGGCCAACTT
ACTTCTGACAACGATCGGAGGACCGAAGGAGCTAACCGCTTTTTTGCACA
ACATGGGGGATCATGTAACTCGCCTTGATCGTTGGGAACCGGAGCTGAAT
GAAGCCATACCAAACGACGAGCGTGACACCACGATGCCTACAGCAATGGC
AACAACGTTGCGCAAACTATTAACTGGCGAACTACTTACTCTAGCTTCCC
GGCAACAATTAATAGACTGGATGGAGGCGGATAAAGTTGCAGGACCACTT
CTGCGCTCGGCCCTTCCGGCTGGCTGGTTTATTGCTGATAAATCTGGAGC
CGGTGAGCGTGGGTCTCGCGGTATCATTGCAGCACTGGGGCCAGATGGTA
AGCCCTCCCGTATCGTAGTTATCTACACGACGGGGAGTCAGGCAACTATG
GATGAACGAAATAGACAGATCGCTGAGATAGGTGCCTCACTGATTAAGCA
TTGGTAACTGTCAGACCAAGTTTACTCATATATACTTTAGATTGATTTAA
AACTTCATTTTTAATTTAAAAGGATCTAGGTGAAGATCCTTTTTGATAAT
CTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGT
TTGCCGGATCAAGAGCTACCAACTCTTTTTCCGAAGGTAACTGGCTTCAG
CAGAGCGCAGATACCAAATACTGTCCTTCTAGTGTAGCCGTAGTTAGGCC
ACCACTTCAAGAACTCTGTAGCACCGCCTACATACCTCGCTCTGCTAATC
CTGTTACCAGTGGCTGCTGCCAGTGGCGATAAGTCGTGTCTTACCGGGTT
GGACTCAAGACGATAGTTACCGGATAAGGCGCAGCGGTCGGGCTGAACGG
GGGGTTCGTGCACACAGCCCAGCTTGGAGCGAACGACCTACACCGAACTG
AGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGAT

TCTGTGGATAACCGTATTACCGCCTTTGAGTGAGCTGATACCGCTCGCCG

CAGCCGAACGACCGAGCGCAGCGAGTCAGTGAGCGAGGAAGCGGAAGAGC

GCCTGATGCGGTATTTTCTCCTTACGCATCTGTGCGGTATTTCACACCG

Example 14

A chimeric OmpA: SFTI RBS E3 Lysis. The chimeric sunflower trypsin inhibitor: OmpA fusion is made by methods known to those skilled in the art. The complete sequence of a tetracycline inducible OmpA: SFTI fusion of which the coding sequence begins with an ATG start codon that begins at 725 and the TAG stop codon ends at 1008 followed by a Shine Delgarno sequence (RBS) and coding sequence for the E3 Lysis sequence of which begins with an ATG start codon that begins at 865 and ends with a TAA stop codon at 1008 that can be inserted into an expression vector is given by:

SEQ ID NO.: 019

CATATGGGGGCGGCCGCCTAAGACCCACTTTCACATTTAAGTIGTTTTTC

TAATCCGCATATAATCAATTCAAGGCCGAATAAGAAGGCTGGCTCTGCAC

CTTGGTGTTCAAATAATTCGATAGCTTGTCGTAATAATGCCGGCATACTA

TCAGTAGTAGGTGTTTCCCTTTCTTCTTTAGCGACTTGATGCTCTTGATC

TTCCAATACGCAACCTAAAGTAAAATGCCCCACAGCGCTGAGTGCATATA

ATGCATTCTCTAGTGAAAAACCTTGTTGGCATAAAAAGGCTAATTGATTT

TCGAGAGTTTCATACTGTTTTTCTGTAGGCCGTGTACCTAAATGTACTTT

TGCTCCATCGCGATGACTTAGTAAAGCACATCTAAAACTTTTAGCGTTAT

TACGTAAAAAATCTTGCCAGCTTTCCCCTTCTAAAGGGCAAAAGTGAGTA

TGGTGCCTATCTAACATCTCAATGGCTAAGGCGTCGAGCAAAGCCCGCTT

ATTTTTTACATGCCAATACAATGTAGGCTGCTCTACACCCAGTTTCTGGG

CGAGTTTACGGGTTTTTAAACCTTCGATTCCGACCTCATTAAGCAGCTCT

AATGCGCTGTTAATCACTTTACTTTTATCTAATCTGGACATCATAAATTC

CTAATTTTTGTTGACACTCTATCATTGATAGAGTTATTTTACCACTCCCT

ATCAGTGATAGAGAAAAGTGAACCATGGCTAAAAAGACAGCTATCGCGAT

TGCAGTGGCACTGGCTGGTTTCGCTACCGTAGCGCAGGCCGCTCCGAAAG

ATGGCCGCTGCACCAAAAGCATTCCGCCGATTTGCTTTCCGGATTAGTCT

AGAAAGGAGTCGTTATGAAAAAAATAACAGGGATTATTTTATTGCTTCTT

GCAGTCATTATTCTGTCTGCATGTCAGGCAAACTATATCCGGGATGTTCA

GGGCGGGACCGTATCTCCGTCATCAACAGCTGAAGTGACCGGATTAGCAA

CGCAGTAACTGCAGGCATGCAAGCTTGGCTGTTTTGGCGGATGAGAGAAG

ATTTTCAGCCTGATACAGATTAAATCAGAACGCAGAAGCGGTCTGATAAA

ACAGAATTTGCCTGGCGGCAGTAGCGCGGTGGTCCCACCTGACCCCATGC

CGAACTCAGAAGTGAAACGCCGTAGCGCCGATGGTAGTGTGGGGTCTCCC

CATGCGAGAGTAGGGAACTGCCAGGCATCAAATAAAACGAAAGGCTCAGT

CGAAAGACTGGGCCTTTCGTTTTATCTGTTGTTTGTCGGTGAACGCTCTC

CTGAGTAGGACAAATCCGCCGGGAGCGGATTTGAACGTTGCGAAGCAACG

GCCCGGAGGGTGGCGGGCAGGACGCCCGCCATAAACTGCCAGGCATCAAA

TTAAGCAGAAGGCCATCCTGACGGATGGCCTTTTTGCGTTTCTACAAACT

CTTTTTGTTTATTTTTCTAAATACATTCAAATATGTATCCGCTCATGAGA

CAATAACCCTGATAAATGCTTCAATAATATTGAAAAAGGAAGAGTATGAG

TATTCAACATTTCCGTGTCGCCCTTATTCCCTTTTTTGCGGCATTTTGCC

TTCCTGTTTTTGCTCACCCAGAAACGCTGGTGAAAGTAAAAGATGCTGAA

GATCAGTTGGGTGCACGAGTGGGTTACATCGAACTGGATCTCAACAGCGG

TAAGATCCTTGAGAGTTTTCGCCCCGAAGAACGTTTTCCAATGATGAGCA

CTTTTAAAGTTCTGCTATGTGGCGCGGTATTATCCCGTGTTGACGCCGGG

CAAGAGCAACTCGGTCGCCGCATACACTATTCTCAGAATGACTTGGTTGA

GTACTCACCAGTCACAGAAAAGCATCTTACGGATGGCATGACAGTAAGAG

AATTATGCAGTGCTGCCATAACCATGAGTGATAACACTGCGGCCAACTTA

CTTCTGACAACGATCGGAGGACCGAAGGAGCTAACCGCTTTTTTGCACAA

CATGGGGGATCATGTAACTCGCCTTGATCGTTGGGAACCGGAGCTGAATG

AAGCCATACCAAACGACGAGCGTGACACCACGATGCCTACAGCAATGGCA

ACAACGTTGCGCAAACTATTAACTGGCGAACTACTTACTCTAGCTTCCCG

GCAACAATTAATAGACTGGATGGAGGCGGATAAAGTTGCAGGACCACTTC

TGCGCTCGGCCCTTCCGGCTGGCTGGTTTATTGCTGATAAATCTGGAGCC

GGTGAGCGTGGGTCTCGCGGTATCATTGCAGCACTGGGGCCAGATGGTAA

GCCCTCCCGTATCGTAGTTATCTACACGACGGGGAGTCAGGCAACTATGG

ATGAACGAAATAGACAGATCGCTGAGATAGGTGCCTCACTGATTAAGCAT

TGGTAACTGTCAGACCAAGTTTACTCATATATACTTTAGATTGATTTAAA

ACTTCATTTTTAATTTAAAAGGATCTAGGTGAAGATCCTTTTTGATAATC

TCATGACCAAAATCCCTTAACGTGAGTTTTCGTTCCACTGAGCGTCAGAC

CCCGTAGAAAAGATCAAAGGATCTTCTTGAGATCCTTTTTTTCTGCGCGT

AATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGC

AGAGCGCAGATACCAAATACTGTCCTTCTAGTGTAGCCGTAGTTAGGCCA

CCACTTCAAGAACTCTGTAGCACCGCCTACATACCTCGCTCTGCTAATCC

TGTTACCAGTGGCTGCTGCCAGTGGCGATAAGTCGTGTCTTACCGGGTTG

GACTCAAGACGATAGTTACCGGATAAGGCGCAGCGGTCGGGCTGAACGGG

GGGTTCGTGCACACAGCCCAGCTTGGAGCGAACGACCTACACCGAACTGA

GATACCTACAGCGTGAGCTATGAGAAAGCGCCACGCTTCCCGAAGGGAGA

AAGGCGGACAGGTATCCGGTAAGCGGCAGGGTCGGAACAGGAGAGCGCAC

GAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGG

CGGAGCCTATGGAAAAACGCCAGCAACGCGGCCTTTTTACGGTTCCTGGC

CTTTTGCTGGCCTTTTGCTCACATGTTCTTTCCTGCGTTATCCCCTGATT

-continued

CTGTGGATAACCGTATTACCGCCTTTGAGTGAGCTGATACCGCTCGCCGC

AGCCGAACGACCGAGCGCAGCGAGTCAGTGAGCGAGGAAGCGGAAGAGCG

CCTGATGCGGTATTTTCTCCTTACGCATCTGTGCGGTATTTCACACCG

While the invention is shown by way of various examples and explanations, it should be understood that this specification and the drawings are intended to encompass the various combinations, sub-combinations, and permutations of the various features disclosed, and not limited by the particular combinations and sequences presented by way of example.

What is claimed is:

1. A chimeric protease inhibitor comprising:

a bacterial secretion signal peptide comprising YebF; and a serine protease inhibitor peptide comprising sunflower trypsin inhibitor;

wherein the bacterial secretion signal peptide and the serine protease inhibitor peptide are fused to form a chimeric peptide.

2. The chimeric protease inhibitor according to claim 1, wherein the chimeric peptide has a sequence that encodes the nucleotide sequence of SEQ ID NO: 017.

3. The chimeric protease inhibitor according to claim 1, in a purified form.

4. The chimeric protease inhibitor according to claim 1, in combination with a live genetically engineered bacterium comprising a genetic sequence encoding the chimeric peptide and an inducible promoter adapted to promote transcription of the chimeric protease inhibitor within the genetically engineered bacterium.

5. The chimeric protease inhibitor according to claim 4, wherein the genetically engineered bacterium is alive within a pharmaceutically acceptable dosage form.

6. The chimeric protease inhibitor according to claim 1, in a pharmaceutically acceptable formulation further comprising a cytotoxic peptide comprising a chimeric cytolethal distending toxin:apoptin peptide degradable by a protease inhibited by the serine protease inhibitor.

7. The chimeric protease inhibitor according to claim 1, further comprising a chimeric *Pseudomonas* ToxA therapeutic molecule peptide degradable by a protease inhibited by the serine protease inhibitor.

8. The chimeric protease inhibitor according to claim 1, in a pharmaceutically effective dosage form comprising at least $10^9$ live genetically engineered bacteria that produce and secrete the chimeric protease inhibitor.

9. A chimeric protease inhibitor comprising a bacterial secretion signal comprising YebF, linked through at least one amino acid to a serine protease inhibitor peptide sequence comprising sunflower trypsin inhibitor.

10. The chimeric protease inhibitor according to claim 9, transcribed from a nucleic acid comprising the nucleotide sequence of SEQ ID NO: 017.

11. The chimeric protease inhibitor according to claim 9, in combination with a live genetically engineered bacterium in a pharmaceutically acceptable formulation, the live genetically engineered bacterium comprising an inducible promoter for inducing production of the chimeric protease inhibitor by the live genetically engineered bacterium.

12. The chimeric protease inhibitor according to claim 9, in combination with a live genetically engineered bacterium in a pharmaceutically acceptable formulation, the live genetically engineered bacterium comprising a nucleic acid which encodes a reorganized polycistronic cytolethal distending toxin fusion expressed or secreted in an absence of sty and ttsa.

13. The chimeric protease inhibitor according to claim 9, in combination with a live genetically engineered bacterium in a pharmaceutically acceptable formulation, the live genetically engineered bacterium comprising a nucleic acid which encodes a modified chimeric cytolethal distending toxin:apoptin fusion expressed or secreted in an absence of in an absence of sty and ttsa.

14. The chimeric protease inhibitor according to claim 9, in combination with a live genetically engineered bacterium in a pharmaceutically acceptable formulation, the live genetically engineered bacterium comprising a nucleic acid which encodes a functionally active modified chimeric *Pseudomonas* ToxA therapeutic molecule.

15. The chimeric protease inhibitor according to claim 9, in combination with a live genetically engineered bacterium in a pharmaceutically acceptable formulation, the live genetically engineered bacterium being a tumor targeting bacterium.

* * * * *